United States Patent
Anderson et al.

(10) Patent No.: US 10,239,835 B2
(45) Date of Patent: Mar. 26, 2019

(54) N-ALKYLARYL-5-OXYARYL-OCTAHYDRO-CYCLOPENTA[C]PYRROLE NEGATIVE ALLOSTERIC MODULATORS OF NR2B

(71) Applicant: Luc Therapeutics, Inc., Cambridge, MA (US)

(72) Inventors: David R. Anderson, Salem, CT (US); Robert A. Volkmann, Mystic, CT (US); Frank S. Menniti, Mystic, CT (US)

(73) Assignee: CADENT THERAPEUTICS, INC., Cambridge, MA (US)

( * ) Notice: Subject to any disclaimer, the term of this patent is extended or adjusted under 35 U.S.C. 154(b) by 0 days.

(21) Appl. No.: 15/506,592

(22) PCT Filed: Sep. 23, 2015

(86) PCT No.: PCT/US2015/051694
§ 371 (c)(1),
(2) Date: Feb. 24, 2017

(87) PCT Pub. No.: WO2016/049165
PCT Pub. Date: Mar. 31, 2016

(65) Prior Publication Data
US 2018/0111902 A1   Apr. 26, 2018

Related U.S. Application Data

(60) Provisional application No. 62/056,284, filed on Sep. 26, 2014.

(51) Int. Cl.
| | |
|---|---|
| C07D 209/52 | (2006.01) |
| C07D 403/12 | (2006.01) |
| C07D 401/14 | (2006.01) |
| C07D 401/06 | (2006.01) |
| C07D 401/12 | (2006.01) |
| C07D 403/06 | (2006.01) |
| A61P 25/22 | (2006.01) |
| A61P 25/24 | (2006.01) |
| A61P 25/00 | (2006.01) |
| A61P 25/16 | (2006.01) |
| A61P 25/28 | (2006.01) |

(52) U.S. Cl.
CPC .......... C07D 209/52 (2013.01); A61P 25/00 (2018.01); A61P 25/16 (2018.01); A61P 25/22 (2018.01); A61P 25/24 (2018.01); A61P 25/28 (2018.01); C07D 401/06 (2013.01); C07D 401/12 (2013.01); C07D 401/14 (2013.01); C07D 403/06 (2013.01); C07D 403/12 (2013.01)

(58) Field of Classification Search
CPC .................................................. C07D 209/52
See application file for complete search history.

(56) References Cited

U.S. PATENT DOCUMENTS

| | | | |
|---|---|---|---|
| 5,532,243 | A | 7/1996 | Gilligan |
| 5,726,172 | A | 3/1998 | Sparks et al. |
| 2006/0014767 | A1 | 1/2006 | Lee et al. |
| 2012/0095040 | A1 | 4/2012 | Abouabdellah et al. |
| 2012/0136026 | A1 | 5/2012 | Abouabdellah et al. |
| 2013/0012705 | A1 | 1/2013 | Tang et al. |

FOREIGN PATENT DOCUMENTS

| | | |
|---|---|---|
| EA | 2011/71386 A1 | 11/2010 |
| EP | 0626949 A1 | 12/1994 |
| JP | 2003-513040 A | 4/2003 |
| JP | 2008-536927 A | 9/2008 |
| JP | 2012-526783 A | 11/2012 |
| WO | WO 1993/016050 | 8/1993 |
| WO | WO 1995/015327 | 6/1995 |
| WO | WO 01/32171 A1 | 5/2001 |

(Continued)

OTHER PUBLICATIONS

Taylor el al. (Drug Metabolism and Disposition (1996), 24(1), 55-64).*
International Search Report and Written Opinion to PCT/US2015/051694, dated Jan. 6, 2016.
International Search Report to Singapore Application No. 11201702023Q, dated Jan. 26, 2018, (3p).
Extended European Search Report to EP Application No. 15844057.8, dated Mar. 9, 2018, (10p).
Bhattarai, Deepak, et al., "Synthesis and in Vitro Evaluation of the Antitubercular and Antibacterial Activity of Novel Oxazolidinones Bearing Octahydrocyclopenta[c]pyrrol-2-yl Moieties"; Center for Neuro-Medicine, Brain Science Institute, Korea Institute of Science and Technology (KIST), Seoul, 136-791, S. Korea; *Chemical & Pharmaceutical Bulletin* (2014), 62(12), pp. 1214-1224.

(Continued)

*Primary Examiner* — Bruck Kifle
(74) *Attorney, Agent, or Firm* — Brinks Gilson & Lione; Yuezhong Feng

(57) ABSTRACT

The present invention relates to N-alkylaryl-5-oxyaryl-octadihydrocyclopent[c]pyrrole negative allosteric modulators of NR2B receptors useful in the treatment of neurological diseases having the Formula I where R1, R2, L1, L2, X, Y, and Y' are described therein. In an aspect, compounds of formula I are described and pharmaceutically acceptable salts, prodrugs, solvates, hydrates, tautomers, or stereoisomers thereof wherein: L1 is straight or branched C1-C5 alkyl optionally substituted with one or more substituents selected from the group consisting of OH, ORIO, NH2, NHRio, and N(Rlo)(Rio') provided that no more than one oxygen or nitrogen is attached to any carbon.

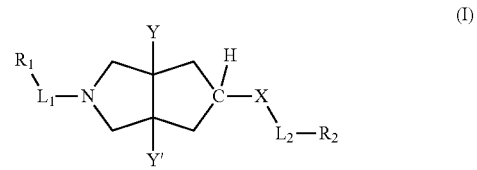

(I)

22 Claims, 1 Drawing Sheet

(56) References Cited

FOREIGN PATENT DOCUMENTS

| | | |
|---|---|---|
| WO | WO 2001/32171 A1 | 5/2001 |
| WO | WO 2005/084667 A1 | 9/2005 |
| WO | WO 2005/086735 A2 | 9/2005 |
| WO | WO 2006/010965 A1 | 2/2006 |
| WO | WO 2006/012396 A1 | 2/2006 |
| WO | WO 2006/113471 A2 | 10/2006 |
| WO | WO 2007/128458 A1 | 11/2007 |
| WO | WO 2007/128459 A1 | 11/2007 |
| WO | WO 2008/121686 A1 | 10/2008 |
| WO | WO 2009/055331 A2 | 4/2009 |
| WO | WO 2010/068851 A1 | 6/2010 |
| WO | WO 2010/130944 A1 | 11/2010 |
| WO | WO 2011/085170 A1 | 7/2011 |
| WO | WO 2011/149993 A2 | 12/2011 |
| WO | WO 2012/156339 A1 | 11/2012 |
| WO | WO 2013/021054 A1 | 2/2013 |
| WO | WO 2013/091539 A1 | 6/2013 |
| WO | WO 2014/048865 A1 | 4/2014 |
| WO | WO 2014/139978 A1 | 9/2014 |
| WO | WO 2015/023441 A2 | 2/2015 |
| WO | WO 2015/048507 A1 | 4/2015 |
| WO | WO 2015/144605 A1 | 10/2015 |

OTHER PUBLICATIONS

Taylor, Albert R. et al., "Synthesis of Putative Metabolites and Investigation of the Metabolic Fate of Gliclazide, [1-(3-azabicyclo(3,3,0)oct-3-yl)-3-(4-Methylphenylsulfonyl)Urea], in Diabetic Patients"; Servier Research and Development Ltd., Fulmer, Slough, SL3 6HH, UK; *Drug Metabolism and Disposition* (1996), 24(1), pp. 55-64.

Paoletti, Pierre, et al., "*NMDA Receptor Subunit Diversity: Impact on Receptor Properties, Synaptic Plasticity and Disease*," Nature Reviews/Neuroscience, vol. 14, Jun. 2013, pp. 383-400.

Preskorn, Sheldon H. et al., "*An Innovative Design to Establish Proof of Concept of the Antidepressant Effects of the NR2B Subunit Selective N-Methyl-D-Aspartate Antagonist, CP-101,606, in Patients With Treatment-Refractory Major Depressive Disorder*," Journal of Clinical Psychopharmacology, vol. 28, No. 6, Dec. 2008, pp. 631-637.

Schinkel, Alfred H., "*P-Glycoprotein, a Gatekeeper in the Blood-Brain Barrier*," Advanced Drug Delivery Reviews, vol. 36, 1999, pp. 179-194.

\* cited by examiner

N-ALKYLARYL-5-OXYARYL-OCTAHYDRO-CYCLOPENTA[C]PYRROLE NEGATIVE ALLOSTERIC MODULATORS OF NR2B

This application is the national phase application of PCT Application No. PCT/US2015/051694, filed Sep. 23, 2015, which claims priority to U.S. Provisional Patent Application Ser. No. 62/056,284, filed Sep. 26, 2014, the entireties of both of which are incorporated herein by reference.

FIELD OF THE INVENTION

The present disclosure relates to compounds that selectively modulate the activity of NR1/NR2B receptors.

BACKGROUND OF THE INVENTION

The NMDA receptor is arguably an important signaling mechanism in the human brain. The brain processes a complex array of information to allow humans to function, storing information from the past and analyzing this information in the context of the present to respond and plan for the future. These incredibly complex computations are mediated at the molecular level by the continual adjustment of the strength of synapses, the nodes for communication between nerve cells (estimated at about 60 trillion in the human brain).

Glutamate is the major excitatory neurotransmitter in the brain, utilized at 80% of these synapses. NMDA receptors are one of three classes that mediate synaptic transmission using glutamate. NMDA receptors play a critical role in regulating the strength of synapses, that is, in regulating synaptic plasticity. Thus, the NMDA receptor is at the molecular core of brain function, and in particular the cognitive functions of learning and memory. These facts underlie the tremendous therapeutic utility of modulating NMDA receptor function with new drugs to treat a broad range of neuropsychiatric disease and cognitive dysfunction.

The molecular basis of NMDA receptor function is increasingly well understood. The NMDA receptor is composed of four protein subunits, two NR1 subunits and two NR2 subunits. An NR1 subunit derived from a single gene is ubiquitously expressed throughout the brain and is common to all NMDA receptors. However, the four different NR2 subunits, NR2A-D, are derived from separate genes that are differentially expressed in different brain regions and by distinct populations of neurons within a particular region. Furthermore, individual neurons may express more than one NR2 subunit and individual NMDA receptors expressed by such neurons may contain two of the same NR2 subunits (for example, 2 NR2B subunits) or two different subunits (one NR2A and one NR2B subunit). Therefore, a drug that selectively modulates the activity of one NR2 subunit may do so at receptors that express two of the targeted subunits, or only one of the targeted subunits. Thus there is a need for new treatments for diseases related to the NR1/NR2B receptor.

SUMMARY OF THE INVENTION

In an aspect, compounds of formula I are described:

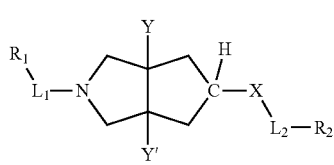

(I)

and pharmaceutically acceptable salts, prodrugs, solvates, hydrates, tautomers, or stereoisomers thereof
wherein:
$L_1$ is straight or branched $C_1$-$C_5$ alkyl optionally substituted with one or more substituents selected from the group consisting of OH, $OR_{10}$, $NH_2$, $NHR_{10}$, and $N(R_{10})(R_{10}')$ provided that no more than one oxygen or nitrogen is attached to any carbon; or $L_1$ is selected from the group consisting of —C(O)—, —C(O)—$C_1$-$C_3$alkylenyl-, —C(O)O—$C_1$-$C_3$alkylenyl-, —S(O)$_2$—, —S(O)$_2$NH—, —C(O)NH—, —C(O)NR$_{10}$—, and a bond;

Each $R_{10}$ and $R_{10}'$ is independently selected from the group consisting of H; $C_1$-$C_6$ alkyl optionally substituted with one or more substituents selected from the group consisting of OH, O—$C_1$-$C_5$ alkyl, $OPO_3^{-2}M_2$, $OP(O)(OH)_2$, OC(O)alkyl, and OC(O)O-alkyl where M is a monovalent metal cation; and cycloalkyl optionally substituted with one or more substituents selected from the group consisting of OH and O—$C_1$-$C_5$ alkyl provided that no more than one oxygen is attached to any carbon; or $R_{10}$ and $R_{10}'$, together with the nitrogen to which they are attached, may form a heterocycle;

$R_1$ is cycloalkyl, aryl, or heteroaryl, any of which optionally substituted with one or more substituents selected from the group consisting of OH, CN, halogen, —$C_1$-$C_6$alkylaryl, —O—$C_1$-$C_6$alkylaryl, O—$R_{10}$, $OPO_3^{-2}M_2$, $OP(O)(OH)_2$, SH, S—$R_{10}$, $C_1$-$C_5$ alkyl, branched alkyl, $NH_2$, $NHR_{10}$, $NHS(O)_2R_{10}$, $N(R_{10})(NR_{10}')$, and $NHCOR_{10}$ where M is a monovalent metal cation;

Y and Y' are independently H, halogen, or $C_1$-$C_5$ alkyl;
X is selected from O, S, —S(O)—, and —S(O)$_2$—;
$L_2$ is a bond, —(CH$_2$)$_n$— or —(CHR$_{11}$)$_n$—;
Each $R_{11}$ is independently selected from the group consisting of H, —$C_1$-$C_5$ alkylenyl-, —CO—$C_1$-$C_5$alkylenyl-, and -alkylenyl-CO-alkylenyl-;
$R_2$ is phenyl, naphthyl, heteroaryl or bicyclic heteroaryl, each of which is optionally substituted with one or more substituents selected from the group consisting of halogen, OH, $C_1$-$C_6$alkyl, $OR_{10}$, CN, $NH_2$, $NHR_{10}$, $N(R_{10})(R_{10}')$, -nitro, SH, $SR_{10}$, $SOR_{10}$, $SO_2R_{10}$, $SO_2NHR_{10}$, $SO_2N(R_{10})(R_{10}')$, $CONH_2$, $CONR_{10}$, and $CON(R_{10})(R_{10}')$; and
n is 1, 2, or 3.

The present disclosure further pertains to compounds that selectively modulate the activity of NMDA receptors that contain an NR2B subunit, which encompasses receptors containing two NR2B subunits or one NR2B subunit in combination with one other NR2 subunit (i.e., NR2A/NR2B, NR2B/NR2C, or NR2B/NR2D receptors). Such compounds can decrease the activity of NR2B-containing NMDA receptors. The present invention also pertains to the therapeutic uses of such compounds. Also described are pharmaceutical formulations, comprising at least one of the disclosed compounds.

Also described herein are methods of treating a disease susceptible to treatment with a disclosed compound in a patient in need thereof by administering to the patient an effective amount of a disclosed compound. Such diseases include, without limitation, neurological dysfunction such as Parkinson's disease, Huntington's disease, amyotrophic lateral sclerosis, multiple sclerosis, and seizure disorders; emotional disorders; depression; bipolar disorder; obsessive-compulsive disorder; and other anxiety disorders.

Compounds or pharmaceutical compositions of the present invention may be used to treat individuals that experience dysfunction caused by abnormal brain development, including but not limited to those suffering from autism and autism spectrum disorders, Fragile X syndrome, Rett Syndrome, Angelman syndrome, tuberous sclerosis, Down's syndrome and other forms of mental retardation.

The invention further pertains to pharmaceutical compositions that comprise an effective amount of a disclosed compound and a pharmaceutically acceptable carrier. The compositions are useful for treating or preventing a disease or disorder. The invention includes a disclosed compound provided as a pharmaceutically acceptable prodrug, hydrate, salt, stereoisomer, or mixtures thereof.

DETAILED DESCRIPTION OF THE INVENTION

Figure 1:
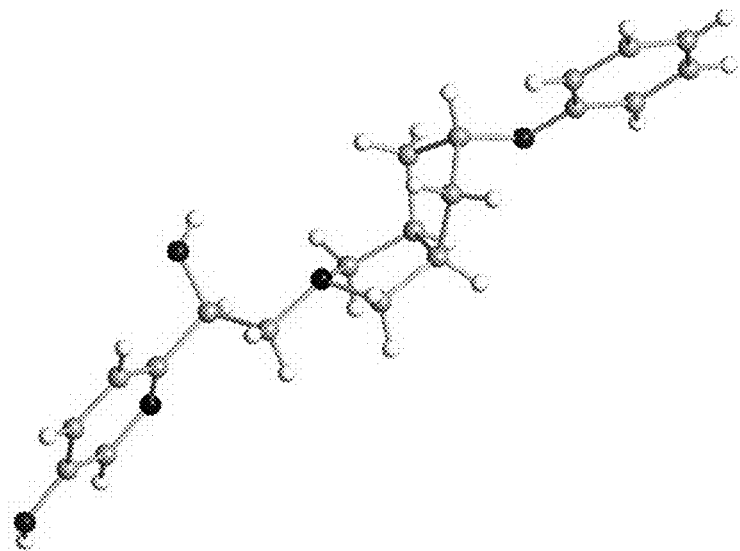
FIG. 1 is the X-ray crystallograph of the compound of Example 8.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g. an alkyl group) can (but is not required to) be bonded other substituents (e.g. heteroatoms). For instance, an alkyl group that is optionally substituted can be a fully saturated alkyl chain (i.e. a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus the term "optionally substituted" means that a given chemical moiety has the potential to contain other functional groups, but does not necessarily have any further functional groups. Suitable substituents used in the optional substitution of the described groups include, without limitation, halogen, oxo, CN, —COOH, —CH$_2$CN, —O—C$_1$-C$_6$alkyl, C$_1$-C$_6$alkyl, —OC$_1$-C$_6$alkenyl, —OC$_1$-C$_6$alkynyl, —C$_1$-C$_6$alkenyl, —C$_1$-C$_6$alkynyl, —OH, —OP(O)(OH)$_2$, —OC(O)C$_1$-C$_6$alkyl, —C(O)C$_1$-C$_6$alkyl, —OC(O)OC$_1$-C$_6$alkyl, NH$_2$, NH(C$_1$-C$_6$alkyl), N(C$_1$-C$_6$alkyl)$_2$, —NHC(O)C$_1$-C$_6$alkyl, —C(O)NHC$_1$-C$_6$alkyl, —S(O)$_2$—C$_1$-C$_6$alkyl, —S(O)NHC$_1$-C$_6$alkyl, and S(O)N(C$_1$-C$_6$alkyl)$_2$ Unless otherwise specifically defined, the term "aryl" refers to cyclic, aromatic hydrocarbon groups that have 1 to 2 aromatic rings, including monocyclic or bicyclic groups such as phenyl, biphenyl or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—C$_1$-C$_6$alkyl, C$_1$-C$_6$alkyl, —OC$_1$-C$_6$alkenyl, —OC$_1$-C$_6$alkynyl, —C$_1$-C$_6$alkenyl, —C$_1$-C$_6$alkynyl, —OH, —OP(O)(OH)$_2$, —OC(O)C$_1$-C$_6$alkyl, —C(O)C$_1$-C$_6$alkyl, —OC(O)OC$_1$-C$_6$alkyl, NH$_2$, NH(C$_1$-C$_6$alkyl), N(C$_1$-C$_6$alkyl)$_2$, —S(O)$_2$—C$_1$-C$_6$alkyl, —S(O)NHC$_1$-C$_6$alkyl, and S(O)N(C$_1$-C$_6$alkyl)$_2$. The substituents can themselves be optionally substituted. Furthermore when containing two fused rings the aryl groups herein defined may have an unsaturated or partially saturated ring fused with a fully saturated ring. Exemplary ring systems of these aryl groups include indanyl, indenyl, tetrahydronaphthalenyl, and tetrahydrobenzoannulenyl.

Unless otherwise specifically defined, "heteroaryl" means a monovalent monocyclic aromatic radical of 5 to 10 ring atoms or a polycyclic aromatic radical, containing one or more ring heteroatoms selected from N, O, or S, the remaining ring atoms being C. Heteroaryl as herein defined also means a bicyclic heteroaromatic group wherein the heteroatom is selected from N, O, or S. The aromatic radical is optionally substituted independently with one or more substituents described herein. Examples include, but are not limited to, furyl, thienyl, pyrrolyl, pyridyl, pyrazolyl, pyrimidinyl, imidazolyl, pyrazinyl, indolyl, thiophen-2-yl, quinolyl, benzopyranyl, thiazolyl, and derivatives thereof. Furthermore when containing two fused rings the aryl groups herein defined may have an unsaturated or partially saturated ring fused with a fully saturated ring. Exemplary ring systems of these heteroaryl groups include indolinyl, indolinonyl, dihydrobenzothiophenyl, dihydrobenzofuran, chromanyl, thiochromanyl, tetrahydroquinolinyl, dihydrobenzothiazine, and dihydrobenzoxanyl.

"C$_1$-C$_3$ alkyl" refers to a straight or branched chain saturated hydrocarbon containing 1-3 carbon atoms. Examples of a C$_1$-C3alkyl group include, but are not limited to, methyl, ethyl, propyl and isopropyl.

"C$_1$-C$_5$ alkyl" refers to a straight or branched chain saturated hydrocarbon containing 1-5 carbon atoms. Examples of a C$_1$-C$_5$alkyl group include, but are not limited to, methyl, ethyl, propyl, butyl, pentyl, isopropyl, isobutyl, sec-butyl and tert-butyl, isopentyl and neopentyl.

Alkyl is generally lower alkyl, or C$_1$-C$_6$ alkyl. Examples of a C$_1$-C$_6$ alkyl group include, but are not limited to, methyl, ethyl, propyl, butyl, pentyl, hexyl, isopropyl, isobutyl, sec-butyl, tert-butyl, isopentyl, neopentyl, and isohexyl.

Halogen or "halo" refers to fluorine, chlorine, bromine and iodine.

"Alkylenyl" as herein defined refers to groups of general formula —(CH$_2$)n- where n is an integer from 1 to 6. Suitable examples of alkylenyl groups include methylenyl, ethylenyl, and propylenyl.

"Alkenyl" refers to a straight or branched chain unsaturated hydrocarbon containing 2-12 carbon atoms. The "alkenyl" group contains at least one double bond in the chain. Examples of alkenyl groups include ethenyl, propenyl, n-butenyl, iso-butenyl, pentenyl, or hexenyl.

"Alkynyl" refers to a straight or branched chain unsaturated hydrocarbon containing 2-12 carbon atoms. The "alkynyl" group contains at least one triplebond in the chain.

Examples of alkynyl groups include ethynyl, propargyl, n-butynyl, iso-butynyl, pentynyl, or hexynyl.

The term "haloalkyl" refers to straight or branched saturated hydrocarbon chains containing 1-5 carbon atoms which are substituted at least one of the carbon with halogen groups such fluorine, chlorine, bromine, iodide. Examples of haloalkyl groups as herein defined include without limitation trifluoromethyl, tribromomethyl, and 1,1,1-trifluoroethyl.

The term "hydroxyalkyl" refers to straight or branched saturated hydrocarbon chains containing 1-5 carbon atoms which are substituted at least one of the carbon with the hydroxyl group.

The term "-alkylaryl" refers to aryl groups connected to an adjacent C1-C6alkyl wherein the linkage is located at the alkyl end. Accordingly, groups such as benzyl, phenylethyl, or mesitylenyl constitute exemplary representatives of alkylaryl of the present invention.

"Cycloalkyl" means monocyclic saturated carbon rings containing 3-18 carbon atoms. Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, or bicyclo[2.2.2]octenyl.

"Heterocyclyl" or "heterocycloalkyl" or "heterocycle" monocyclic rings containing carbon and heteroatoms taken from oxygen, nitrogen, or sulfur and wherein there is not delocalized 2n electrons (aromaticity) shared among the ring carbon or heteroatoms; heterocyclyl rings include, but are not limited to, oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl.

"Spirocycle" means bicyclic ring systems with both rings connected through a single atom. The ring can be different in size and nature, or identical in size and nature. Examples include spiropentane, spriohexane, spiroheptane, spirooctane, spirononane, or spirodecane.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

The term "monovalent metal cation" refers to atomic elements that are positively charged (atoms which have more protons than electrons because they have lost electrons). Examples of metal cations include, without limitation, monovalent metal and metalloids of the periodic table. These metal cations include monovalent alkaline metals such Li, K, Na, Rb, or Cs, monovalent transition metals such as Cu, Au, or Ag.

The term "stereoisomers" refers to the set of compounds which have the same number and type of atoms and share the same bond connectivity between those atoms, but differ in three dimensional structure. The term "stereoisomer" refers to any member of this set of compounds.

The term "diastereomers" refers to the set of stereoisomers which cannot be made superimposable by rotation around single bonds. For example, cis- and trans-double bonds, endo- and exo-substitution on bicyclic ring systems, and compounds containing multiple stereogenic centers with different relative configurations are considered to be diastereomer. The term "diastereomer" refers to any member of this set of compounds. In some examples presented, the synthetic route may produce a single diasteromer or a mixture of diastereomer. In some cases these diasteromers were separated and in other cases a wavy bond is used to indicate the structural element where configuration is variable.

The term "enantiomers" refers to a pair of stereoisomers which are non-superimposable mirror images of one another. The term "enantiomer" refers to a single member of this pair of stereoisomers. The term "racemic" refers to a 1:1 mixture of a pair of enantiomers.

The term "tautomers" refers to a set of compounds that have the same number and type of atoms, but differ in bond connectivity and are in equilibrium with one another. A "tautomer" is a single member of this set of compounds. Typically a single tautomer is drawn but it is understood that this single structure is meant to represent all possible tautomers that might exist. Examples include enol-ketone tautomerism. When a ketone is drawn it is understood that both the enol and ketone forms are part of the invention.

A "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound. Furthermore, as used herein a prodrug is a drug which is inactive in the body, but is transformed in the body typically either during absorption or after absorption from the gastrointestinal tract into the active compound. The conversion of the prodrug into the active compound in the body may be done chemically or biologically (i.e., using an enzyme).

One aspect of the invention relates to compounds of Formula I:

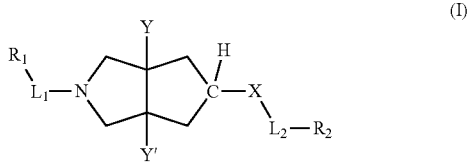

and pharmaceutically acceptable salts, prodrugs, solvates, hydrates, tautomers, or stereoisomers thereof, where $R_1$, $R_2$, $L_1$, $L_2$, X, Y, and Y' are described above.

In one embodiment of the compounds of Formula I, $R_1$ is aryl or heteroaryl each of which is substituted with one or more substituents selected from the group consisting of OH, halogen, $OR_{10}$, SH, $SR_{10}$, $NH_2$, $NHR_{10}$ and $NHCOR_{10}$.

In another embodiment, wherein $R_1$ is aryl substituted with one substituent selected from the group consisting of OH, $OR_{10}$, SH, $SR_{10}$, $NH_2$, $NHR_{10}$ and $NHCOR_{10}$.

In another embodiment of the compounds of Formula I, Y and Y' are hydrogen.

In another embodiment of the compounds of Formula I, Y and Y' are halogen. In other embodiments of the compounds of Formula I, Y and Y' are fluorine.

In another embodiment of the compounds $L_2$ is a bond.

In another embodiment of the compounds of Formula I, n is 1.

In another embodiment of the compounds of Formula I, n is 2.

In yet another embodiment of the compounds of Formula I, $R_2$ is phenyl optionally substituted with one or more halogen, OH, $OR_{10}$, CN, $NH_2$, $NHR_{10}$, $N(R_{10})(R_{10}')$, SH, $SR_{10}$, $SOR_{10}$, $SO_2R_{10}$, $SO_2NHR_{10}$, $SO_2N(R_{10})(R_{10}')$, $CONH_2$, $CONR_{10}$, $CON(R_{10})(R_{10}')$.

In another embodiment, $R_2$ is phenyl substituted with one or more halogen.

In another embodiment of the compounds of Formula I, $L_1$ is branched $C_1$-$C_5$ alkyl substituted with one or more substituents selected from the group consisting of OH, $OR_{10}$, $NH_2$, $NHR_{10}$, and $N(R_{10})(R_{10}')$ provided that no more than one oxygen or nitrogen is attached to any carbon of $L_1$.

In another embodiment of the compounds of Formula I, $L_1$ is straight $C_1$-$C_5$ alkyl substituted with one or more substituents selected from the group consisting of OH, $OR_{10}$, $NH_2$, $NHR_{10}$, and $N(R_{10})(R_{10}')$ provided that no more than one oxygen or nitrogen is attached to any carbon of $L_1$.

Other embodiments of the invention relate to compounds of Formula I where $L_1$ is straight or branched $C_1$-$C_5$ alkyl substituted with OH.

In some embodiments of the compounds of Formula I, $L_1$ is —C(O)—$C_1$-$C_3$alkylenyl-.

In other embodiments of the compounds of Formula I, $L_2$ is unsubstituted straight or branched $C_1$-$C_5$ alkyl.

In some embodiments of the compounds of Formula I, $L_2$ is —$CH_2$—.

Yet in other embodiments, the invention describes compounds of Formula I where X is O.

In some embodiments of the compounds of Formula I, X is S.

In other embodiments, the invention relates to compounds of Formula I where $R_1$ is aryl or heteroaryl, both of which are optionally substituted with one or more substituents selected from the group consisting of OH and halogen.

In other embodiments of the compounds of Formula I, $R_1$ is phenyl substituted with OH and halogen.

In yet another embodiment of the compounds of Formula I, $R_1$ is a bicyclic heteroaryl substituted with OH and halogen.

In some embodiments, the present disclosure rather includes compounds of Formula I where any hydrogen atom may be replaced with a deuterium atom.

In other embodiments, tautomers of the compounds of Formula I are also described.

Other embodiments of Formula I relate to compounds of Formula (Ia):

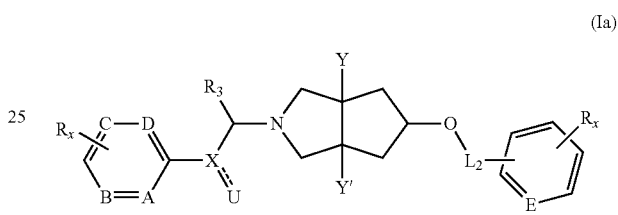

wherein:
A, B, C, D, and E are independently N or $CR_x$;
------ is an optional double bond;
X is CH or C;
U is OH or O;
Y and Y' are independently H, halogen, or $C_1$-$C_6$ alkyl;
$R_3$ is H;
each $R_x$ is independently H, $C_1$-$C_6$ alkyl, halogen, —OH, —$NHS(O)_2R_{10}$, or —$OC_1$-$C_6$ alkyl; and
$L_2$ is a bond or $(CH_2)_n$, wherein n is 1 or 2.

In other embodiments, the compounds of invention have the Formula (Ib):

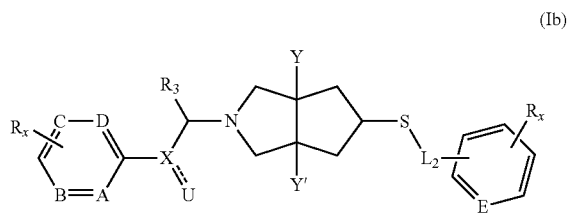

wherein:
A, B, C, D, and E are independently N or $CR_x$;
------ is an optional double bond;
X is CH or C;
U is OH or O;
Y and Y' are independently H, halogen, or $C_1$-$C_6$ alkyl;
$R_3$ is H;
each $R_x$ is independently H, $C_1$-$C_6$ alkyl, halogen, —OH, —$NHS(O)_2R_{10}$, or —$OC_1$-$C_6$ alkyl; and
$L_2$ is $(CH_2)_n$, wherein n is 0, 1 or 2.

In other embodiments of the invention the compounds herein described have the Formula (Ic):

(Ic)

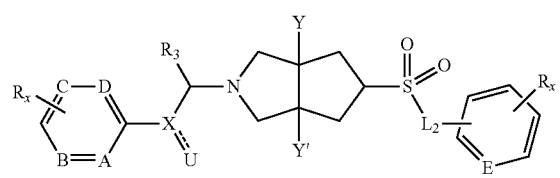

A, B, C, D, and E are independently N or CR$_x$;
------ is an optional double bond;
X is CH or C;
U is OH or O;
Y and Y' are independently H, halogen, or C$_1$-C$_6$ alkyl;
R$_3$ is H;
each R$_x$ is independently H, C$_1$-C$_6$ alkyl, halogen, —OH, —NHS(O)$_2$R$_{10}$, or —OC$_1$-C$_6$ alkyl; and
L$_2$ is a bond or (CH$_2$)$_n$, wherein n is 1 or 2.

In yet another embodiment, the compounds of the invention have the Formula (Id):

(Id)

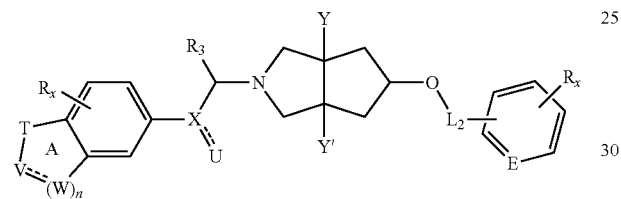

wherein:
------ is an optional double bond which allows the A ring to be partially or fully saturated;
E is independently N or CR$_x$;
T is O, S, NR$_y$, C═O, or C(R$_x$)$_n$;
V is O, S, N, NR$_y$, C═O, or C(R$_x$)$_n$;
each W is independently selected from O, S, C═O, N, NR$_y$ or C(R$_x$)$_n$;
X is CH or C;
U is OH or O;
Y and Y' are independently H, halogen, or C$_1$-C$_6$ alkyl;
R$_3$ is H;
each R$_x$ is independently H, C$_1$-C$_6$ alkyl, halogen, —OH, or —OC$_1$-C$_6$ alkyl;
R$_y$ is H, or C$_{1-6}$ alkyl;
L$_2$ is a bond or (CH$_2$)$_n$; and
each n is independently 1, or 2.

In another embodiment, illustrative compounds of Formula I include:

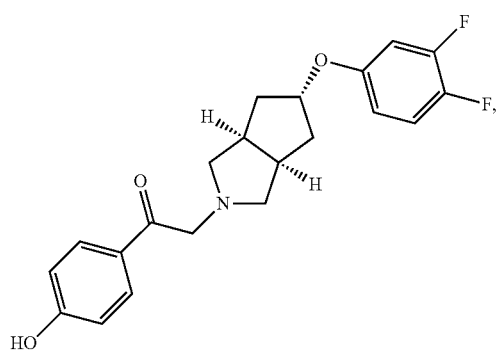

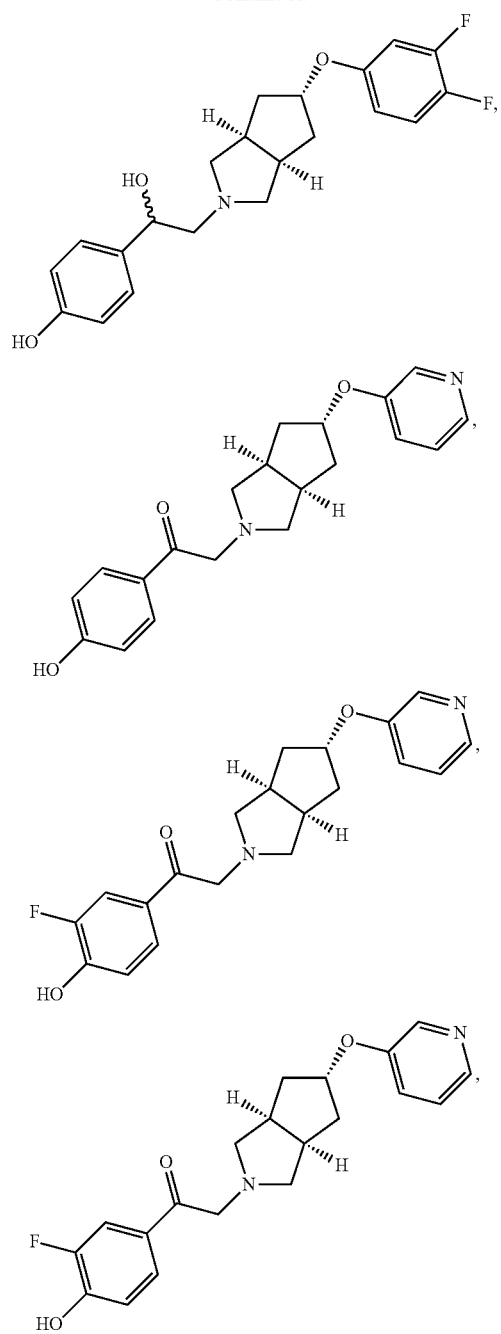

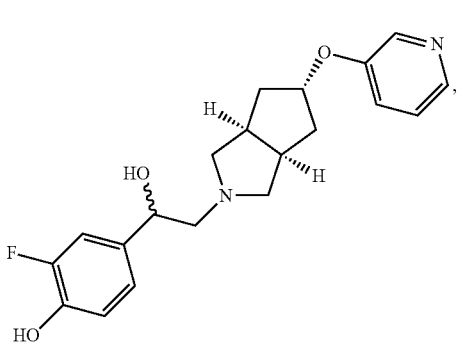

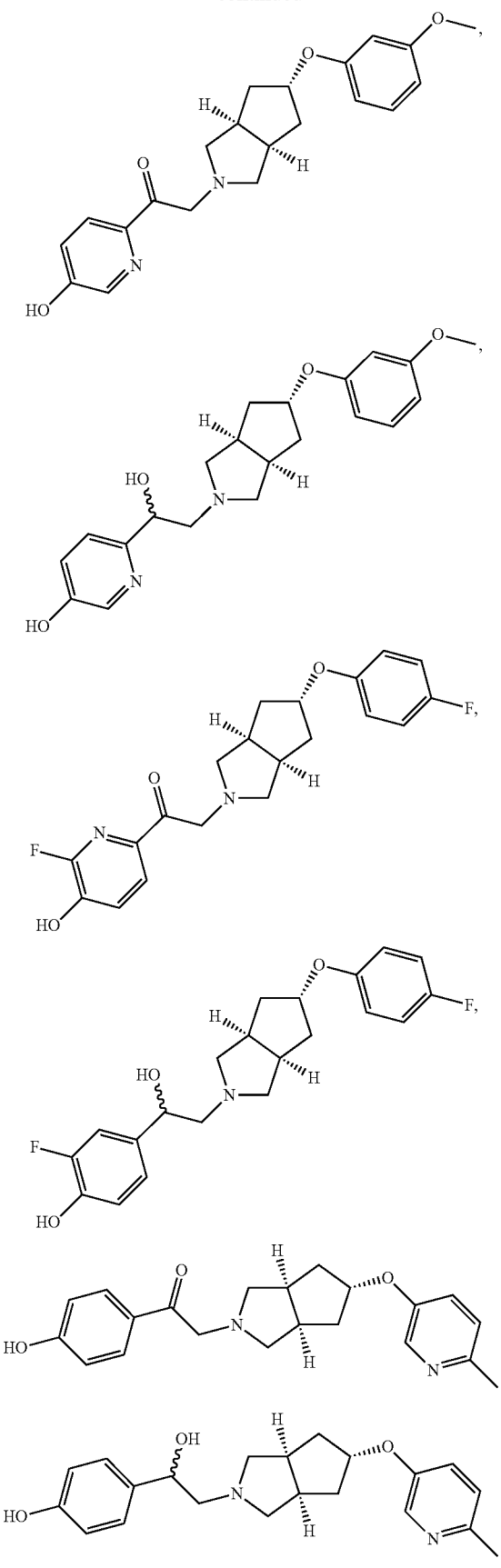

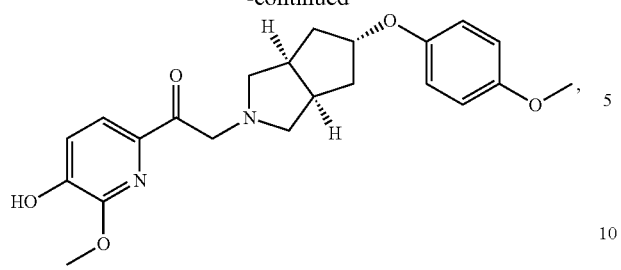
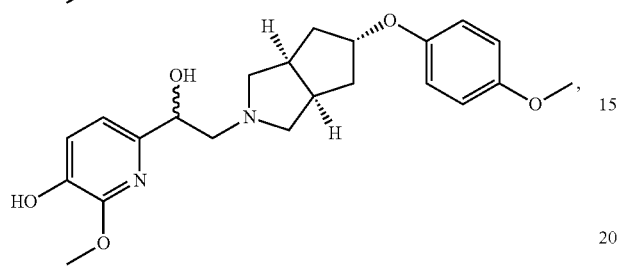
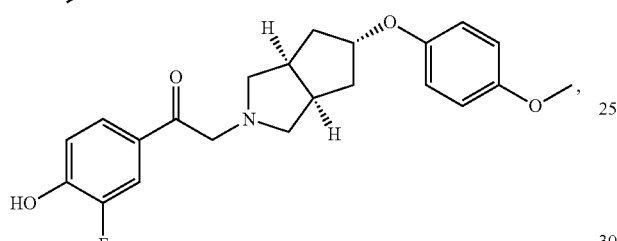
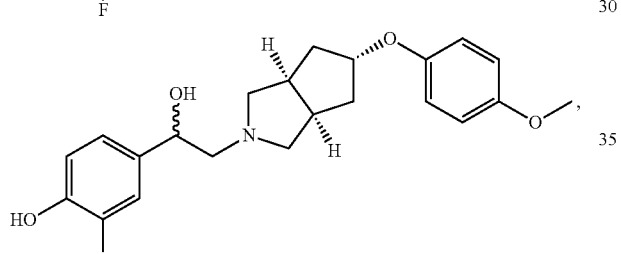
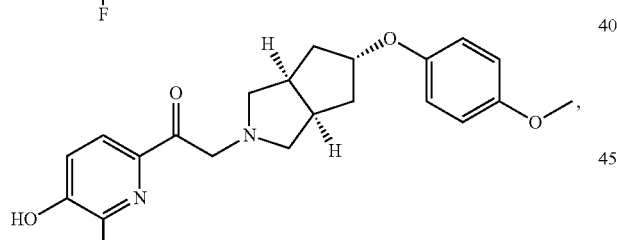
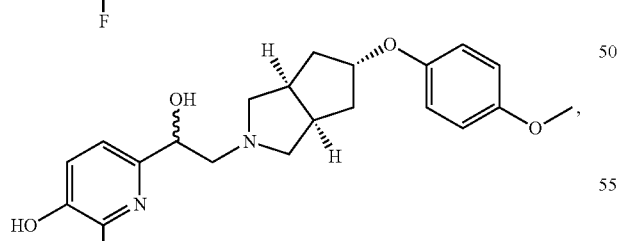
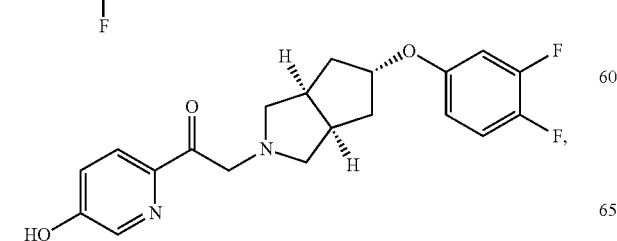
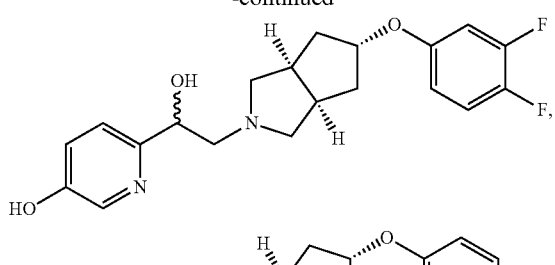
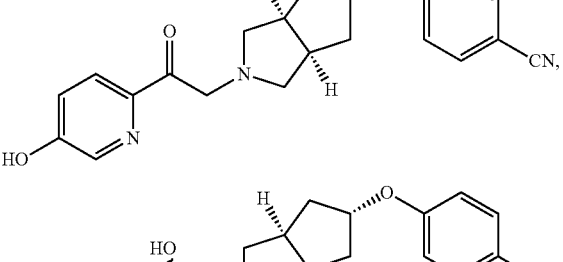
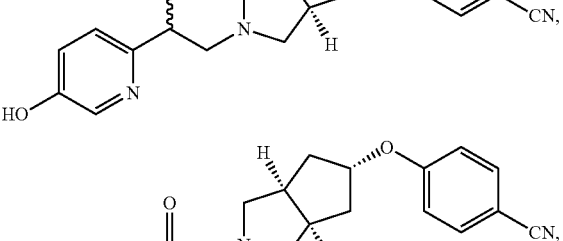
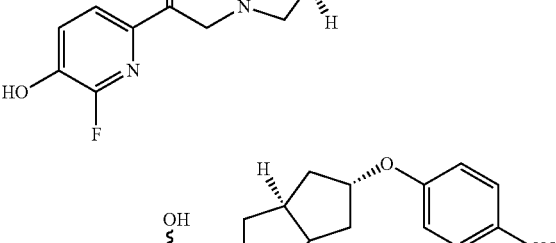
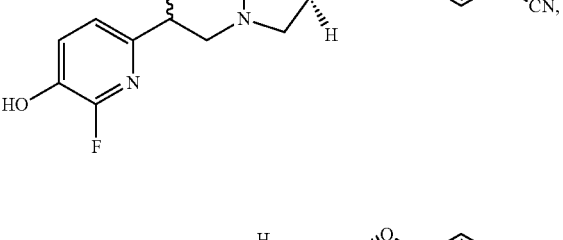
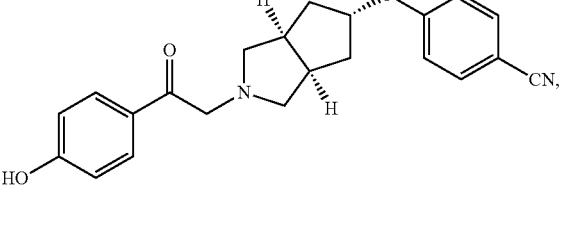
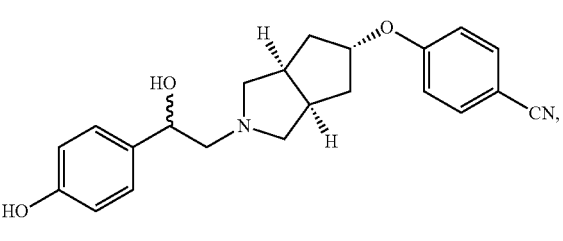

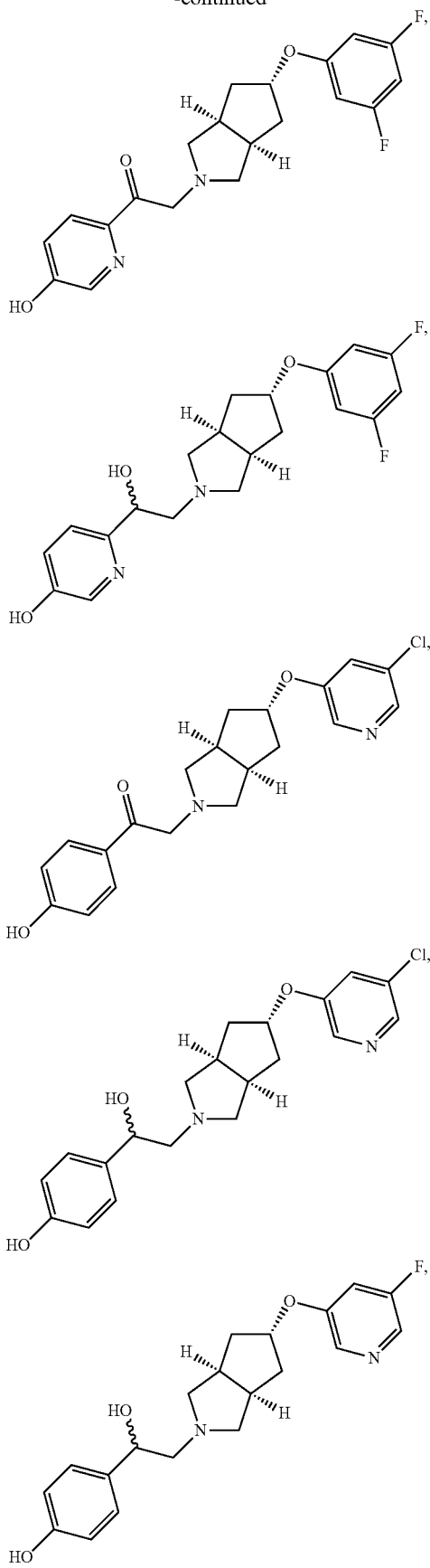
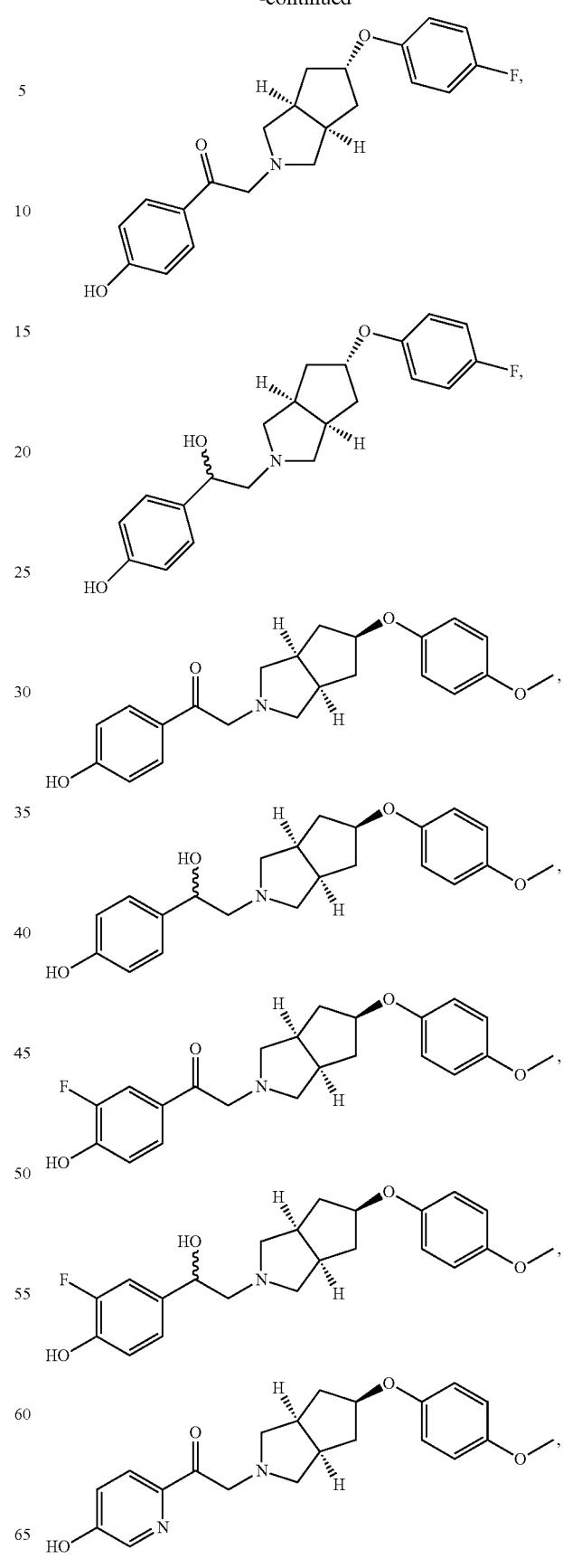

-continued
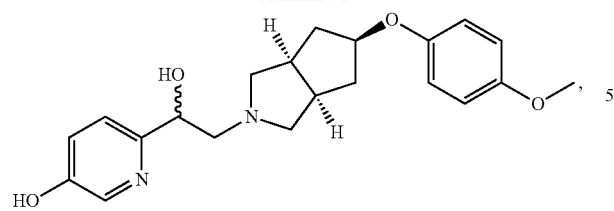
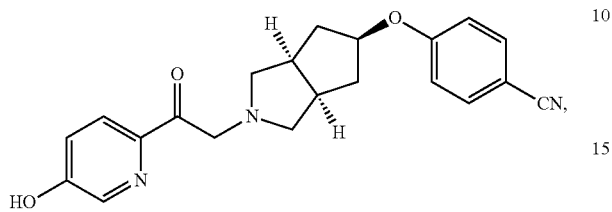
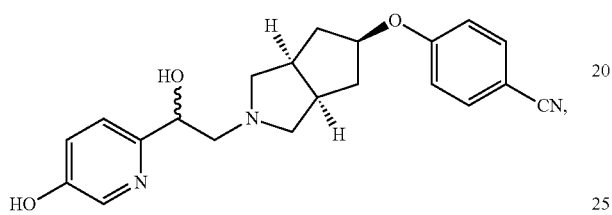
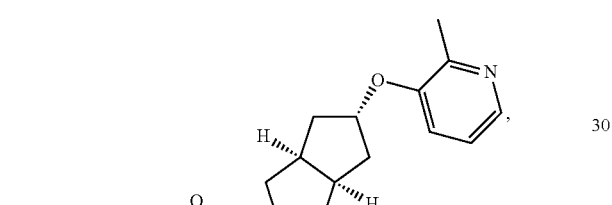
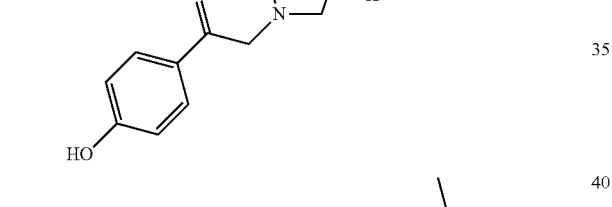
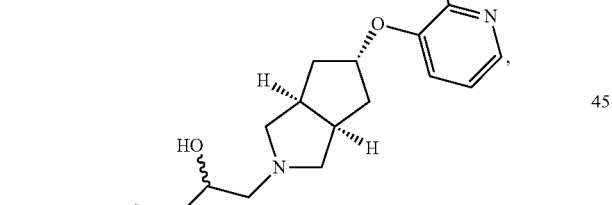
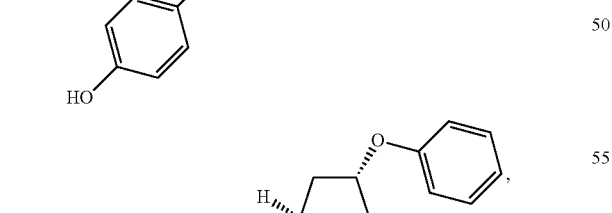
-continued
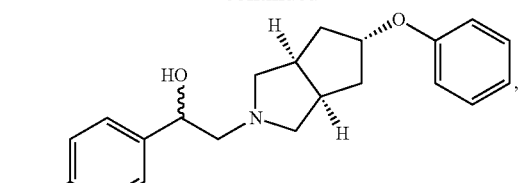
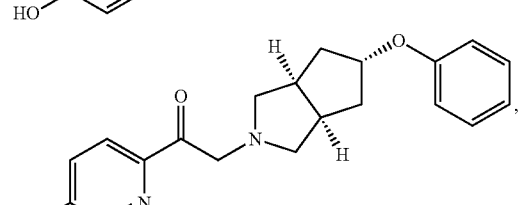
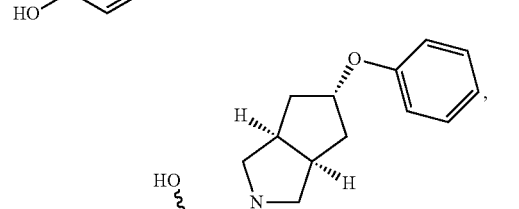
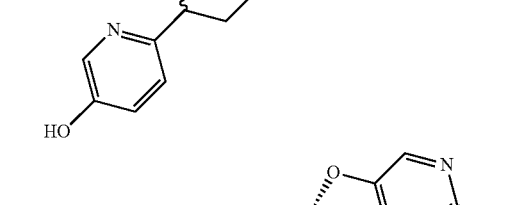
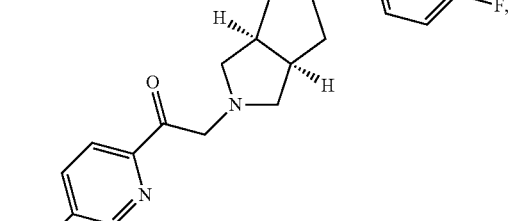
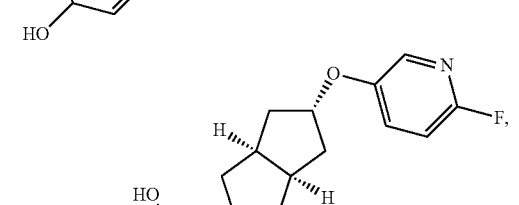
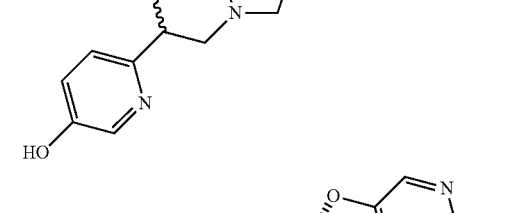
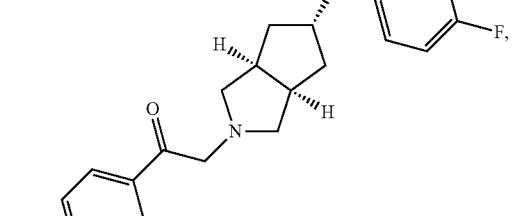

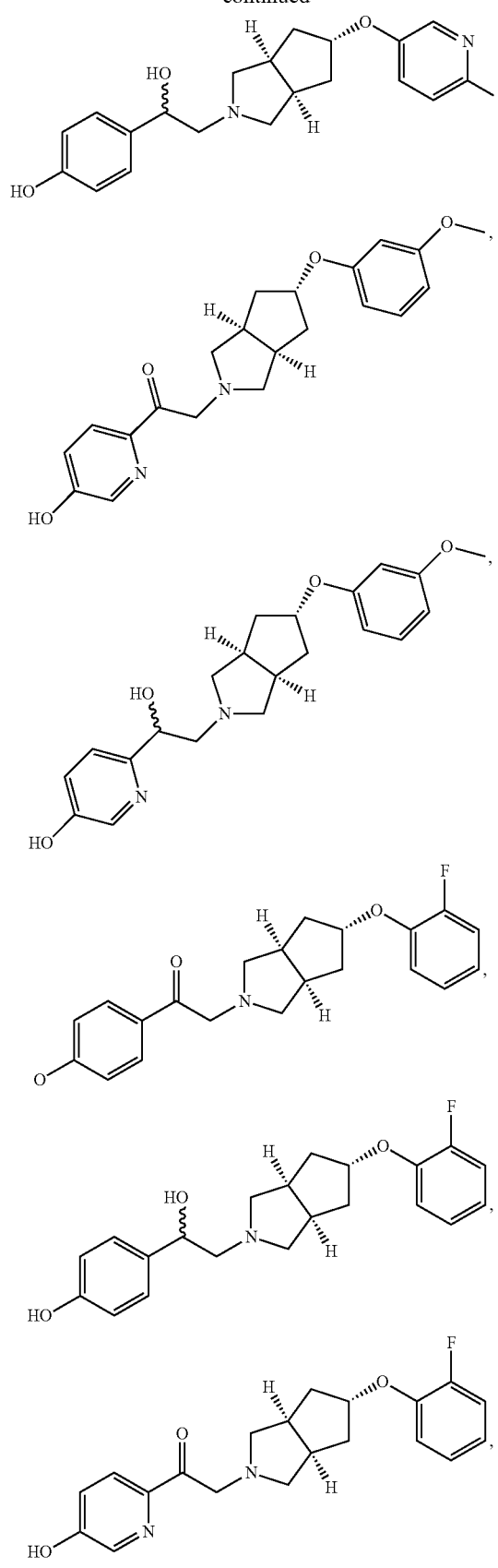
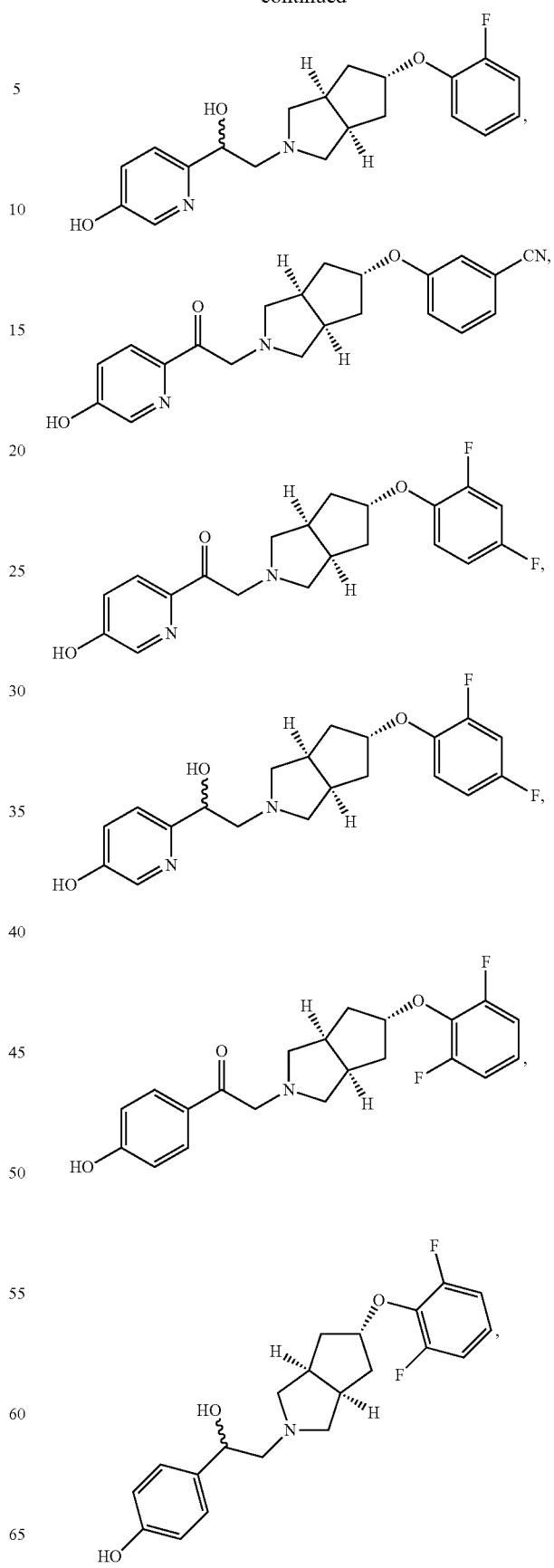

-continued
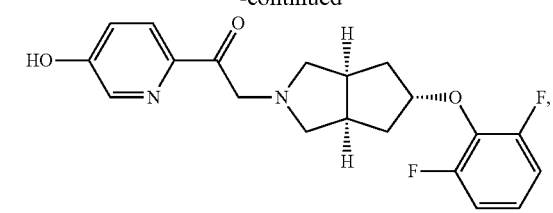
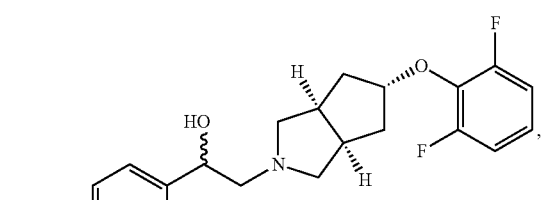
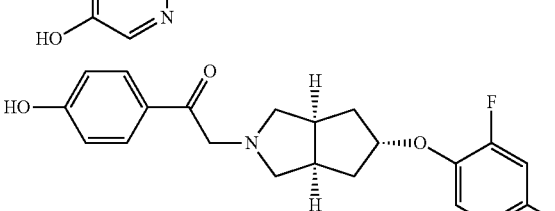
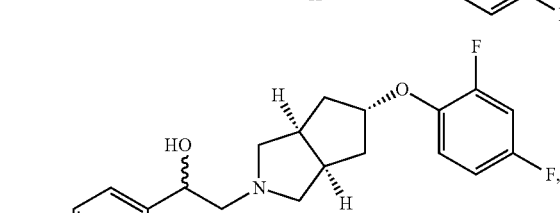
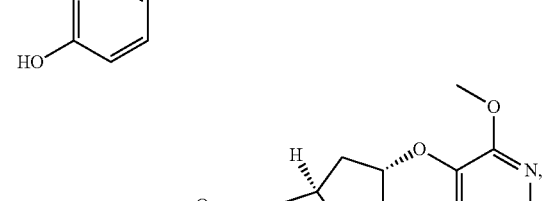
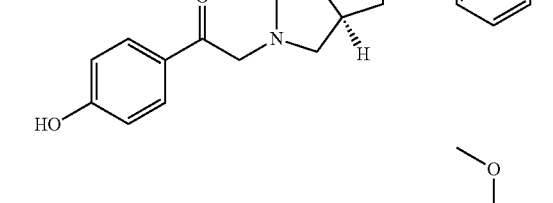
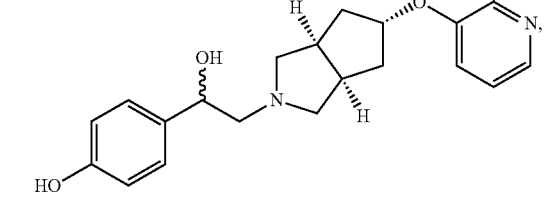
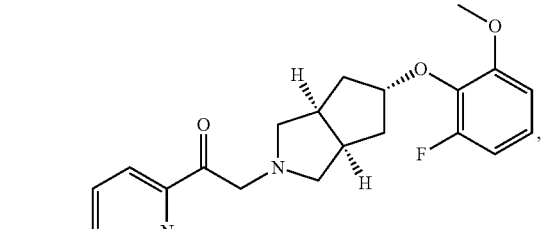
-continued
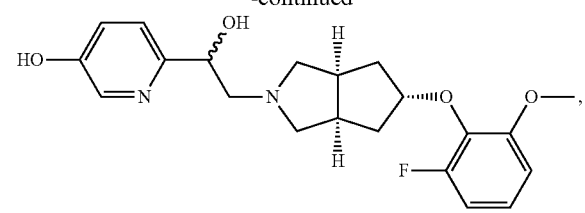
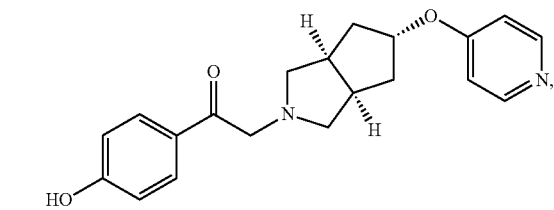
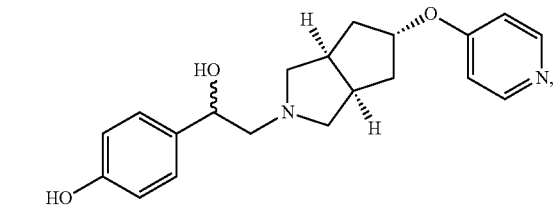
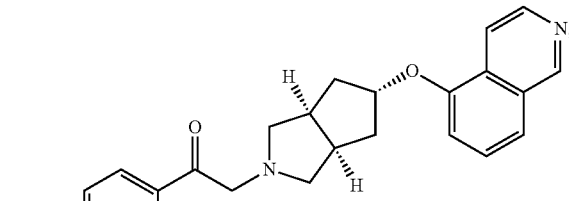
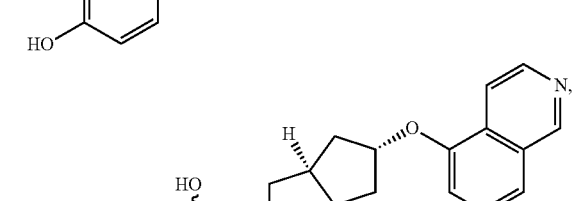
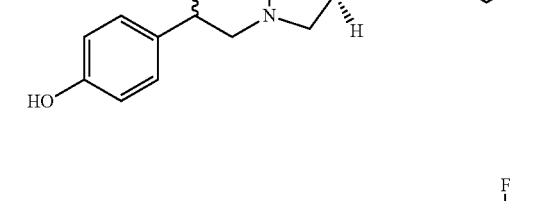
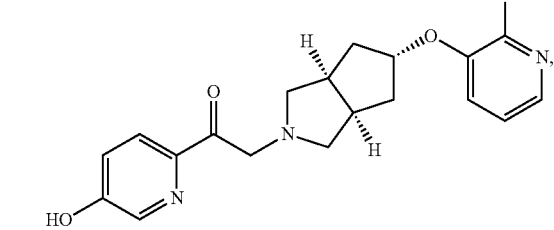
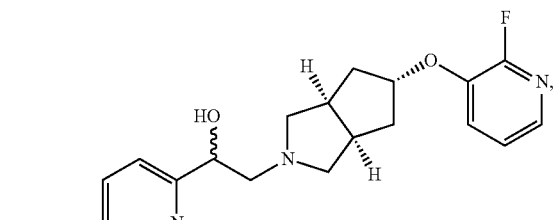

23
-continued
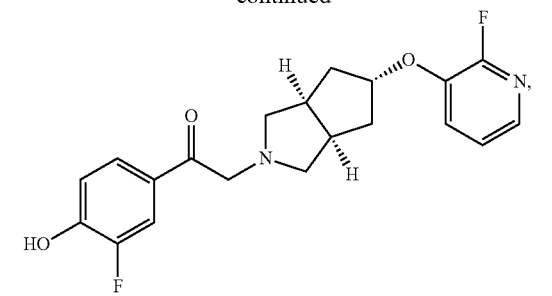
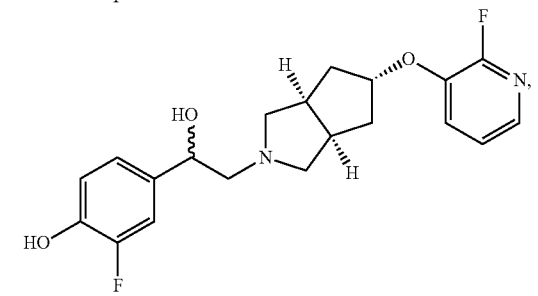
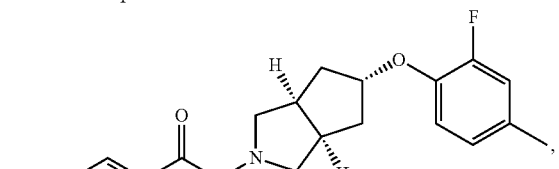
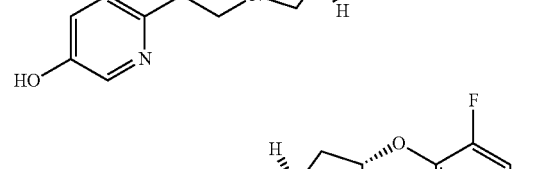
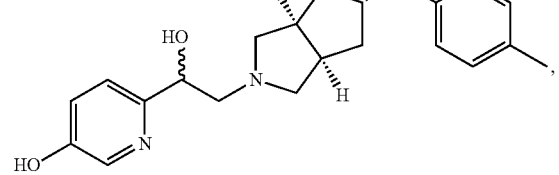
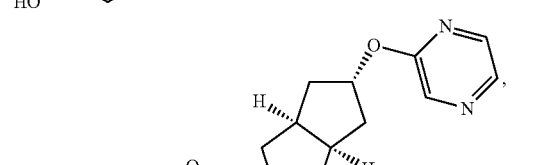
24
-continued
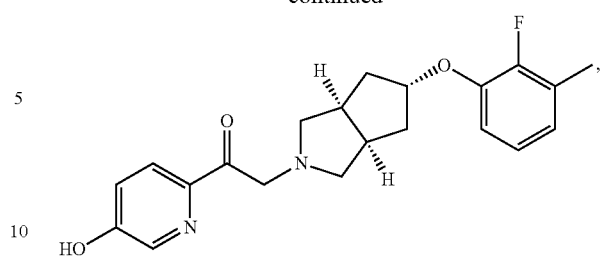
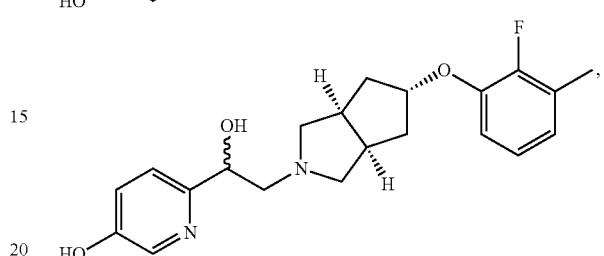
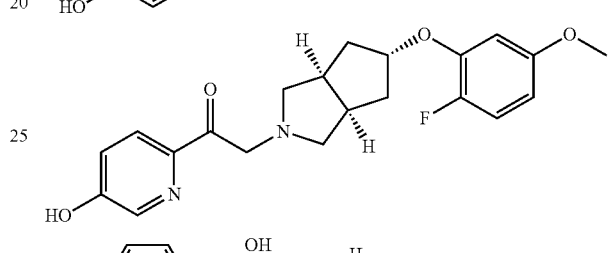
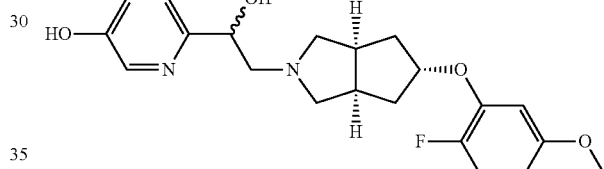
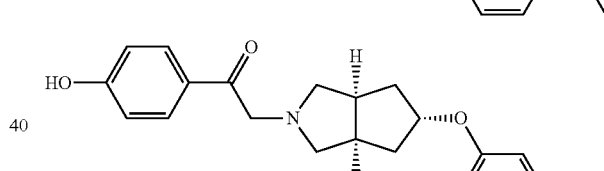
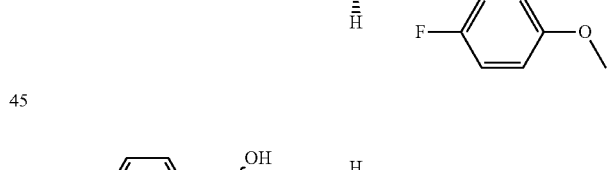
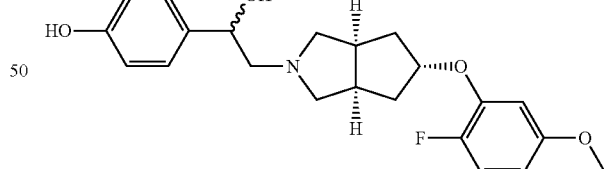
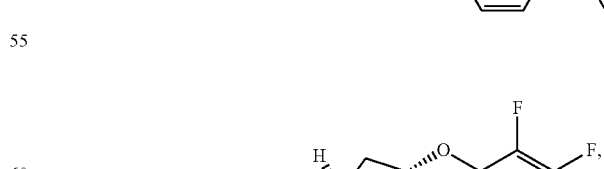
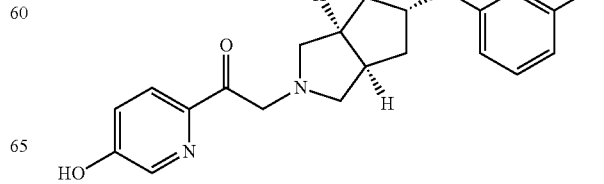

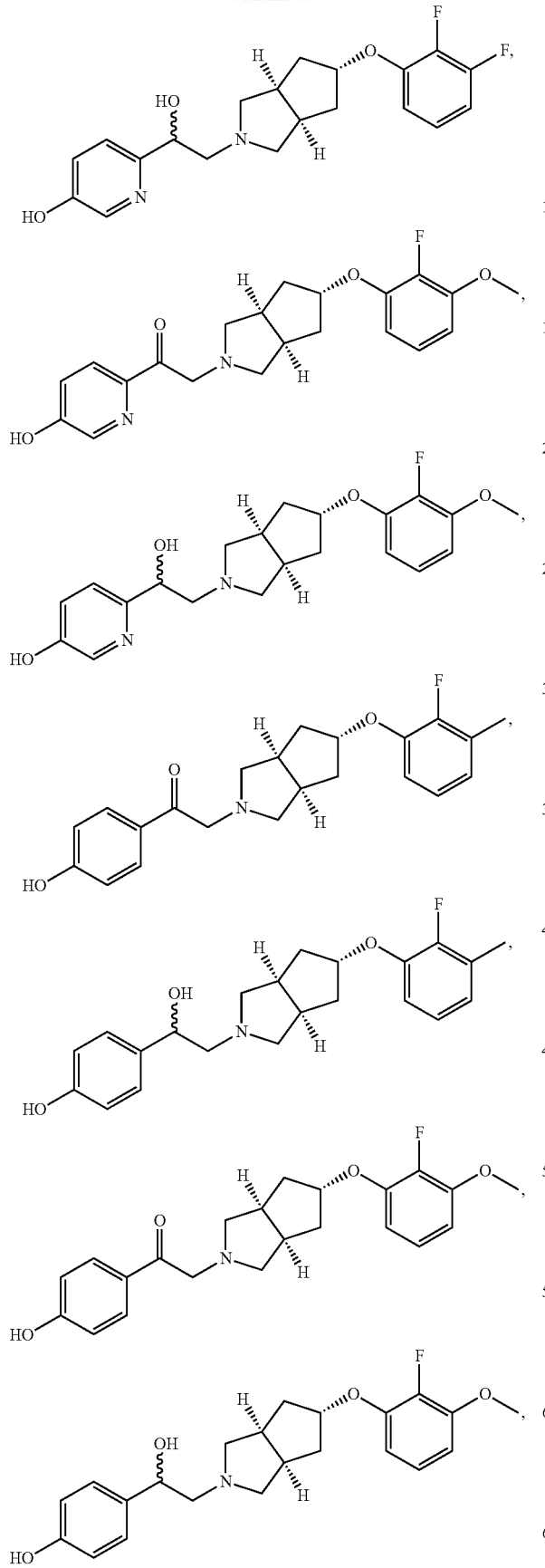
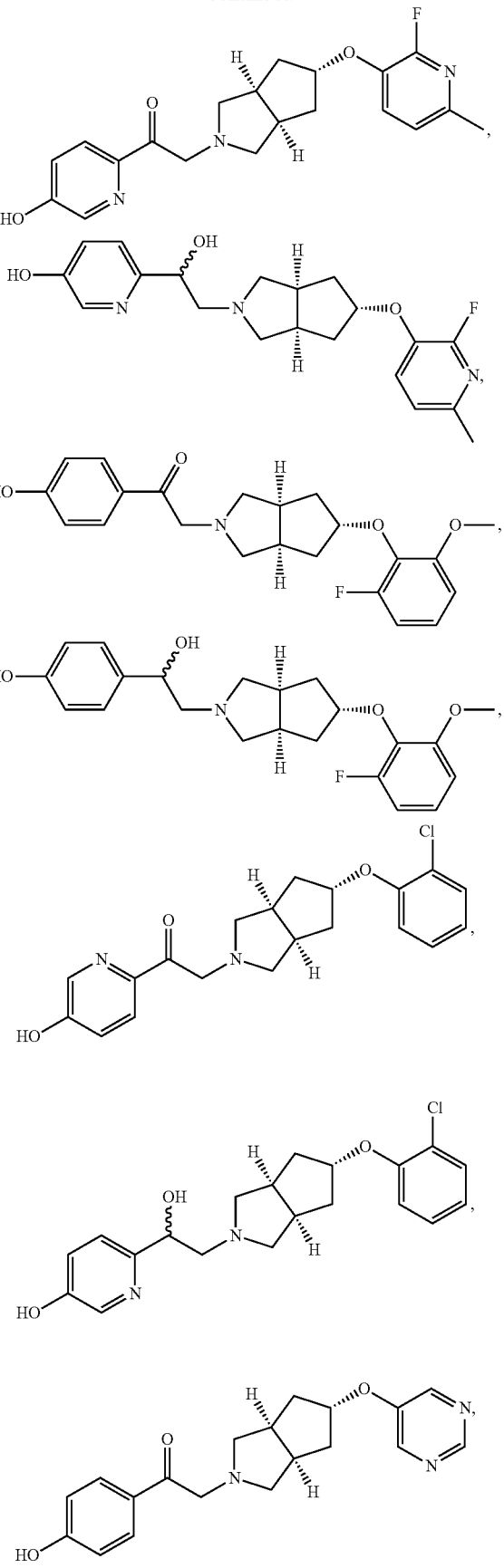

-continued
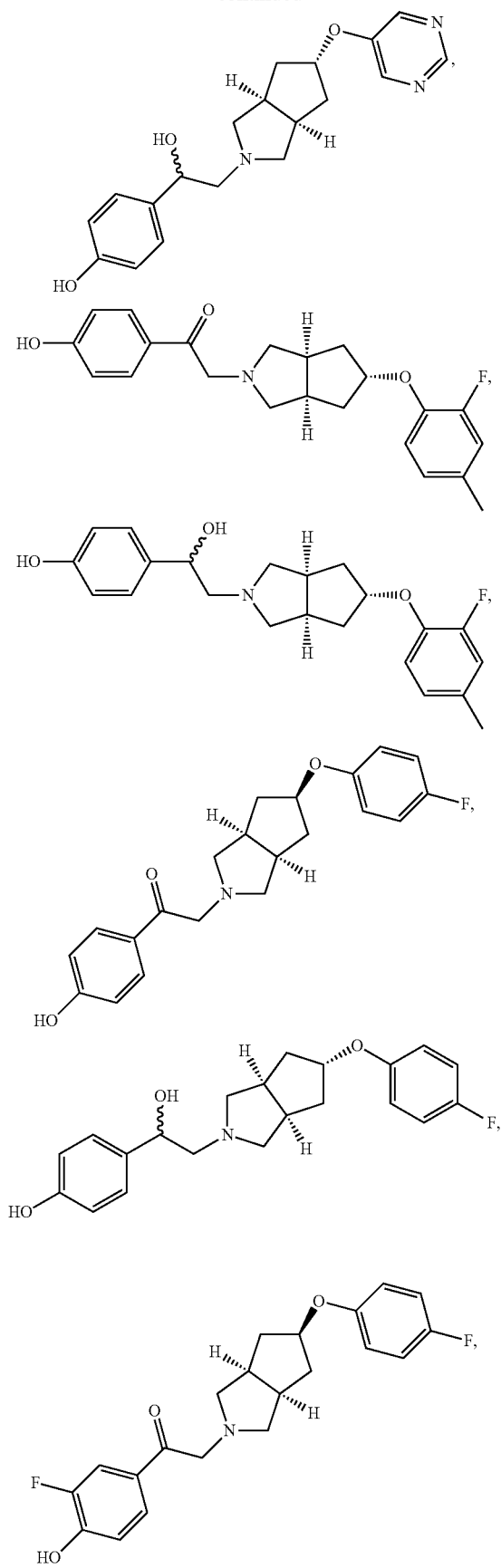
-continued
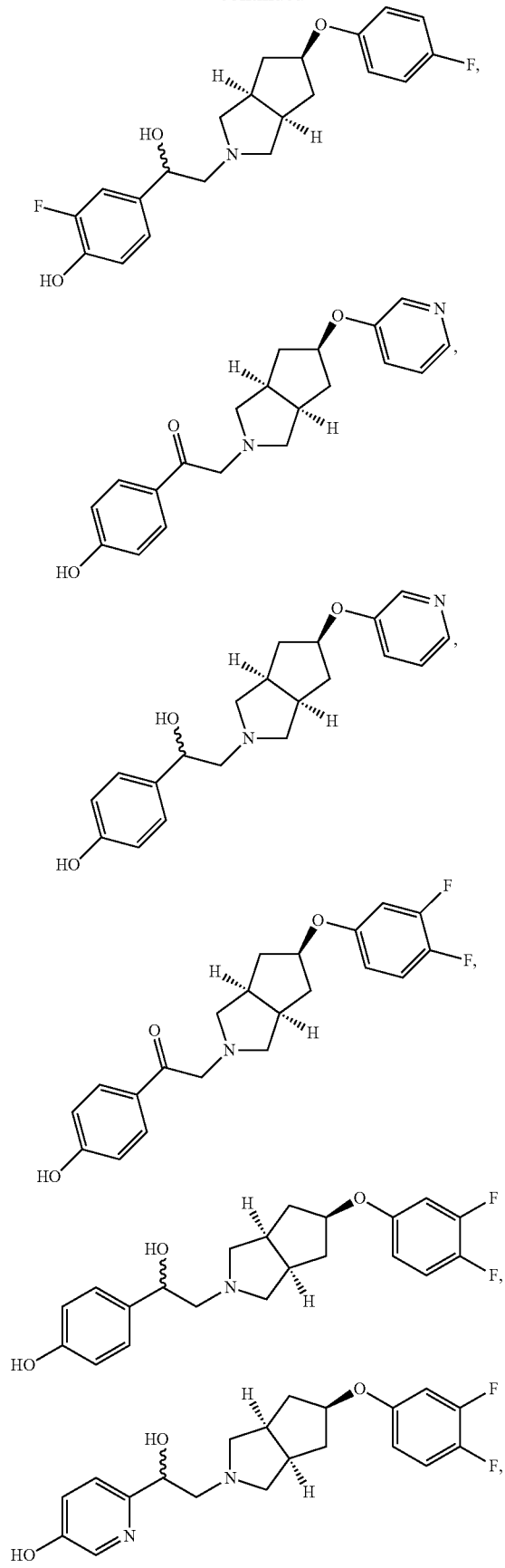

-continued
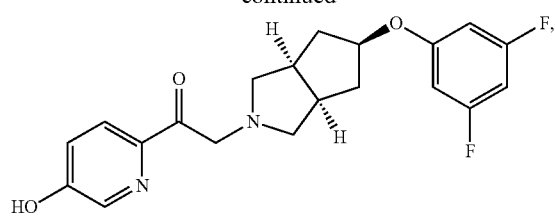
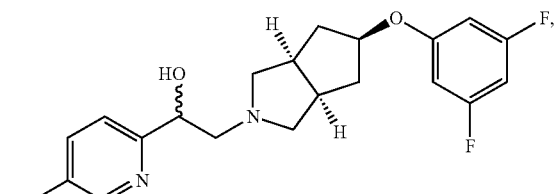
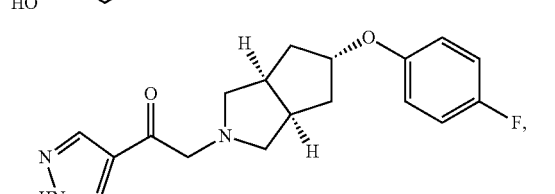
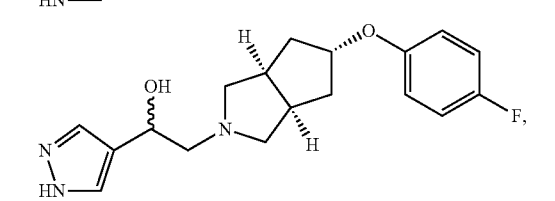
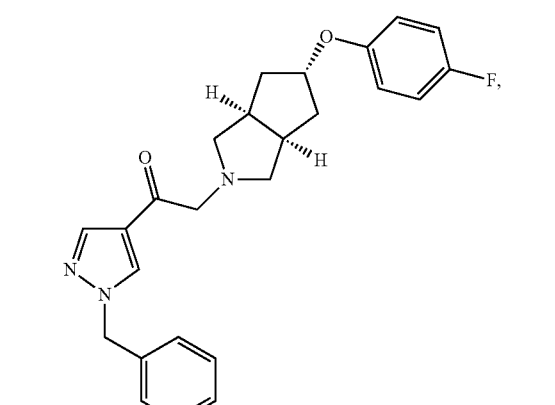
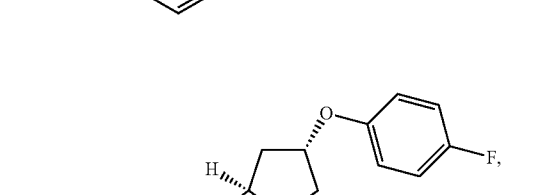
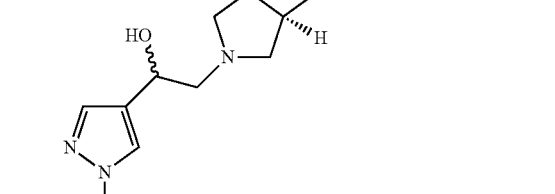
-continued
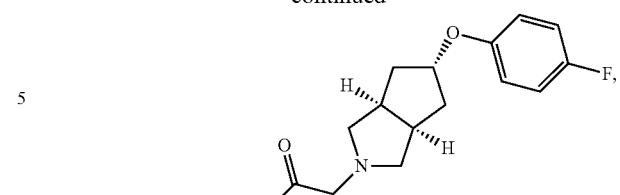
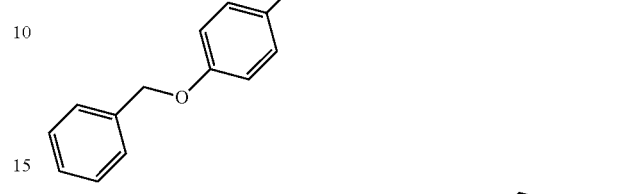
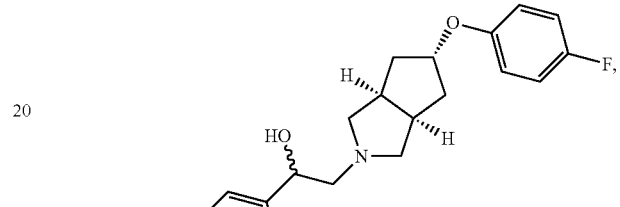
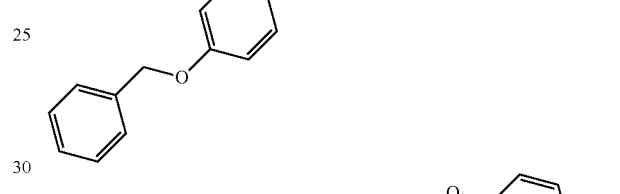
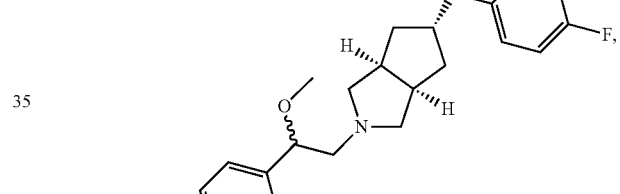
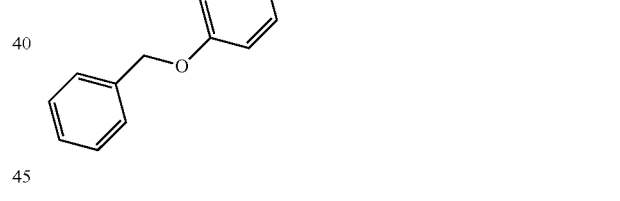
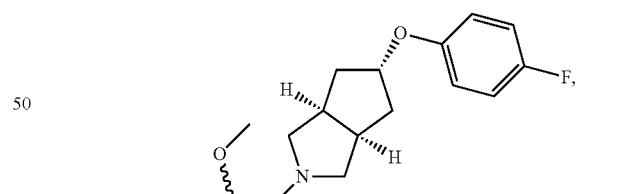
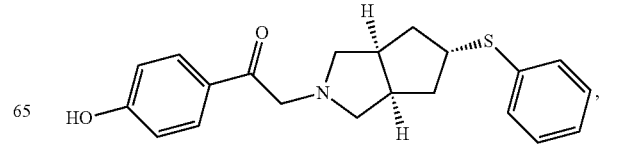

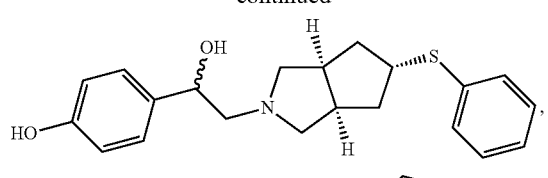,

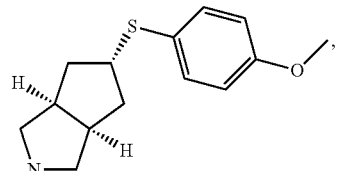,

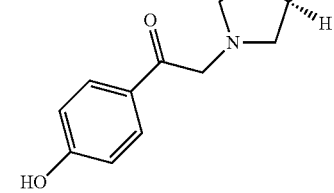,

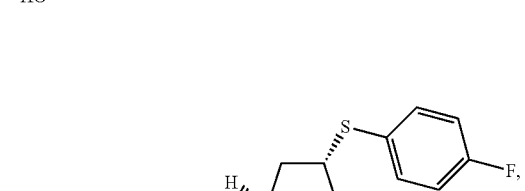,

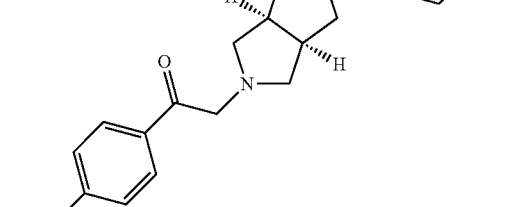,

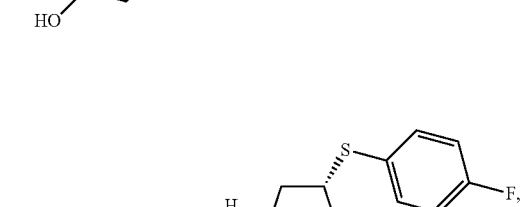,

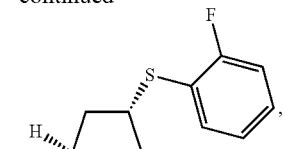,

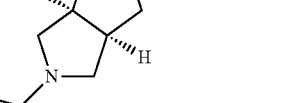,

,

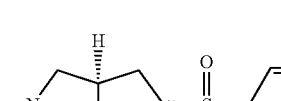,

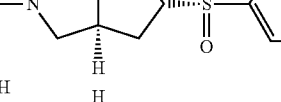, and

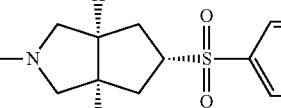.

In another embodiment of the invention, the compounds of Formula I are enantiomers. In some embodiments the compounds are (R)-enantiomer. In other embodiments the compounds may also be (S)-enantiomer. In yet other embodiments, the compounds of Formula I may be (+) or (−) enantiomers.

Another embodiment of the present invention is rac-4-(1-hydroxy-2-((3aR,5s,6aS)-5-phenoxyhexahydrocyclopenta[c]pyrrol-2(1H)-yl)ethyl)phenol or a pharmaceutically acceptable salt thereof.

Another embodiment of the present invention is 6-((S)-1-hydroxy-2-((3aR,5R,6aS)-5-phenoxyhexahydrocyclopenta[c]pyrrol-2(1H)-yl)ethyl)pyridin-3-ol or a pharmaceutically acceptable salt thereof.

Another embodiment of the present invention is 6-((R)-1-hydroxy-2-((3aR,5S,6aS)-5-phenoxyhexahydrocyclopenta[c]pyrrol-2(1H)-yl)ethyl)pyridin-3-ol or a pharmaceutically acceptable salt thereof.

Another embodiment of the present invention is rac-6-(2-((3aR,5s,6aS)-5-(2-fluorophenoxy)hexahydrocyclopenta[c]pyrrol-2(1H)-yl)-1-hydroxyethyl)pyridin-3-ol or a pharmaceutically acceptable salt thereof.

Another embodiment of the present invention is 6-((S)-2-((3aR,5R,6aS)-5-(2-fluorophenoxy)hexahydrocyclopenta[c]pyrrol-2(1H)-yl)-1-hydroxyethyl)pyridin-3-ol or a pharmaceutically acceptable salt thereof.

Another embodiment of the present invention is 6-((R)-2-((3aR,5S,6aS)-5-(2-fluorophenoxy)hexahydrocyclopenta[c]pyrrol-2(1H)-yl)-1-hydroxyethyl)pyridin-3-ol or a pharmaceutically acceptable salt thereof.

Another embodiment of the present invention is rac-6-(2-((3aR,5s,6aS)-5-((2-fluoropyridin-3-yl)oxy)hexahydrocyclopenta[c]pyrrol-2(1H)-yl)-1-hydroxyethyl)pyridin-3-ol or a pharmaceutically acceptable salt thereof.

Another embodiment of the present invention is 6-((S)-2-((3aR,5R,6aS)-5-((2-fluoropyridin-3-yl)oxy)hexahydrocyclopenta[c]pyrrol-2(1H)-yl)-1-hydroxyethyl)pyridin-3-ol or a pharmaceutically acceptable salt thereof.

Methods of Using the Disclosed Compounds

In another aspect, the present invention is directed to a method of treating a neurological disease, and abnormal brain function, and/or an emotional disorder in a subject. In some embodiments, the method comprises administering to a subject in need thereof an effective amount of a compound according to Formula I including any of the embodiments of Formula I described herein. The method can also comprise administering to the subject in need thereof a pharmaceutical composition of a compound of Formula I as described herein.

In an embodiment, the present disclosure pertains to compounds that selectively modulate the activity of NMDA receptors that contain an NR2B subunit, which encompasses receptors containing two NR2B subunits or one NR2B subunit in combination with one other NR2 subunit (i.e., NR2A/NR2B, NR2B/NR2C, or NR2B/NR2D receptors). The present disclosure also relates to the therapeutic uses of such compounds.

One therapeutic use of a compound of the present invention that modulates the activity of NR2B-containing NMDA receptors is to treat patients suffering from Major Depressive Disorder (MDD, or depression). Depression is the prolonged experience of sadness, hopelessness, or worthlessness to a degree that significantly impairs quality of life and the ability to function Major Depressive Disorder is now commonly treated with Selective Serotonin Reuptake Inhibitors (SSRIs) such as Prozac, Zoloft and newer variants, but these agents are of limited effectiveness. Of additional concern is that even when these drugs are effective, the onset of action is may be delayed 4-6 weeks or more, during which time patients are at increased risk of suicide. Consequently, the Food and Drug Administration has inserted a black-box warning on all antidepressants concerning suicide risk. There is a need for new agents with greater antidepressant efficacy and faster onset of action.

In some embodiments, the neurological disease is selected from Parkinson's disease, Huntington's disease, amyotrophic lateral sclerosis, multiple sclerosis, or seizure disorders.

Another therapeutic use of a compound of the present invention that modulates the activity of NR2B-containing NMDA receptors is to treat patients suffering from Alzheimer's disease.

In one or more embodiments, the abnormal brain function is selected from autism and autism spectrum disorders, Fragile X syndrome, tuberous sclerosis, Down's syndrome or other forms of mental retardation.

The emotional disorder can be selected from bipolar disorder, obsessive-compulsive disorder, or other anxiety disorders. Other anxiety disorders include general anxiety disorder, social anxiety disorder, phobias and panic disorder.

Another therapeutic use for compounds of the present invention is in the treatment of schizophrenia. Schizophrenia is a debilitating mental disorder encompassing three symptom domains: positive (hallucination, delusions), negative (withdrawal), and cognitive (pervasive reduction in cognitive ability). Schizophrenia typically strikes in early adulthood with the emergence of positive symptoms; however, it is the chronic cognitive deficits that prevent patients from resuming normal activities after the initial onset of symptoms and largely accounts for a lifetime disability.

Given the fundamental role of NR2B containing NMDA receptors in brain function (vide supra), there are many other therapeutic uses for compounds of the present invention that modulate the activity of NR2B-containing NMDA receptors. Compounds of the present invention may improve cognitive function in individuals suffering from cognitive deficits in addition to schizophrenia, including but not limited to those suffering from Alzheimer's disease. Such compounds may also be used in the treatment of post-traumatic stress syndrome. Compounds of the present invention may be used to treat individuals suffering from neurological dysfunction, including but not limited to those suffering from Parkinson's disease, Huntington's disease, amyotrophic lateral sclerosis, multiple sclerosis, and seizure disorders. Compounds of the present invention may be used to treat individuals suffering from emotional disorders in addition to depression, including but not limited to those suffering from bipolar disorder, obsessive-compulsive disorder and other anxiety disorders. Compounds of the present invention may be used to treat individuals that experience dysfunction caused by abnormal brain development, including but not limited to those suffering from autism and autism spectrum disorders, Fragile X syndrome, tuberous sclerosis, Down's syndrome and other forms of mental retardation. Such compounds may also be used to treat abnormal brain function that results from infections of the central nervous system, exposure to toxic agents or other xenobiotics or naturally occurring toxins.

Compounds of the present invention may also improve cognitive dysfunction such as in Alzheimer's disease, mild cognitive impairment, frontotemporal dementia, multi-infarct dementia, or cognitive dysfunction that occurs after stroke or traumatic brain injury and may be useful in the treatment of these conditions.

Compounds of the present invention may also be useful in treating pain such as neuropathic pain, pain after nerve or spinal cord injury, pain after tissue damage or burn, or associated pain with diabetes or cardiovascular disease.

Compounds of the present invention may also be useful in treating depression Depression associated neurodegenerative diseases like Parkinson's (PD) and Alzheimer's disease.

The disclosed compounds can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes. Additional modes of administration include sublingual, inhalation and intramuscular.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, aerosol, oral dispersible films or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin and/or HPMC capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, aliginic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parenteralinjectable administration is generally used for subcutaneous, intramuscular or intravenous injections and infusions. Injectables can be prepared in conventional forms, either as liquid solutions or suspensions or solid forms suitable for dissolving in liquid prior to injection.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

In accordance with the foregoing, in a further aspect, the invention relates to a compound of the present invention for use as a medicament, e. g. for the treatment or prevention of a neurological disease, abnormal brain function or an emotional disorder in which modulation of NR2B plays a role. In a further embodiment, the invention relates to a compound of the present invention for use in the treatment of a disease or disorder mediated by negative allosteric modulation or inhibition of NR2B. In a further embodiment, the disease or disorder is major depressive disorder, refractory and/or treatment resistant depression. In another embodiment the disease or disorder is ADHD. In another embodiment the disease or disorder is bipolar disease. In another embodiment the disease or disorder is post-traumatic stress disorder. In another embodiment the disease or disorder is depression associated with a neurodegenerative disease, such as Parkinson's disease (PD) or Alzheimer's disease (AD). In another embodiment the disease or disorder is neuropathic pain, fibromyalgia, or peripheral neuropathy.

In a further aspect, the invention relates to the use of a compound of the present invention as an active pharmaceutical ingredient in a medicament, e. g. for the treatment or prevention of a neurological disease, abnormal brain function or an emotional disorder in which modulation of NR2B plays a role. In a further embodiment, the invention relates to the use of a compound of the present invention as an active pharmaceutical ingredient in a medicament for the treatment or prevention of a disease or disorder mediated by negative allosteric modulation or inhibition of NR2B. In a further embodiment the disease or disorder is major depressive disorder, refractory and/or treatment resistant depression. In another embodiment the disease or disorder is ADHD. In another embodiment the disease or disorder is bipolar disease. In another embodiment the disease or disorder is post-traumatic stress disorder. In another embodiment the disease or disorder is depression associated with a neurodegenerative disease, such as Parkinson's disease (PD) or Alzheimer's disease (AD). In another embodiment the disease or disorder is neuropathic pain, fibromyalgia, or peripheral neuropathy.

In a further aspect, the invention relates to the use of a compound of the present invention for the manufacture of a medicament for the treatment or prevention of a neurological disease, abnormal brain function or an emotional disorder in which modulation of NR2B plays a role. In a further embodiment, the invention relates to the use of a compound of the present invention for the manufacture of a medicament for the treatment or prevention of a disease or disorder mediated by negative allosteric modulation or inhibition of NR2B. In a further embodiment, the disease or disorder is major depressive disorder, refractory and/or treatment resistant depression. In another embodiment the disease or disorder is ADHD. In another embodiment the disease or disorder is bipolar disease. In another embodiment the disease or disorder is post-traumatic stress disorder. In another embodiment the disease or disorder is depression associated with a neurodegenerative disease, such as Parkinson's disease (PD) and Alzheimer's disease (AD). In another embodiment the disease or disorder is neuropathic pain, fibromyalgia, or peripheral neuropathy.

In a further aspect, the invention relates to a method for the treatment or prevention of a neurological disease, abnormal brain function or an emotional disorder in which modulation of NR2B plays a role, in a subject in need of such treatment or prevention which method comprises administering to such subject an effective amount of a compound of the present invention. In one embodiment, the invention relates to a method for the treatment of a disease or disorder mediated by negative allosteric modulation or inhibition of NR2B in a subject, wherein the method comprises administering to the subject a therapeutically effective amount of a compound of the present invention. In a further embodiment the disease or disorder is major depressive disorder, refractory and/or treatment resistant depression. In another embodiment the disease or disorder is ADHD. In another embodiment the disease or disorder is bipolar disease. In another embodiment the disease or disorder is post-traumatic stress disorder. In another embodiment the disease or disorder is depression associated with a neurodegenerative disease, such as Parkinson's disease (PD) and Alzheimer's disease (AD). In another embodiment the disease or disorder is neuropathic pain, fibromyalgia, or peripheral neuropathy.

A compound of the present invention can be administered as sole active pharmaceutical ingredient or as a combination with at least one other active pharmaceutical ingredient effective, e. g., in the treatment or prevention of a neurological disease, abnormal brain function or an emotional disorder in which modulation of NR2B plays a role. Such a pharmaceutical combination may be in the form of a unit dosage form, which unit dosage form comprises a predetermined quantity of each of the at least two active components in association with at least one pharmaceutically acceptable carrier or diluent. Alternatively, the pharmaceutical combination may be in the form of a package comprising the at least two active components separately, e. g. a pack or dispenser-device adapted for the concomitant or separate administration of the at least two active components, in which these active components are separately arranged. In a further aspect, the invention relates to such pharmaceutical combinations.

In a further aspect, the invention therefore relates to a pharmaceutical combination comprising a therapeutically effective amount of a compound of the present invention and a second drug substance, for simultaneous or sequential administration.

In one embodiment, the invention provides a product comprising a compound of the present invention and at least one other therapeutic agent as a combined preparation for simultaneous, separate or sequential use in therapy. In one embodiment, the therapy is the treatment of a disease or condition in which modulation of NR2B plays a role.

In one embodiment, the invention provides a pharmaceutical composition comprising a compound of the present invention and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound of the present invention. In one embodiment, the kit comprises means for separately retaining said compositions, such as a container, divided bottle, or divided foil packet. An example of such a kit is a blister pack, as typically used for the packaging of tablets, capsules and the like. The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the present invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent. Accordingly, the invention provides an agent of the invention for use in the treatment of a disease or condition in which modulation of NR2B plays a role, wherein the medicament is prepared for administration with another therapeutic agent. The invention also provides the use of another therapeutic agent for treating a disease or condition in which modulation of NR2B plays a role, wherein the medicament is administered with a compound of the present invention.

The invention also provides a compound of the present invention for use in a method of treating a disease or condition in which modulation of NR2B plays a role, wherein the compound of the present invention is prepared for administration with another therapeutic agent. The invention also provides another therapeutic agent for use in a method of treating a disease or condition in which modulation of NR2B plays a role, wherein the other therapeutic agent is prepared for administration with a compound of the present invention. The invention also provides a compound of the present invention for use in a method of treating a disease or condition in which modulation of NR2B plays a role, wherein the compound of the present invention is administered with another therapeutic agent. The invention also provides another therapeutic agent for use in a method of treating a disease or condition in which modulation of NR2B plays a role, wherein the other therapeutic agent is administered with a compound of the invention.

The invention also provides the use of an agent of the invention for treating a disease or condition in which modulation of NR2B plays a role, wherein the patient has previously (e.g. within 24 hours) been treated with another therapeutic agent. The invention also provides the use of another therapeutic agent for treating a disease or condition in which modulation of NR2B plays a role, wherein the patient has previously (e.g. within 24 hours) been treated with a compound of the invention.

In one embodiment, the invention relates to a compound of the present invention in combination with another therapeutic agent wherein the other therapeutic agent is selected from:
(a) lithium;
(b) stimulants, such as amphetamine and dextroamphetamine, (Adderall™) or methylphenidate (Ritalin™);
(c) acetylcholinesterase inhibitors, such as donepezil (Aricept™), rivastigmine (Exelon™) and galantamine (Razadyne™);
(d) antidepressant medications for low mood and irritability, such as citalopram (Celexa™), fluoxetine (Prozac™), paroxeine (Paxil™), sertraline (Zoloft™), trazodone (Desyrel™), and tricyclic antidepressants such as amitriptyline (Elavil™);
(e) anxiolytics for anxiety, restlessness, verbally disruptive behavior and resistance, such as lorazepam (Ativan™) and oxazepam (Serax™);
(f) antipsychotic medications for hallucinations, delusions, aggression, agitation, hostility and uncooperativeness, such as aripiprazole (Abilify™), clozapine (Clozaril™), haloperidol (Haldol™), olanzapine (Zyprexa™), quetiapine (Seroquel™), risperidone (Risperdal™) and ziprasidone (Geodon™);
(g) mood stabilizers, such as carbamazepine (Tegretol™) and divalproex (Depakote™);
(h) pregabalin;
(i) gabapentin (Neurontin™);
(j) dopamine agonists such as L-DOPA, pramipexole (Mirapex™) and ropinerol (Requip™);
(k) analgesics including opiates and non-opiates;
(k) carbidopa;
(l) triptans such as sumatriptan (Imitrex™) and zolmitriptan (Zomig™);
(m) nicotinic alpha—7 agonists;
(n) mGluR5 antagonists;
(o) H3 agonists;
(p) amyloid therapy vaccines; and
(q) chemotherapy agents.

Methods for Making the N-alkylaryl-5-oxyaryl-octahydro-cyclopenta[c]pyrrole

Examples of synthetic pathways useful for making N-alkylaryl-5-oxyaryl-octahydro-cyclopenta[c]pyrrole derivatives of Formula I, Formula Ia, Formula Ib, Formula Ic, and Formula Id are set forth in the Examples below and generalized in the following Schemes.

Scheme 1:

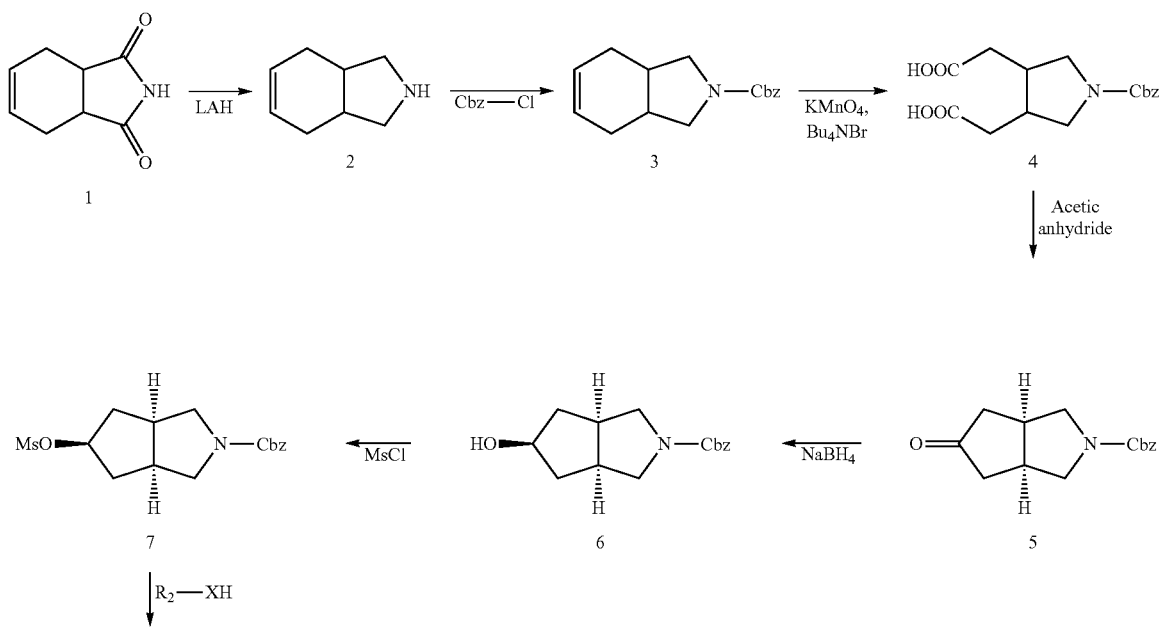

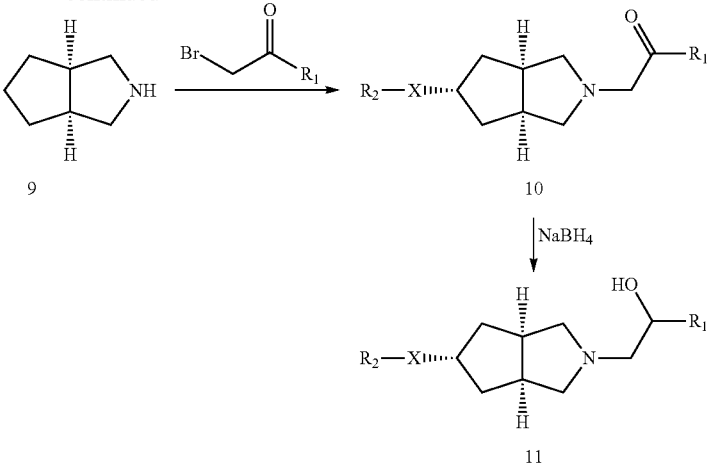

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

In many examples and intermediates, there is a plane of symmetry present in the molecules presented resulting in an achiral, meso compound. There is, however, relative stereochemistry between groups which is described. For example, (2-((3aR, 5s, 6aS)-5-(3,4-difluorophenoxy) hexahydrocyclopenta[c]pyrrol-2(1H)-yl)-1-(4-hydroxyphenyl) ethanone) has a core structure that is designated with absolute configuration designations. This nomenclature is used to describe the relative configurations of the aryl ether with respect to the bridgehead hydrogens. In this example, the substituent is exo with respect to the larger pyrrolidine ring of the bicyclic system. Conversely, (1-(4-hydroxyphenyl)-2-((3aR,5r,6aS)-5-(4-methoxyphenoxy)hexahydrocyclopenta[c]pyrrol-2(1H)-yl)ethanone) describes the opposite configuration where the oxygen substituent is endo with respect to the pyrrolidine ring and on the opposite side of the bridgehead hydrogens. It is understood that when multiple stereoisomers may exist, all are included within the scope of the invention.

In cases where any substituent also contains a stereogenic center, the compound becomes chiral and we use the designator "rac" to denote the synthesis of racemic mixtures of these examples. It is understood that the single enantiomers can be separated from this mixture and are included within the scope of the invention.

LCMS Instrumentation and Methods
Method A
Instrument: Agilent 1290 Infinity
Column: Kinetex C18 (50 mm×2.1 mm×1.7 μm)
Mobile phase (A): 0.01% TFA in water
Mobile phase (B): Acetonitrile
Flow rate: 0.3 mL/min Method B
Instrument: Waters 2695
Column: Eclipse XDB-C18 (150 mm×4.6 mm×3.5 μm)
Mobile phase (A): 0.01% NH$_4$OH
Mobile phase (B): Acetonitrile
Flow rate: 1.0 mL/min Method C
Instrument: Waters 2695
Column: Zorbax XDB C18 (150 mm×4.6 mm×3.5 μm)
Mobile phase (A): 0.01% NH$_4$OH
Mobile phase (B): Acetonitrile
Flow rate: 1.0 mL/min Method D
Instrument: Waters 2695
Column: Accentis Express (50 mm×4.6 mm×2.7 μm)
Mobile Phase (A): 0.01% Formic acid in water
Mobile Phase (B): Acetonitrile
Flow rate: 0.5 ml/min Method E
Instrument: Agilent 1290 Infinity
Column: Zorbax Eclipse Plus C18 RRHD (50 mm×2.1 mm×1.8 μm)
Mobile Phase (A): 0.01% TFA in water
Mobile Phase (B): Acetonitrile
Flow rate: 0.3 mL/min Method F
Instrument: Waters 2695
Column: Gemini (50 mm×3 mm×3 μm)
Mobile Phase (A): 0.01% Formic acid in water
Mobile Phase (B): Acetonitrile
Flow rate: 0.5 ml/min Method G
Instrument: Waters 2695
Column: Gemini C18 (50 mm×3.0 mm×3 μm)
Mobile Phase (A): 0.01% TFA in w ater
Mobile Phase (B): Acetonitrile
Flow rate: 0.5 ml/min Method H
Instrument: Waters 2695
Column: XTERRA C18(250 mm×4.6 mm×5 μm)
Mobile phase (A): Ammonia in water
Mobile phase (B): Acetonitrile
Flow rate: 1.0 mL/min Method I
Instrument: Agilent 1290 Infinity
Column: Kinetex C18 (50 mm×2.1 mm×2.6 μm)
Mobile phase (A): 0.01% acetic acid in water
Mobile phase (B): Acetonitrile
Flow rate: 0.3 mL/min
Method J
Instrument: Agilent 1290 Infinity
Column: Kinetex C18 (100 mm×4.6 mm×2.1 μm)
Mobile phase (A): 0.01% TFA in water
Mobile phase (B): Acetonitrile
Flow rate: 0.7 mL/min
Method K
Instrument: Agilent 1290 Infinity
Column: Kinetex C18 (100 mm×4.6 mm×2.6 μm)
Mobile phase (A): 0.01% TFA in water
Mobile phase (B): Acetonitrile
Flow rate: 0.7 mL/min
Method L
Instrument: Agilent 1290 Infinity
Column: Denali C18 (50 mm×2.1 m×5 μm)
Mobile phase (A): 0.01% NH4OH
Mobile phase (B): Acetonitrile
Flow rate: 0.7 mL/min
Method M
Instrument: Agilent 1290 Infinity
Column: Zorbax RRHD C18 (50 mm×2.1 mm×1.8 μm)
Mobile phase (A): 0.01% Acetic acid in water
Mobile phase (B): Acetonitrile
Flow rate: 0.3 mL/min
Method N
Instrument: Waters 2695
Column: Xbridge C18 (250 mm×4.6 mm×5 μm)
Mobile phase (A): 0.01% TFA in w ater
Mobile phase (B): Acetonitrile
Flow rate: 1.0 mL/min
Method O
Instrument: Waters 2695
Column: Ascentis Express C18 (50 mm×2.1 mm×2.7 μm)
Mobile phase (A): 0.01% Formic acid in water
Mobile phase (B): Acetonitrile
Flow rate: 0.5 mL/min
Method P
Instrument: Agilent 1290 Infinity
Column: Kinetex C18 (50 mm×2.1 mm×1.7 μm)
Mobile phase (A): Water
Mobile phase (B): Acetonitrile
Flow rate: 0.3 mL/min
Method Q
Instrument: Agilent 1290 Infinity
Column: Kinetex C18 (50 mm×2.1 mm×1.7 μm)
Mobile phase (A): 5 mM Ammonium acetate in water
Mobile phase (B): Acetonitrile
Flow rate: 0.3 mL/min
Method R
Instrument: Waters Acquity SDS
Run time: 5.20 min
Column: ACQUITY UPLC BEH C18, 130 Å, 1.7 μm, 2.1 mm×50 mm—50° C.
Mobile phase (A): Water+0.1% formic acid
Mobile phase (B): Acetonitrile+0.1% formic acid
Method S
Preparative SFC
Column: AD-H 250×21 mm
Flow rate: 80 g per minute
Cosolvent: 35% EtOH 10 mM NH4OH Detection: 207 nm
ABPR 100

Example 1—Preparation of rac-4-(2-((3aR,5s,6aS)-5-(3,4-difluorophenoxy)hexahydrocyclopenta[c]pyrrol-2(1H)-yl)-1-hydroxyethyl)phenol

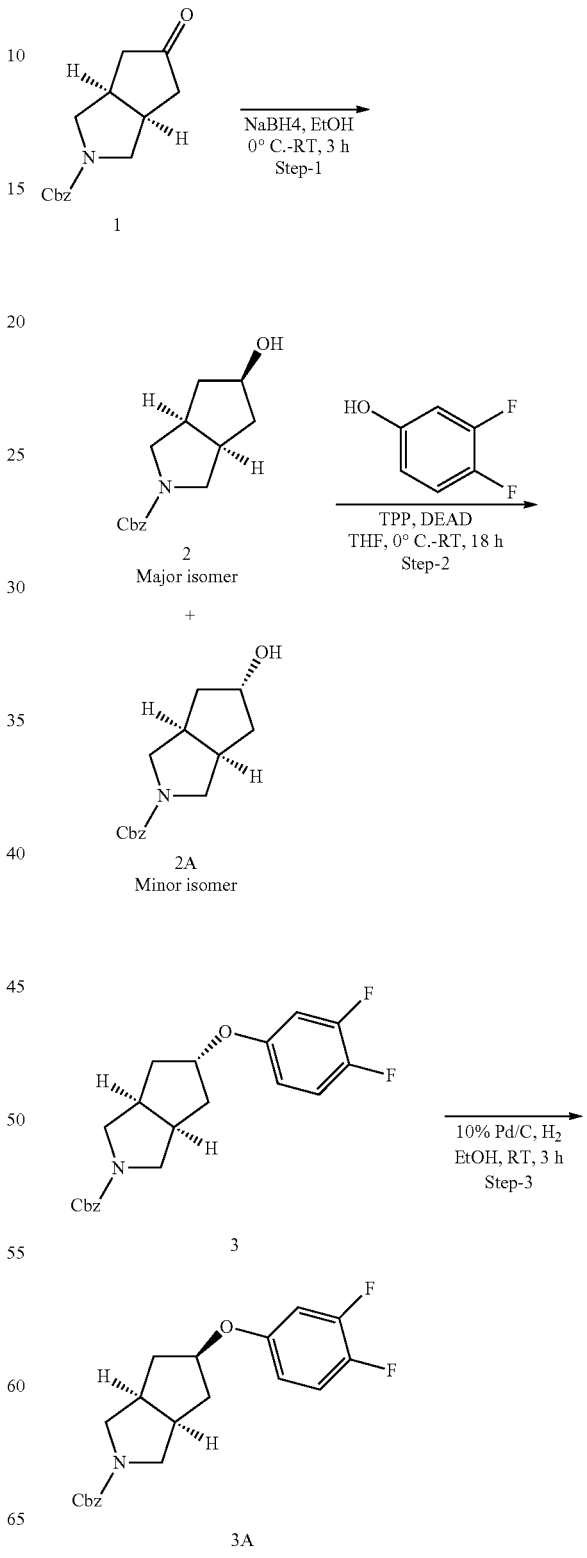

Scheme 2:

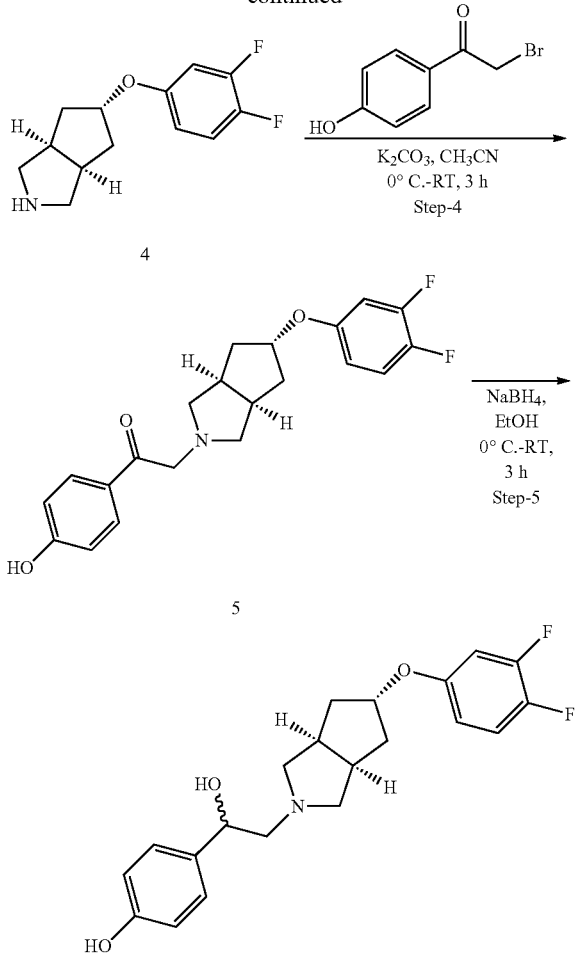

Compound 1 can be purchased from a commercial vender. It can also be synthesized based on Scheme 1, PCT Int. Appl. 2014048865 or PCT Int. Appl. 2013091539.

Step 1

Preparation of (3aR,5r,6aS)-benzyl 5-hydroxyhexahydrocyclopenta[c]pyrrole-2(1H)-carboxylate

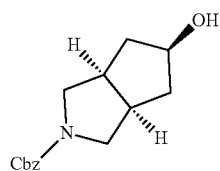 [SMILES: O=C(OCc1ccccc1)N1C[C@H]2C[C@@H](O)C[C@H]2C1]

To a solution of (3aR,6aS)-benzyl 5-oxohexahydrocyclopenta[c]pyrrole-2(1H)-carboxylate (9.5 g, 36.63 mmol) in ethanol (300 mL) was added sodium borohydride (11.8 g, 310.52 mmol)) at 0° C. The reaction mixture was stirred at room temperature for 3 h and concentrated. The residue was diluted with water (300 mL) and extracted with dichloromethane (500 mL×3). The combined organic layer was dried over anhydrous sodium sulfate, filtered and concentrated. The crude material was purified by chiral HPLC column chromatography (analytical conditions: column: CHIRALPAK IA (250 mm×4.6 mm×5 m), mobile phase: n-Hexane: 0.1% DEA in ethanol (50:50), Flow rate: 1.0 mL/min) to afford title compound (3aR,5r,6aS)-benzyl 5-hydroxyhexahydrocyclopenta[c]pyrrole-2(1H)-carboxylate (7.2 g, 75% yield, major isomer 2) as a white solid. Calculated M+H: 262.32; Found M+H: 262.1.

During purification the minor isomer 2A (3aR,5s,6aS)-benzyl 5-hydroxyhexahydrocyclopenta[c]pyrrole-2(1H)-carboxylate (0.65 g, 6.8% yield) was also isolated as a colourless liquid.

A crystallization method was used to separate the major isomer from minor isomer. Ethyl acetate (180 mL) was added portion wise to a mixture of diasteriomers (42 g, 16.09 mmol) in hexane (400 mL) at 75° C. The mixture was heated at same temperature with stirring until all of the solid dissolved. Then the mixture was concentrated at 75° C. to one third of the initial volume, seeded with authentic product and kept for recrystallisation at room temperature for 15 h. The crystallized product was filtered, washed with 20% ethyl acetate in hexane (200 mL) and dried to afford the title compound 2 (36 g, 98.5% chiral purity) as a white solid. This material was again recrystallised from ethyl acetate-hexane using above condition to afford the title compound (3aR,5r,6aS)-benzyl 5-hydroxyhexahydrocyclopenta[c]pyrrole-2(1H)-carboxylate (34 g, 99.5% chiral purity) as a white solid.

Step 2

Preparation of (3aR,5s,6aS)-benzyl 5-(3,4-Difluorophenoxy)hexahydrocyclopenta[c]pyrrole-2(1H)-carboxylate

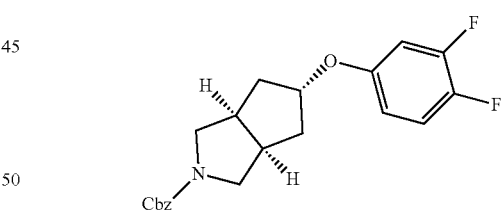

To a solution of (3aR,5r,6aS)-benzyl 5-hydroxyhexahydrocyclopenta[c]pyrrole-2(1H)-carboxylate (0.6 g, 2.298 mmol) in tetrahydrofuran (20 mL) at 0° C. were added 3,4-difluorophenol (0.6 g, 4.59 mmol), triphenylphosphine (0.66 g, 2.528 mmol) and diethyl azo dicarboxylate (0.54 mL, 3.44 mmol). The reaction mixture was stirred at room temperature for 18 h and concentrated. Then crude was purified by combiflash purifier using 20-25% ethyl acetate in hexane to afford the title compound (3aR,5s,6aS)-benzyl 5-(3,4-difluorophenoxy)hexahydrocyclopenta[c]pyrrole-2 (1H)-carboxylate (0.34 g, 39.67% yield) as a pale yellow liquid. Calculated M+H: 374.39; Found M+H: 374.2.

Step 3

Preparation of (3aR, 5s, 6aS)-5-(3,4-difluorophenoxy) octahydrocyclopenta[c]pyrrole

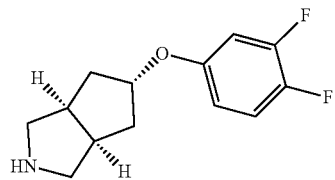 [SMILES: Fc1ccc(O[C@@H]2C[C@H]3CNC[C@H]3C2)cc1F]

To a solution of (3aR,5s,6aS)-benzyl-5-(3,4-difluorophenoxy)hexahydrocyclopenta[c]pyrrole-2(1H)-carboxylate (0.34 g, 0.911 mmol) in ethanol (5 mL) was added 10% Pd/C (0.1 g, 50% wet). The reaction mixture was stirred at room temperature for 3 h under hydrogen atmosphere. The suspension was filtered through celite and the bed was washed with methanol. The combined filtrate was concentrated to afford the title compound (3aR, 5s, 6aS)-5-(3,4-difluorophenoxy) octahydrocyclopenta[c]pyrrole (0.2 g, crude) as a colorless liquid. Calculated M+H: 240.26; Found M+H: 240.1.

Step 4

Preparation of 2-((3aR, 5s, 6aS)-5-(3,4-difluorophenoxy) hexahydrocyclopenta[c]pyrrol-2(1H)-yl)-1-(4-hydroxyphenyl) ethanone

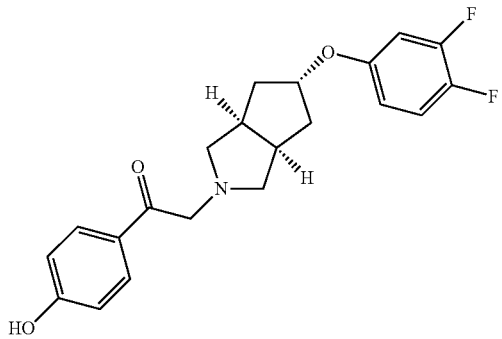

To a solution of (3aR, 5s, 6aS)-5-(3,4-difluorophenoxy) octahydrocyclopenta[c]pyrrole (0.2 g, 0.878 mmol) in acetonitrile (10 mL) was added potassium carbonate (0.36 g, 2.63 mmol) followed by 2-bromo-1-(4-hydroxyphenyl) ethanone (0.18 g, 0.878 mmol). The resulting suspension was stirred at room temperature for 3 h. The reaction mixture was filtered and the filtrate was concentrated. The crude was purified by combiflash purifier using 3% methanol in dichloromethane to afford the title compound 2-((3 aR,5s,6aS)-5-(3,4-difluorophenoxy) hexahydrocyclopenta[c]pyrrol-2 (1H)-yl)-1-(4-hydroxyphenyl) ethanone (0.28 g, 85.36% yield) as a white solid. Calculated M+H: 374.39; Found M+H: 374.2.

Step 5

Preparation of rac-4-(2-((3aR, 5s, 6aS)-5-(3,4-difluorophenoxy) hexahydrocyclopenta[c]pyrrol-2(1H)-yl)-1-hydroxyethyl) phenol

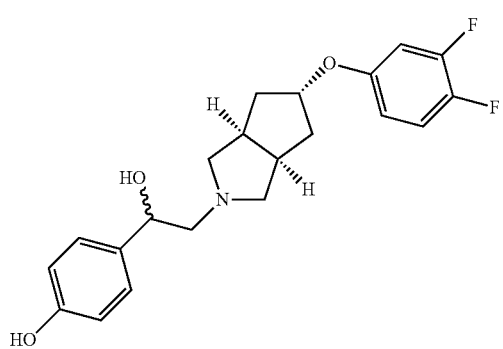 [SMILES: Oc1ccc(C(O)CN2C[C@H]3C[C@H](Oc4ccc(F)c(F)c4)C[C@H]3C2)cc1]

To a solution of 2-((3aR,5s,6aS)-5-(3,4-difluorophenoxy) hexahydrocyclopenta[c]pyrrol-2(1H)-yl)-1-(4-hydroxyphenyl) ethanone (0.25 g, 0.672 mmol) in ethanol (5 mL) was added sodium borohydride (0.25 g, 6.72 mmol)) at 0° C. The reaction mixture was stirred at room temperature for 3 h and concentrated. The residue was diluted with water (50 mL) and extracted with dichloromethane (100 mL×2). The combined organic layer was dried over anhydrous sodium sulfate, filtered and concentrated. The crude was purified by combiflash purifier using 4% methanol in dichloromethane to afford the title compound rac-4-(2-((3 aR,5s,6aS)-5-(3,4-difluorophenoxy) hexahydrocyclopenta[c]pyrrol-2(1H)-yl)-1-hydroxyethyl) phenol (0.12 g, 48.0% yield) as a white solid. Calculated M+H: 376.41; Found M+H: 376.2.

Example 2—Preparation of 2-bromo-1-(5-hydroxypyridin-2-yl)ethanone

Alternative α-halo ketones for use in step 4 above were prepared by the following methods Scheme 3

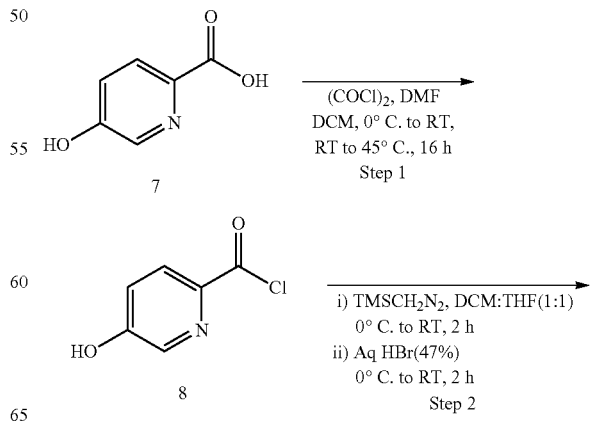

Example 3—Preparation of 2-bromo-1-(3-fluoro-4-hydroxyphenyl) ethanone

Scheme 4:

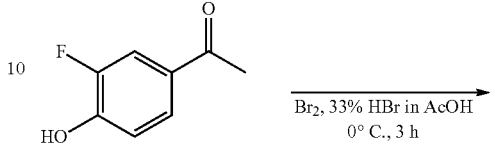

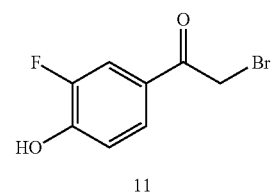

To a suspension of 1-(3-fluoro-4-hydroxyphenyl) ethanone (2.0 g, 12.98 mmol) in 33% hydrobromic acid in acetic acid (200 mL), was added a solution of bromine (0.53 mL, 10.389 mmol) in 20 mL of 33% hydrobromic acid in acetic acid at 0° C. and stirred at the same temperature for 3 h. The reaction mixture was diluted with ice water (100 mL) and extract with ethyl acetate (100 mL×3). The combined organic layer was dried over anhydrous sodium sulfate, filtered and concentrated. The crude was purified by silica gel column chromatography using 3% ethyl acetate in hexane to afford the title compound 2-bromo-1-(3-fluoro-4-hydroxyphenyl) ethanone (1.5 g, 49.66% yield) as a white solid. Calculated M+H: 232.95; Found M+H: 233.0.

Example 4—Preparation of 2-bromo-1-(6-fluoro-5-hydroxypyridin-2-yl)ethanone

Scheme 5:

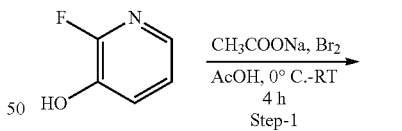

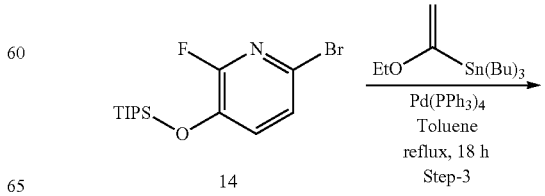

-continued

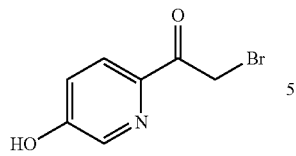

9

Step 1

Preparation of 5-hydroxypicolinoyl chloride

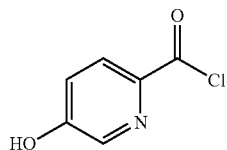

To a suspension of 5-hydroxypicolinic acid (1.0 g, 7.18 mmol) in dichloromethane (70 mL) and catalytic N,N-dimethyl formamide (0.2 mL), was added oxalyl chloride (1.25 mL, 14.37 mmol) slowly at 0° C., the resulting suspension was allowed to warm to room temperature and refluxed for 16 h. The mixture was allowed to cool to room temperature and concentrated under vacuum to afford the title compound 5-hydroxypicolinoyl chloride (1.1 g, crude) which was as such taken for next step without further purification.

Step 2

Preparation of 2-bromo-1-(5-hydroxypyridin-2-yl)ethanone

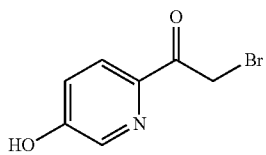 [SMILES: O=C(CBr)c1ccc(O)cn1]

To a suspension of 5-hydroxypicolinoyl chloride (1.1 g, 7.18 mmol, crude) in dichloromethane: tetrahydrofuran mixture (1:1, 50 mL) was added trimethyl silyl diazomethane (9.5 mL, 19.04 mmol, 2M in hexane) slowly at 0° C. and the reaction mixture was stirred at room temperature for 2 h. The reaction mixture was cooled to 0° C. and aqueous hydrobromic acid (47%, 3 mL, 19.04 mmol) was added. The reaction mixture was allowed warm to room temperature and stirred for 2 h. The solid formed was filtered, the washed with dichloromethane, diethyl ether and dried to obtain the title compound 2-bromo-1-(5-hydroxypyridin-2-yl)ethanone (0.6 g, crude) as pale brown solid. Calculated M+H: 215.96; Found M+H: 216.0.

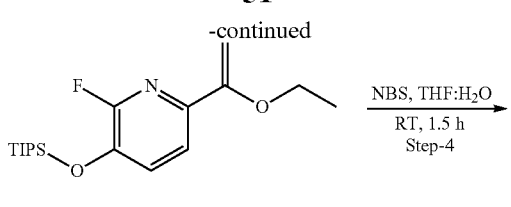

NBS, THF:H₂O
RT, 1.5 h
Step-4

15

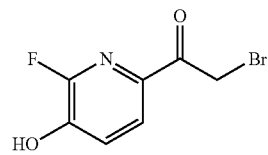

16

Step-1

Preparation of 6-bromo-2-fluoropyridin-3-ol

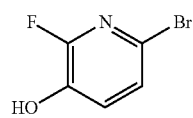

To a solution of 2-fluoropyridin-3-ol (1 g, 8.842 mmol) and sodium acetate (0.72 g, 8.842 mmol) in acetic acid (10 mL) was added bromine (0.23 mL, 8.842 mmol) at 0° C. and the reaction mixture was stirred at room temperature for 4 h. The solution was poured into ice, pH was adjusted to 6 using 2N sodium hydroxide solution and extracted with ethyl acetate (50 mL×2). The combined organic layer was dried over anhydrous sodium sulfate, filtered and concentrated to afford the crude product, which was purified by silica gel column chromatography (10% ethyl acetate/hexane) to obtain the title compound 6-bromo-2-fluoropyridin-3-ol (0.5 g, 30% yield) as a colorless liquid. Calculated (M+H): 193; Found (M+1): 193.9.

Step-2

Preparation of 6-bromo-2-fluoro-3-((triisopropylsilyl)oxy)pyridine

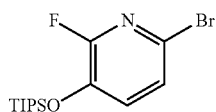

To a solution of 6-bromo-2-fluoropyridin-3-ol (0.5 g, 2.604 mmol) in tetrahydrofuran (20 mL) was added triethylamine (0.54 mL, 3.906 mmol) and the reaction mixture was cooled to 0° C. Chlorotriisopropylsilane (0.73 mL, 3.385 mmol) was added drop wise and the solution was stirred at room temperature for 2 h. The reaction mixture was diluted with water (30 mL) and extracted with ethyl acetate (50 ml×2). The combined organic layer was dried over anhydrous sodium sulfate, filtered and concentrated to afford the crude product, which was purified by silica gel column chromatography (5% ethyl acetate/hexane) to obtain the title compound 6-bromo-2-fluoro-3-((triisopropylsilyl)oxy)pyridine (0.8 g, 87% yield) as a colorless liquid. Calculated (M+H): 348.07; Found (M+1): 348.1.

Step-3

Preparation of 6-(1-ethoxyvinyl)-2-fluoro-3-((triisopropylsilyl)oxy)pyridine

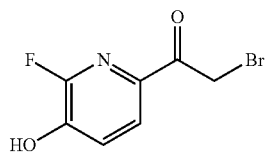 [SMILES: O=C(CBr)c1ccc(O)c(F)n1]

To a solution of 6-bromo-2-fluoro-3-((triisopropylsilyl)oxy)pyridine (0.4 g, 1.148 mmol) and tributyl(1-ethoxyvinyl)stannane (0.43 mL, 1.263 mmol) in toluene argon was purged for 10 minutes. Tetrakis(triphenylphosphine)palladium(0) was added and the reaction mixture was heated at 100° C. for 18 h. The solution was filtered through celite and filtrate was concentrated to afford the title compound 6-(1-ethoxyvinyl)-2-fluoro-3-((triisopropylsilyl)oxy)pyridine (0.36 g, crude) as brownish gum. Calculated (M+H): 340.5; Found (M+1): 340.2.

Step-4

Preparation of 2-bromo-1-(6-fluoro-5-hydroxypyridin-2-yl)ethanone

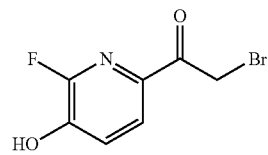

To a solution of 6-(1-ethoxyvinyl)-2-fluoro-3-((triisopropylsilyl)oxy)pyridine (8.46 g, 24.93 mmol) in tetrahydrofuran:water (280 ml, 3:1) mixture was added N-bromosuccinimide and the reaction mixture was stirred at room temperature for 1.5 h. The reaction mixture was diluted with water (150 mL) and extracted with ethyl acetate (300 mL×2). The combined organic layer was dried over anhydrous sodium sulfate, filtered and concentrated to afford the crude product, which was purified by silica gel column chromatography (40% ethyl acetate/hexane) to obtain the title compound 2-bromo-1-(6-fluoro-5-hydroxypyridin-2-yl)ethanone (5.5 g, 95% yield) as brownish gum. Calculated (M+H): 235.02; Found (M+1): 235.9.

These α-halo ketones were used in Steps 4 and 5 of Example 1 to prepare the following compounds.

TABLE 1

Compounds prepared using the α-halo ketones of Examples 2-4.

| Structure | IUPAC Name | Calculated M + H | Found M + H | Retention time (min) | Method |
|---|---|---|---|---|---|
| (structure) | 1-(4-hydroxyphenyl)-2-((3aR,5s,6aS)-5-(pyridin-3-yloxy)hexahydrocyclopenta[c]pyrrol-2(1H)-yl)ethanone | 339.4 | 339.2 | 1.392 | G |
| (structure) | rac-4-(1-hydroxy-2-((3aR,5s,6aS)-5-(pyridin-3-yloxy)hexahydrocyclopenta[c]pyrrol-2(1H)-yl)ethyl)phenol | 341.42 | 341.2 | 4.719 | H |
| (structure) | 1-(3-fluoro-4-hydroxyphenyl)-2-((3aR,5s,6aS)-5-(pyridin-3-yloxy)hexahydrocyclopenta[c]pyrrol-2(1H)-yl)ethanone | 357.39 | 357.1 | 1.165 | I |
| (structure) | rac-2-fluoro-4-(1-hydroxy-2-((3aR,5s,6aS)-5-(pyridin-3-yloxy)hexahydrocyclopenta[c]pyrrol-2(1H)-yl)ethyl)phenol | 359.41 | 359.92 | 0.915 | A |

TABLE 1-continued

Compounds prepared using the α-halo ketones of Examples 2-4.

| Structure | IUPAC Name | Calculated M + H | Found M + H | Retention time (min) | Method |
| --- | --- | --- | --- | --- | --- |
| | 1-(5-hydroxy-pyridin-2-yl)-2-((3aR,5s,6aS)-5-(3-methoxy-phenoxy)hexahydrocyclopenta[c]pyrrol-2(1)-yl)ethanone | 369.43 | 369.5 | 1.953 | A |
| | rac-6-(1-hydroxy-2-((3aR,5s,6aS)-5-(3-methoxy-phenoxy)hexahydrocyclopenta[c]pyrrol-2(1H)-yl)ethyl)pyridin-3-ol | 371.44 | 371.5 | 1.699 | A |
| | 1-(6-fluoro-5-hydroxypyridin-2-yl)-2-((3aR,5s,6aS)-5-(4-fluoro-phenoxy)hexahydrocyclopenta[c]pyrrol-2(1H)-yl)ethanone | 375.38 | 375.1 | 2.038 | A |
| | rac-2-fluoro-6-(2-((3aR,5s,6aS)-5-(4-fluoro-phenoxy)hexahydrocyclopenta[c]pyrrol-2(1H)-yl)-1-hydroxy-ethyl)pyridin-3-ol | 377.39 | 377.4 | 1.99 | A |
| | 1-(4-hydroxy-phenyl)-2-((3aR,5s,6aS)-5-((6-methyl-pyridin-3-yl)oxy)hexahydrocyclopenta[c]pyrrol-2(1H)-yl)ethanone | 353.43 | 353.2 | 1.163 | A |

TABLE 1-continued

Compounds prepared using the α-halo ketones of Examples 2-4.

| Structure | IUPAC Name | Calculated M + H | Found M + H | Retention time (min) | Method |
|---|---|---|---|---|---|
| 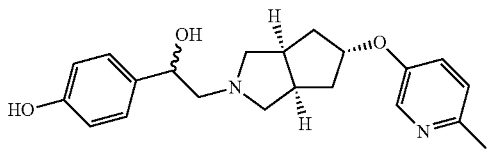 [SMILES: Cc1ccc(O[C@H]2C[C@@H]3CN(CC(O)c4ccc(O)cc4)C[C@@H]3C2)cn1] | rac-4-(1-hydroxy-2-((3aR,5s,6aS)-5-((6-methyl-pyridin-3-yl)oxy)hexahydrocyclo-penta[c]pyrrol-2(1H)-yl)ethyl)phenol | 355.45 | 355.2 | 7.816 | C |
| 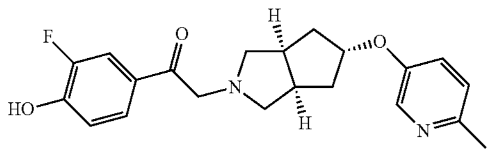 [SMILES: Cc1ccc(O[C@H]2C[C@@H]3CN(CC(=O)c4ccc(O)c(F)c4)C[C@@H]3C2)cn1] | 1-(3-fluoro-4-hydroxyphenyl)-2-((3aR,5s,6aS)-5-((6-methyl-pyridin-3-yl)oxy)hexahydrocyclo-penta[c]pyrrol-2(1H)-yl)ethanone | 371.41 | 371.4 | 1.184 | A |
| 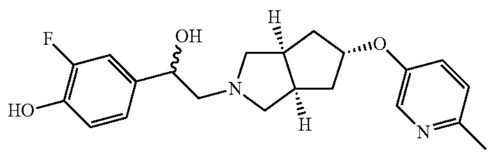 [SMILES: Cc1ccc(O[C@H]2C[C@@H]3CN(CC(O)c4ccc(O)c(F)c4)C[C@@H]3C2)cn1] | rac-2-fluoro-4-(1-hydroxy-2-((3aR,5s,6aS)-5-((6-methylpyridin-3-yl)oxy)hexa-hydrocyclopenta[c]pyrrol-2(1H)-yl)ethyl)phenol | 373.43 | 373.2 | 1.077 | A |
| 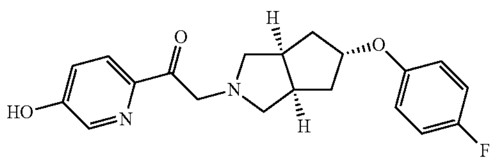 [SMILES: O=C(CN1C[C@H]2C[C@H](Oc3ccc(F)cc3)C[C@H]2C1)c1ccc(O)cn1] | 2-((3aR,5s,6aS)-5-(4-fluorophenoxy)hexahydrocyclo-penta[c]pyrrol-2(1H)-yl)-1-(5-hydroxypyridin-2-yl)ethanone | 357.39 | 357.2 | 1.593 | G |
| 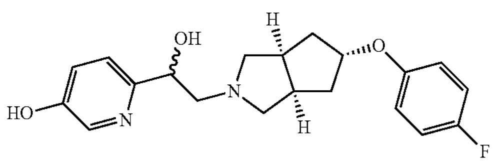 [SMILES: Oc1ccc(C(O)CN2C[C@H]3C[C@H](Oc4ccc(F)cc4)C[C@H]3C2)nc1] | rac-6-(2-((3aR,5s,6aS)-5-(4-fluorophenoxy)hexa-hydrocyclopenta[c]pyrrol-2(1H)-yl)-1-hydroxyethyl)pyridin-3-ol | 359.40 | 359.2 | 2.697 | J |
| 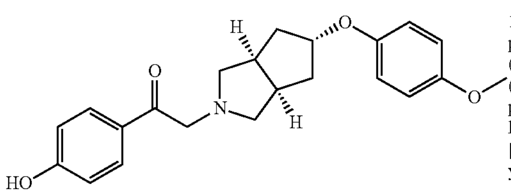 | 1-(4-hydroxy-phenyl)-2-((3aR,5s,6aS)-5-(4-methoxy-phenoxy)hexa-hydrocyclopenta[c]pyrrol-2(1H)-yl)ethanone | 368.44 | 368.2 | 1.934 | A |
| 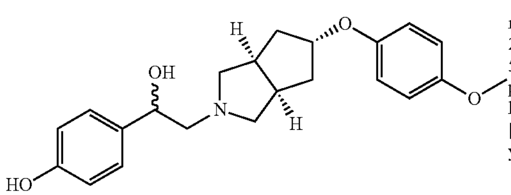 | rac-4-(1-hydroxy-2-((3aR,5s,6aS)-5-(4-methoxy-phenoxy)hexa-hydrocyclopenta[c]pyrrol-2(1H)-yl)ethyl)phenol | 370.45 | 370.2 | 1.942 | A |
| 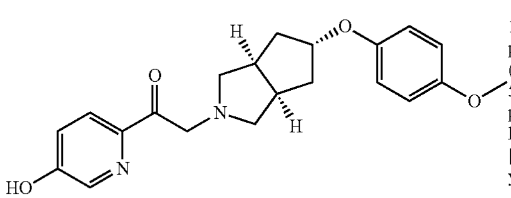 | 1-(5-hydroxy-pyridin-2-yl)-2-((3aR,5s,6aS)-5-(4-methoxy-phenoxy)hexa-hydrocyclopenta[c]pyrrol-2(1H)-yl)ethanone | 369.43 | 369.5 | 1.953 | A |

TABLE 1-continued

*Compounds prepared using the α-halo ketones of Examples 2-4.*

| Structure | IUPAC Name | Calculated M + H | Found M + H | Retention time (min) | Method |
|---|---|---|---|---|---|
| | rac-6-(1-hydroxy-2-((3aR,5s,6aS)-5-(4-methoxyphenoxy)hexahydrocyclopenta[c]pyrrol-2(1H)-yl)ethyl)pyridin-3-ol | 371.44 | 371.5 | 1.668 | A |
| | 1-(5-hydroxy-6-methoxypyridin-2-yl)-2-((3aR,5s,6aS)-5-(4-methoxyphenoxy)hexahydrocyclopenta[c]pyrrol-2(1H)-yl)ethanone | 399.45 | 399.2 | 1.986 | A |
| | rac-6-(1-hydroxy-2-((3aR,5s,6aS)-5-(4-methoxyphenoxy)hexahydrocyclopenta[c]pyrrol-2(1H)-yl)ethyl)-2-methoxypyridin-3-ol | 401.47 | 401.5 | 1.841 | A |
| | 1-(3-fluoro-4-hydroxyphenyl)-2-((3aR,5s,6aS)-5-(4-methoxyphenoxy)hexahydrocyclopenta[c]pyrrol-2(1H)-yl)ethanone | 386.43 | 386.5 | 2.033 | A |
| | rac-2-fluoro-4-(1-hydroxy-2-((3aR,5s,6aS)-5-(4-methoxyphenoxy)hexahydrocyclopenta[c]pyrrol-2(1H)-yl)ethyl)phenol | 388.44 | 388.5 | 1.929 | A |
| | 1-(6-fluoro-5-hydroxypyridin-2-yl)-2-((3aR,5s,6aS)-5-(4-methoxyphenoxy)hexahydrocyclopenta[c]pyrrol-2(1H)-yl)ethanone | 385.42 (M − H) | 385.2 (M − 1H) | 2.062 | A |

TABLE 1-continued

Compounds prepared using the α-halo ketones of Examples 2-4.

| Structure | IUPAC Name | Calculated M + H | Found M + H | Retention time (min) | Method |
|---|---|---|---|---|---|
| | rac-2-fluoro-6-(1-hydroxy-2-((3aR,5s,6aS)-5-(4-methoxyphenoxy)hexahydrocyclopenta[c]pyrrol-2(1H)-yl)ethyl)pyridin-3-ol | 389.43 | 389.5 | 1.913 | A |
| | 2-((3aR,5s,6aS)-5-(3,4-difluorophenoxy)hexahydrocyclopenta[c]pyrrol-2(1H)-yl)-1-(5-hydroxypyridin-2-yl)ethanone | 375.38 | 375.1 | 2.779 | A |
| | rac-6-(2-((3aR,5s,6aS)-5-(3,4-difluorophenoxy)hexahydrocyclopenta[c]pyrrol-2(1H)-yl)-1-hydroxyethyl)pyridin-3-ol | 377.4 | 377.2 | 1.535 | G |
| | 4-(((3aR,5s,6aS)-2-(2-(5-hydroxypyridin-2-yl)-2-oxoethyl)octahydrocyclopenta[c]pyrrol-5-yl)oxy)benzonitrile | 364.41 | 364.5 | 1.856 | A |
| | rac-4-(((3aR,5s,6aS)-2-(2-hydroxy-2-(5-hydroxypyridin-2-yl)ethyl)octahydrocyclopenta[c]pyrrol-5-yl)oxy)benzonitrile | 366.43 | 366.5 | 1.614 | A |
| | 4-(((3aR,5s,6aS)-2-(2-(6-fluoro-5-hydroxypyridin-2-yl)-2-oxoethyl)octahydrocyclopenta[c]pyrrol-5-yl)oxy)benzonitrile | 382.4 | 382.3 | 1.917 | A |
| | rac-4-(((3aR,5s,6aS)-2-(2-(6-fluoro-5-hydroxypyridin-2-yl)-2-hydroxyethyl)octahydrocyclopenta[c]pyrrol-5-yl)oxy)benzonitrile | 384.42 | 384.2 | 1.82 | A |

TABLE 1-continued

Compounds prepared using the α-halo ketones of Examples 2-4.

| Structure | IUPAC Name | Calculated M + H | Found M + H | Retention time (min) | Method |
|---|---|---|---|---|---|
| | 4-(((3aR,5s,6aS)-2-(2-(4-hydroxyphenyl)-2-oxoethyl)octahydrocyclopenta[c]pyrrol-5-yl)oxy)benzonitrile | 363.42 | 363.2 | 1.969 | A |
| | rac-4-(((3aR,5s,6aS)-2-(2-hydroxy-2-(4-hydroxyphenyl)ethyl)octahydrocyclopenta[c]pyrrol-5-yl)oxy)benzonitrile | 365.44 | 365.2 | 1.92 | A |
| | 2-((3aR,5s,6aS)-5-(3,5-difluorophenoxy)hexahydrocyclopenta[c]pyrrol-2(1H)-yl)-1-(5-hydroxypyridin-2-yl)ethanone | 375.38 | 375.4 | 1.481 | G |
| | rac-6-(2-((3aR,5s,6aS)-5-(3,5-difluorophenoxy)hexahydrocyclopenta[c]pyrrol-2(1H)-yl)-1-hydroxyethyl)pyridin-3-ol | 377.4 | 377.4 | 1.542 | G |
| | 2-((3aR,5s,6aS)-5-((5-chloropyridin-3-yl)oxy)hexahydrocyclopenta[c]pyrrol-2(1H)-yl)-1-(4-hydroxyphenyl)ethanone | 373.85 | 373.3 | 1.835 | A |

TABLE 1-continued

Compounds prepared using the α-halo ketones of Examples 2-4.

| Structure | IUPAC Name | Calculated M + H | Found M + H | Retention time (min) | Method |
|---|---|---|---|---|---|
| | rac-4-(2-((3aR,5s,6aS)-5-((5-chloropyridin-3-yl)oxy)hexahydrocyclopenta[c]pyrrol-2(1H)-yl)-1-hydroxyethyl)phenol | 375.86 | 375.2 | 1.7 | A |
| | rac-4-(2-((3aR,5s,6aS)-5-((5-fluoropyridin-3-yl)oxy)hexahydrocyclopenta[c]pyrrol-2(1H)-yl)-1-hydroxyethyl)phenol | 359.41 | 359.2 | 1.549 | A |
| | 2-((3aR,5s,6aS)-5-(4-fluorophenoxy)hexahydrocyclopenta[c]pyrrol-2(1H)-yl)-1-(4-hydroxyphenyl)ethanone | 356.40 | 356.17 | N/A | N/A |
| | rac-2-((3aR,5s,6aS)-5-(4-fluorophenoxy)hexahydrocyclopenta[c]pyrrol-2(1H)-yl)-1-(4-hydroxyphenyl)ethanol | 358.42 | 358.25 | N/A | N/A |

The minor isomer 2A from step 1 can also be used to create compounds with the opposite relative configuration as shown in the following examples.

Example 6—Preparation of (3aR,5r,6aS)-benzyl 5-(4-methoxyphenoxy)hexahydrocyclopenta[c]pyrrole-2(1H)-carboxylate

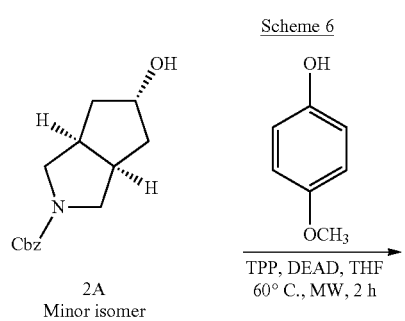

Scheme 6

TPP, DEAD, THF
60° C., MW, 2 h

2A
Minor isomer

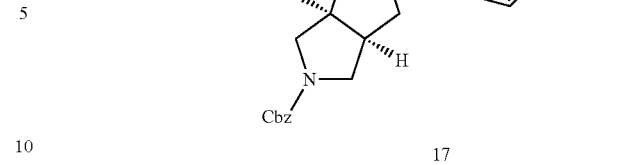

17

To a solution of (3aR,5s,6aS)-benzyl 5-hydroxyhexahydrocyclopenta[c]pyrrole-2(1H)-carboxylate (1.7 g, 6.51 mmol) in tetrahydrofuran (12 mL) at 0° C. were added 4-methoxyphenol (0.81 g, 6.51 mmol), triphenylphosphine (1.87 g, 7.16 mmol) and diethyl azo dicarboxylate (1.53 mL, 9.76 mmol). The reaction mixture was heated at 60° C. in microwave for 2 h and concentrated. Then crude was purified by combiflash purifier using 15% ethyl acetate in dichloromethane to afford the title compound 17 (3aR,5r,6aS)-benzyl 5-(4-methoxyphenoxy)hexahydrocyclopenta[c]pyrrole-2(1H)-carboxylate (1.02 g, 42.0% yield) as a brownish liquid. Calculated M+H: 368.44; Found M+H: 368.2.

17 can be elaborated by the method used to prepare Steps 4 and 5 of Example 1 and the ketones of Examples 2-4 to afford 1-(4-hydroxyphenyl)-2-((3aR,5r,6aS)-5-(4-methoxyphenoxy)hexahydrocyclopenta[c]pyrrol-2(1H)-yl)ethanone and rac-4-(1-hydroxy-2-((3aR,5r,6aS)-5-(4-methoxyphenoxy)hexahydrocyclopenta[c]pyrrol-2(1H)-yl)ethyl)phenol (Table 2). Additional compounds prepared by these procedures are described in Table 2.

TABLE 2

Analogs prepared from 2A.

| Structure | IUPAC Name | Calculated M + H | Found M + H | Retention time (min) | Method |
|---|---|---|---|---|---|
| 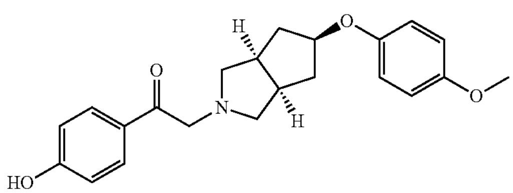 [SMILES: COc1ccc(O[C@@H]2C[C@@H]3CN(CC(=O)c4ccc(O)cc4)C[C@@H]3C2)cc1] | 1-(4-hydroxyphenyl)-2-((3aR,5r,6aS)-5-(4-methoxyphenoxy)hexahydrocyclopenta[c]pyrrol-2(1H)-yl)ethanone | 368.44 | 368.2 | 1.956 | A |
| 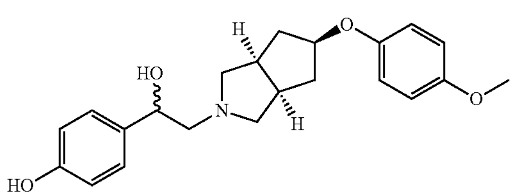 [SMILES: COc1ccc(O[C@@H]2C[C@@H]3CN(CC(O)c4ccc(O)cc4)C[C@@H]3C2)cc1] | rac-4-(1-hydroxy-2-((3aR,5r,6aS)-5-(4-methoxyphenoxy)hexahydrocyclopenta[c]pyrrol-2(1H)-yl)ethyl)phenol | 370.42 | 370.2 | 1.82 | A |
| 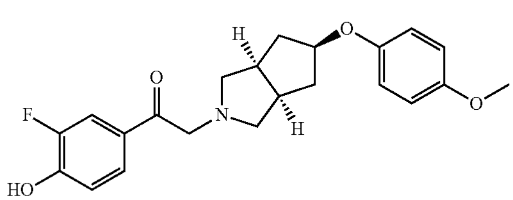 [SMILES: COc1ccc(O[C@@H]2C[C@@H]3CN(CC(=O)c4ccc(O)c(F)c4)C[C@@H]3C2)cc1] | 1-(3-fluoro-4-hydroxyphenyl)-2-((3aR,5r,6aS)-5-(4-methoxyphenoxy)hexahydrocyclopenta[c]pyrrol-2(1H)-yl)ethanone | 386.43 | 386.2 | 2.031 | A |

TABLE 2-continued

Analogs prepared from 2A.

| Structure | IUPAC Name | Calculated M + H | Found M + H | Retention time (min) | Method |
|---|---|---|---|---|---|
| | rac-2-fluoro-4-(1-hydroxy-2-((3aR,5r,6aS)-5-(4-methoxy-phenoxy)hexahydrocyclopenta[c]pyrrol-2(1H)-yl)ethyl)phenol | 388.44 | 388.2 | 1.921 | A |
| | 1-(5-hydroxy-pyridin-2-yl)-2-((3aR,5r,6aS)-5-(4-methoxy-phenoxy)hexahydrocyclopenta[c]pyrrol-2(1H)-yl)ethanone | 369.43 | 369.2 | 2.067 | A |
| | rac-6-(1-hydroxy-2-((3aR,5r,6aS)-5-(4-methoxy-phenoxy)hexahydrocyclopenta[c]pyrrol-2(1H)-yl)ethyl)pyridin-3-ol | 371.44 | 371.2 | 1.738 | A |
| | 4-(((3aR,5r,6aS)-2-(2-(5-hydroxypyridin-2-yl)-2-oxoethyl)octahydrocyclopenta[c]pyrrol-5-yl)oxy)benzonitrile | 364.41 | 364.4 | 1.905 | A |
| | rac-4-(((3aR,5r,6aS)-2-(2-hydroxy-2-(5-hydroxy-pyridin-2-yl)ethyl)octahydrocyclopenta[c]pyrrol-5-yl)oxy)benzonitrile | 366.43 | 366.2 | 1.61 | A |

Example 7—Preparation of rac-4-(2-((3aR,5s,6aS)-5-((2-fluoropyridin-3-yl)oxy)hexahydrocyclopenta[c]pyrrol-2(1H)-yl)-1-hydroxyethyl)phenol An alternative synthetic route was used to prepare the other examples.

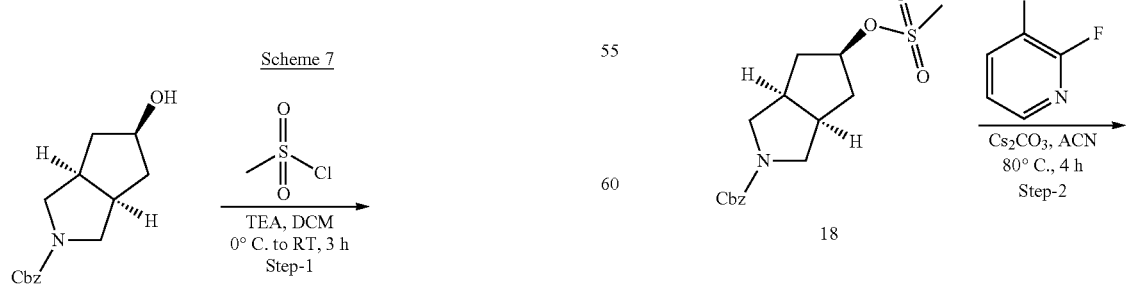

Scheme 7

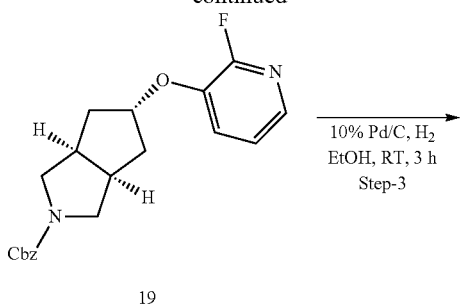

19

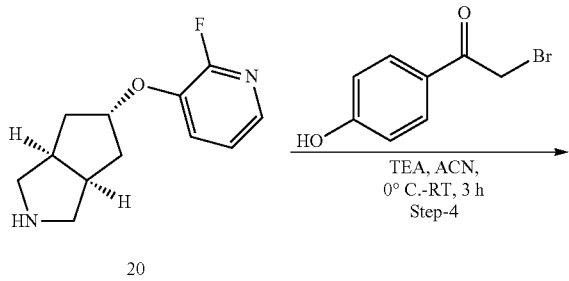

20

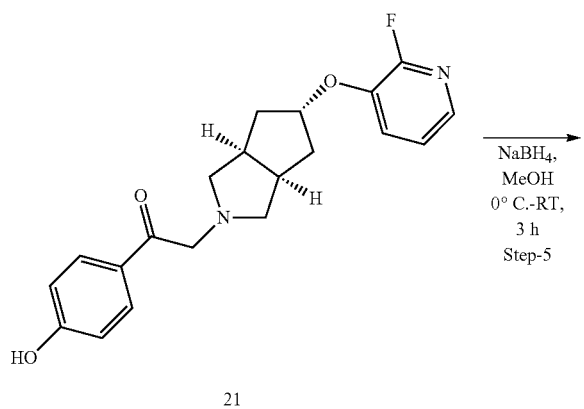

21

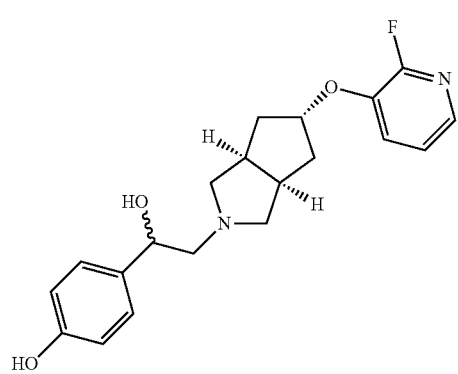

22

Step 1

Preparation of (3aR,5s,6aS)-benzyl 5-((methylsulfonyl) oxy) hexahydrocyclopenta[c]pyrrole-2(1H)-carboxylate To a solution of (3aR, 5r, 6aS)-benzyl 5-hydroxyhexahydrocyclopenta[c]pyrrole-2(1H)-carboxylate (3.1 g, 11.87 mmol) in dichloromethane (30 mL) was added triethylamine (3 mL, 23.74 mmol) at room temperature. The reaction mixture was cooled to 0° C. and methanesulfonyl chloride (2.03 g, 17.82 mmol) was slowly added. The resultant mixture was allowed to warm to room temperature and stirred for 3 h. The solution was quenched with saturated ammonium chloride solution (25 mL) and extracted with dichloromethane (200 mL×3). The combined extracts were washed with brine solution (100 mL), dried over anhydrous sodium sulfate, filtered and concentrated to afford the title compound (3aR, 5s, 6aS)-benzyl 5-((methylsulfonyl) oxy) hexahydrocyclopenta[c]pyrrole-2(1H)-carboxylate (3 g, 75%) as a colorless liquid. Calculated M+H: 340.41; Found M+H: 340.1.

Step 2

Preparation of (3aR,5s,6aS)-benzyl 5-(2-fluoropyridine) hexahydrocyclopenta[c]pyrrole-2(1H)-carboxylate To a solution of (3aR, 5s, 6aS)-benzyl 5-((methylsulfonyl) oxy) hexahydrocyclopenta[c]pyrrole-2(1H)-carboxylate (0.7 g, 2.064 mmol) in acetonitrile (15 mL), 2-fluoropyridine-3-ol (0.349 g, 3.097 mmol) and cesium carbonate (1.353 g, 4.128 mmol) were added at room temperature and the reaction mixture was stirred at 80° C. for 4 h. The reaction mixture was concentrated, the residue was diluted with water (100 mL) and extracted with ethyl acetate (200 mL×2). The combined organic layer was dried over anhydrous sodium sulfate, filtered and concentrated. The crude was purified by combiflash purifier using 20-25% ethyl acetate in hexane to afford the title compound (3aR,5s,6aS)-benzyl 5-(2-fluoropyridine) hexahydrocyclopenta[c]pyrrole- 2(1H)-carboxylate (0.8 g, crude) as a pale yellow liquid. Calculated M+H: 357.16; Found M+H: 357.2.

Step 3

Preparation of (3aR,5s,6aS)-5-((2-fluoropyridin-3-yl)oxy) octahydrocyclopenta[c]pyrrole

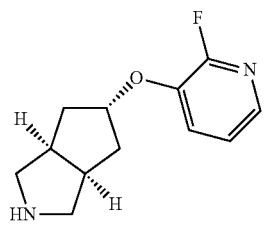 [SMILES: Fc1ncccc1O[C@@H]1C[C@H]2CNC[C@H]2C1]

To a solution of (3aR, 5s, 6aS)-benzyl 5-(2-fluoropyridine) hexahydrocyclopenta[c]pyrrole-2(1H)-carboxylate (0.8 g, 1.40 mmol) in ethanol (40 mL) was added 10% Pd/C (50% wet) (0.4 g) and the reaction mixture was stirred at room temperature for 3 h under hydrogen atmosphere. The reaction mixture was filtered through celite and washed with methanol. The combined filtrate was concentrated and dried to afford the title compound (3aR,5s,6aS)-5-((2-fluoropyridin-3-yl)oxy) octahydrocyclopenta[c]pyrrole (0.4 g, crude) as a colorless liquid. Calculated M+H: 223.26; Found M+H: 223.3.

Step 4

Preparation of 2-((3aR, 5s, 6aS)-5-((2-fluoropyridin-3-yl) oxy) hexahydrocyclopenta[c]pyrrol-2(1H)-yl)-1-(4-hydroxyphenyl) ethanone

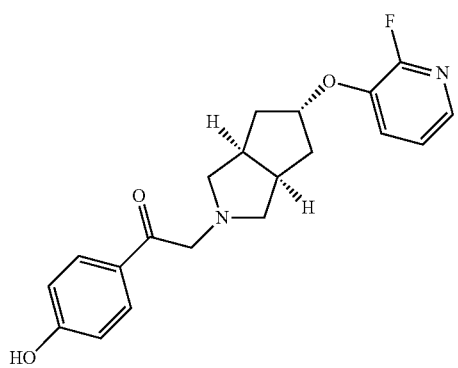 [SMILES: O=C(CN1C[C@H]2C[C@H](Oc3cccnc3F)C[C@H]2C1)c1ccc(O)cc1]

To a solution of (3aR,5s,6aS)-5-((2-fluoropyridin-3-yl) oxy) octahydrocyclopenta[c]pyrrole (0.3 g, 1.35 mmol) in acetonitrile (10 mL) was added triethylamine (0.58 mL, 4.053 mmol) followed by 2-bromo-1-(4-hydroxyphenyl) ethanone (0.232 g, 1.081 mmol) and the resulting suspension was stirred at room temperature for 3 h. The reaction mixture was concentrated, the residue was diluted with water (50 mL) and extracted with ethyl acetate (100 mL×3). The combined organic layer was dried over anhydrous sodium sulfate, filtered and concentrated. The crude was purified by combiflash purifier using 2-3% methanol in dichloromethane to afford the title compound 2-((3aR,5s, 6aS)-5-((2-fluoropyridin-3-yl)oxy)hexahydrocyclopenta[c] pyrrol-2(1H)-yl)-1-(4-hydroxyphenyl) ethanone (0.13 g, 27% yield) as a white solid. Calculated M+H: 357.4; Found M+H: 357.2.

Step 5

Preparation of rac-4-(2-((3aR, 5s, 6aS)-5-(2-fluoropyridin-3-yl)oxy hexahydrocyclopenta[c]pyrrol-2 (1H)-yl)-1-hydroxyethyl) phenol

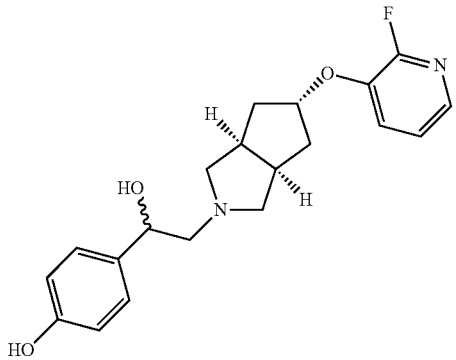

To a solution of 2-((3aR,5s,6aS)-5-((2-fluoropyridin-3-yl) oxy) hexahydrocyclopenta[c]pyrrol-2(1H)-yl)-1-(4-hydroxyphenyl) ethanone (0.15 g, 0.421 mmol) in methanol (10 mL) was added sodium borohydride (0.15 g, 4.21 mmol) at 0° C. and the suspension was stirred at room temperature for 3 h. The reaction mixture was concentrated; the residue was diluted with water (50 mL) and extracted with dichloromethane (100 mL×2). The combined organic layer was dried over anhydrous sodium sulfate, filtered and concentrated. The crude was purified by combiflash purifier using 4% methanol in dichloromethane to afford the title compound 4-(2-((3aR,5s,6aS)-5-(2-fluoropyridin-3-yl)oxyhexahydrocyclopenta[c]pyrrol-2(1H)-yl)-1-hydroxyethyl) phenol (0.10 g, 66.0% yield) as a white solid. Calculated M+H: 359.41; Found M+H: 359.2.

Example 8—Preparation of 6-((S)-1-hydroxy-2-((3aR,5R,6aS)-5-phenoxyhexahydrocyclopenta[c] pyrrol-2(1H)-yl)ethyl)pyridin-3-ol Scheme 8:

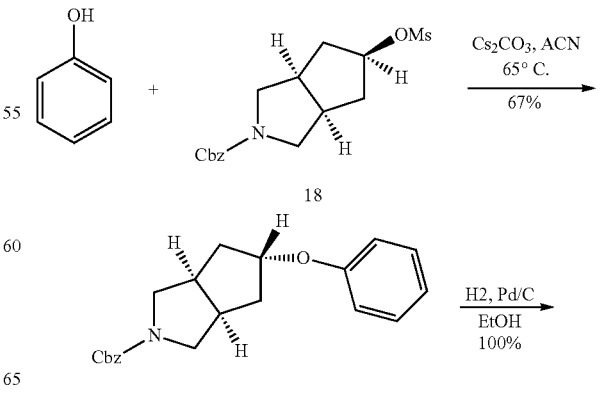

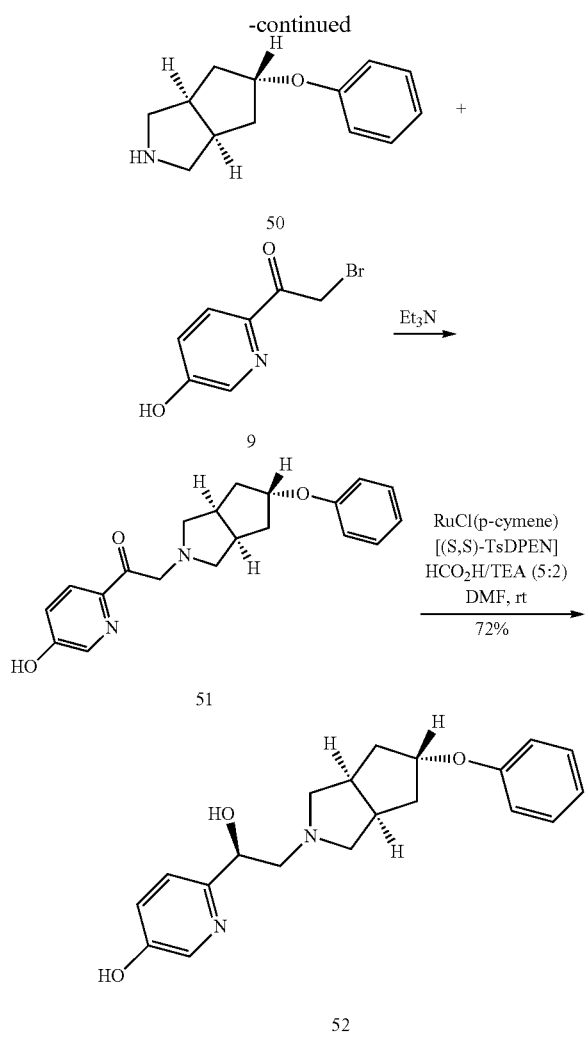

Step 1

Preparation of benzyl (3aR,5s,6aS)-5-phenoxyhexahydrocyclopenta[c]pyrrole-2(1H)-carboxylate To a stirred solution of benzyl (3aR,5r,6aS)-5 ((methylsulfonyl)oxy)hexahydrocyclopenta[c]pyrrole-2(1H)-carboxylate (30.35 g, 90 mmol) in 600 mL of acetonitrile was added phenol (9.27 g, 98 mmol) and cesium carbonate (58.3 g, 179 mmol). The mixture was stirred with heating at 65° C. for two hours and filtered through a pad of Celite. The Celite was washed with acetonitrile. The filtrate was combined and concentrated. The residue was chromatographed twice on silica gel eluting with heptane/ethyl acetate to afford 20.15 g (67%) of benzyl (3aR,5s,6aS)-5-phenoxyhexahydrocyclopenta[c]pyrrole-2(1H)-carboxylate. LCMS [M+H]$^+$ 338.3, 1.35 min, method R.

Step 2

Preparation of (3aR,5s,6aS)-5-phenoxyoctahydrocyclopenta[c]pyrrole

To a stirred suspension of benzyl (3aR,5s,6aS)-5-phenoxyhexahydrocyclopenta[c]pyrrole-2(1H)-carboxylate (20.08 g, 59.6 mmol) in 700 mL of ethanol was added 2.9 g of 10% palladium on carbon (wet degussa type). The mixture was degassed, purged and exposed to one atmosphere of hydrogen gas for 1 hour. Another 2.7 g of 10% palladium on carbon was added and the reaction mixture was stirred for an hour. The catalyst was filtered with the aid of wet ethanol and the filtrate was concentrated to afford 12.23 g (100%) of (3aR,5s,6aS)-5-phenoxyoctahydrocyclopenta[c]pyrrole. LCMS [M+H]$^+$ 204.3, 0.84 min, method R.

Step 3

Preparation of 1-(5-hydroxypyridin-2-yl)-2-((3aR, 5s,6aS)-5-phenoxyhexahydrocyclopenta[c]pyrrol-2 (1H)-yl)ethan-1-one Two independent solutions of 2-bromo-1-(5-hydroxypyridin-2-yl)ethan-1-one (8.75 g, 29.6 mmol) in 30 mL of DMF and (3aR,5s,6aS)-5-phenoxyoctahydrocyclopenta[c]pyrrole (8.22 g, 40.5 mmol) in 40 mL of DMF/2-methyltetrahydrofuran (1:3) were added separately at the same rate to a stirring solution of triethylamine (3.09 mL, 22.18 mmol) in 20 mL of 2-methyltetrahydrofuran in an ice bath over 1 hour. After 1.5 hours of stirring from the start of the addition, the reaction mixture was quenched with saturated potassium dihydrogen phosphate solution. The aqueous layer was extracted with dichloromethane. The organic layer was washed with brine, dried (Na$_2$SO$_4$), filtered through a pad of florisil with the aid of ethyl acetate-ethanol and concentrated to an orange oil. The oil was chromatographed on silica gel eluting with dichloromethane-ethyl acetate-EtOH.

Brine was added to the aqueous phosphate solution. It was extracted with ethyl acetate, The organic layer was dried (N$_2$SO$_4$) and filtered through a pad of florisil with the aid of ethyl acetate-EtOH. The organic solution was concentrated until crystallization was observed. The solid was collected by filtration and dried. In combination 7.19 g (72%) of 1-(5-hydroxypyridin-2-yl)-2-((3aR,5s,6aS)-5-phenoxyhexahydrocyclopenta[c]pyrrol-2(1H)-yl)ethan-1-one was obtained. LCMS [M+H]$^+$ 339.3, 1.13 min, method R.

Step 4

Preparation of 6-((S)-1-hydroxy-2-((3aR,5R,6aS)-5-phenoxyhexahydrocyclopenta[c]pyrrol-2(1H)-yl) ethyl)pyridin-3-ol To a stirred nitrogen-flushed solution of 1-(5-hydroxypyridin-2-yl)-2-((3aR,5s,6aS)-5-phenoxyhexahydrocyclopenta[c]pyrrol-2(1H)-yl)ethan-1-one (7.19 g, 21.27 mmol) and RuCl(p-cymene)[(S,S)-TsDPEN] (0.541 g, 0.851 mmol) in 100 mL of DMF was added a solution of formic acid (4.01 mL, 106 mmol) and triethylamine (5.94 mL, 42.5 mmol). The reaction mixture was stirred at room temperature overnight. The reaction was quenched with aqueous NaHCO$_3$ solution. Ethyl acetate was added and the organic phase was washed with brine, dried (Na$_2$SO$_4$) and filtered. The filtrate was passed through a pad of florisil with the aid of ethyl acetate-ethanol and concentrated. The residue was then chromatographed on silica gel eluting with MeOH-DCM and concentrated until crystallization was observed. The solid was collected by filtration, washed with heptane, ether, and dried. Concentration of the filtrate afforded another crop, which was combined to afford 5.15 g of 6-((S)-1-hydroxy-2-((3 aR,5R,6aS)-5-phenoxyhexahydrocyclopenta [c]pyrrol-2(1H)-yl)ethyl)pyridin-3-ol as a solid. The solid was further purified by preparative SFC (method S). The obtained methanolic solution was treated with 400 mg of Si-Triamine scavenger reagent for over 8 hours, filtered and concentrated to afford 4.07 g (80%) of 6-((S)-1-hydroxy-2-((3aR,5R,6aS)-5-phenoxyhexahydrocyclopenta[c]pyrrol-2 (1H)-yl)ethyl)pyridin-3-ol. Purity was >98% and Ruthenium level was found to be 54 ppm. $^1$H NMR (400 MHz, DMSO-d6) δ ppm 1.66 (dt, J=12.75, 4.75 Hz, 2H) 1.83-1.94 (m, 2H) 2.30 (dt, J=8.74, 6.69 Hz, 2H) 2.52-2.60 (m, 4H) 2.65 (dd, J=12.10, 5.01 Hz, 1H) 4.60 (dd, J=7.34, 5.14 Hz, 1H) 4.80 (quin, J=4.62 Hz, 1H) 4.99 (br s, 1H) 6.82-6.91 (m, 3H) 7.13 (dd, J=8.56, 2.81 Hz, 1H) 7.23-7.31 (m, 3H) 8.03 (d, J=2.45 Hz, 1H) 9.67 (br s, 1H); LCMS [M+H]$^+$ 341.4, 0.91 min, method R The absolute stereochemistry was confirmed by x-ray crystallography (FIG. 1).

Example 9—Preparation of 6-((R)-1-hydroxy-2-((3aR,5S,6aS)-5-phenoxyhexahydrocyclopenta[c]pyrrol-2(1H)-yl)ethyl)pyridin-3-ol

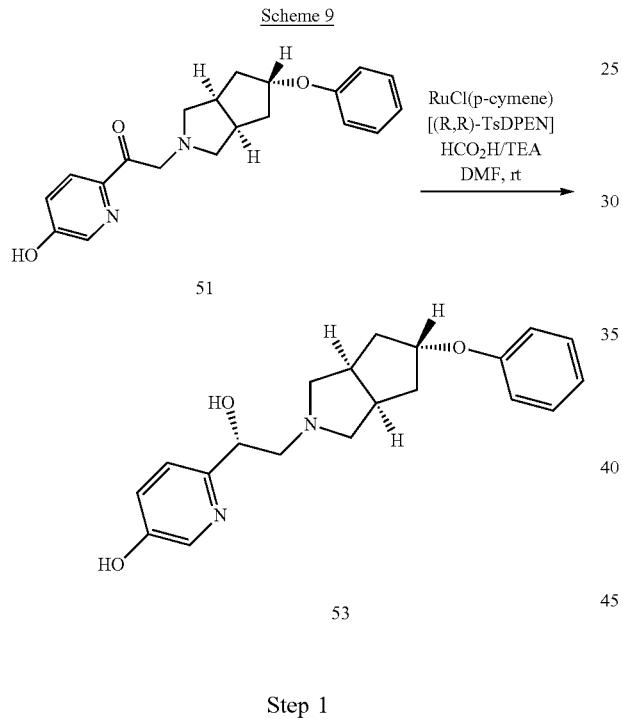

Step 1

Preparation of 6-((R)-1-hydroxy-2-((3aR,5S,6aS)-5-phenoxyhexahydrocyclopenta[c]pyrrol-2(1H)-yl)ethyl)pyridin-3-ol To a stirred nitrogen-flushed solution of 1-(5-hydroxypyridin-2-yl)-2-((3aR,5s,6aS)-5-phenoxyhexahydrocyclopenta[c]pyrrol-2(1H)-yl)ethan-1-one (0.20 g, 0.59 mmol) and RuCl(p-cymene)[(R,R)-TsDPEN] (0.015 g, 0.024 mmol) in 15 mL of DMF was added a solution of formic acid (0.112 mL, 2.96 mmol) and TEA (0.165 mL, 1.18 mmol). The reaction mixture was stirred at room temperature overnight. The reaction was quenched with aqueous NaHCO$_3$ solution. Ethyl acetate was added and the organic phase was washed with brine, dried (Na$_2$SO$_4$) and filtered. The filtrate was passed through a pad of florisil with the aid of ethyl acetate-ethanol and concentrated. The residue was purified by preparative SFC (method S) to afford 71 mg (35%) of 6-((R)-1-hydroxy-2-((3aR,5S,6aS)-5-phenoxyhexahydrocyclopenta[c]pyrrol-2(1H)-yl)ethyl)pyridin-3-ol. $^1$H NMR (400 MHz, DMSO-d6) δ 9.68 (s, 1H), 8.02 (d, J=2.5 Hz, 1H), 7.55-7.20 (m, 3H), 7.13 (dd, J=2.8, 8.5 Hz, 1H), 6.97-6.76 (m, 3H), 5.00 (s, 1H), 4.81 (p, J=4.6 Hz, 1H), 4.60 (t, J=5.6 Hz, 1H), 2.79-2.44 (m, 5H), 2.44-2.18 (m, 2H), 2.04-1.79 (m, 2H), 1.66 (dt, J=4.6, 12.7 Hz, 2H); LCMS [M+H]$^+$ 341.3, 0.92 min, method R.

Example 10—Preparation of 6-((S)-2-((3aR,5R,6aS)-5-(2-fluorophenoxy)hexahydrocyclopenta[c]pyrrol-2(1H)-yl)-1-hydroxyethyl)pyridin-3-ol

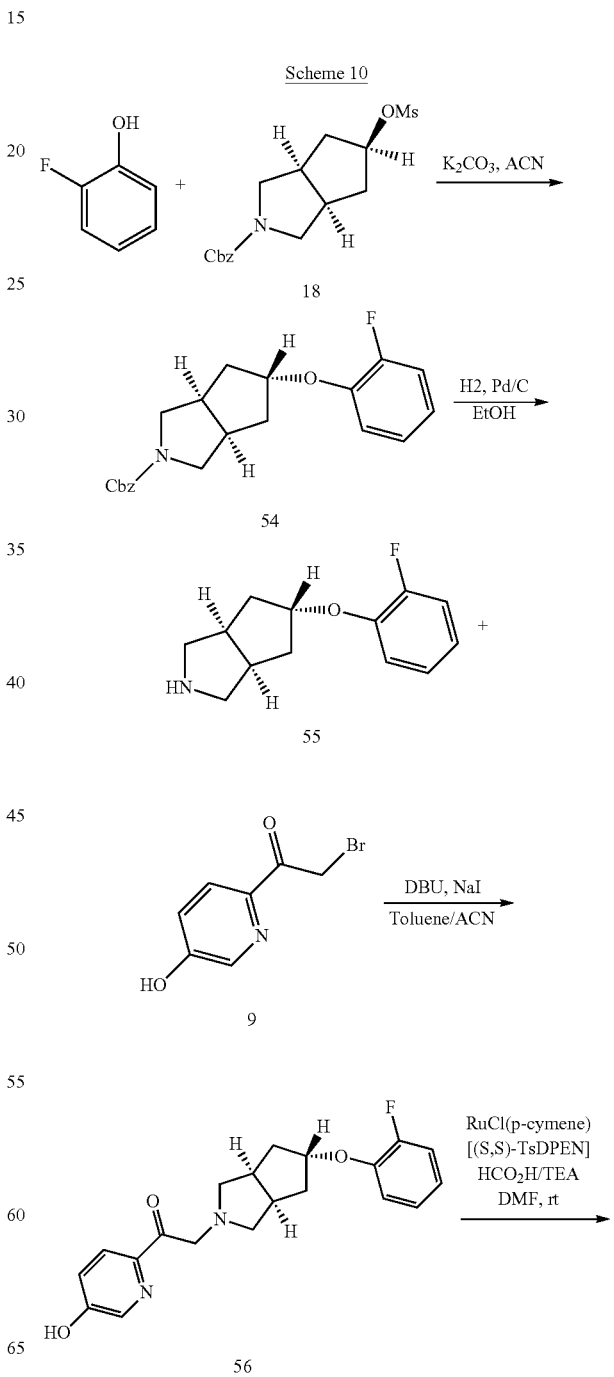

-continued

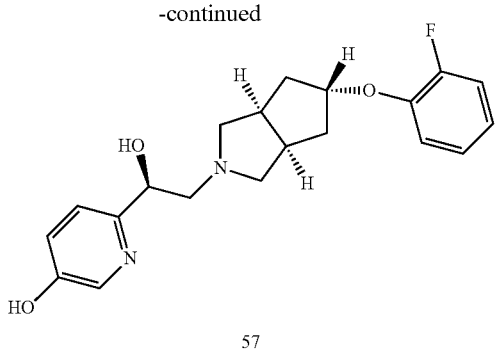

57

Step 1

Preparation of benzyl (3aR,5s,6aS)-5-(2-fluorophenoxy)hexahydrocyclopenta[c]pyrrole-2(1H)-carboxylate To a stirred suspension of potassium carbonate (26.9 g, 194 mmol) in MeCN (Volume: 400 mL) was added 2-fluorophenol (7.89 mL, 88 mmol). The reaction mixture was stirred at room temperature for 15 minutes, then to this was added benzyl (3aR,5r,6aS)-5-((methylsulfonyl)oxy)hexahydrocyclopenta[c]pyrrole-2(1H)-carboxylate (30 g, 88 mmol) as a solid. The suspension was stirred at room temperature for 10 minutes and heated at 60° C. overnight and then an additional 6 hours. The reaction was diluted with additional acetonitrile (200 mL) and heated overnight. The suspension was allowed to cool to room temperature and filtered over Celite plug. The filtrate was partially evaporated and diluted with EtOAc (200 mL) and water (200 mL). The organic layer was washed with saturated NaHCO₃ solution, dried over MgSO₄, filtered and concentrated. The residue was loaded onto a 750 g Redisep column and eluted with n-heptane: EtOAc gradient (0-40%). Fractions were collected, combined and evaporated to give a pale yellow oil, which crystallized on standing to give benzyl (3aR,5s,6aS)-5-(2-fluorophenoxy)hexahydrocyclopenta[c]pyrrole-2(1H)-carboxylate (22.6 g; 72% yield). LC-MS: [M+H]⁺ 356.3, Rt=1.88 min, method R.

Step 2

Preparation of (3aR,5s,6aS)-5-(2-fluorophenoxy)octahydrocyclopenta[c]pyrrole

To a stirred solution of benzyl (3aR,5s,6aS)-5-(2-fluorophenoxy)hexahydrocyclopenta[c]pyrrole-2(1H)-carboxylate (22.6 g, 60.5 mmol) in ethanol (Volume: 400 mL) under nitrogen was charged 10% palladium on carbon (wet—degussa) (0.644 g, 0.605 mmol; 10 mol %). The stirred suspension was then placed under a balloon of hydrogen gas (several evacuation/charging phases completed) and then was allowed to stir at room temperature for 2 hours. The reaction mixture was placed under N₂ atmosphere. The catalyst was removed via suction filtration over Celite plug, and the filtrate was concentrated in vacuo to give (3aR,5s,6aS)-5-(2-fluorophenoxy)octahydrocyclopenta[c]pyrrole as a pale yellow oil (14.2 g; 100% yield). LC-MS: [M+H]⁺ 222.2 Rt=0.85 min, method R.

Step 3

Preparation of 2-((3aR,5s,6aS)-5-(2-fluorophenoxy)hexahydrocyclopenta[c]pyrrol-2(1H)-yl)-1-(5-hydroxypyridin-2-yl)ethan-1-one Solution A: (3aR,5s,6aS)-5-(2-fluorophenoxy)octahydrocyclopenta[c]pyrrole (9.48 g, 42.9 mmol) and triethylamine (3.45 ml, 24.74 mmol) in DMF (45 mL). Solution B: 2-bromo-1-(5-hydroxypyridin-2-yl)ethan-1-one (9.5 g, 33.0 mmol) in DMF (45 mL).

Solution A and Solution B were pumped together (at 1.0 ml/min) mixing at a T-piece mixer, followed by a 10 ml reaction loop (total residence time 5 min), and output was collected into a stirred reaction vial containing dichloromethane and 10% KH₂PO₄ solution. The biphasic solution was separated, and the organic layer was dried over Na₂SO₄, evaporated under high vacuum to remove as much solvent as possible without heating water bath above 20° C. The dark orange/brown solution was then loaded onto a large dry silica plug, and washed with DCM, followed by elution through a 750 g Redisep column using a DCM/[EtOAc/EtOH (3:1)] gradient column to give 2-((3aR,5s,6aS)-5-(2-fluorophenoxy)hexahydrocyclopenta[c]pyrrol-2(1H)-yl)-1-(5-hydroxypyridin-2-yl)ethan-1-one as an orange foam (6.7 g). LC-MS: [M+H]⁺ 357.3, Rt=1.08 min, method R.

Step 4

Preparation of 6-((S)-2-((3aR,5R,6aS)-5-(2-fluorophenoxy)hexahydrocyclopenta[c]pyrrol-2(1H)-yl)-1-hydroxyethyl)pyridin-3-ol 2-((3 aR,5s,6aS)-5-(2-fluorophenoxy)hexahydrocyclopenta[c]pyrrol-2(1H)-yl)-1-(5-hydroxypyridin-2-yl)ethan-1-one (6.7 g, 18.8 mmol) in DMF (Volume: 94 ml) was de-gassed under N₂ flow for 10 minutes. The reaction mixture was charged with a preformed mixture of formic acid (3.55 ml, 94 mmol) and triethylamine (5.24 ml, 37.6 mmol). This was then followed by catalyst RuCl(p-Cymene)-[(S,S-pTs-DPEN)] (0.359 g, 0.564 mmol), and reaction was allowed to stir at room temperature under inert N₂ atmosphere. After 16 hours additional catalyst was added (1 mol %) (total 4 mol % added for reaction) and the reaction was stirred for an additional 7 hours. The reaction was quenched with saturated NaHCO₃ solution and diluted with EtOAc. The organic layer was dried over Na₂SO₄, filtered and concentrated (40° C. water bath) to a dark brown crude residue, which was loaded directly onto dry silica (as DMF concentrate) and eluted down a 330 g Redisep column with DCM/MeOH (0-30%) to yield a pale green solid. The solid was taken up in refluxing methyl tert-butyl either (MTBE), and was hot filtered. The filtrate was treated with charcoal, filtered and evaporated to give a solid. The solid was taken back up in hot MTBE (150 ml), followed by addition of n-heptane (150 mL), and was recrystallized overnight, which upon filtration and washing with n-heptane yielded an off-white solid. The solid was dried in a vacuum oven for 3 days (at 40° C.) to give 6-((S)-2-((3aR,5R,6aS)-5-(2-fluorophenoxy)hexahydrocyclopenta[c]pyrrol-2(1H)-yl)-1-hydroxyethyl)pyridin-3-ol (3.38 g). ¹H NMR (400 MHz, DMSO-d6) δ 9.67 (s, 1H), 8.13-7.87 (m, 1H), 7.29 (d, J=8.5 Hz, 1H), 7.22-7.00 (m, 4H), 7.00-6.77 (m, 1H), 4.99 (s, 1H), 4.84 (q, J=4.4 Hz, 1H), 4.60 (s, 1H), 2.77-2.40 (m, 5H), 2.39-2.20 (m, 2H), 1.93 (dd, J=4.3, 8.8 Hz, 2H), 1.65 (dt, J=4.8, 13.0 Hz, 2H). LC-MS: [M+H]⁺ 359.4 Rt=0.93 min, method R.

Figure 2:
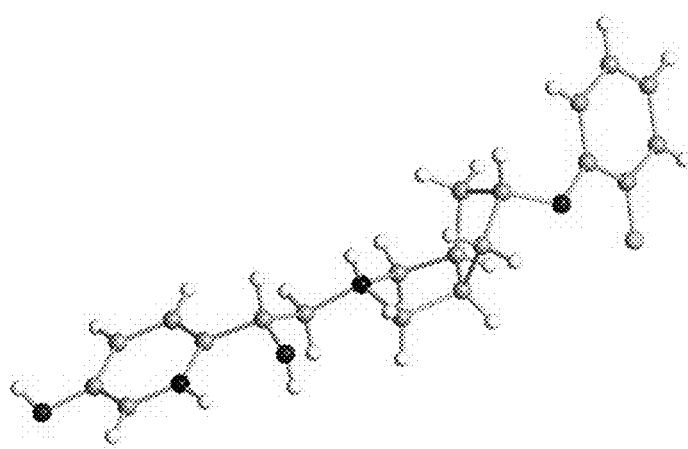
FIG. 2 is the X-ray crystallograph of the compound of Example 10.

The absolute stereochemistry was confirmed by x-ray crystallography (FIG. 2).

Example 11—Preparation of 6-((R)-2-((3aR,5S,6aS)-5-(2-fluorophenoxy)hexahydrocyclopenta[c]pyrrol-2(1H)-yl)-1-hydroxyethyl)pyridin-3-ol

Step 1

Preparation of 6-((R)-2-((3aR,5S,6aS)-5-(2-fluorophenoxy)hexahydrocyclopenta[c]pyrrol-2(1H)-yl)-1-hydroxyethyl)pyridin-3-ol

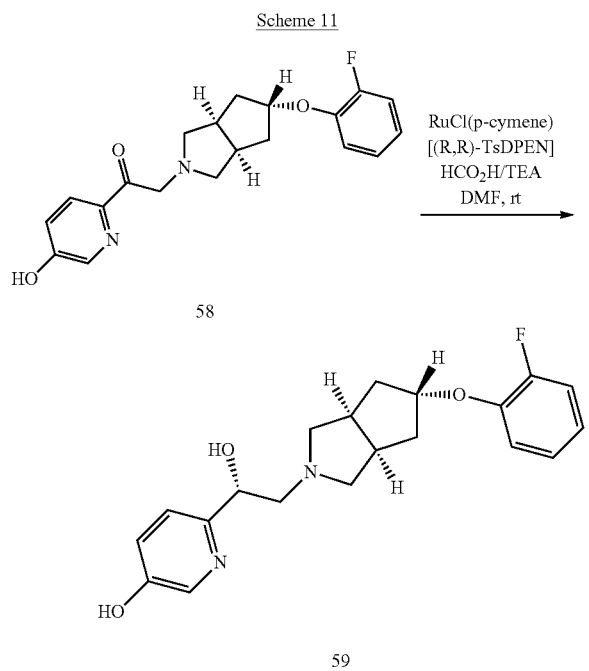

Scheme 11

2-((3aR,5s,6aS)-5-(2-fluorophenoxy)hexahydrocyclopenta[c]pyrrol-2(1H)-yl)-1-(5-hydroxypyridin-2-yl)ethan-1-one (0.25 g, 0.70 mmol) in DMF (Volume: 1 ml) was de-gassed under $N_2$ flow for 10 minutes. The reaction mixture was charged with a preformed mixture of formic acid (49.9 mg, 0.70 mmol) and triethylamine (0.196 ml, 1.40 mmol). This was then followed by catalyst RuCl(p-Cymene)-[(R,R-pTs-DPEN)] (13.4 mg, 0.021 mmol), and reaction was allowed to stir at room temperature under inert $N_2$ atmosphere overnight. The reaction was quenched with saturated $NaHCO_3$ solution and diluted with EtOAc. The organic layer was dried over $Na_2SO_4$, filtered and concentrated. The residue was purified by SFC (method S) to give 6-((R)-2-((3aR,5S,6aS)-5-(2-fluorophenoxy)hexahydrocyclopenta[c]pyrrol-2(1H)-yl)-1-hydroxyethyl)pyridin-3-ol as a beige foam (121 mg, 46%). $^1$H NMR (400 MHz, DMSO-d6) δ 9.69 (s, 1H), 8.02 (d, J=2.4 Hz, 1H), 7.29 (d, J=8.5 Hz, 1H), 7.24-6.99 (m, 4H), 6.99-6.80 (m, 1H), 4.98 (d, J=4.4 Hz, 1H), 4.92-4.77 (m, 1H), 4.60 (dt, J=4.5, 8.4 Hz, 1H), 2.74-2.44 (m, 5H), 2.42-2.18 (m, 2H), 2.06-1.82 (m, 2H), 1.65 (dt, J=4.9, 13.1 Hz, 2H). LC-MS: [M+H]$^+$ 359.4 Rt=0.99 min, method R.

TABLE 3

The following compounds were prepared by the method described above.

| Structure | IUPAC Name | Calculated M + H | Found M + H | Retention time (min) | Method |
|---|---|---|---|---|---|
| 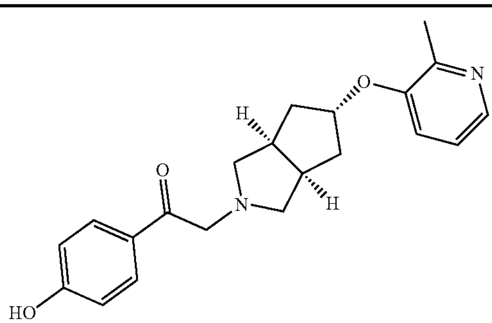 | 1-(4-hydroxyphenyl)-2-((3aR,5s,6aS)-5-((2-methylpyridin-3-yl)oxy)hexahydrocyclopenta[c]pyrrol-2(1H)-yl)ethanone | 353.4 | 353.2 | 0.864 | M |
| 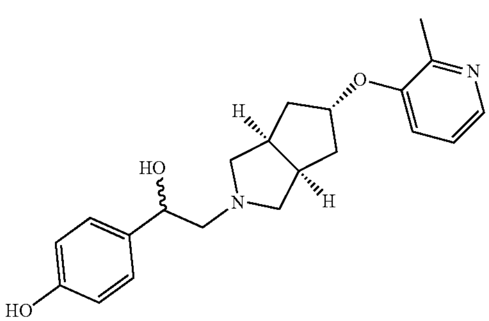 [SMILES: Cc1ncccc1O[C@H]1C[C@@H]2CN(CC(O)c3ccc(O)cc3)C[C@@H]2C1] | rac-4-(1-hydroxy-2-((3aR,5s,6aS)-5-((2-methylpyridin-3-yl)oxy)hexahydrocyclopenta[c]pyrrol-2(1H)-yl)ethyl)phenol | 355.44 | 355.2 | 1.091 | A |

TABLE 3-continued

The following compounds were prepared by the method described above.

| Structure | IUPAC Name | Calculated M + H | Found M + H | Retention time (min) | Method |
|---|---|---|---|---|---|
| 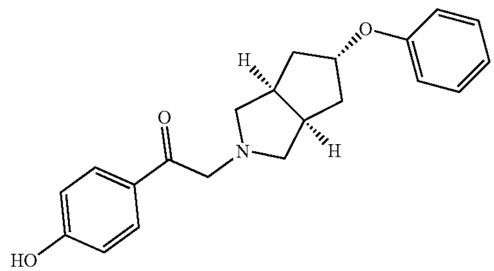 [SMILES: O=C(CN1C[C@H]2C[C@H](Oc3ccccc3)C[C@H]2C1)c1ccc(O)cc1] | 1-(4-hydroxyphenyl)-2-((3aR,5s,6aS)-5-phenoxyhexahydro-cyclopenta[c]pyrrol-2(1H)-yl)ethanone | 338.41 | 338.2 | 1.964 | A |
| 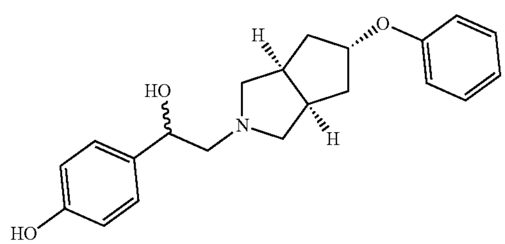 [SMILES: Oc1ccc(C(O)CN2C[C@H]3C[C@H](Oc4ccccc4)C[C@H]3C2)cc1] | rac-A-(1-hydroxy-2-((3aR,5s,6aS)-5-phenoxyhexahydro-cyclopenta[c]pyrrol-2(1H)-yl)ethyl)phenol | 340.42 | 340.2 | 1.822 | A |
| 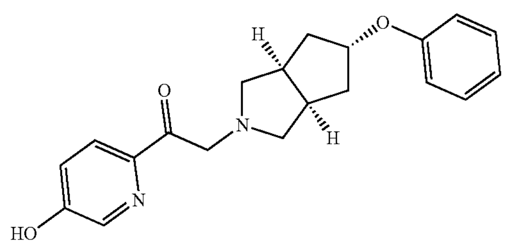 [SMILES: O=C(CN1C[C@H]2C[C@H](Oc3ccccc3)C[C@H]2C1)c1ccc(O)cn1] | 1-(5-hydroxypyridin-2-yl)-2-((3aR,5s,6aS)-5-phenoxyhexahydro-cyclopenta[c]pyrrol-2(1H)-yl)ethanone | 339.40 | 339.2 | 6.337 | N |
| 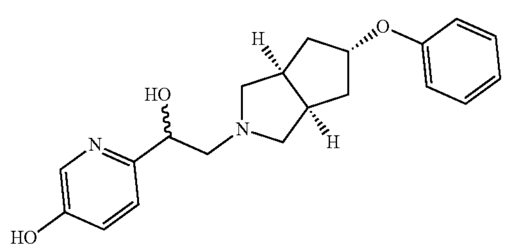 [SMILES: Oc1ccc(C(O)CN2C[C@H]3C[C@H](Oc4ccccc4)C[C@H]3C2)nc1] | rac-4-(1-hydroxy-2-((3aR,5s,6aS)-5-phenoxyhexahydro-cyclopenta[c]pyrrol-2(1H)-yl)ethyl)phenol | 341.42 | 341.2 | 1.936 | A |
| 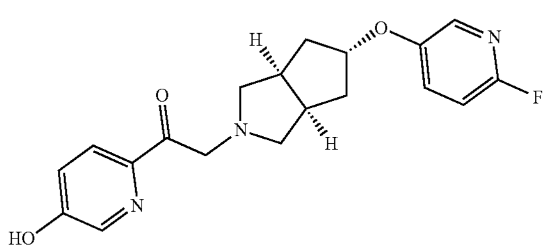 [SMILES: O=C(CN1C[C@H]2C[C@H](Oc3ccc(F)nc3)C[C@H]2C1)c1ccc(O)cn1] | 2-((3aR,5s,6aS)-5-((6-fluoropyridin-3-yl)oxy)hexahydro-cyclopenta[c]pyrrol-2(1H)-yl)-1-(5-hydroxypyridin-2-yl)ethanone | 358.38 | 358.2 | 1.744 | A |
| 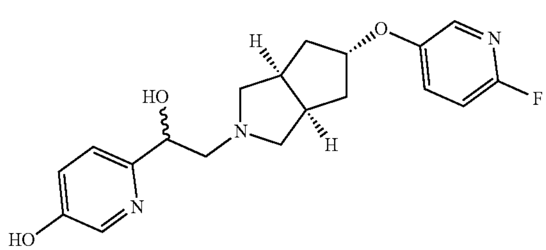 [SMILES: Oc1ccc(C(O)CN2C[C@H]3C[C@H](Oc4ccc(F)nc4)C[C@H]3C2)nc1] | rac-6-(2-((3aR,5s,6aS)-5-((6-fluoropyridin-3-yl)oxy)hexahydro-cyclopenta[c]pyrrol-2(1H)-yl)-1-hydroxyethyl)pyridin-3-ol | 360.39 | 360.2 | 1.487 | A |

TABLE 3-continued

The following compounds were prepared by the method described above.

| Structure | IUPAC Name | Calculated M + H | Found M + H | Retention time (min) | Method |
|---|---|---|---|---|---|
| | 1-(3-fluoro-4-hydroxyphenyl)-2-((3aR,5s,6aS)-5-(pyridin-3-yloxy)hexahydrocyclopenta[c]pyrrol-2(1H)-yl)ethanone | 357.39 | 357.2 | 2.284 | A |
| | rac-4-(2-((3aR,5s,6aS)-5-((6-fluoropyridin-3-yl)oxy)hexahydrocyclopenta[c]pyrrol-2(1H)-yl)-1-hydroxyethyl)phenol | 359.41 | 359.2 | 2.095 | A |
| | 1-(5-hydroxypyridin-2-yl)-2-((3aR,5s,6aS)-5-(3-methoxyphenoxy)hexahydrocyclopenta[c]pyrrol-2(1H)-yl)ethanone | 369.43 | 369.5 | 1.953 | A |
| | rac-6-(1-hydroxy-2-((3aR,5s,6aS)-5-(3-methoxyphenoxy)hexahydrocyclopenta[c]pyrrol-2(1H)-yl)ethyl)pyridin-3-ol | 371.44 | 371.5 | 1.699 | A |
| | 2-((3aR,5s,6aS)-5-(2-fluorophenoxy)hexahydrocyclopenta[c]pyrrol-2(1H)-yl)-1-(4-hydroxyphenyl)ethanone | 356.4 | 356.2 | 1.991 | A |

TABLE 3-continued

The following compounds were prepared by the method described above.

| Structure | IUPAC Name | Calculated M + H | Found M + H | Retention time (min) | Method |
|---|---|---|---|---|---|
| 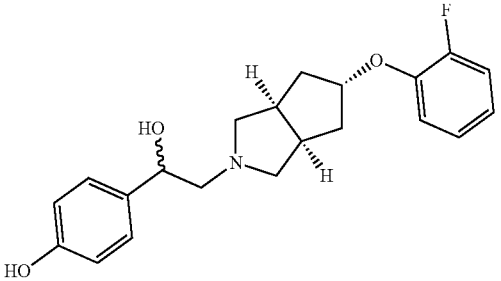 | rac-4-(2-((3aR,5s,6aS)-5-(2-fluorophenoxy)hexahydrocyclopenta[c]pyrrol-2(1H)-yl)-1-hydroxyethyl)phenol | 358.4 | 358.2 | 1.839 | A |
| 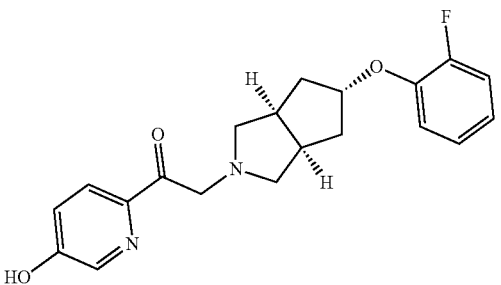 [SMILES: O=C(CN1C[C@H]2C[C@H](Oc3ccccc3F)C[C@H]2C1)c1ccc(O)cc1] | 2-((3aR,5s,6aS)-5-(2-fluorophenoxy)hexahydrocyclopenta[c]pyrrol-2(1H)-yl)-1-(5-hydroxypyridin-2-yl)ethanone | 357.3 | 357.2 | 2.022 | A |
| 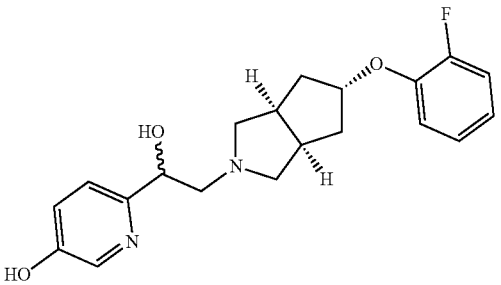 [SMILES: Oc1ccc(C(O)CN2C[C@H]3C[C@H](Oc4ccccc4F)C[C@H]3C2)nc1] | rac-6-(2-((3aR,5s,6aS)-5-(2-fluorophenoxy)hexahydrocyclopenta[c]pyrrol-2(1H)-yl)-1-hydroxyethyl)pyridin-3-ol | 359.4 | 359.2 | 1.755 | A |
| 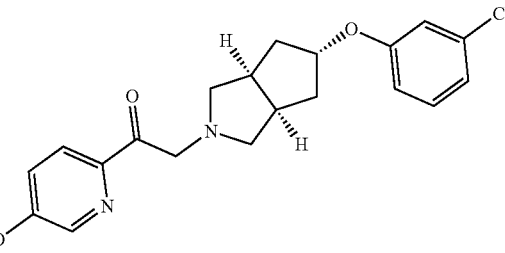 | 3-(((3aR,5s,6aS)-2-(2-(5-hydroxypyridin-2-yl)-2-oxoethyl)octahydrocyclopenta[c]pyrrol-5-yl)oxy)benzonitrile | 364.4 | 364.2 | 1.965 | A |
| 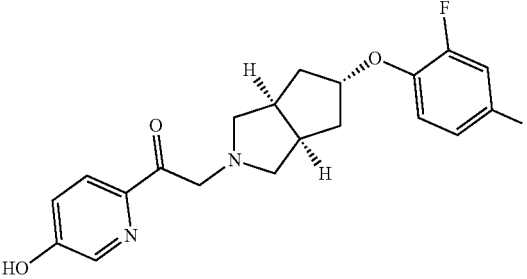 | 2-((3aR,5s,6aS)-5-(2,4-difluorophenoxy)hexahydrocyclopenta[c]pyrrol-2(1H)-yl)-1-(5-hydroxypyridin-2-yl)ethanone | 375.39 | 375.4 | 2.084 | A |

TABLE 3-continued

The following compounds were prepared by the method described above.

| Structure | IUPAC Name | Calculated M + H | Found M + H | Retention time (min) | Method |
|---|---|---|---|---|---|
| 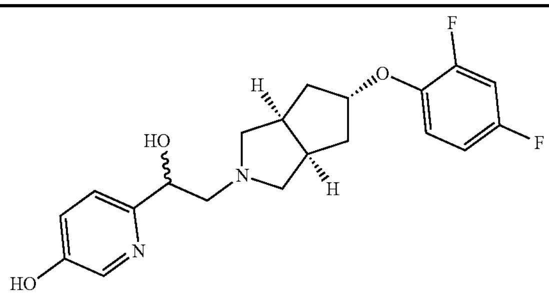 | rac-6-(2-((3aR,5r,6aS)-5-(2,4-difluorophenoxy)hexahydrocyclopenta[c]pyrrol-2(1H)-yl)-1-hydroxyethyl)pyridin-3-ol | 377.16 | 377.2 | 2.374 | J |
| 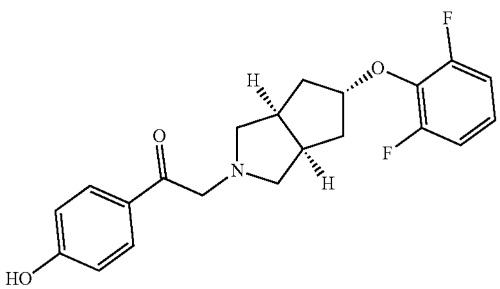 [SMILES: O=C(CN1C[C@H]2C[C@H](Oc3c(F)cccc3F)C[C@H]2C1)c1ccc(O)cc1] | 2-((3aR,5s,6aS)-5-(2,6-difluorophenoxy)hexahydrocyclopenta[c]pyrrol-2(1H)-yl)-1-(4-hydroxyphenyl)ethanone | 374.4 | 374.2 | 3.024 | K |
| 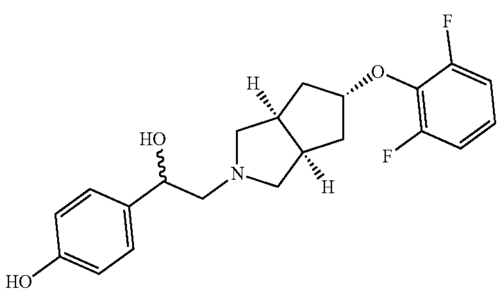 [SMILES: Oc1ccc(C(O)CN2C[C@H]3C[C@H](Oc4c(F)cccc4F)C[C@H]3C2)cc1] | rac-4-(2-((3aR,5s,6aS)-5-(2,6-difluorophenoxy)hexahydrocyclopenta[c]pyrrol-2(1H)-yl)-1-hydroxyethyl)phenol | 376.41 | 376.2 | 2.756 | A |
| 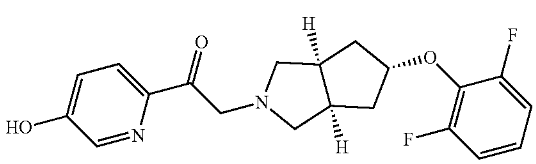 [SMILES: O=C(CN1C[C@H]2C[C@H](Oc3c(F)cccc3F)C[C@H]2C1)c1ccc(O)cn1] | 2-((3aR,5s,6aS)-5-(2,6-difluorophenoxy)hexahydrocyclopenta[c]pyrrol-2(1H)-yl)-1-(5-hydroxypyridin-2-yl)ethanone | 375.38 | 375.1 | 2.876 | K |
| 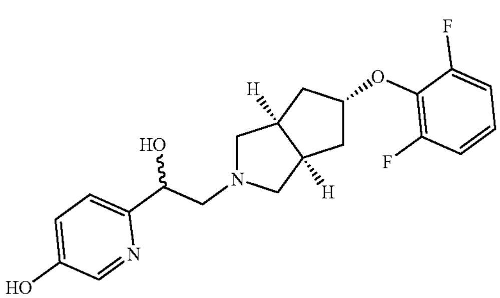 [SMILES: Oc1ccc(C(O)CN2C[C@H]3C[C@H](Oc4c(F)cccc4F)C[C@H]3C2)nc1] | rac-6-(2-((3aR,5s,6aS)-5-(2,6-difluorophenoxy)hexahydrocyclopenta[c]pyrrol-2(1H)-yl)-1-hydroxyethyl)pyridin-3-ol | 377.4 | 377.2 | 2.672 | K |
| 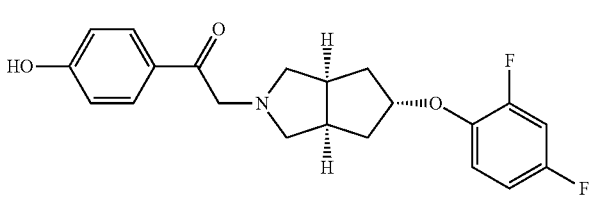 [SMILES: O=C(CN1C[C@H]2C[C@H](Oc3ccc(F)cc3F)C[C@H]2C1)c1ccc(O)cc1] | 2-((3aR,5s,6aS)-5-(2,4-difluorophenoxy)hexahydrocyclopenta[c]pyrrol-2(1H)-yl)-1-(4-hydroxyphenyl)ethanone | 374.39 | 374.1 | 1.514 | O |

TABLE 3-continued

The following compounds were prepared by the method described above.

| Structure | IUPAC Name | Calculated M + H | Found M + H | Retention time (min) | Method |
|---|---|---|---|---|---|
| 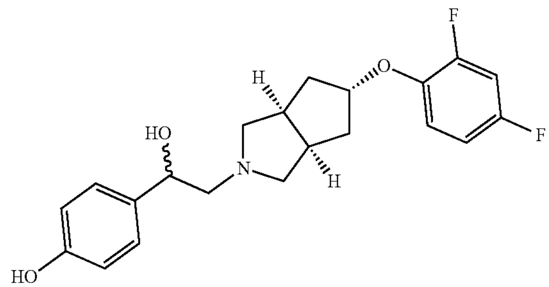 [SMILES: Oc1ccc(C(O)CN2C[C@H]3C[C@H](Oc4ccc(F)cc4F)C[C@H]3C2)cc1] | rac-4-(2-((3aR,5s,6aS)-5-(2,4-difluorophenoxy)hexahydrocyclopenta[c]pyrrol-2(1H)-yl)-1-hydroxyethyl)phenol | 376.42 | 376.1 | 2.957 | K |
| 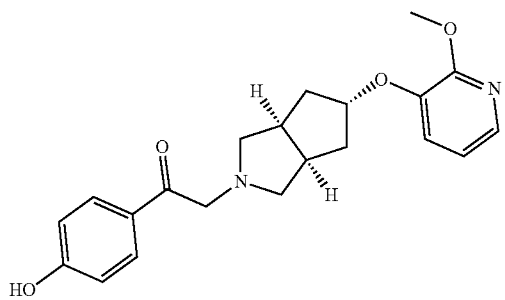 [SMILES: COc1ncccc1O[C@H]1C[C@@H]2CN(CC(=O)c3ccc(O)cc3)C[C@@H]2C1] | 1-(4-hydroxyphenyl)-2-((3aR,5s,6aS)-5-((2-methoxypyridin-3-yl)oxy)hexahydrocyclopenta[c]pyrrol-2(1H)-yl)ethanone | 369.43 | 369.2 | 1.856 | A |
| 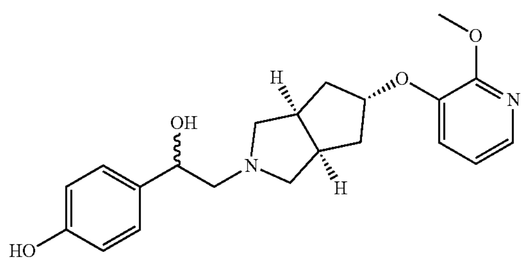 [SMILES: COc1ncccc1O[C@H]1C[C@@H]2CN(CC(O)c3ccc(O)cc3)C[C@@H]2C1] | rac-4-(1-hydroxy-2-((3aR,5s,6aS)-5-((2-methoxypyridin-3-yl)oxy)hexahydrocyclopenta[c]pyrrol-2(1H)-yl)ethyl)phenol | 371.44 | 371.2 | 1.652 | A |
| 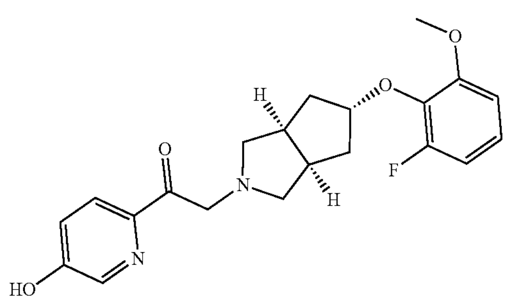 [SMILES: COc1cccc(F)c1O[C@H]1C[C@@H]2CN(CC(=O)c3ccc(O)cn3)C[C@@H]2C1] | 2-((3aR,5s,6aS)-5-(2-fluoro-6-methoxyphenoxy)hexahydrocyclopenta[c]pyrrol-2(1H)-yl)-1-(5-hydroxypyridin-2-yl)ethanone | 387.42 | 387.1 | 2.973 | J |
| 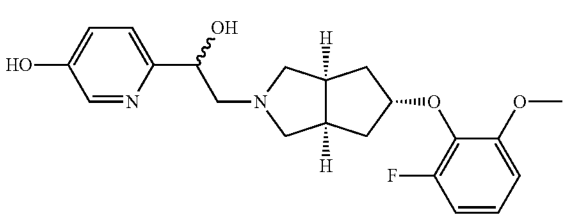 | rac-6-(2-((3aR,5s,6aS)-5-(2-fluoro-6-methoxyphenoxy)hexahydrocyclopenta[c]pyrrol-2(1H)-yl)-1-hydroxyethyl)pyridin-3-ol | 389.43 | 389.2 | 2.503 | J |

TABLE 3-continued

The following compounds were prepared by the method described above.

| Structure | IUPAC Name | Calculated M + H | Found M + H | Retention time (min) | Method |
|---|---|---|---|---|---|
| 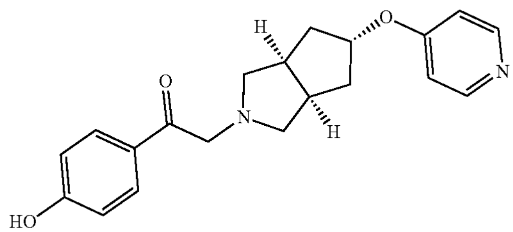 [SMILES: O=C(CN1C[C@H]2C[C@H](Oc3ccncc3)C[C@H]2C1)c1ccc(O)cc1] | 1-(4-hydroxyphenyl)-2-((3aR,5s,6aS)-5-(pyridin-4-yloxy)hexahydrocyclopenta[c]pyrrol-2(1H)-yl)ethanone | 339.0 | 339.2 | 3.141 | C |
| 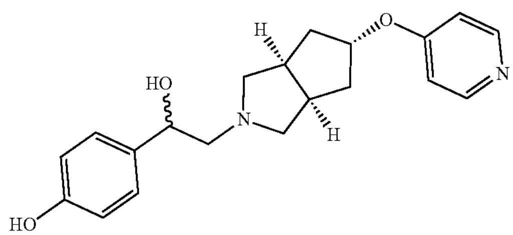 [SMILES: Oc1ccc(C(O)CN2C[C@H]3C[C@H](Oc4ccncc4)C[C@H]3C2)cc1] | rac-4-(1-hydroxy-2-((3aR,5s,6aS)-5-(pyridin-4-yloxy)hexahydrocyclopenta[c]pyrrol-2(1H)-yl)ethyl)phenol | 341.42 | 341.2 | 3.532 | L |
| 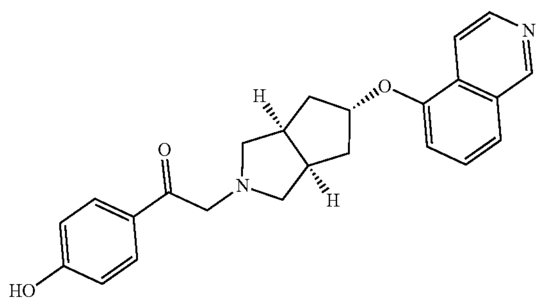 [SMILES: O=C(CN1C[C@H]2C[C@H](Oc3cccc4cnccc34)C[C@H]2C1)c1ccc(O)cc1] | 1-(4-hydroxyphenyl)-2-((3aR,5s,6aS)-5-(isoquinolin-5-yloxy)hexahydrocyclopenta[c]pyrrol-2(1H)-yl)ethanone | 389.46 | 389.2 | 1.462 | A |
| 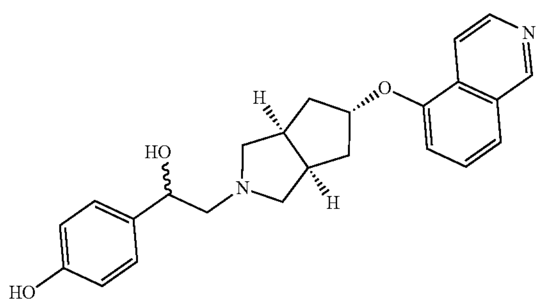 [SMILES: Oc1ccc(C(O)CN2C[C@H]3C[C@H](Oc4cccc5cnccc45)C[C@H]3C2)cc1] | rac-4-(1-hydroxy-2-((3aR,5s,6aS)-5-(isoquinolin-5-yloxy)hexahydrocyclopenta[c]pyrrol-2(1H)-yl)ethyl)phenol | 391.47 | 391.2 | 1.326 | A |
| 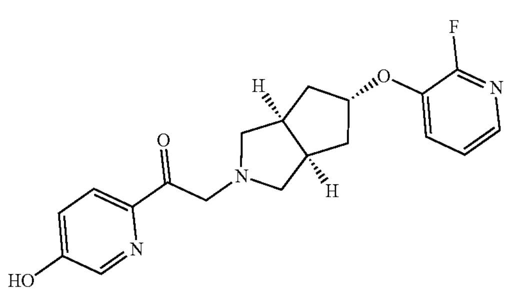 [SMILES: O=C(CN1C[C@H]2C[C@H](Oc3cccnc3F)C[C@H]2C1)c1ccc(O)cn1] | 2-((3aR,5s,6aS)-5-((2-fluoropyridin-3-yl)oxy)hexahydrocyclopenta[c]pyrrol-2(1H)-yl)-1-(5-hydroxypyridin-2-yl)ethanone | 358.38 | 358.2 | 1.853 | A |

TABLE 3-continued

The following compounds were prepared by the method described above.

| Structure | IUPAC Name | Calculated M + H | Found M + H | Retention time (min) | Method |
|---|---|---|---|---|---|
| 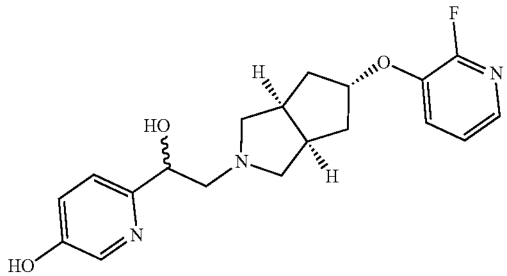 [SMILES: Oc1ccc(C(O)CN2C[C@H]3C[C@H](Oc4cccnc4F)C[C@H]3C2)nc1] | rac-6-(2-((3aR,5s,6aS)-5-((2-fluoropyridin-3-yl)oxy)hexahydrocyclopenta[c]pyrrol-2(1H)-yl)-1-hydroxyethyl)pyridin-3-ol | 360.39 | 360.2 | 1.386 | A |
| 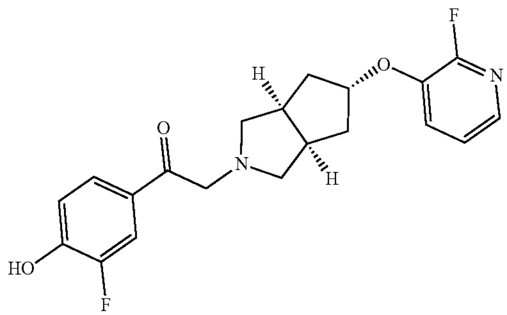 [SMILES: O=C(CN1C[C@H]2C[C@H](Oc3cccnc3F)C[C@H]2C1)c1ccc(O)c(F)c1] | 1-(3-fluoro-4-hydroxyphenyl)-2-((3aR,5s,6aS)-5-((2-fluoropyridin-3-yl)oxy)hexahydrocyclopenta[c]pyrrol-2(1H)-yl)ethanone | 375.38 | 375.1 | 1.72 | A |
| 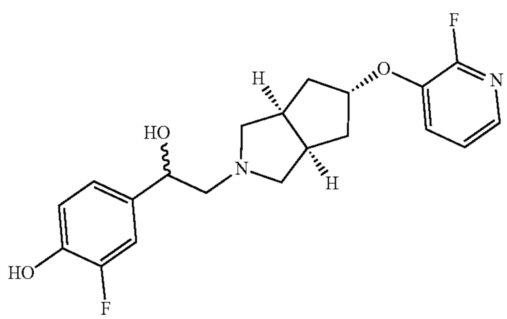 [SMILES: Oc1ccc(C(O)CN2C[C@H]3C[C@H](Oc4cccnc4F)C[C@H]3C2)cc1F] | rac-2-fluoro-4-(2-((3aR,5s,6aS)-5-((2-fluoropyridin-3-yl)oxy)hexahydrocyclopenta[c]pyrrol-2(1H)-yl)-1-hydroxyethyl)phenol | 377.4 | 377.2 | 1.67 | A |
| 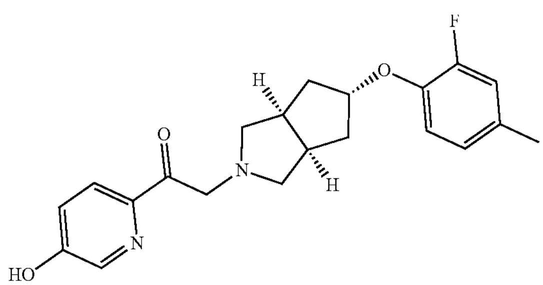 [SMILES: Cc1ccc(O[C@H]2C[C@@H]3CN(CC(=O)c4ccc(O)cn4)C[C@@H]3C2)c(F)c1] | 2-((3aR,5s,6aS)-5-(2-fluoro-4-methylphenoxy)hexahydrocyclopenta[c]pyrrol-2(1H)-yl)-1-(5-hydroxypyridin-2-yl)ethanone | 371.17 | 371.2 | 3.109 | A |
| 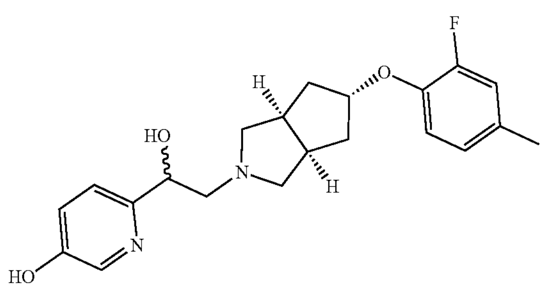 [SMILES: Cc1ccc(O[C@H]2C[C@@H]3CN(CC(O)c4ccc(O)cn4)C[C@@H]3C2)c(F)c1] | rac-6-(2-((3aR,5s,6aS)-5-(2-fluoro-4-methylphenoxy)hexahydrocyclopenta[c]pyrrol-2(1H)-yl)-1-hydroxyethyl)pyridin-3-ol | 373.43 | 373.2 | 2.628 | J |

TABLE 3-continued

The following compounds were prepared by the method described above.

| Structure | IUPAC Name | Calculated M + H | Found M + H | Retention time (min) | Method |
|---|---|---|---|---|---|
| 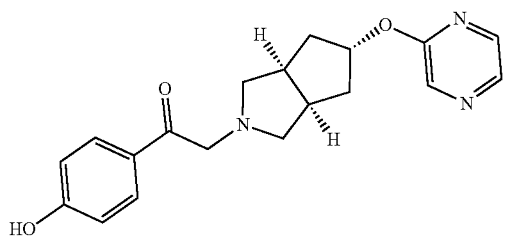 [SMILES: O=C(CN1C[C@H]2C[C@H](Oc3cnccn3)C[C@H]2C1)c1ccc(O)cc1] | 1-(4-hydroxyphenyl)-2-((3aR,5s,6aS)-5-(pyrazin-2-yloxy)hexahydrocyclopenta[c]pyrrol-2(1H)-yl)ethanone | 340.38 | 340.2 | 2.517 | J |
| 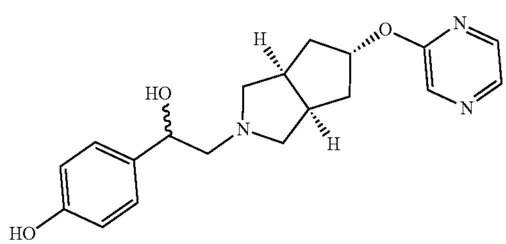 [SMILES: Oc1ccc(C(O)CN2C[C@H]3C[C@H](Oc4cnccn4)C[C@H]3C2)cc1] | rac-4-(1-hydroxy-2-((3aR,5s,6aS)-5-(pyrazin-2-yloxy)hexahydrocyclopenta[c]pyrrol-2(1H)-yl)ethyl)phenol | 342.40 | 342.3 | 6.803 | C |
| 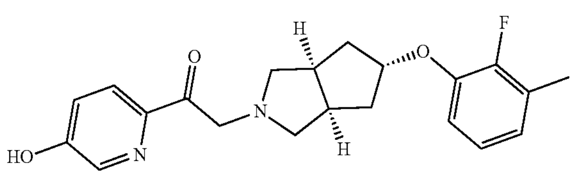 [SMILES: Cc1cccc(O[C@H]2C[C@@H]3CN(CC(=O)c4ccc(O)cn4)C[C@@H]3C2)c1F] | 2-((3aR,5s,6aS)-5-(2-fluoro-3-methylphenoxy)hexahydrocyclopenta[c]pyrrol-2(1H)-yl)-1-(5-hydroxypyridin-2-yl)ethanone | 371.42 | 371.2 | 3.109 | K |
| 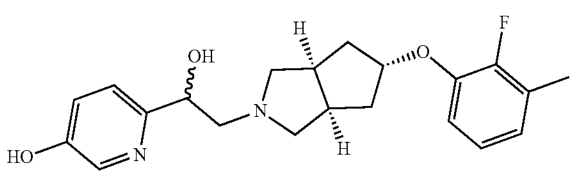 [SMILES: Cc1cccc(O[C@H]2C[C@@H]3CN(CC(O)c4ccc(O)cn4)C[C@@H]3C2)c1F] | rac-6-(2-((3aR,5s,6aS)-5-(2-fluoro-3-methylphenoxy)hexahydrocyclopenta[c]pyrrol-2(1H)-yl)-1-hydroxyethyl)pyridin-3-ol | 373.43 | 373.5 | 2.616 | J |
| 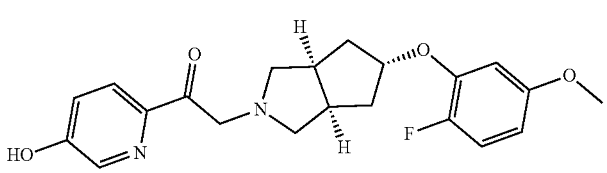 [SMILES: COc1ccc(F)c(O[C@H]2C[C@@H]3CN(CC(=O)c4ccc(O)cn4)C[C@@H]3C2)c1] | 2-((3aR,5s,6aS)-5-(2-fluoro-5-methoxyphenoxy)hexahydrocyclopenta[c]pyrrol-2(1H)-yl)-1-(5-hydroxypyridin-2-yl)ethanone | 387.42 | 387.2 | 3.011 | J |
| 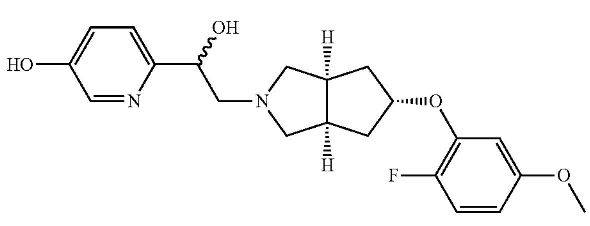 | rac-6-(2-((3aR,5s,6aS)-5-(2-fluoro-5-methoxyphenoxy)hexahydrocyclopenta[c]pyrrol-2(1H)-yl)-1-hydroxyethyl)pyridin-3-ol | 389.43 | 389.2 | 2.535 | J |
| 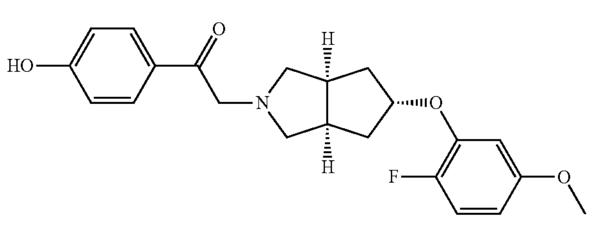 [SMILES: COc1ccc(F)c(O[C@H]2C[C@@H]3CN(CC(=O)c4ccc(O)cc4)C[C@@H]3C2)c1] | 2-((3aR,5s,6aS)-5-(2-fluoro-5-methoxyphenoxy)hexahydrocyclopenta[c]pyrrol-2(1H)-yl)-1-(4-hydroxyphenyl)ethanone | 386.43 | 386.2 | 2.6 | J |

TABLE 3-continued

The following compounds were prepared by the method described above.

| Structure | IUPAC Name | Calculated M + H | Found M + H | Retention time (min) | Method |
|---|---|---|---|---|---|
| 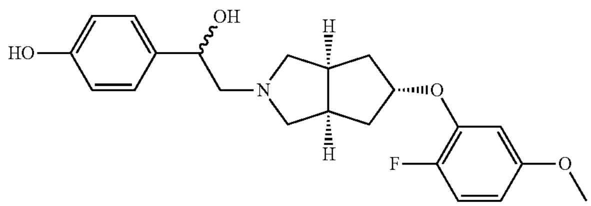 | rac-4-(2-((3aR,5s,6aS)-5-(2-fluoro-5-methoxy-phenoxy)hexahydro-cyclopenta[c]pyrrol-2(1H)-yl)-1-hydroxyethyl)phenol | 388.44 | 388.3 | 2.752 | J |
| 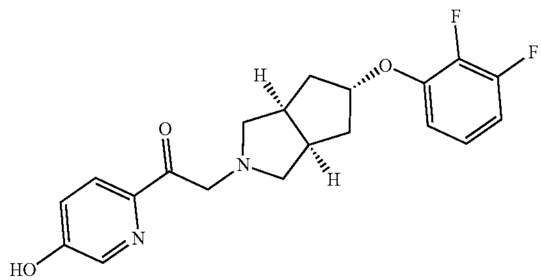 [SMILES: O=C(CN1C[C@H]2C[C@H](Oc3cccc(F)c3F)C[C@H]2C1)c1ccc(O)cn1] | 2-((3aR,5r,6aS)-5-(2,3-difluorophenoxy)hexahy-drocyclopenta[c]pyrrol-2(1H)-yl)-1-(5-hydroxypyridin-2-yl)ethanone | 375.14 | 375.4 | 1.477 | O |
| 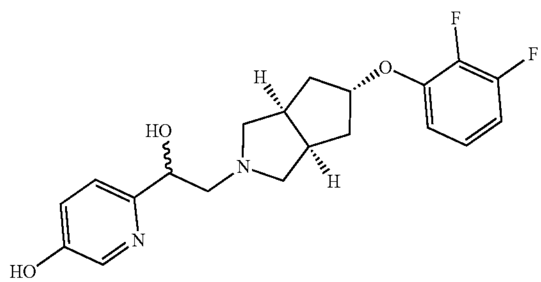 [SMILES: Oc1ccc(C(O)CN2C[C@H]3C[C@H](Oc4cccc(F)c4F)C[C@H]3C2)nc1] | rac-6-(2-((3aR,5s,6aS)-5-(2,3-difluorophenoxy)hexahy-drocyclopenta[c]pyrrol-2(1H)-yl)-1-hydroxyethyl)pyridin-3-ol | 377.16 | 377.2 | 2.585 | A |
| 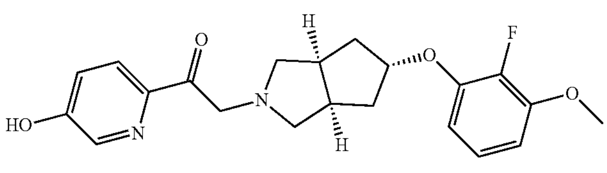 [SMILES: COc1cccc(O[C@H]2C[C@@H]3CN(CC(=O)c4ccc(O)cn4)C[C@@H]3C2)c1F] | 2-((3aR,5s,6aS)-5-(2-fluoro-3-methoxy-phenoxy)hexahydro-cyclopenta[c]pyrrol-2(1H)-yl)-1-(5-hydroxypyridin-2-yl)ethanone | 387.42 | 387.2 | 2.54 | J |
| 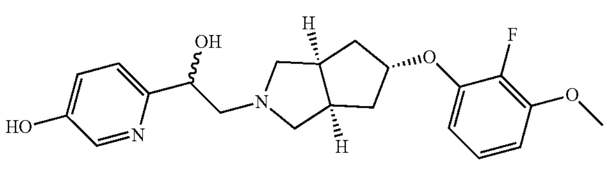 [SMILES: COc1cccc(O[C@H]2C[C@@H]3CN(CC(O)c4ccc(O)cn4)C[C@@H]3C2)c1F] | rac-6-(2-((3aR,5s,6aS)-5-(2-fluoro-3-methoxy-phenoxy)hexahydro-cyclopenta[c]pyrrol-2(1H)-yl)-1-hydroxyethyl)pyridin-3-ol | 389.43 | 389.2 | 2.493 | A |
| 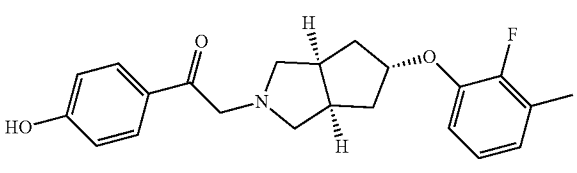 [SMILES: Cc1cccc(O[C@H]2C[C@@H]3CN(CC(=O)c4ccc(O)cc4)C[C@@H]3C2)c1F] | 2-((3aR,5s,6aS)-5-(2-fluoro-3-methyl-phenoxy)hexahydro-cyclopenta[c]pyrrol-2(1H)-yl)-1-(4-hydroxyphenyl)ethanone | 370.43 | 370.2 | 2.9 | K |
| 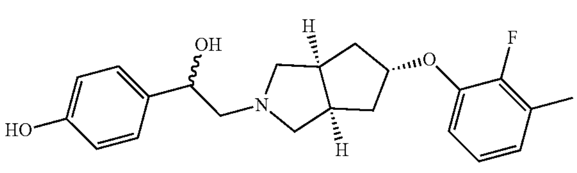 | rac-4-(2-((3aR,5s,6aS)-5-(2-fluoro-3-methyl-phenoxy)hexahydro-cyclopenta[c]pyrrol-2(1H)-yl)-1-hydroxyethyl)phenol | 372.45 | 372.2 | 2.851 | A |

TABLE 3-continued

The following compounds were prepared by the method described above.

| Structure | IUPAC Name | Calculated M + H | Found M + H | Retention time (min) | Method |
|---|---|---|---|---|---|
| | 2-((3aR,5s,6aS)-5-(2-fluoro-3-methoxyphenoxy)hexahydrocyclopenta[c]pyrrol-2(1H)-yl)-1-(4-hydroxyphenyl)ethanone | 386.43 | 386.2 | 2.795 | A |
| | rac-4-(2-((3aR,5s,6aS)-5-(2-fluoro-3-methoxyphenoxy)hexahydrocyclopenta[c]pyrrol-2(1H)-yl)-1-hydroxyethyl)phenol | 388.44 | 388.5 | 2.717 | A |
| | 2-((3aR,5s,6aS)-5-((2-fluoro-6-methylpyridin-3-yl)oxy)hexahydrocyclopenta[c]pyrrol-2(1H)-yl)-1-(5-hydroxypyridin-2-yl)ethanone | 372.41 | 372.2 | 2.63 | A |
| | rac-6-(2-((3aR,5s,6aS)-5-((2-fluoro-6-methylpyridin-3-yl)oxy)hexahydrocyclopenta[c]pyrrol-2(1H)-yl)-1-hydroxyethyl)pyridin-3-ol | 374.42 | 374.2 | 2.36 | A |
| | 2-((3aR,5s,6aS)-5-(2-fluoro-6-methoxyphenoxy)hexahydrocyclopenta[c]pyrrol-2(1H)-yl)-1-(4-hydroxyphenyl)ethanone | 386.43 | 386.2 | 2.807 | K |
| | rac-4-(2-((3aR,5s,6aS)-5-(2-fluoro-6-methoxyphenoxy)hexahydrocyclopenta[c]pyrrol-2(1H)-yl)-1-hydroxyethyl)phenol | 388.44 | 388.3 | 2.727 | A |
| | 2-((3aR,5s,6aS)-5-(2-chlorophenoxy)hexahydrocyclopenta[c]pyrrol-2(1H)-yl)-1-(5-hydroxypyridin-2-yl)ethanone | 373.85 | 373.1 | 2.891 | K |

TABLE 3-continued

The following compounds were prepared by the method described above.

| Structure | IUPAC Name | Calculated M + H | Found M + H | Retention time (min) | Method |
|---|---|---|---|---|---|
| 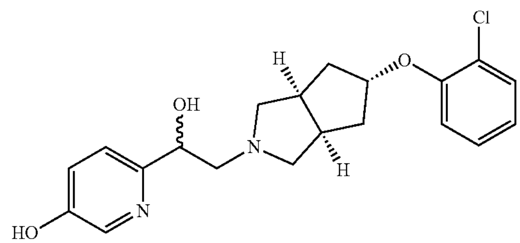 [SMILES: Oc1ccc(C(O)CN2C[C@H]3C[C@H](Oc4ccccc4Cl)C[C@H]3C2)nc1] | rac-6-(2-((3aR,5s,6aS)-5-(2-chlorophenoxy)hexahydrocyclopenta[c]pyrrol-2(1H)-yl)-1-hydroxyethyl)pyridin-3-ol | 375.86 | 375.1 | 2.613 | A |
| 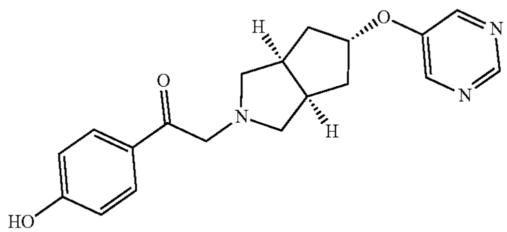 [SMILES: O=C(CN1C[C@H]2C[C@H](Oc3cncnc3)C[C@H]2C1)c1ccc(O)cc1] | 1-(4-hydroxyphenyl)-2-((3aR,5s,6aS)-5-(pyrimidin-5-yloxy)hexahydrocyclopenta[c]pyrrol-2(1H)-yl)ethanone | 340.16 | 340.2 | 2.262 | A |
| 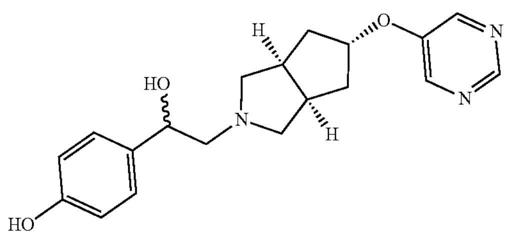 [SMILES: Oc1ccc(C(O)CN2C[C@H]3C[C@H](Oc4cncnc4)C[C@H]3C2)cc1] | rac-4-(1-hydroxy-2-((3aR,5s,6aS)-5-(pyrimidin-5-yloxy)hexahydrocyclopenta[c]pyrrol-2(1H)-yl)ethyl)phenol | 342.40 | 342.3 | 2.05 | P |
| 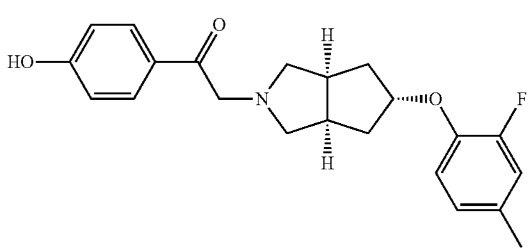 [SMILES: Cc1ccc(O[C@H]2C[C@@H]3CN(CC(=O)c4ccc(O)cc4)C[C@@H]3C2)c(F)c1] | 2-((3aR,5s,6aS)-5-(2-fluoro-4-methylphenoxy)hexahydrocyclopenta[c]pyrrol-2(1H)-yl)-1-(4-hydroxyphenyl)ethanone | 370.43 | 370.2 | 2.913 | A |
| 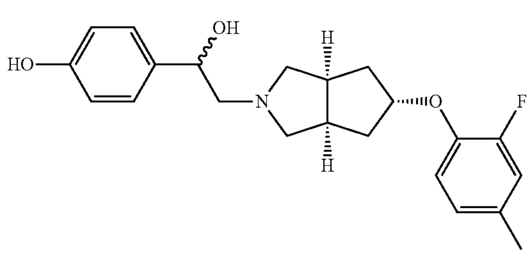 | rac-4-(2-((3aR,5s,6aS)-5-(2-fluoro-4-methylphenoxy)hexahydrocyclopenta[c]pyrrol-2(1H)-yl)-1-hydroxyethyl)phenol | 372.45 | 372.2 | 2.852 | Q |

TABLE 3-continued

The following compounds were prepared by the method described above.

| Structure | IUPAC Name | Calculated M + H | Found M + H | Retention time (min) | Method |
|---|---|---|---|---|---|
| 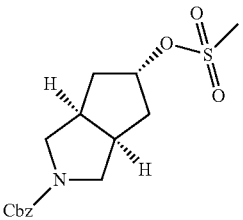 [SMILES: CS(=O)(=O)O[C@H]1C[C@@H]2CN(C(=O)OCc3ccccc3)C[C@@H]2C1] | 6-((S)-2-((3aR,5R,6aS)-5-((2-fluoropyridin-3-yl)oxy)hexahydrocyclopenta[c]pyrrol-2(1H)-yl)-1-hydroxyethyl)pyridin-3-ol | 360.16 | 360.2 | 1.276 | A |

The minor isomer 2A can also be used to create compounds with the opposite relative configuration as shown in the following examples

Example 12—Preparation of (3aR,5r,6aS)-benzyl 5-(4-fluorophenoxy)hexahydrocyclopenta[c]pyrrole-2(1H)-carboxylate Scheme 12:

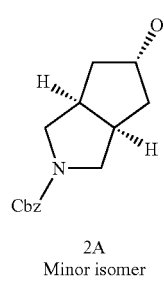

2A
Minor isomer

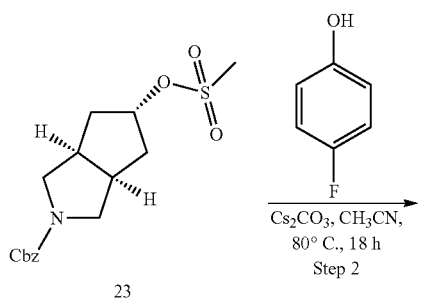

Step 1

Preparation of (3aR,5s,6aS)-benzyl 5-((methylsulfonyl)oxy)hexahydrocyclopenta[c]pyrrole-2(1H)-carboxylate

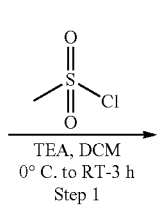

To a solution of (3aR,5s,6aS)-benzyl 5-hydroxyhexahydrocyclopenta[c]pyrrole-2(1H)-carboxylate (1.4 g, 5.364 mmol) in dichloromethane (30 mL) was added triethylamine (2.24 mL, 16.091 mmol) at room temperature. The reaction mixture was cooled to 0° C. and methanesulfonyl chloride (1.1 mL, 10.727 mmol) was slowly added. The resultant mixture was allowed to warm to room temperature and stirred for 3 h. The solution was diluted with ice-water (25 mL) and extracted with dichloromethane (100 mL×3). The combined extracts were washed with sodium bicarbonate solution (100 mL), dried over anhydrous sodium sulfate, filtered and concentrated to afford the title compound (3aR,5s,6aS)-benzyl 5-((methylsulfonyl)oxy)hexahydrocyclopenta[c]pyrrole-2(1H)-carboxylate (1.8 g, 98.9%) as a brownish liquid. Calculated M+H: 340.4; Found M+H: 340.1.

Step 2

Preparation of (3aR,5r,6aS)-benzyl 5-(4-fluorophenoxy)hexahydrocyclopenta[c]pyrrole-2(1H)-carboxylate

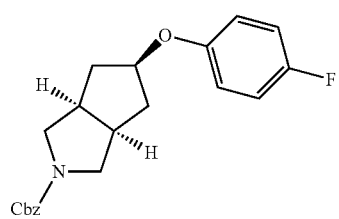

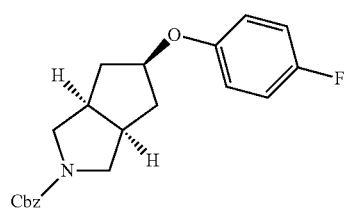 [SMILES: O=C(OCc1ccccc1)N1C[C@H]2C[C@@H](Oc3ccc(F)cc3)C[C@H]2C1]

To a solution of (3aR,5s,6aS)-benzyl 5-((methylsulfonyl)oxy)hexahydrocyclopenta[c]pyrrole-2(1H)-carboxylate (1.5 g, 4.424 mmol) in acetonitrile (20 mL) were added 4-fluorophenol (1.0 g, 8.849 mmol) and cesium carbonate (2.87 g, 8.849 mmol) at room temperature. The reaction mixture was heated at 80° C. for 18 h. After completion of the reaction (monitored by TLC), the reaction mixture was filtered and the filtrate was concentrated. The residue was purified by combiflash purifier using 10% ethyl acetate in hexane to afford the title compound (3aR,5r,6aS)-benzyl 5-(4-fluorophenoxy)hexahydrocyclopenta[c]pyrrole-2(1H)-carboxylate (0.7 g, 44.58% yield) as a colorless liquid. Calculated M+H: 356.4; Found M+H: 356.3.

TABLE 4

The following compounds were prepared by the method of Example 12.

| Structure | IUPAC Name | Calculated M + H | Found M + H | Retention time (min) | Method |
|---|---|---|---|---|---|
| 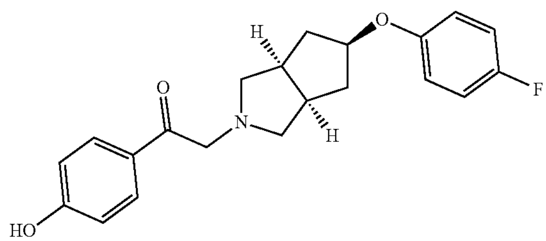 [SMILES: O=C(CN1C[C@H]2C[C@@H](Oc3ccc(F)cc3)C[C@H]2C1)c1ccc(O)cc1] | 2-((3aR,5r,6aS)-5-(4-fluorophenoxy)hexahydrocyclopenta[c]pyrrol-2(1H)-yl)-1-(4-hydroxyphenyl)ethanone | 356.4 | 356.2 | 2.061 | A |
| | rac-2-fluoro-4-(2-((3aR,5r,6aS)-5-(4-fluorophenoxy)hexahydrocyclopenta[c]pyrrol-2(1H)-yl)-1-hydroxyethyl)phenol | 358.4 | 358.2 | 1.886 | A |
| 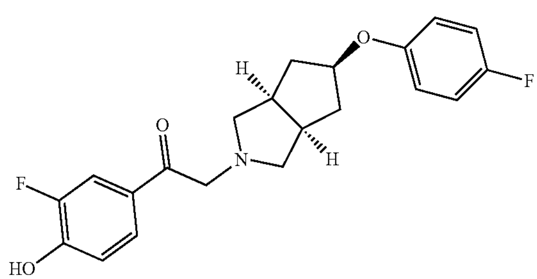 [SMILES: O=C(CN1C[C@H]2C[C@@H](Oc3ccc(F)cc3)C[C@H]2C1)c1ccc(O)c(F)c1] | 1-(3-fluoro-4-hydroxyphenyl)-2-((3aR,5r,6aS)-5-(4-fluorophenoxy)hexahydrocyclopenta[c]pyrrol-2(1H)-yl)ethanone | 374.39 | 374.5 | 2.055 | A |
| | rac-2-fluoro-4-(2-((3aR,5r,6aS)-5-(4-fluorophenoxy)hexahydrocyclopenta[c]pyrrol-2(1H)-yl)-1-hydroxyethyl)phenol | 376.41 | 376.3 | 8.537 | B |
| 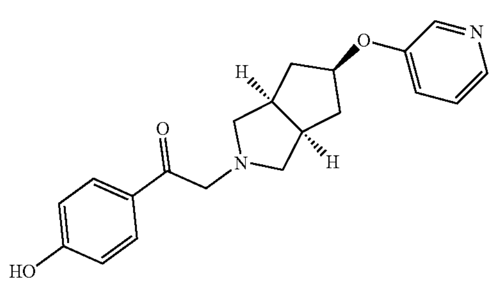 [SMILES: O=C(CN1C[C@H]2C[C@@H](Oc3cccnc3)C[C@H]2C1)c1ccc(O)cc1] | 1-(4-hydroxyphenyl)-2-((3aR,5s,6aS)-5-(pyridin-3-yloxy)hexahydrocyclopenta[c]pyrrol-2(1H)-yl)ethanone | 339.40 | 339.2 | 1.063 | A |

TABLE 4-continued

The following compounds were prepared by the method of Example 12.

| Structure | IUPAC Name | Calculated M + H | Found M + H | Retention time (min) | Method |
|---|---|---|---|---|---|
| 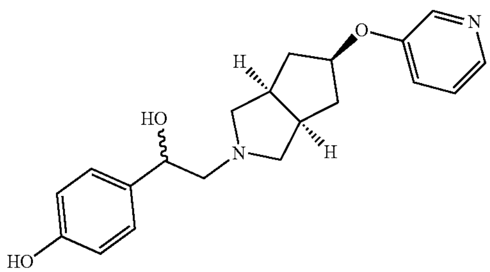 [SMILES: Oc1ccc(C(O)CN2C[C@H]3C[C@@H](Oc4cccnc4)C[C@H]3C2)cc1] | rac-4-(1-hydroxy-2-((3aR,5r,6aS)-5-(pyridin-3-yloxy)hexahydro-cyclopenta[c]pyrrol-2(1H)-yl)ethyl)phenol | 341.42 | 341.2 | 7.231 | C |
| | 2-((3aR,5r,6aS)-5-(3,4-difluoro-phenoxy)hexahydro-cyclopenta[c]pyrrol-2(1H)-yl)-1-(4-hydroxyphenyl)ethanone | 374.39 | 374.4 | 2.105 | A |
| 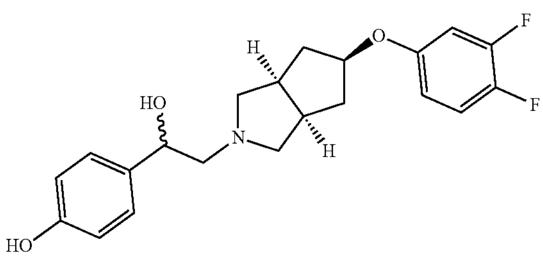 [SMILES: Oc1ccc(C(O)CN2C[C@H]3C[C@@H](Oc4ccc(F)c(F)c4)C[C@H]3C2)cc1] | rac-4-(2-((3aR,5r,6aS)-5-(3,4-difluoro-phenoxy)hexahydro-cyclopenta[c]pyrrol-2(1H)-yl)-1-hydroxyethyl)phenol | 376.4 | 376.2 | 1.348 | D |
| 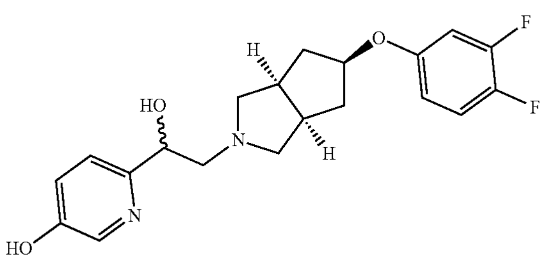 | rac-6-(2-((3aR,5r,6aS)-5-(3,4-difluoro-phenoxy)hexahydro-cyclopenta[c]pyrrol-2(1H)-yl)-1-hydroxyethyl)pyridin-3-ol | 377.39 | 377.4 | 1.863 | A |
| 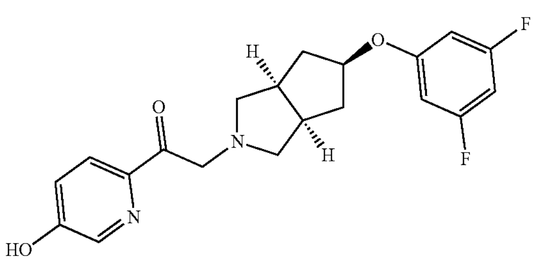 [SMILES: O=C(CN1C[C@H]2C[C@@H](Oc3cc(F)cc(F)c3)C[C@H]2C1)c1ccc(O)cn1] | 2-((3aR,5r,6aS)-5-(3,5-difluoro-phenoxy)hexahydro-cyclopenta[c]pyrrol-2(1H)-yl)-1-(5-hydroxypyridin-2-yl)ethanone | 375.38 | 375.4 | 1.988 | A |

TABLE 4-continued

The following compounds were prepared by the method of Example 12.

| Structure | IUPAC Name | Calculated M + H | Found M + H | Retention time (min) | Method |
|---|---|---|---|---|---|
| 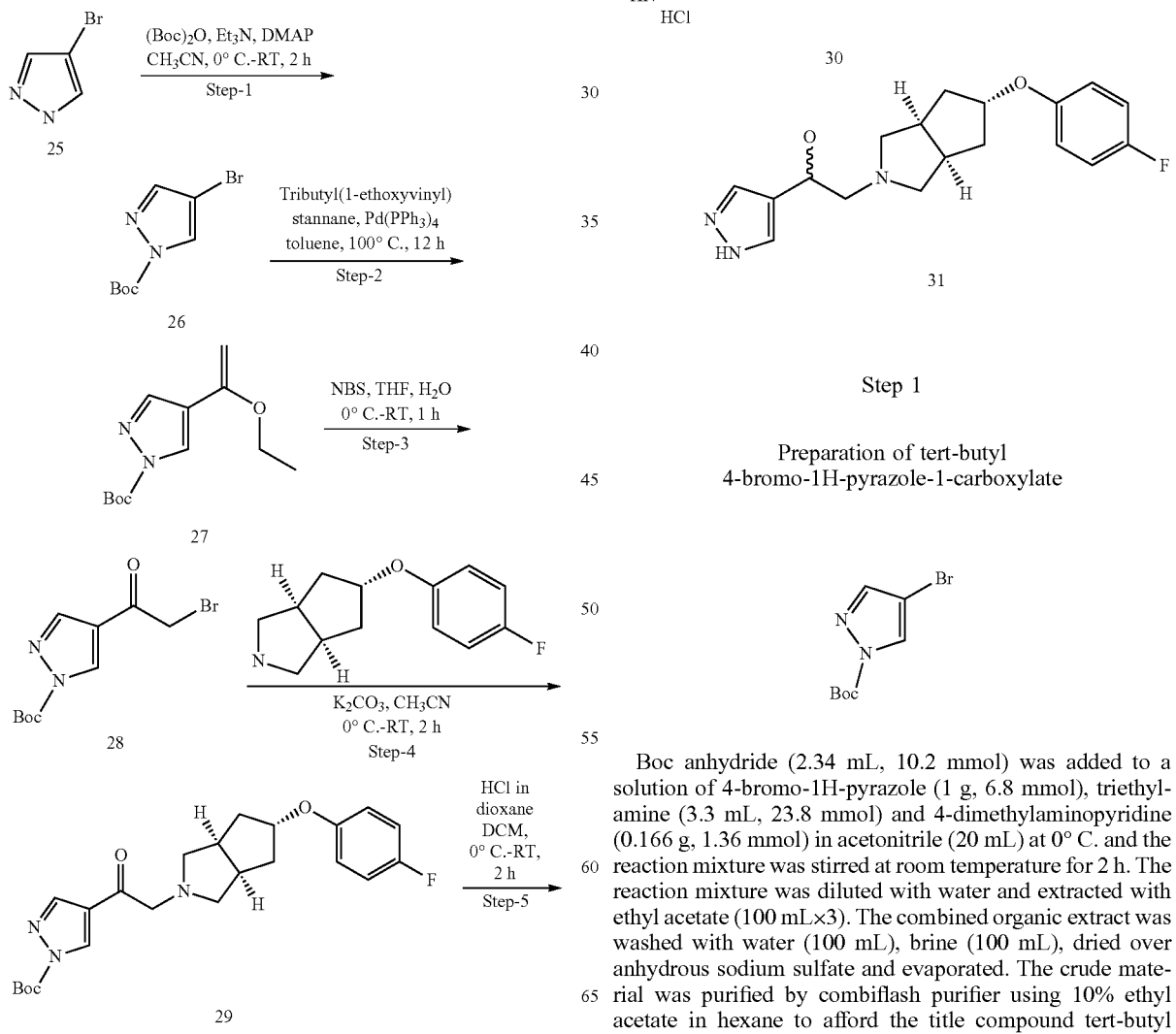 | rac-6-(2-((3aR,5r,6aS)-5-(3,5-difluoro-phenoxy)hexahydro-cyclopenta[c]pyrrol-2(1H)-yl)-1-hydroxyethyl)pyridin-3-ol | 377.4 | 377.4 | 1.845 | A |

Example 13—Preparation of rac-2-((3aR,5s,6aS)-5-(4-fluorophenoxy)hexahydrocyclopenta[c]pyrrol-2(1H)-yl)-1-(1H-pyrazol-4-yl)ethanol Scheme 13:

Step 1

Preparation of tert-butyl 4-bromo-1H-pyrazole-1-carboxylate

Boc anhydride (2.34 mL, 10.2 mmol) was added to a solution of 4-bromo-1H-pyrazole (1 g, 6.8 mmol), triethylamine (3.3 mL, 23.8 mmol) and 4-dimethylaminopyridine (0.166 g, 1.36 mmol) in acetonitrile (20 mL) at 0° C. and the reaction mixture was stirred at room temperature for 2 h. The reaction mixture was diluted with water and extracted with ethyl acetate (100 mL×3). The combined organic extract was washed with water (100 mL), brine (100 mL), dried over anhydrous sodium sulfate and evaporated. The crude material was purified by combiflash purifier using 10% ethyl acetate in hexane to afford the title compound tert-butyl 4-bromo-1H-pyrazole-1-carboxylate (1.65 g, 98% yield) as a colorless liquid. ¹H NMR (400 MHz, CDCl₃) δ 8.09 (s, 1H), 7.66 (s, 1H), 1.65 (s, 9H).

Step 2

Preparation of tert-butyl 4-(1-ethoxyvinyl)-1H-pyrazole-1-carboxylate

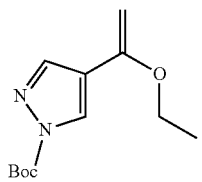 [SMILES: C=C(OCC)c1cnn(C(=O)OC(C)(C)C)c1]

Nitrogen was purged into a solution of tert-butyl 4-bromo-1H-pyrazole-1-carboxylate (0.75 g, 3.03 mmol) and tributyl(1-ethoxyvinyl)stannane (1.13 mL, 3.34 mmol) in toluene (10 mL) for 15 minutes. Tetrakis(triphenylphosphine)palladium(0) (0.175 g, 0.152 mmol) was added and the reaction mixture was heated at 110° C. for 12 h. The reaction mixture was filtered through celite and the filtrate was evaporated to afford the title compound tert-butyl 4-(1-ethoxyvinyl)-1H-pyrazole-1-carboxylate (0.7 g, crude) as a black liquid. The crude material was as such taken for next step without further purification.

Step 3

Preparation of tert-butyl 4-(2-bromoacetyl)-1H-pyrazole-1-carboxylate

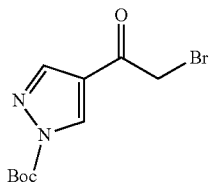

N-Bromosuccinimide (0.52 g, 2.94 mmol) was added to a solution of tert-butyl 4-(1-ethoxyvinyl)-1H-pyrazole-1-carboxylate (0.7 g, 2.94 mmol) in tetrahydrofuran (15 mL) and water (5 mL) at 0° C. and the reaction mixture was stirred at room temperature for 1 h. The reaction mixture was diluted with water and extracted with ethyl acetate (100 mL×2). The combined organic extract was washed with brine (50 mL), dried over anhydrous sodium sulfate and evaporated. The crude material was purified by combiflash purifier using 20% ethyl acetate in hexane to afford the title compound tert-butyl 4-(2-bromoacetyl)-1H-pyrazole-1-carboxylate as a colorless liquid (0.31 g, 35% yield). ¹H NMR (400 MHz, CDCl₃) δ 8.66 (s, 1H), 8.14 (s, 1H), 4.42 (s, 2H), 1.68 (s, 9H).

Step 4

Preparation of tert-butyl 4-(2-((3aR,5s,6aS)-5-(4-fluorophenoxy)hexahydrocyclopenta[c]pyrrol-2(1H)-yl)acetyl)-1H-pyrazole-1-carboxylate

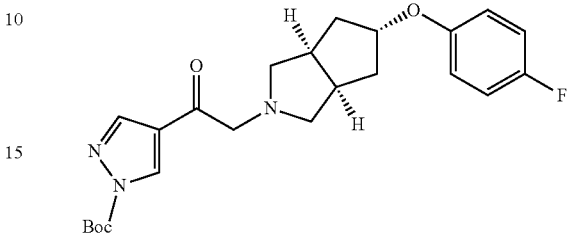

To a solution of (3aR,5s,6aS)-5-(4-fluorophenoxy)octahydrocyclopenta[c]pyrrole (0.24 g, 1.08 mmol) in acetonitrile (10 mL) was added potassium carbonate (0.45 g, 3.25 mmol) followed by tert-butyl 4-(2-bromoacetyl)-1H-pyrazole-1-carboxylate (0.31 g, 1.08 mmol). The resulting suspension was stirred at room temperature for 2 h. The reaction mixture was filtered and the filtrate was concentrated. The crude was purified by combiflash purifier using 3% methanol in dichloromethane to afford the title compound tert-butyl 4-(2-((3aR,5s,6aS)-5-(4-fluorophenoxy)hexahydrocyclopenta[c]pyrrol-2(1H)-yl)acetyl)-1H-pyrazole-1-carboxylate (0.2 g, 43% yield) as a gummy material. Calculated (M+H)-boc: 330.38; Found (M+H)-boc: 330.4.

Step 5

Preparation of 2-((3aR,5s,6aS)-5-(4-fluorophenoxy) hexahydrocyclopenta[c]pyrrol-2(1H)-yl)-1-(1H-pyrazol-4-yl)ethanone hydrochloride

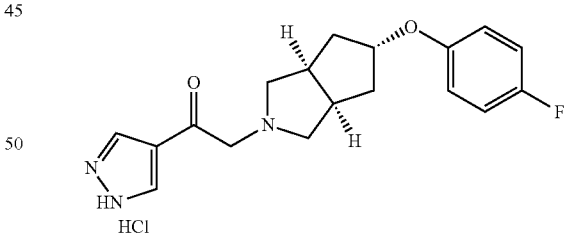

Hydrochloric acid in dioxane (1.5 mL) was added to a solution of tert-butyl 4-(2-((3aR,5s,6aS)-5-(4-fluorophenoxy)hexahydrocyclopenta[c]pyrrol-2(1H)-yl)acetyl)-1H-pyrazole-1-carboxylate (0.15 g, 0.35 mmol) in dichloromethane (10 mL) at 0° C. and the reaction mixture was stirred at room temperature for 2 h. The reaction mixture was evaporated to dryness. The crude material was triturated with diethyl ether in pentane (50 mL, 50%) and dried to afford the title compound 2-((3aR,5s,6aS)-5-(4-fluorophenoxy)hexahydrocyclopenta[c]pyrrol-2(1H)-yl)-1-(1H-pyrazol-4-yl)ethanone hydrochloride (0.09 g, 70% yield) as a white solid. Calculated M+H: 330.38; Found M+H: 330.4.

Step 6

Preparation of rac-2-((3aR,5s,6aS)-5-(4-fluorophe-noxy)hexahydrocyclopenta[c]pyrrol-2(1H)-yl)-1-(1H-pyrazol-4-yl)ethanol

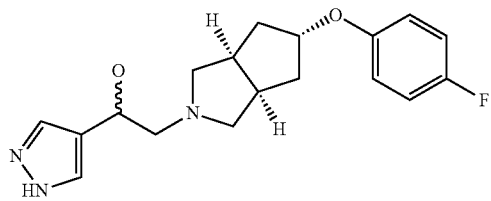 [SMILES: OC(CN1C[C@H]2C[C@H](Oc3ccc(F)cc3)C[C@H]2C1)c1cn[nH]c1]

To a solution of 2-((3aR,5s,6aS)-5-(4-fluorophenoxy)hexahydrocyclopenta[c]pyrrol-2(1H)-yl)-1-(1H-pyrazol-4-yl)ethanone hydrochloride (0.09 g, 0.246 mmol) in methanol (10 mL) was added sodium borohydride (0.09 g, 2.46 mmol)) at 0° C. The reaction mixture was stirred at room temperature for 2 h and concentrated. The residue was diluted with water (50 mL) and extracted with dichloromethane (100 mL×2). The combined organic layer was dried over anhydrous sodium sulfate, filtered and concentrated. The crude was washed with ether in pentane (50 mL, 50%) to afford the title compound 2-((3aR,5s,6aS)-5-(4-fluorophenoxy)hexahydrocyclopenta[c]pyrrol-2(1H)-yl)-1-(1H-pyrazol-4-yl)ethanol (0.065 g, 80.0% yield) as a white solid. Calculated M+H: 332.39; Found M+H: 332.4.

Example 14—Preparation of 1-(1-benzyl-1H-pyrazol-4-yl)-2-bromoethanone

Scheme 14:

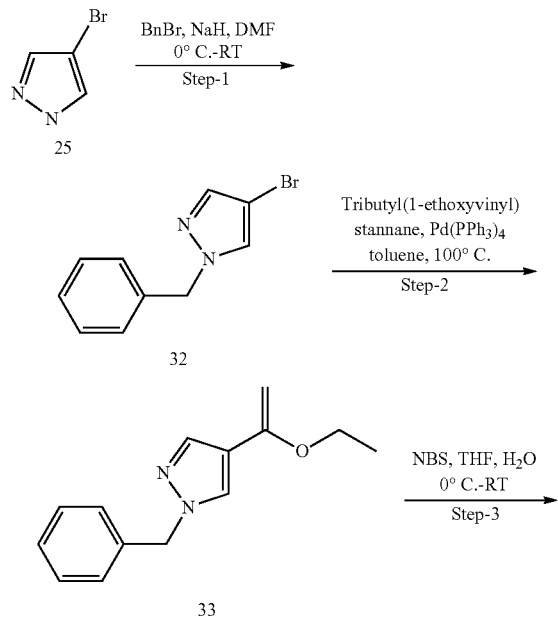

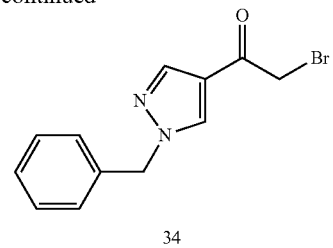

34

Step 1

Preparation of 1-benzyl-4-bromo-1H-pyrazole

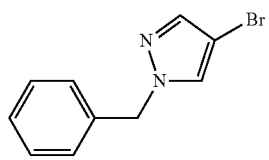 [SMILES: Brc1cnn(Cc2ccccc2)c1]

Sodium hydride (0.2 g, 60%, 5.1 mmol) was added to a solution of 4-bromo-1H-pyrazole (0.5 g, 3.4 mmol) in N,N-dimethylformamide (10 mL) at 0° C. and stirred at room temperature for 30 minutes. The reaction mixture was cooled to 0° C., added benzyl bromide (0.485 mL, 4.08 mmol) and stirred at room temperature for 2 h. The reaction mixture was diluted with ice-water (30 mL) and extracted with ethyl acetate (50 mL×2). The combined organic extract was washed with water (30 mL), brine (30 mL), dried over anhydrous sodium sulfate and evaporated. The crude material was purified by combiflash purifier using 7% ethyl acetate in hexane to afford the title compound 1-benzyl-4-bromo-1H-pyrazole (0.7 g, 87% yield) as a colorless liquid. Calculated M+H: 236.99; Found M+H: 236.9.

Step 2

Preparation of 1-benzyl-4-(1-ethoxyvinyl)-1H-pyrazole

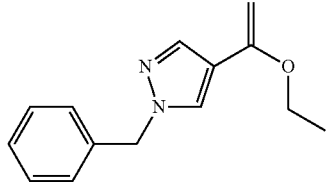 [SMILES: C=C(OCC)c1cnn(Cc2ccccc2)c1]

Nitrogen was purged into a solution of 1-benzyl-4-bromo-1H-pyrazole (0.55 g, 2.32 mmol) and tributyl(1-ethoxyvinyl)stannane (0.862 mL, 2.55 mmol) in toluene (15 mL) for 15 minutes. Then tetrakis(triphenylphosphine)palladium(0) (0.134 g, 0.116 mmol) was added and the reaction mixture was heated at 110° C. for 12 h. The reaction mixture was filtered through celite and the filtrate was evaporated to afford the title compound 1-benzyl-4-(1-ethoxyvinyl)-1H-pyrazole (0.52 g, crude) as a black liquid. The crude material was as such taken for next step without further purification.

Step 3

Preparation of 1-(1-benzyl-1H-pyrazol-4-yl)-2-bromoethanone

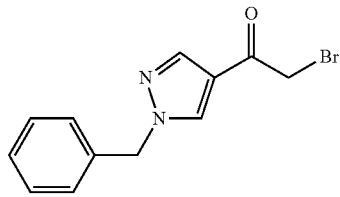 [SMILES: O=C(CBr)c1cnn(Cc2ccccc2)c1]

N-Bromosuccinimide (0.487 g, 2.74 mmol) was added to a solution of 1-benzyl-4-(1-ethoxyvinyl)-1H-pyrazole (0.52 g, 2.28 mmol) in tetrahydrofuran (15 mL) and water (5 mL) at 0° C. and the reaction mixture was stirred at room temperature for 1 h. The reaction mixture was diluted with water (30 mL) and extracted with ethyl acetate (50 mL×2). The combined organic extract was washed with brine (30 mL), dried over anhydrous sodium sulfate and evaporated. The crude material was purified by combiflash purifier using 20% ethyl acetate in hexane to afford the title compound 1-(1-benzyl-1H-pyrazol-4-yl)-2-bromoethanone (0.23 g, 36% yield) as a colorless liquid. Calculated M+H: 279.01; Found M+H: 279.0.

Example 15—Preparation of rac-4-(2-((3aR,5s,6aS)-5-(4-fluorophenoxy)hexahydrocyclopenta[c]pyrrol-2(1H)-yl)-1-methoxyethyl)phenol Scheme 15:

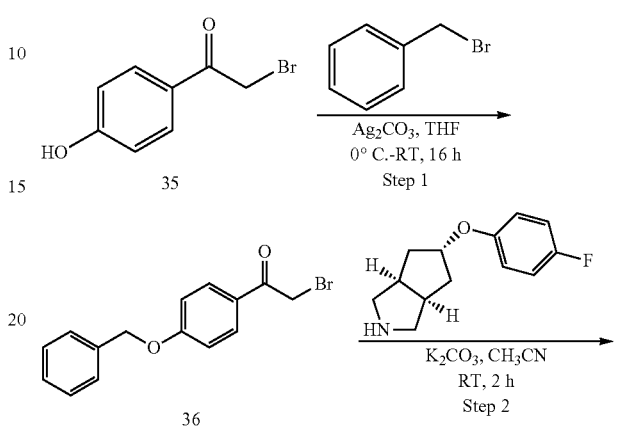

TABLE 5

The following compounds were prepared by the method of Example 14.

| Structure | IUPAC Name | Calculated M + H | Found M + H | Retention time (min) | Method |
|---|---|---|---|---|---|
| 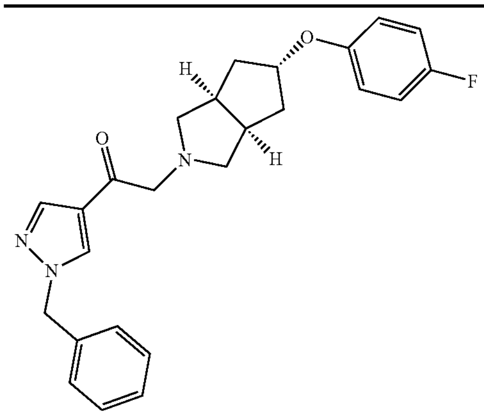 | 1-(1-benzyl-1H-pyrazol-4-yl)-2-((3aR,5s,6aS)-5-(4-fluorophenoxy)hexahydro-cyclopenta[c]pyrrol-2(1H)-yl)ethanone | 420.49 | 420.5 | 2.248 | A |
| 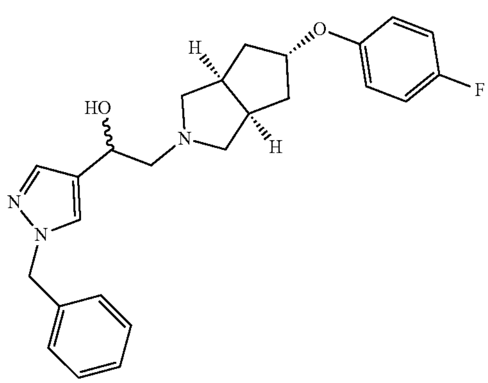 [SMILES: OC(CN1C[C@H]2C[C@H](Oc3ccc(F)cc3)C[C@H]2C1)c1cnn(Cc2ccccc2)c1] | rac-1-(1-benzyl-1H-pyrazol-4-yl)-2-((3aR,5s,6aS)-5-(4-fluorophenoxy)hexahy-drocyclopenta[c]pyrrol-2(1H)-yl)ethanol | 422.51 | 422.2 | 2.104 | A |

119
-continued

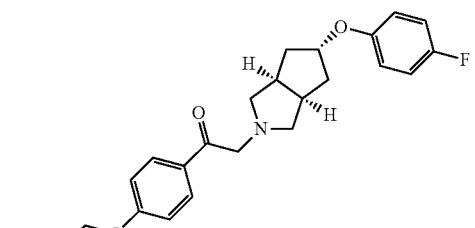

37

NaBH₄
EtOH,
RT, 4 h
Step 3

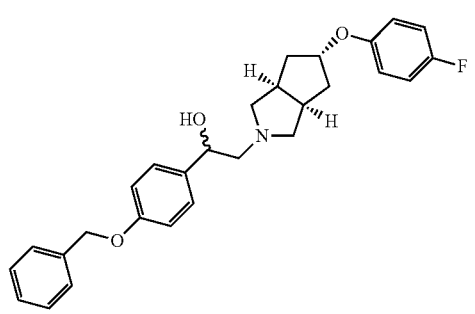

38

Me₂SO₄
K₂CO₃,
DMF
0° C.-RT,
1.5 h
Step 4

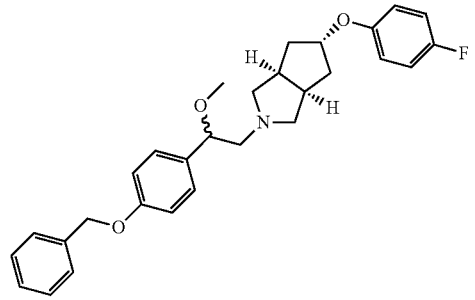

39

Et₃SiH
Pd/C,
MeOH
RT, 18 h
Step 5

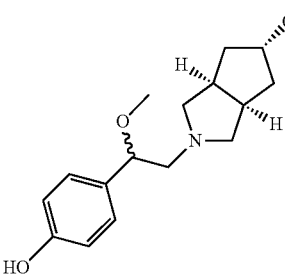

40

120
Step 1

Preparation of
1-(4-(benzyloxy)phenyl)-2-bromoethanone

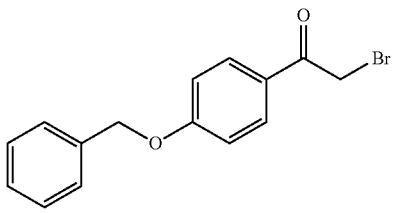 [SMILES: O=C(CBr)c1ccc(OCc2ccccc2)cc1]

To a solution of 2-bromo-1-(4-hydroxyphenyl)ethanone (2 g, 9.3 mmol) in tetrahydrofuran (70 mL) was added silver carbonate (5.128 g, 18.6 mmol) and the reaction mixture was cooled to 0° C. Benzyl bromide (1.32 mL, 11.16 mmol) was added drop wise and the reaction mixture was stirred at room temperature for 16 h. The reaction mixture was filtered through celite, the filtrate was diluted with ethyl acetate (200 mL) and washed with water (60 mL×2). The organic layer was dried over anhydrous sodium sulfate, filtered and concentrated. The crude was purified by column chromatography using 6% ethyl acetate in hexane to afford title 1-(4-(benzyloxy)phenyl)-2-bromoethanone (1.22 g, 43% yield) as a white solid. Calculated M+H: 306.17; Found M+H: 306.

Step 2

Preparation of 1-(4-(benzyloxy)phenyl)-2-((3aR,5s,6aS)-5-(4-fluorophenoxy)hexahydrocyclopenta[c]pyrrol-2(1H)-yl)ethanone

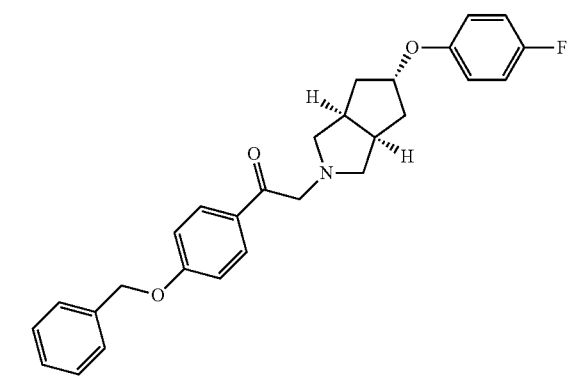 [SMILES: O=C(CN1C[C@H]2C[C@H](Oc3ccc(F)cc3)C[C@H]2C1)c1ccc(OCc2ccccc2)cc1]

To a solution of (3aR,5s,6aS)-5-(4-fluorophenoxy)octahydrocyclopenta[c]pyrrole (0.7 g, 3.165 mmol) in acetonitrile (25 mL) was added potassium carbonate (1.312 g, 9.495 mmol) followed by 1-(4-(benzyloxy)phenyl)-2-bromoethanone (0.866 g, 2.849 mmol). The resulting suspension was stirred at room temperature for 2 h. The reaction mixture was filtered and the filtrate was concentrated. The crude was purified by column chromatography using 15% ethyl acetate in hexane to afford the title compound 1-(4-(benzyloxy)phenyl)-2-((3aR,5s,6aS)-5-(4-fluorophenoxy)hexahydrocyclopenta[c]pyrrol-2(1H)-yl)ethanone (1.06 g, 75% yield) as a white solid. Calculated M+H: 446.53; Found M+H: 446.2.

Step 3

Preparation of rac-1-(4-(benzyloxy)phenyl)-2-((3aR,5s,6aS)-5-(4-fluorophenoxy)hexahydrocyclopenta[c]pyrrol-2(1H)-yl)ethanol

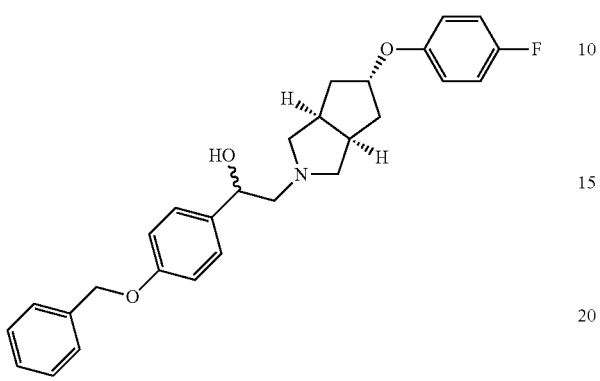

To a solution of 1-(4-(benzyloxy)phenyl)-2-((3aR,5s,6aS)-5-(4-fluorophenoxy)hexahydrocyclopenta[c]pyrrol-2(1H)-yl)ethanone (1.06 g, 2.38 mmol) in ethanol (50 mL) was added sodium borohydride (1.35 g, 35.713 mmol). The reaction mixture was stirred at room temperature for 4 h and concentrated. The residue was diluted with water (50 mL) and extracted with ethyl acetate (100 mL×3). The combined organic layer was dried over anhydrous sodium sulfate, filtered and concentrated. The crude was purified column chromatography using 22% ethyl acetate in hexane to afford the title compound 1-(4-(benzyloxy)phenyl)-2-((3aR,5s,6aS)-5-(4-fluorophenoxy)hexahydrocyclopenta[c]pyrrol-2(1H)-yl)ethanol (0.63 g, 59% yield) as a white solid. Calculated M+H: 448.54; Found M+H: 448.2.

Step 4

Preparation of rac-(3aR,5s,6aS)-2-(2-(4-(benzyloxy)phenyl)-2-methoxyethyl)-5-(4-fluorophenoxy)octahydrocyclopenta[c]pyrrole

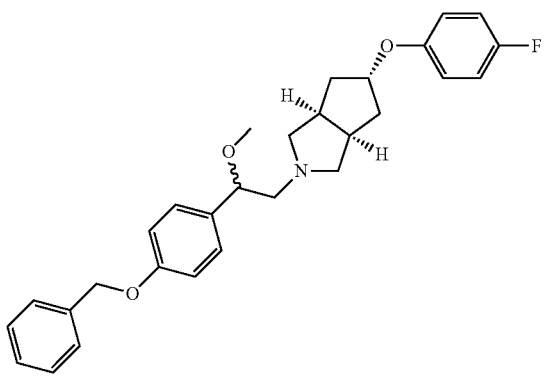 [SMILES: COC(CN1C[C@H]2C[C@H](Oc3ccc(F)cc3)C[C@H]2C1)c1ccc(OCc2ccccc2)cc1]

To a solution of 1-(4-(benzyloxy)phenyl)-2-((3aR,5s,6aS)-5-(4-fluorophenoxy)hexahydrocyclopenta[c]pyrrol-2(1H)-yl)ethanol (0.23 g, 0.514 mmol) in N,N-dimethyl formamide (6 mL) was added potassium carbonate (0.213 g, 1.543 mmol). The reaction mixture was cooled to 0° C. and dimethyl sulfate (0.146 mL, 1.543 mmol) was added drop wise. The resulting suspension was stirred at room temperature for 1.5 h. The reaction mixture was diluted with ethyl acetate (200 mL) washed with water (40 mL×2). The organic layer was dried over anhydrous sodium sulfate filtered and concentrated to afford the title compound (3aR,5s,6aS)-2-(2-(4-(benzyloxy)phenyl)-2-methoxyethyl)-5-(4-fluorophenoxy)octahydrocyclopenta[c]pyrrole (0.24 g, crude) as a white solid. Calculated M+H: 462.57; Found M+H: 462.2.

Step 5

Preparation of rac-4-(2-((3aR,5s,6aS)-5-(4-fluorophenoxy)hexahydrocyclopenta[c]pyrrol-2(1H)-yl)-1-methoxyethyl)phenol

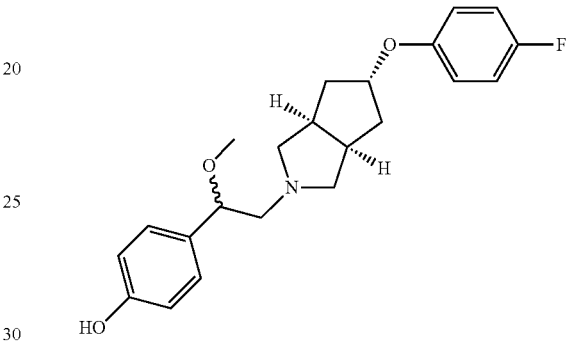

To a solution of (3aR,5s,6aS)-2-(2-(4-(benzyloxy)phenyl)-2-methoxyethyl)-5-(4-fluorophenoxy)octahydrocyclopenta[c]pyrrole (0.24 g, 0.52 mmol) in methanol (15 mL), Pd/C (0.04 g, 10% dry) and triethylsilane (1.65 mL, 10.4 mmol) were added. The resulting suspension was stirred at room temperature for 18 h. The reaction mixture was filtered through celite and the filtrate was concentrated. The crude was purified by preparative HPLC (analytical conditions: column: Zorbax XDB C18 (150 mm×4.6 mm×3.5 μm), mobile phase (A): 5 mM ammonium acetate in water, mobile phase (B): acetonitrile, flow rate: 1.0 mL/min T/% B: 0/20,10/70, 25/70,27/20,30/20) to afford the title compound 4-(2-((3aR,5s,6aS)-5-(4-fluorophenoxy)hexahydrocyclopenta[c]pyrrol-2(1H)-yl)-1-methoxyethyl)phenol (0.015 g, 7%) as a brown solid. Calculated M+H: 372.45; Found M+H: 372.5.

Example 16—Preparation of (3aR,5s,6aS)-benzyl 5-((4-nitrobenzoyl)oxy)hexahydrocyclopenta[c]pyrrole-2(1H)-carboxylate Scheme 16:

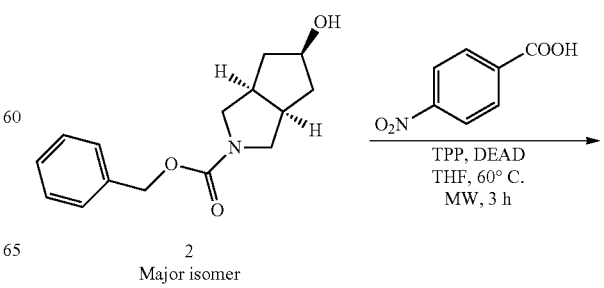

2
Major isomer

-continued

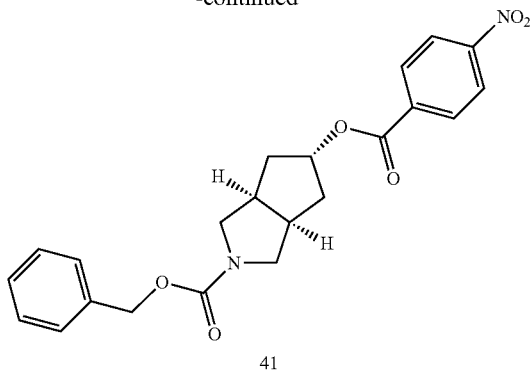

41

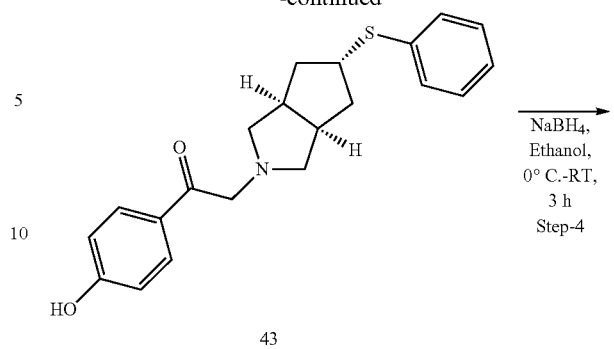

43

To a solution of (3aR,5r,6aS)-benzyl 5-hydroxyhexahydrocyclopenta[c]pyrrole-2(1H)-carboxylate (0.5 g, 1.915 mmol) in tetrahydrofuran (5 mL) cooled at 0° C., were added 4-nitrobenzoic acid (0.32 g, 1.915 mmol), triphenylphosphine (0.6 g, 2.29 mmol) and diethyl azo dicarboxylate (0.45 mL, 2.87 mmol). The reaction mixture was heated at 60° C. in microwave for 3 h and concentrated. Then the crude material was purified by combiflash purifier using 20% ethyl acetate in hexane to afford the title compound (3aR,5s,6aS)-benzyl 5-((4-nitrobenzoyl)oxy)hexahydrocyclopenta[c]pyrrole-2(1H)-carboxylate (0.65 g, 83.33% yield) as a white solid. Calculated M+H: 411.42; Found M+H: 411.2.

Example 17—Preparation of rac-4-(1-hydroxy-2-((3aR,5s,6aS)-5-(phenylthio)hexahydrocyclopenta[c]pyrrol-2(1H)-yl)ethyl)phenol

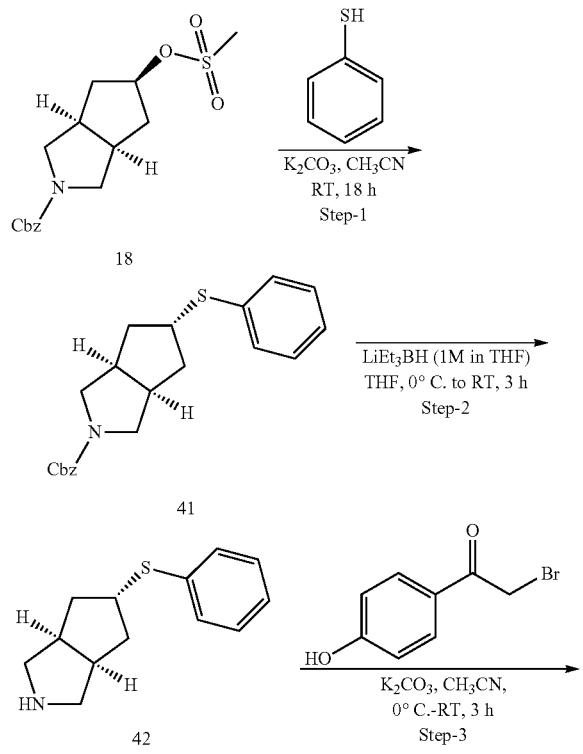

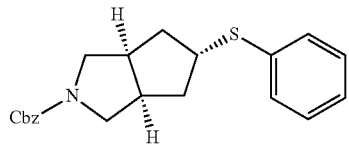 [SMILES: O=C(OCc1ccccc1)N1C[C@H]2C[C@H](Sc3ccccc3)C[C@H]2C1]

44

Step 1

Preparation of (3aR,5s,6aS)-benzyl 5-(phenylthio)hexahydrocyclopenta[c]pyrrole-2(1H)-carboxylate To a mixture of (3aR,5r,6aS)-benzyl 5-((methylsulfonyl)oxy)hexahydrocyclopenta[c]pyrrole-2(1H)-carboxylate (2.7 g, 7.954 mmol) and potassium carbonate (2.74 g, 19.88 mmol) in acetonitrile (50 mL) was added benzenethiol (1.22 mL, 11.93 mmol) at 0° C. The reaction mixture was allowed to warm to room temperature and stirred for 18 h. The progress of the reaction was monitored by TLC. The reaction mixture was filtered through celite pad, the bed was washed with ethyl acetate and the combined filtrate was concentrated to afford the crude product which was purified by silica gel column chromatography using 8% ethyl acetate in hexane to obtain the title compound (3aR,5s,6aS)-benzyl 5-(phenylthio)hexahydrocyclopenta[c]pyrrole-2(1H)-carboxylate (1.6 g, 56% yield) as a colorless semi solid. Calculated (M+H): 354.48; Found (M+H): 354.4.

Step 2

Preparation of (3aR,5s,6aS)-5-(phenylthio)octahydrocyclopenta[c]pyrrole

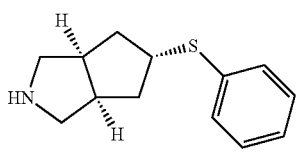 [SMILES: c1ccc(S[C@@H]2C[C@H]3CNC[C@H]3C2)cc1]

To a solution of (3aR,5s,6aS)-benzyl 5-(phenylthio)hexahydrocyclopenta[c]pyrrole-2(1H)-carboxylate (1.0 g, 2.82 mmol) in tetrahydrofuran (10 mL) was added lithium triethylborohydride, (1M solution in tetrahydrofuran, 1.49 g, 14.14 mmol) under nitrogen atmosphere at 0° C. The reaction mixture was allowed to warm to room temperature and stirred for 3 h. The mixture was quenched with saturated solution of ammonium chloride (10 ml), extracted with ethyl acetate (100 mL×3), dried over sodium sulfate, filtered and concentrated to afford crude product (3aR,5s,6aS)-5-(phenylthio)octahydrocyclopenta[c]pyrrole (1.2 g, crude) which was taken as such to the next step without further purification. Calculated (M+H): 220.11; Found (M+H): 220.3.

Step 3

Preparation of 1-(4-hydroxyphenyl)-2-((3aR,5s,6aS)-5-(phenylthio)hexahydrocyclopenta[c]pyrrol-2(1H)-yl)ethanone

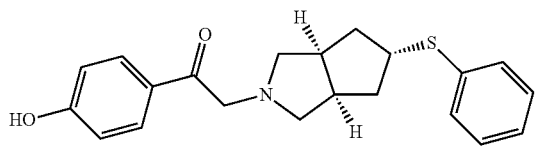 [SMILES: O=C(CN1C[C@H]2C[C@H](Sc3ccccc3)C[C@H]2C1)c1ccc(O)cc1]

To a solution of (3aR,5s,6aS)-5-(phenylthio)octahydrocyclopenta[c]pyrrole (0.3 g, 1.36 mmol) in acetonitrile (10 mL) was added potassium carbonate (0.47 g, 3.42 mmol) at 0° C., followed by the addition of 2-bromo-1-(4-hydroxyphenyl) ethanone (0.29 g, 1.36 mmol). The resulting suspension was gradually allowed to warm to room temperature and stirred for 3 h. The reaction mixture was filtered and washed with 10% methanol in dichloromethane, the combined filtrate was concentrated under vacuum to afford crude product, which was purified by silica gel column chromatography using 10% methanol in dichloromethane and again purified by preparative HPLC (Column: Zorbax XDB C18 (150 mm×4.6 mm×3.5 m), Mobile phase (A): 0.01% Formic acid in water, Mobile phase (B): acetonitrile, Flow rate: 1.0 mL/min, T/% B: 0/20,10/70,25/70,27/20,30/20) to obtain the title compound 1-(4-hydroxyphenyl)-2-((3aR,5s,6aS)-5-(phenylthio)hexahydrocyclopenta[c]pyrrol-2(1H)-yl)ethanone (0.14 g, 29% yield) as a colorless solid. Calculated (M+H): 354.48; Found (M+H): 354.4.

Step 4

Preparation of rac-4-(1-hydroxy-2-((3aR,5s,6aS)-5-(phenylthio)hexahydrocyclopenta[c]pyrrol-2(1H)-yl)ethyl)phenol

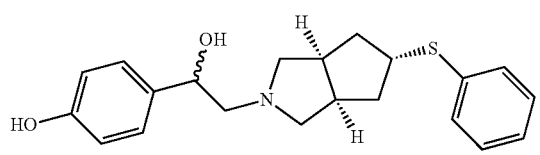 [SMILES: Oc1ccc(C(O)CN2C[C@H]3C[C@H](Sc4ccccc4)C[C@H]3C2)cc1]

To a solution of 1-(4-hydroxyphenyl)-2-((3aR,5s,6aS)-5-(phenylthio)hexahydrocyclopenta[c]pyrrol-2(1H)-yl)ethanone (0.1 g, 0.28 mmol) in ethanol (10 mL) was added sodium borohydride (0.21 g, 5.65 mmol) at room temperature and stirred for 3 h. The reaction mixture was diluted with water (25 mL) and concentrated under vacuum. The aqueous residue was extracted with dichloromethane (50 mL×3), the combined organic layer was dried over anhydrous sodium sulfate, filtered and concentrated under vacuum to afford crude product which was purified by silica gel column chromatography using 4% methanol in dichloromethane to afford the title compound 4-(1-hydroxy-2-((3aR,5s,6aS)-5-(phenylthio)hexahydrocyclopenta[c]pyrrol-2(1H)-yl)ethyl)phenol (0.045 g, 45% yield) as a white solid. Calculated (M+H): 356.49; Found (M+1): 356.3.

TABLE 6

The following compounds were prepared by the method described above.

| Structure | IUPAC Name | Calculated (M + H) | Found (M + H) | Retention time (min) | Method |
|---|---|---|---|---|---|
| 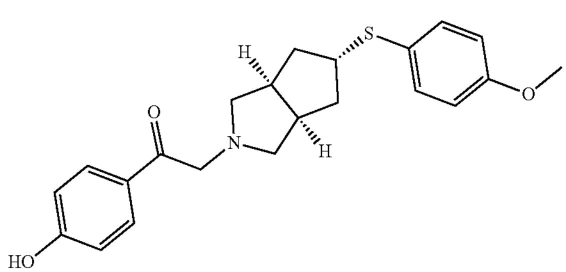 [SMILES: COc1ccc(S[C@H]2C[C@@H]3CN(CC(=O)c4ccc(O)cc4)C[C@@H]3C2)cc1] | 1-(4-hydroxyphenyl)-2-((3aR,5s,6aS)-5-((4-methoxyphenyl)thio)hexahydrocyclopenta[c]pyrrol-2(1H)-yl)ethanone | 384.16 | 384.2 | 1.602 | D |

TABLE 6-continued

The following compounds were prepared by the method described above.

| Structure | IUPAC Name | Calculated (M + H) | Found (M + H) | Retention time (min) | Method |
|---|---|---|---|---|---|
| 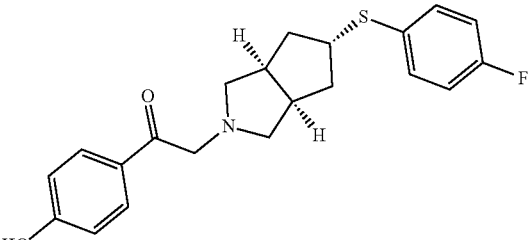 | 2-((3aR,5s,6aS)-5-((4-fluorophenyl)thio)hexahydrocyclopenta[c]pyrrol-2(1H)-yl)-1-(4-hydroxyphenyl)ethanone | 372.14 | 372.1 | 2.096 | E |
| 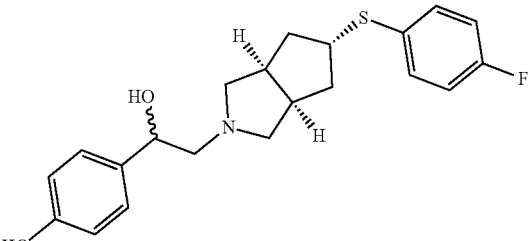 | rac-4-(2-((3aR,5s,6aS)-5-((4-fluorophenyl)thio)hexahydrocyclopenta[c]pyrrol-2(1H)-yl)-1-hydroxyethyl)phenol | 374.15 | 374.1 | 1.975 | A |
| 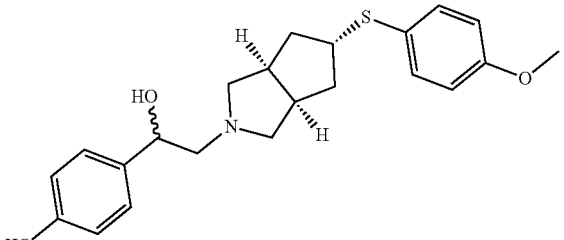 | rac-4-(1-hydroxy-2-((3aR,5s,6aS)-5-((4-methoxyphenyl)thio)hexahydrocyclopenta[c]pyrrol-2(1H)-yl)ethyl)phenol | 386.17 | 386.2 | 2.086 | A |
| 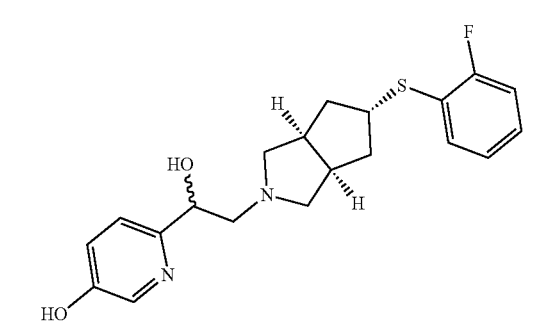 [SMILES: Oc1ccc(C(O)CN2C[C@H]3C[C@H](Sc4ccccc4F)C[C@H]3C2)nc1] | rac-6-(2-((3aR,5s,6aS)-5-((2-fluorophenyl)thio)hexahydrocyclopenta[c]pyrrol-2(1H)-yl)-1-hydroxyethyl)pyridin-3-ol | 375.15 | 375.1 | 1.302 | D |

Example 18—Preparation of rac-4-(1-hydroxy-2-((3aR,5s,6aS)-5-(phenylsulfonyl)hexahydrocyclopenta[c]pyrrol-2(1H)-yl)ethyl)phenol Scheme 18

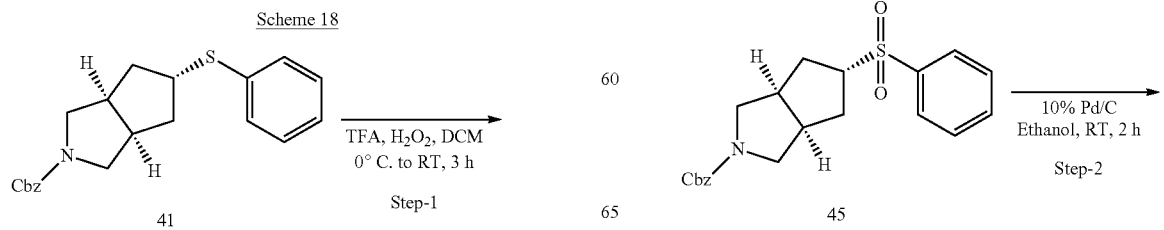

129

-continued

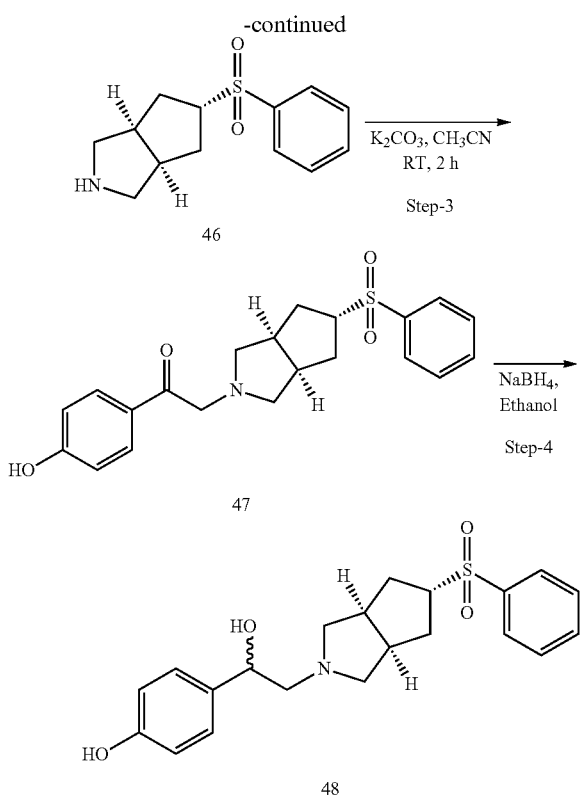

Step 1

Preparation of (3aR,5s,6aS)-benzyl 5-(phenylsulfonyl)hexahydrocyclopenta[c]pyrrole-2(1H)-carboxylate

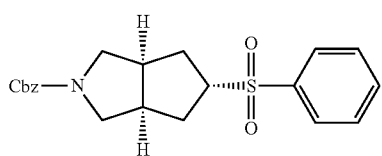 [SMILES: O=C(OCc1ccccc1)N1C[C@H]2C[C@H](S(=O)(=O)c3ccccc3)C[C@H]2C1]

To a mixture of (3aR,5s,6aS)-benzyl 5-(phenylthio)hexahydrocyclopenta[c]pyrrole-2(1H)-carboxylate (0.7 g, 1.98 mmol), trifluoro acetic acid (5 mL) and dichloromethane (5 mL) was added hydrogen peroxide (1.12 mL, 9.95 mmol, aqueous 35%) at 0° C. The reaction mixture was allowed to warm to room temperature and stirred for 3 h. The progress of the reaction was monitored by TLC. The reaction mixture was cooled to 0° C. and neutralized with saturated sodium bicarbonate solution to pH=7. The mixture was extracted with dichloromethane (150 mL×3), the combined organic layer was washed with water (100 mL), brine solution (100 mL), dried over anhydrous sodium sulfate, filtered and concentrated under vacuum to afford the crude product which was purified by silica gel column chromatography using 35% ethyl acetate in hexane to obtain title compound (3aR,5s,6aS)-benzyl 5-(phenylsulfonyl)hexahydrocyclopenta[c]pyrrole-2(1H)-carboxylate (0.63 g, 83% yield) as a colorless semi solid. Calculated (M+H): 386.53; Found (M+H): 386.1.

130

Step 2

Preparation of (3aR,5s,6aS)-5-(phenylsulfonyl)octahydrocyclopenta[c]pyrrole

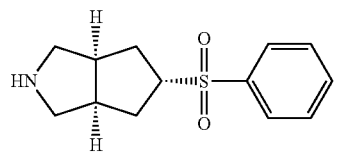 [SMILES: O=S(=O)(c1ccccc1)[C@@H]1C[C@H]2CNC[C@H]2C1]

To a stirred solution of (3aR,5s,6aS)-benzyl 5-(phenylsulfonyl)hexahydrocyclopenta[c]pyrrole-2(1H)-carboxylate (0.38 g, 0.98 mmol) in ethanol (10 mL), was added 10% Pd/C (0.1 g) under nitrogen atmosphere. The reaction was subjected to hydrogenation in balloon and stirred for 2 h. After completion of reaction, the mixture was filtered through celite and the bed was washed with methanol. The combined filtrate was concentrated under vacuum to obtain the title compound (3aR,5s,6aS)-5-(phenylsulfonyl)octahydrocyclopenta[c]pyrrole (0.22 g, crude) as a colorless gum. Calculated (M+H): 252.1; Found (M+H): 252.2.

Step 3

Preparation of 1-(4-hydroxyphenyl)-2-((3aR,5s,6aS)-5-(phenylsulfonyl)hexahydrocyclopenta[c]pyrrol-2(1H)-yl)ethanone

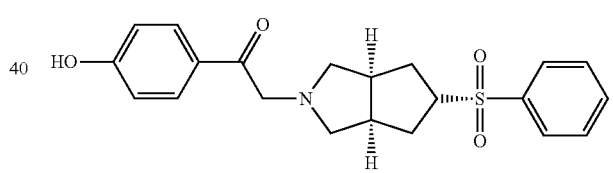

To a solution of (3aR,5s,6aS)-5-(phenylsulfonyl)octahydrocyclopenta[c]pyrrole (0.21 g, 0.83 mmol) in acetonitrile (10 mL) was added potassium carbonate (0.28 g, 2.08 mmol) at 0° C. followed by the addition of 2-bromo-1-(4-hydroxyphenyl) ethanone (0.18 g, 0.835 mmol). The resulting suspension was gradually allowed to warm to room temperature and stirred for 2 h. The reaction mixture was filtered and washed with 10% methanol in dichloromethane. The combined filtrate was concentrated under vacuum to afford crude product, which was purified by silica gel column chromatography using 10% methanol in dichloromethane and again purified by preparative HPLC; (Column: Zorbax XDB C18 (150 mm×4.6 mm×3.5 μm), Mobile phase (A): 0.01% Formic acid, Mobile phase (B): Acetonitrile, Flow rate: 1.0 mL/min, T/% B: 0/20,10/70, 25/70,27/20,30/20) to obtain title compound 1-(4-hydroxyphenyl)-2-((3aR,5s,6aS)-5-(phenylsulfonyl)hexahydrocyclopenta[c]pyrrol-2(1H)-yl) ethanone (0.14 g, 43% yield) as a colorless solid. Calculated (M+H): 386.13; Found (M+H): 386.1.

Step 4

Preparation of rac-4-(1-hydroxy-2-((3aR,5s,6aS)-5-(phenylsulfonyl)hexahydrocyclopenta[c]pyrrol-2(1H)-yl)ethyl)phenol

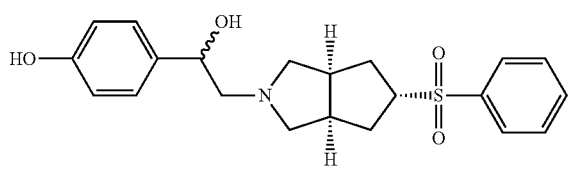 [SMILES: O=S(=O)(c1ccccc1)[C@H]1C[C@@H]2CN(CC(O)c3ccc(O)cc3)C[C@@H]2C1]

To a solution of 1-(4-hydroxyphenyl)-2-((3aR,5s,6aS)-5-(phenylsulfonyl)hexahydrocyclopenta[c]pyrrol-2(1H)-yl) ethanone (0.15 g, 0.39 mmol) in ethanol (10 mL) was added sodium borohydride (0.29 g, 7.78 mmol)) at room temperature and stirred for 4 h. The reaction mixture was diluted with water (25 mL) and concentrated under vacuum. The aqueous residue was extracted with dichloromethane (50 mL×3), the combined organic layer was dried over anhydrous sodium sulfate, filtered, concentrated under vacuum to afford crude product which was purified by silica gel column chromatography using 7% methanol in dichloromethane to afford the title compound 4-(1-hydroxy-2-((3aR,5s,6aS)-5-(phenylsulfonyl)hexahydrocyclopenta[c]pyrrol-2(1H)-yl) ethyl)phenol (0.042 g, 28% yield) as a white solid. Calculated (M+H): 388.15; Found (M+H): 388.4.

confluency as an adherent monolayer in standard tissue culture flasks at 37° C., 5% $CO_2$ per supplier's instructions. NR2B expression was induced by incubation with 0.3-0.4 μg/ml tetracycline in the presence of 4 mM ARL-15896 for 18-24 hours under the same growth conditions, then transferred to 30° C. for another 3-5 hours.

After induction, cell culture medium was removed and cells were rinsed once with $Ca^{2+}$ and $Mg^{2+}$-free Dulbecco's phosphate buffered saline. Cells were then removed from the flask using TrypLE™ Express (Life Technologies) according to the manufacturer's instructions and collected to 50 ml centrifuge tubes. Following two washes in $Ca^{2+}/Mg^{2+}$-free HBSS with 20 mM HEPES (HHnoCa), cells were counted and viability assessed using trypan blue. To load cells with $Ca^{2+}$-sensitive dye, they were resuspended in fluo-8 plus Component B (AAT Bioquest Products) diluted in HHnoCa and incubated 15 minutes at 37° C., followed by 30 minutes at room temp (in dark). Cells were then washed and resuspended in HHnoCa to remove extracellular dye and plated in 384-well plates (Falcon, uncoated) at 20,000-30,000 cells/well in a final volume of 25 μl/well.

FDSS Assay: To each well of the plate, 10 μL test compound, control (MK801) or HHnoCa buffer was added at different concentrations to yield final concentrations of 0.001, 0.003, 0.010, 0.030, 0.100, 0.300, 1.000, 3.000, 10.000, or 30.000 uM final concentration of DMSO of 0.1%. Following 10 minutes pre-incubation in the dark, plates are loaded onto the Hamamatsu FDSS 6000. After collecting baseline fluorescence images, 3 μM glutamate, 3 μM glycine, and 1 mM $Ca^{2+}$ in HHnoCa buffer is added to each

TABLE 7

The following compounds were prepared by the method described above.

| Structure | IUPAC Name | Calculated (M + H) | Found (M + H) | Retention time (min) | Method |
|---|---|---|---|---|---|
| | 1-(3-fluoro-4-hydroxyphenyl)-2-((3aR,5s,6aS)-5-(phenylsulfonyl)hexahydrocyclopenta[c]pyrrol-2(1H)-yl)ethanone | 404.13 | 404.1 | 1.795 | A |
| | rac-2-fluoro-4-(1-hydroxy-2-((3aR,5s,6aS)-5-(phenylsulfonyl)hexahydrocyclopenta[c]pyrrol-2(1H)-yl)ethyl)phenol | 406.14 | 406.1 | 4.11 | C |

Example 19—Cell Assay

Cell Culture and plating: HEK293 cells expressing NR1/NR2B (Chantest, Cleveland, Ohio) were grown to 70-80% well, and $Ca^{2+}$ is recorded for 3 minutes. Data were processed by computing ratio of fluorescence at the end of data collection to baseline fluorescence to assess degree of $Ca^{2+}$ influx inhibition relative to that observed in MK801.

Table 8 below provides activity of each compound according to the legend that "++++" indicates inhibition at a concentration<100 nM; "+++" indicates inhibition at a concentration between 100 nM and 1 μM of the disclosed compound; "++" indicates inhibition at a concentration of from 1 μM to 10 μM; and "+" indicates inhibition at a concentration>10 μM.

TABLE 8

| NR2B NAM Assay | | |
|---|---|---|
| Structure | NR2B NAM IC$_{50}$ (M) | Activity Category |
| | 4.70E−08 | ++++ |
| | 1.30E−08 | ++++ |
| | 6.16E−08 | ++++ |
| | 1.40E−08 | ++++ |
| | 1.26E−06 | ++ |

TABLE 8-continued

NR2B NAM Assay

| Structure | NR2B NAM IC$_{50}$ (M) | Activity Category |
|---|---|---|
| 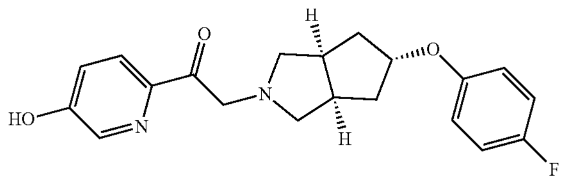 [SMILES: O=C(CN1C[C@H]2C[C@H](Oc3ccc(F)cc3)C[C@H]2C1)c1ccc(O)cn1] | 6.99E−07 | +++ |
| 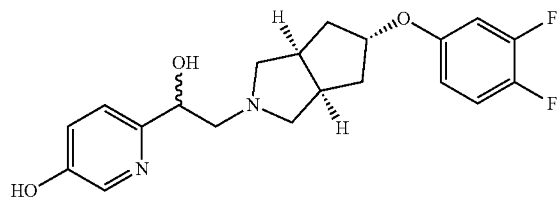 [SMILES: Oc1ccc(C(O)CN2C[C@H]3C[C@H](Oc4ccc(F)c(F)c4)C[C@H]3C2)nc1] | 1.78E−08 | ++++ |
| 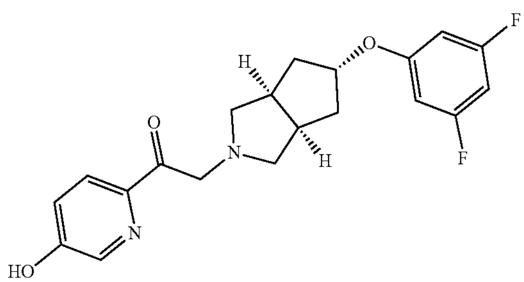 [SMILES: O=C(CN1C[C@H]2C[C@H](Oc3cc(F)cc(F)c3)C[C@H]2C1)c1ccc(O)cn1] | 1.00E−05 | + |
| 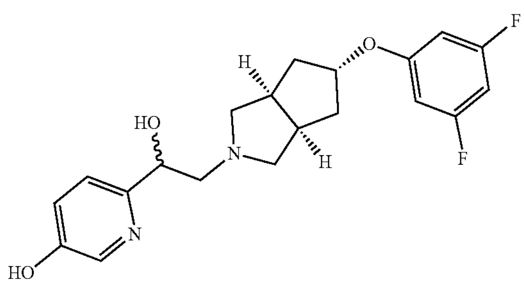 [SMILES: Oc1ccc(C(O)CN2C[C@H]3C[C@H](Oc4cc(F)cc(F)c4)C[C@H]3C2)nc1] | 5.83E−08 | ++++ |
| 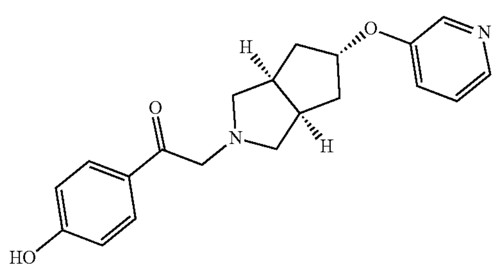 [SMILES: O=C(CN1C[C@H]2C[C@H](Oc3cccnc3)C[C@H]2C1)c1ccc(O)cc1] | 8.15E−08 | ++++ |
| 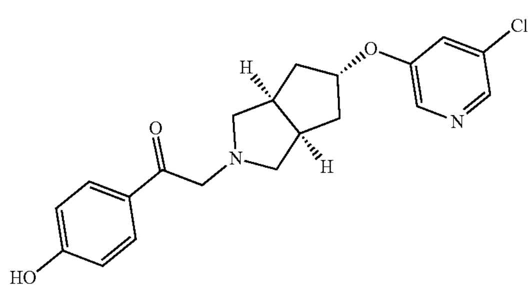 [SMILES: O=C(CN1C[C@H]2C[C@H](Oc3cncc(Cl)c3)C[C@H]2C1)c1ccc(O)cc1] | 2.53E−07 | +++ |

TABLE 8-continued

NR2B NAM Assay

| Structure | NR2B NAM IC$_{50}$ (M) | Activity Category |
|---|---|---|
| (structure) | 4.93E-07 | +++ |
| (structure) | 1.00E-05 | + |
| (structure) | 1.00E-05 | + |
| (structure) | 5.34E-08 | ++++ |

TABLE 8-continued

| NR2B NAM Assay | | |
|---|---|---|
| Structure | NR2B NAM IC$_{50}$ (M) | Activity Category |
| | 9.46E−08 | ++++ |
| | 1.00E−05 | + |
| | 8.45E−08 | ++++ |
| | 1.00E−05 | + |
| | 1.80E−08 | ++++ |
| | 3.67E−07 | +++ |

TABLE 8-continued

NR2B NAM Assay

| Structure | NR2B NAM IC$_{50}$ (M) | Activity Category |
|---|---|---|
| 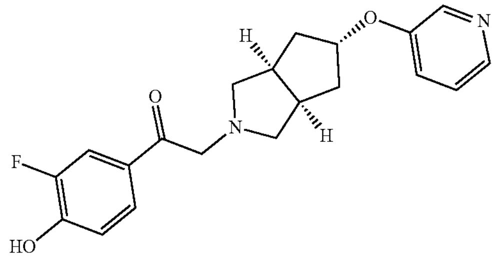 [SMILES: O=C(CN1C[C@H]2C[C@H](Oc3cccnc3)C[C@H]2C1)c1ccc(O)c(F)c1] | 4.34E−07 | +++ |
| | 1.00E−05 | + |
| 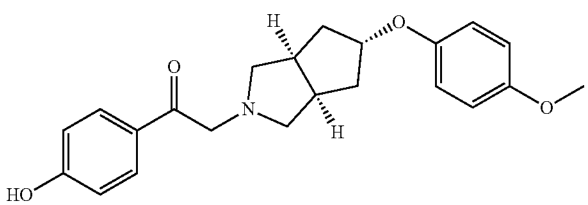 [SMILES: COc1ccc(O[C@H]2C[C@@H]3CN(CC(=O)c4ccc(O)cc4)C[C@@H]3C2)cc1] | 4.64E−08 | ++++ |
| 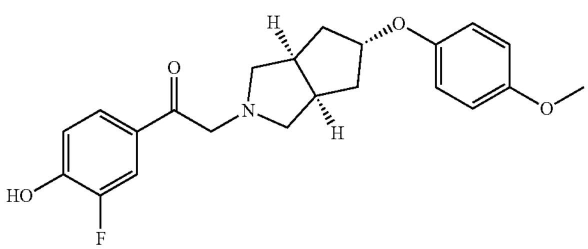 [SMILES: COc1ccc(O[C@H]2C[C@@H]3CN(CC(=O)c4ccc(O)c(F)c4)C[C@@H]3C2)cc1] | 1.02E−07 | +++ |
| | 1.00E−05 | + |
| 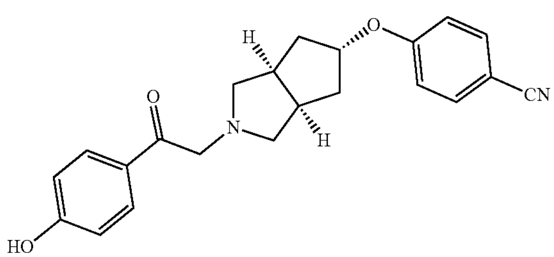 [SMILES: N#Cc1ccc(O[C@H]2C[C@@H]3CN(CC(=O)c4ccc(O)cc4)C[C@@H]3C2)cc1] | 6.82E−08 | ++++ |

TABLE 8-continued

| Structure | NR2B NAM IC$_{50}$ (M) | Activity Category |
|---|---|---|
| (structure) | 4.74E-08 | ++++ |
| (structure) | 2.67E-07 | +++ |
| (structure) | 4.89E-06 | ++ |
| (structure) | 5.21E-08 | ++++ |
| (structure) | 1.00E-05 | + |
| (structure) | 1.40E-07 | +++ |

TABLE 8-continued

| NR2B NAM Assay | | |
|---|---|---|
| Structure | NR2B NAM IC$_{50}$ (M) | Activity Category |
| | 1.00E−05 | + |
| | 1.33E−06 | ++ |
| | 6.58E−08 | ++++ |
| | 4.15E−08 | ++++ |
| | 5.16E−08 | ++++ |
| | 7.07E−08 | ++++ |

TABLE 8-continued

| NR2B NAM Assay | | |
|---|---|---|
| Structure | NR2B NAM IC$_{50}$ (M) | Activity Category |
| | 3.02E−08 | ++++ |
| | 1.00E−05 | + |
| | 1.98E−06 | ++ |
| | 2.92E−06 | ++ |
| | 5.73E−08 | ++++ |
| | 2.50E−07 | +++ |

TABLE 8-continued
NR2B NAM Assay
| Structure | NR2B NAM IC$_{50}$ (M) | Activity Category |
|---|---|---|
| 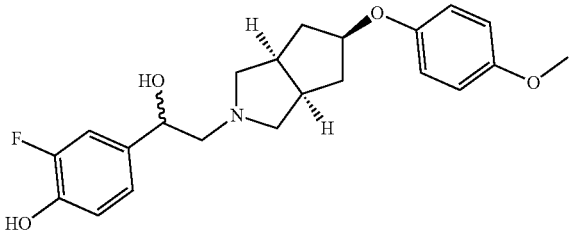 [SMILES: COc1ccc(O[C@@H]2C[C@@H]3CN(CC(O)c4ccc(O)c(F)c4)C[C@@H]3C2)cc1] | 8.39E−08 | ++++ |
| 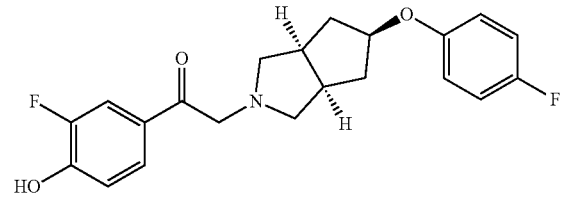 [SMILES: O=C(CN1C[C@H]2C[C@@H](Oc3ccc(F)cc3)C[C@H]2C1)c1ccc(O)c(F)c1] | 5.32E−08 | ++++ |
| 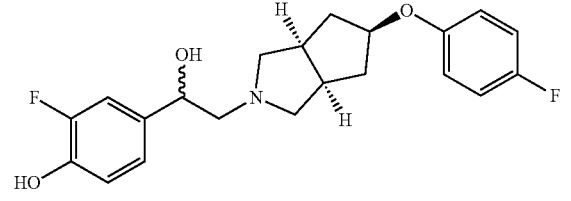 [SMILES: Oc1ccc(C(O)CN2C[C@H]3C[C@@H](Oc4ccc(F)cc4)C[C@H]3C2)cc1F] | 3.05E−08 | ++++ |
| 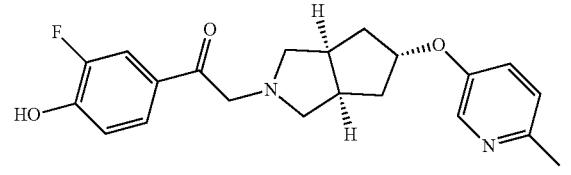 [SMILES: Cc1ccc(O[C@H]2C[C@@H]3CN(CC(=O)c4ccc(O)c(F)c4)C[C@@H]3C2)cn1] | 2.37E−06 | ++ |
| 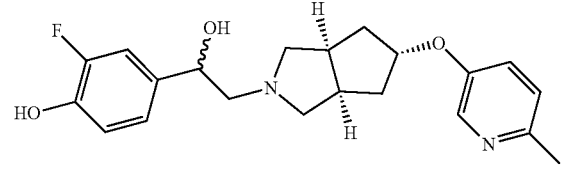 [SMILES: Cc1ccc(O[C@H]2C[C@@H]3CN(CC(O)c4ccc(O)c(F)c4)C[C@@H]3C2)cn1] | 9.00E−08 | ++++ |
| 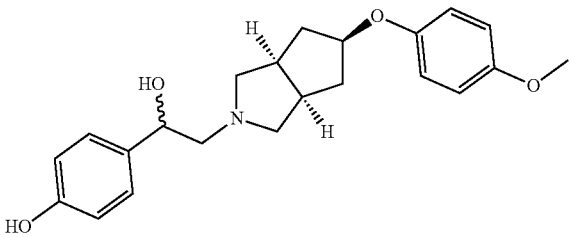 [SMILES: COc1ccc(O[C@@H]2C[C@@H]3CN(CC(O)c4ccc(O)cc4)C[C@@H]3C2)cc1] | 1.12E−07 | +++ |
| 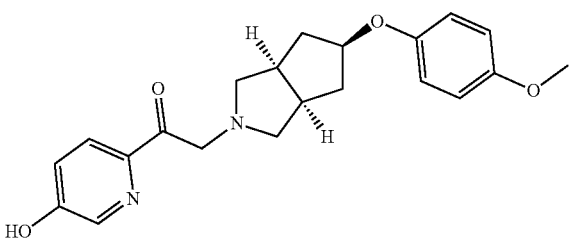 | 7.10E−06 | ++ |

TABLE 8-continued

| NR2B NAM Assay | | |
|---|---|---|
| Structure | NR2B NAM IC$_{50}$ (M) | Activity Category |
| | 1.78E−08 | ++++ |
| | 2.78E−06 | ++ |
| | 4.47E−06 | ++ |
| | 1.34E−07 | +++ |
| | 1.88E−07 | +++ |

TABLE 8-continued

NR2B NAM Assay

| Structure | NR2B NAM IC$_{50}$ (M) | Activity Category |
|---|---|---|
| | 1.00E−05 | + |
| 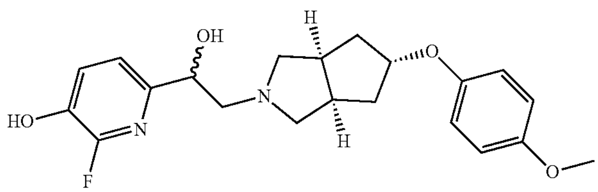 [SMILES: COc1ccc(O[C@H]2C[C@@H]3CN(CC(O)c4ccc(O)c(F)n4)C[C@@H]3C2)cc1] | 3.29E−06 | ++ |
| 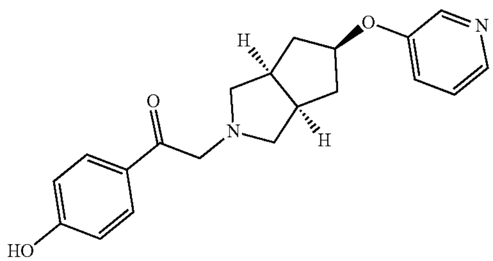 [SMILES: O=C(CN1C[C@H]2C[C@@H](Oc3cccnc3)C[C@H]2C1)c1ccc(O)cc1] | 5.22E−06 | ++ |
| 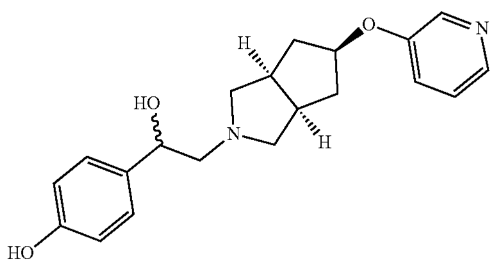 [SMILES: Oc1ccc(C(O)CN2C[C@H]3C[C@@H](Oc4cccnc4)C[C@H]3C2)cc1] | 8.00E−06 | ++ |
| | 1.00E−05 | + |
| 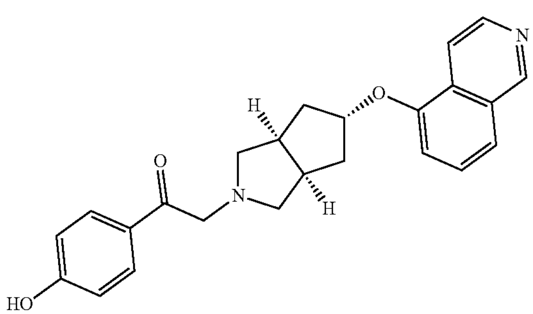 [SMILES: O=C(CN1C[C@H]2C[C@H](Oc3cccc4cnccc34)C[C@H]2C1)c1ccc(O)cc1] | 4.09E−07 | +++ |

TABLE 8-continued

| Structure | NR2B NAM IC$_{50}$ (M) | Activity Category |
|---|---|---|
| 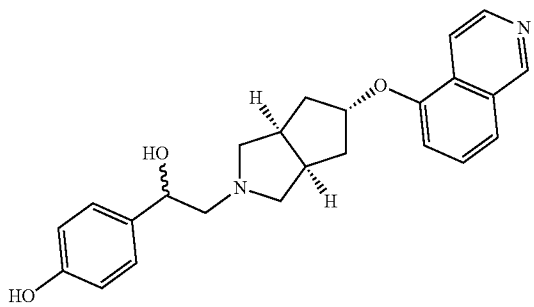 [SMILES: Oc1ccc(C(O)CN2C[C@H]3C[C@H](Oc4cccc5cnccc45)C[C@H]3C2)cc1] | 1.91E−07 | +++ |
| 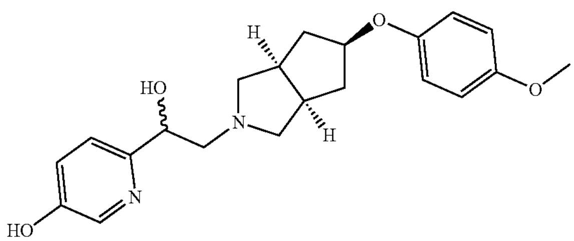 [SMILES: COc1ccc(O[C@@H]2C[C@@H]3CN(CC(O)c4ccc(O)cn4)C[C@@H]3C2)cc1] | 4.40E−07 | +++ |
| 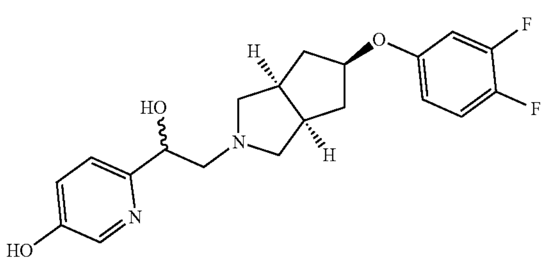 [SMILES: Oc1ccc(C(O)CN2C[C@H]3C[C@@H](Oc4ccc(F)c(F)c4)C[C@H]3C2)nc1] | 3.76E−08 | ++++ |
| 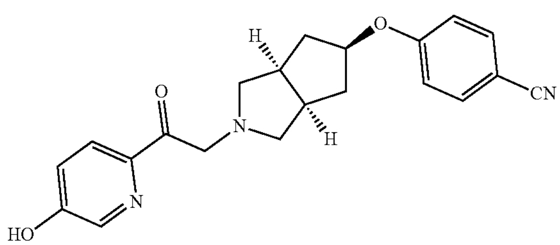 [SMILES: N#Cc1ccc(O[C@@H]2C[C@@H]3CN(CC(=O)c4ccc(O)cn4)C[C@@H]3C2)cc1] | 1.00E−05 | + |
| 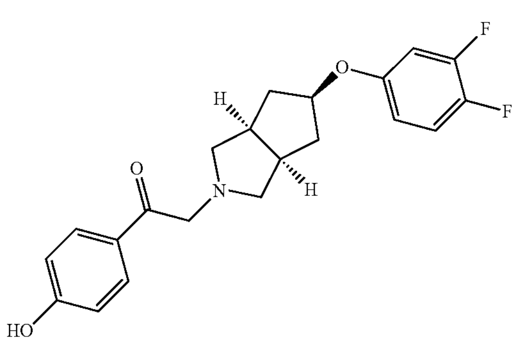 [SMILES: O=C(CN1C[C@H]2C[C@@H](Oc3ccc(F)c(F)c3)C[C@H]2C1)c1ccc(O)cc1] | 6.86E−08 | ++++ |

TABLE 8-continued
| Structure | NR2B NAM IC$_{50}$ (M) | Activity Category |
|---|---|---|
| 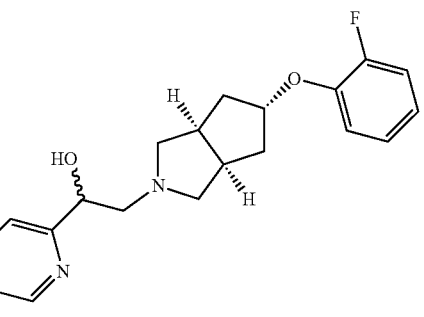 | 6.20E−09 | ++++ |
| 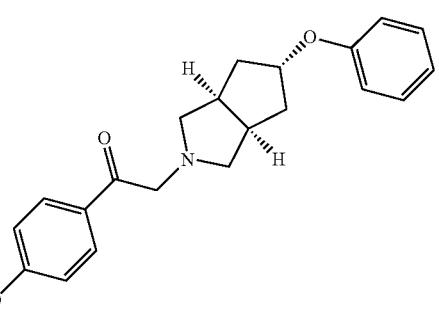 | 1.07E−08 | ++++ |
| 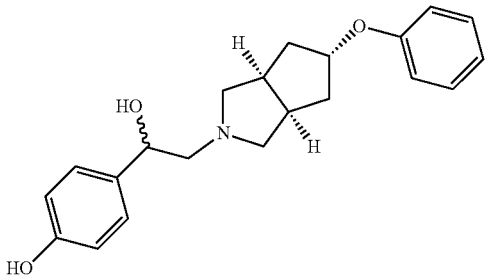 | 5.96E−09 | ++++ |
| 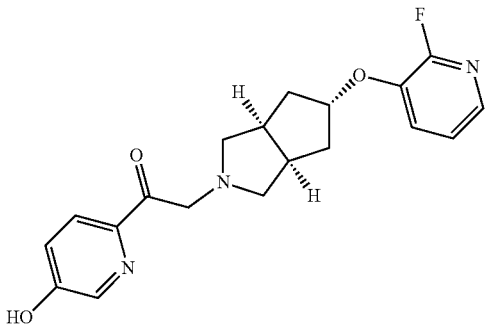 [SMILES: O=C(CN1C[C@H]2C[C@H](Oc3cccnc3F)C[C@H]2C1)c1ccc(O)cn1] | 1.00E−05 | + |

TABLE 8-continued

NR2B NAM Assay

| Structure | NR2B NAM IC$_{50}$ (M) | Activity Category |
|---|---|---|
| | 1.00E−05 | + |
| | 1.00E−05 | + |
| 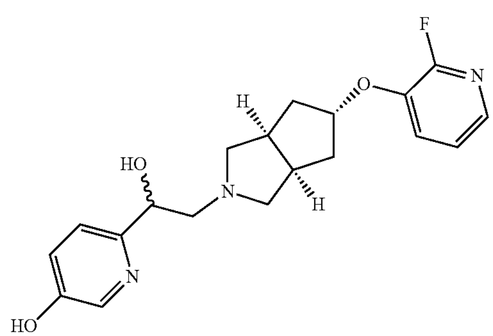 [SMILES: Oc1ccc(C(O)CN2C[C@H]3C[C@H](Oc4cccnc4F)C[C@H]3C2)nc1] | 2.09E−08 | ++++ |
| 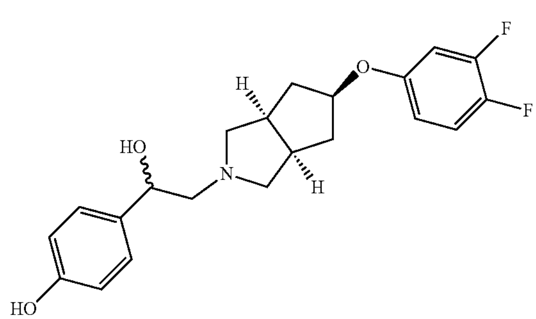 [SMILES: Oc1ccc(C(O)CN2C[C@H]3C[C@@H](Oc4ccc(F)c(F)c4)C[C@H]3C2)cc1] | 8.07E−08 | ++++ |

TABLE 8-continued
| NR2B NAM Assay | | |
|---|---|---|
| Structure | NR2B NAM IC$_{50}$ (M) | Activity Category |
| 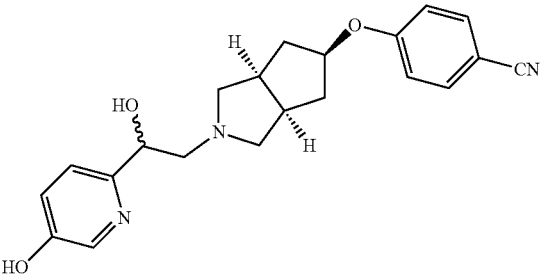 [SMILES: N#Cc1ccc(O[C@@H]2C[C@@H]3CN(CC(O)c4ccc(O)cn4)C[C@@H]3C2)cc1] | 1.00E−05 | + |
| 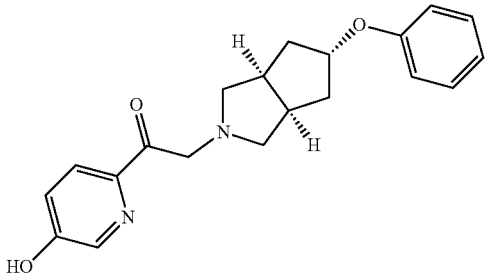 [SMILES: O=C(CN1C[C@H]2C[C@H](Oc3ccccc3)C[C@H]2C1)c1ccc(O)cn1] | 6.24E−06 | ++ |
| 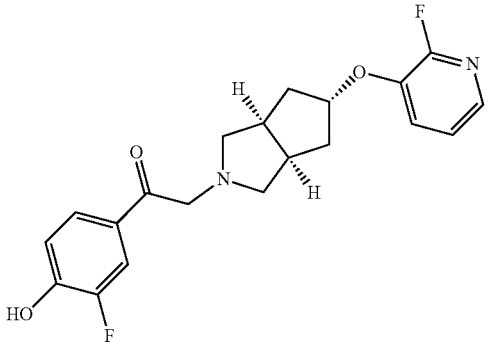 [SMILES: O=C(CN1C[C@H]2C[C@H](Oc3cccnc3F)C[C@H]2C1)c1ccc(O)c(F)c1] | 1.00E−05 | + |
| 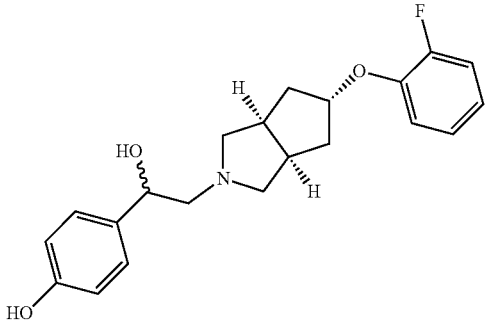 [SMILES: Oc1ccc(C(O)CN2C[C@H]3C[C@H](Oc4ccccc4F)C[C@H]3C2)cc1] | 4.44E−09 | ++++ |

TABLE 8-continued

NR2B NAM Assay

| Structure | NR2B NAM IC$_{50}$ (M) | Activity Category |
|---|---|---|
| 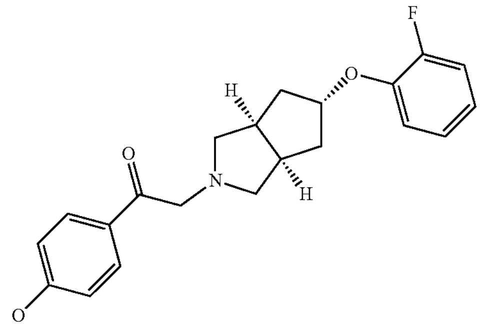 [SMILES: O=C(CN1C[C@H]2C[C@H](Oc3ccccc3F)C[C@H]2C1)c1ccc(O)cc1] | 1.68E-08 | ++++ |
| 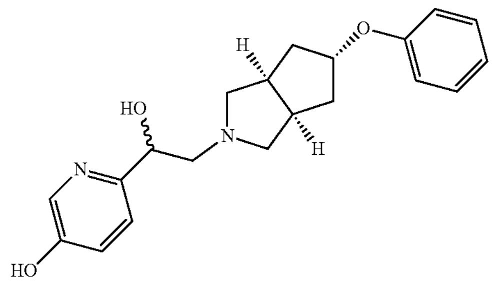 [SMILES: Oc1ccc(C(O)CN2C[C@H]3C[C@H](Oc4ccccc4)C[C@H]3C2)nc1] | 5.72E-09 | ++++ |
| 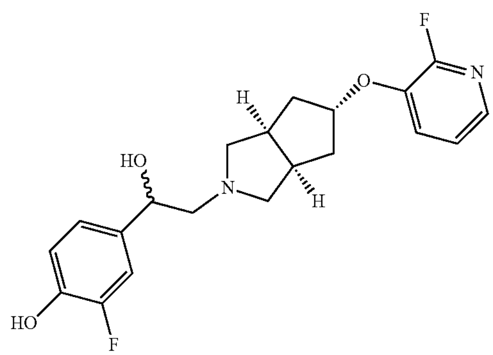 [SMILES: Oc1ccc(C(O)CN2C[C@H]3C[C@H](Oc4cccnc4F)C[C@H]3C2)cc1F] | 2.17E-08 | ++++ |
| 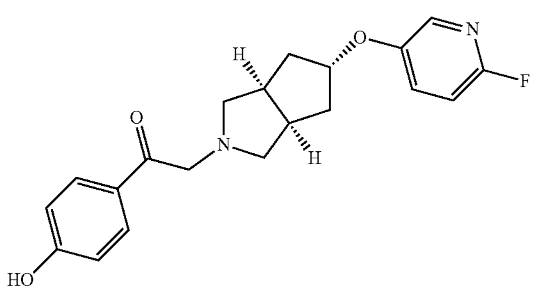 [SMILES: O=C(CN1C[C@H]2C[C@H](Oc3ccc(F)nc3)C[C@H]2C1)c1ccc(O)cc1] | 5.52E-08 | ++++ |
| 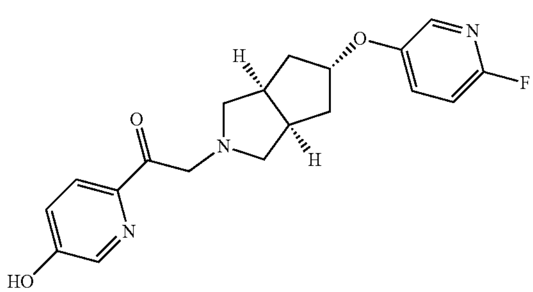 [SMILES: O=C(CN1C[C@H]2C[C@H](Oc3ccc(F)nc3)C[C@H]2C1)c1ccc(O)cn1] | 1.00E-05 | + |

TABLE 8-continued

| NR2B NAM Assay |||
|---|---|---|
| Structure | NR2B NAM IC$_{50}$ (M) | Activity Category |
| *(structure)* | 7.41E−08 | ++++ |
| *(structure)* | 2.19E−07 | +++ |
| *(structure)* | 1.12E−07 | +++ |
| *(structure)* | 1.15E−06 | ++ |
| *(structure)* | 1.08E−06 | ++ |

TABLE 8-continued

| NR2B NAM Assay | | |
|---|---|---|
| Structure | NR2B NAM IC$_{50}$ (M) | Activity Category |
| [structure: 4-hydroxyphenyl ketone-CH$_2$-N-octahydrocyclopenta[c]pyrrole-O-2,4-difluorophenyl] | 4.11E−08 | ++++ |
| [structure: 5-hydroxypyridin-2-yl ketone-CH$_2$-N-octahydrocyclopenta[c]pyrrole-O-2-fluoro-4-methylphenyl] | 2.25E−07 | +++ |
| [structure: 4-hydroxyphenyl ketone-CH$_2$-N-octahydrocyclopenta[c]pyrrole-O-2,6-difluorophenyl] | 2.93E−08 | ++++ |
| [structure: 5-hydroxypyridin-2-yl-CH(OH)-CH$_2$-N-octahydrocyclopenta[c]pyrrole-O-2,6-difluorophenyl] | 9.60E−09 | ++++ |
| [structure: 4-hydroxyphenyl-CH(OH)-CH$_2$-N-octahydrocyclopenta[c]pyrrole-O-2,4-difluorophenyl] | 8.62E−09 | ++++ |

TABLE 8-continued

| NR2B NAM Assay | | |
|---|---|---|
| Structure | NR2B NAM IC$_{50}$ (M) | Activity Category |
| | 1.39E-07 | +++ |
| | 1.49E-07 | +++ |
| | 4.41E-09 | ++++ |
| | 4.35E-07 | +++ |
| | 1.00E-05 | + |
| | 1.00E-05 | + |

TABLE 8-continued

| NR2B NAM Assay | | |
|---|---|---|
| Structure | NR2B NAM IC$_{50}$ (M) | Activity Category |
| | 1.63E−07 | +++ |
| | 5.47E−07 | +++ |
| | 6.31E−07 | +++ |
| | 5.69E−07 | +++ |
| | 3.08E−07 | +++ |
| | 6.81E−09 | ++++ |

TABLE 8-continued

| | NR2B NAM Assay | |
|---|---|---|
| Structure | NR2B NAM IC$_{50}$ (M) | Activity Category |
| (structure) | 1.44E−08 | ++++ |
| (structure) | 3.78E−06 | ++ |
| (structure) | 2.34E−08 | ++++ |
| (structure) | 2.43E−07 | +++ |
| (structure) | 1.77E−07 | +++ |
| (structure) | 5.08E−08 | ++++ |
| (structure) | 1.17E−07 | +++ |

TABLE 8-continued
| NR2B NAM Assay | | |
|---|---|---|
| Structure | NR2B NAM IC$_{50}$ (M) | Activity Category |
| 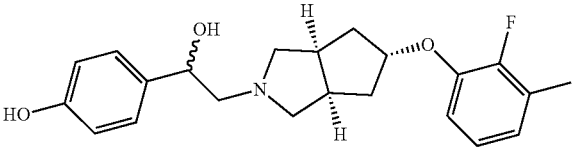 [SMILES: Cc1cccc(O[C@H]2C[C@@H]3CN(CC(O)c4ccc(O)cc4)C[C@@H]3C2)c1F] | 7.26E−08 | ++++ |
| 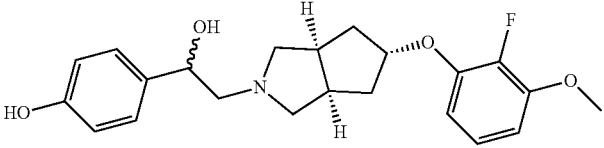 [SMILES: COc1cccc(O[C@H]2C[C@@H]3CN(CC(O)c4ccc(O)cc4)C[C@@H]3C2)c1F] | 7.77E−08 | ++++ |
| 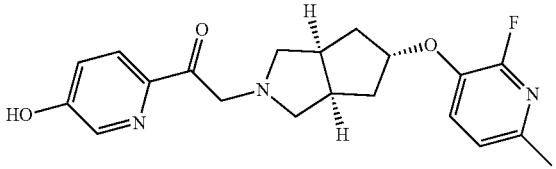 [SMILES: Cc1ccc(O[C@H]2C[C@@H]3CN(CC(=O)c4ccc(O)cn4)C[C@@H]3C2)c(F)n1] | 1.00E−05 | + |
| 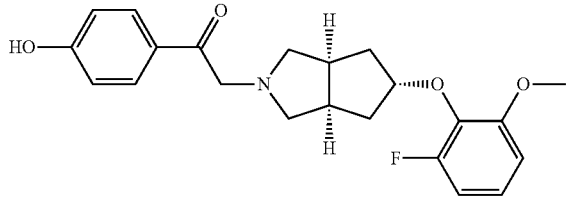 [SMILES: COc1cccc(F)c1O[C@H]1C[C@@H]2CN(CC(=O)c3ccc(O)cc3)C[C@@H]2C1] | 4.66E−07 | +++ |
| 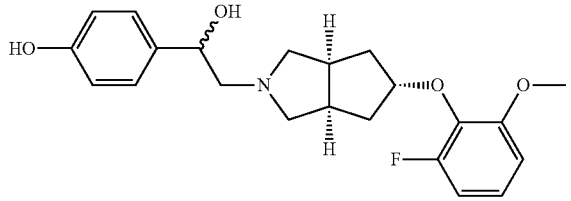 [SMILES: COc1cccc(F)c1O[C@H]1C[C@@H]2CN(CC(O)c3ccc(O)cc3)C[C@@H]2C1] | 2.49E−07 | +++ |
| 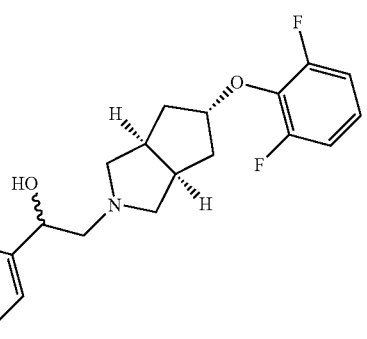 | 2.63E−08 | ++++ |

TABLE 8-continued

| Structure | NR2B NAM IC$_{50}$ (M) | Activity Category |
|---|---|---|
| 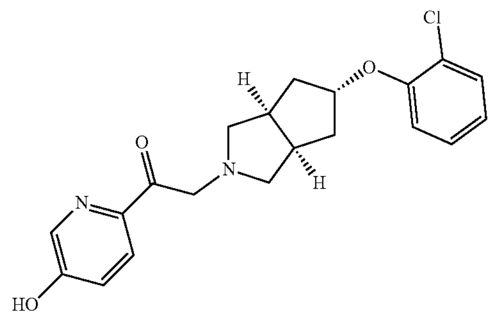 [SMILES: O=C(CN1C[C@H]2C[C@H](Oc3ccccc3Cl)C[C@H]2C1)c1ccc(O)cn1] | 1.66E−06 | ++ |
| 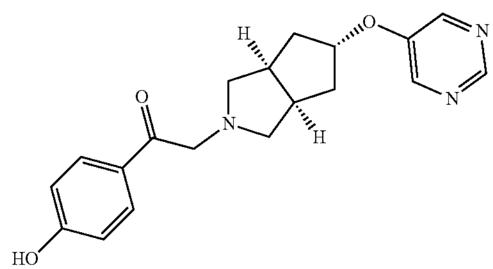 [SMILES: O=C(CN1C[C@H]2C[C@H](Oc3cncnc3)C[C@H]2C1)c1ccc(O)cc1] | 1.04E−06 | ++ |
| 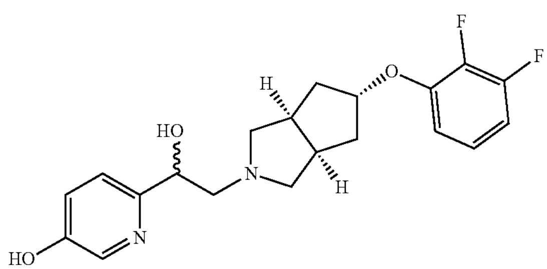 [SMILES: Oc1ccc(C(O)CN2C[C@H]3C[C@H](Oc4cccc(F)c4F)C[C@H]3C2)nc1] | 8.78E−09 | ++++ |
| 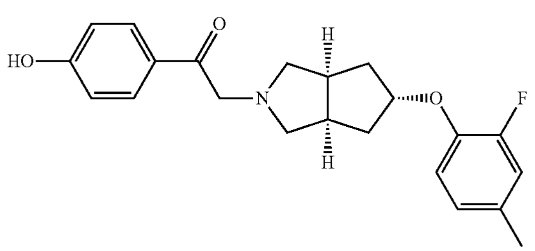 [SMILES: Cc1ccc(O[C@H]2C[C@@H]3CN(CC(=O)c4ccc(O)cc4)C[C@@H]3C2)c(F)c1] | 2.10E−07 | +++ |
| 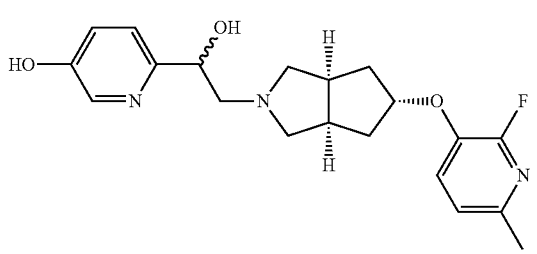 [SMILES: Cc1ccc(O[C@H]2C[C@@H]3CN(CC(O)c4ccc(O)cn4)C[C@@H]3C2)c(F)n1] | 6.02E−08 | ++++ |

TABLE 8-continued

| NR2B NAM Assay | | |
|---|---|---|
| Structure | NR2B NAM IC$_{50}$ (M) | Activity Category |
| | 3.80E−08 | ++++ |
| | 2.67E−08 | ++++ |
| | 9.36E−09 | ++++ |
| | 3.50E−06 | ++ |
| | 4.37E−06 | ++ |
| | 1.00E−05 | + |

TABLE 8-continued

NR2B NAM Assay

| Structure | NR2B NAM IC$_{50}$ (M) | Activity Category |
|---|---|---|
| (structure) | 1.00E−05 | + |
| (structure) | 2.30E−07 | +++ |
| (structure) | 7.40E−08 | ++++ |
| (structure) | 1.92E−08 | ++++ |
| (structure) | 1.13E−07 | +++ |

TABLE 8-continued
NR2B NAM Assay
| Structure | NR2B NAM IC$_{50}$ (M) | Activity Category |
|---|---|---|
| 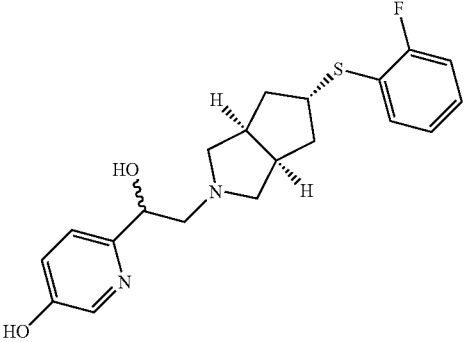 [SMILES: Oc1ccc(C(O)CN2C[C@H]3C[C@H](Sc4ccccc4F)C[C@H]3C2)nc1] | 2.06E−08 | ++++ |
| 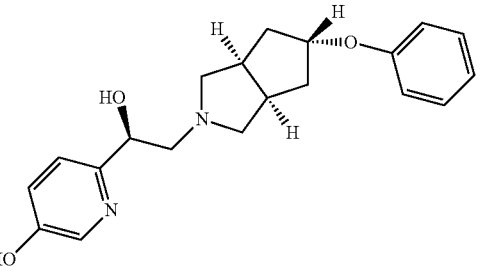 | 5.25E−09 | ++++ |
| 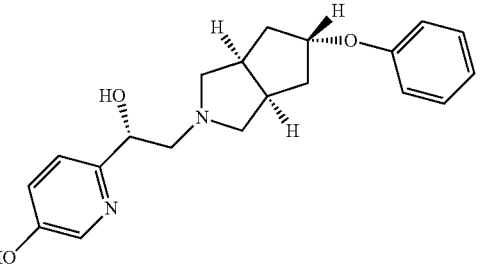 | 5.24E−09 | ++++ |
| 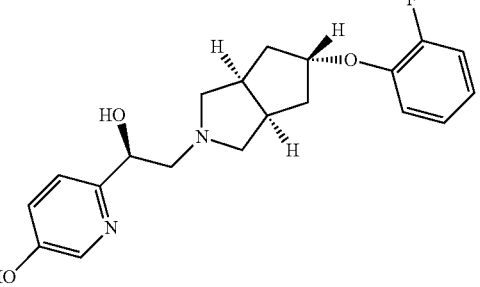 | 8.30E−09 | ++++ |
| 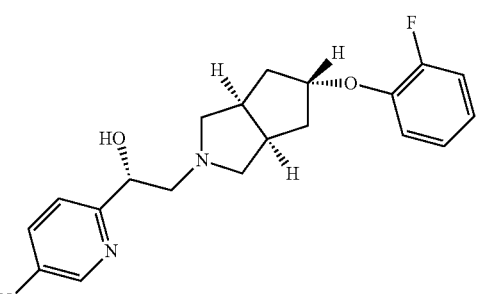 | 8.50E−09 | ++++ |

TABLE 8-continued

NR2B NAM Assay

| Structure | NR2B NAM IC$_{50}$ (M) | Activity Category |
|---|---|---|
| 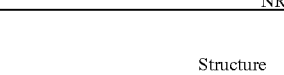 | 2.00E−08 | ++++ |

Example 20: PGP Efflux Assay

PgP is a protein present at the blood brain barrier and its substrates are subjected to efflux from the barrier, thereby limiting their distribution or partitioning into the CNS.

MDCK cells transfected with MDR1 (MDCK-MDR1) were seeded onto Costar permeable support plates at a density of approximately 260,000 cell/cm$^2$, and monolayers were ready for experimental use four days later. Compounds dissolved at 10 mM in 100% DMSO were diluted for experiments and prepared in transport buffer (Hank's Balanced Salt Solution, 0.02% bovine serum albumin, 10 mM HEPES, pH 7.4). Compounds were tested at 10 µM concentration and independently measured in two directions (apical to basal and basal to apical) in triplicate. Prior to initiation of the experiment, cells were washed three times in transport buffer. Monolayer efflux studies were conducted at 37° C. for 120 minutes. Markers for membrane integrity (bestatin) and efflux (quinidine) were included in each experiment. Experimental samples plus internal standard (glyburide) were centrifuged for 10 minutes at 4000 rpm at 4° C. The samples were then subject to analysis by mass spectroscopy using a RapidFire High-throughput MS System (Agilent RapidFire coupled to Sciex ABI4000 mass spectrometer). The apparent permeability (P$_{app}$) was calculated with the equation P$_{app}$=V$_r$/AC$_0$×(C$_r$/t), where A is membrane surface area, C$_0$ is donor drug concentration at t=0, and C$_r$ is the concentration of the receiver compartment at time (t) 120 minutes. If the ratio of Papp in the basal to apical to the Papp apical to basal direction exceeds two in the assay (e.g. P$_{app\ B>A}$/P$_{appA>B}$>2), the molecule is considered to be a substrate of MDR1 (P-gP).

Certain compounds of the present invention have little PGP efflux liability and are readily partitioned across the blood brain barrier.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:
1. A compound of formula I:

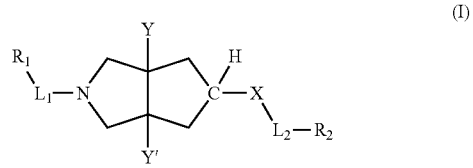

(I)

or a pharmaceutically acceptable salt, tautomer, or stereoisomer thereof
wherein:
L$_1$ is straight or branched C$_1$-C$_5$ alkylene substituted with OH;
each R$_{10}$ and R$_{10}$' is independently selected from the group consisting of H;
C$_1$-C$_6$ alkyl optionally substituted with one or more substituents selected from the group consisting of OH, O—C$_1$-C$_5$ alkyl, OPO$_3^{-2}$M$_2$, OP(O)(OH)$_2$, OC(O) alkyl, and OC(O)O-alkyl where M is a monovalent metal cation; and
cycloalkyl optionally substituted with one or more substituents selected from the group consisting of OH and O—C$_1$-C$_5$ alkyl provided that no more than one oxygen is attached to any carbon; or R$_{10}$ and R$_{10}$', together with the nitrogen to which they are attached, may form a heterocycle selected from the group consisting of oxetanyl, azetadinyl, tetrahydrofuranyl, pyrrolidinyl, oxazolinyl, oxazolidinyl, thiazolinyl, thiazolidinyl, pyranyl, thiopyranyl, tetrahydropyranyl, dioxalinyl, piperidinyl, morpholinyl, thiomorpholinyl, thiomorpholinyl S-oxide, thiomorpholinyl S-dioxide, piperazinyl, azepinyl, oxepinyl, diazepinyl, tropanyl, and homotropanyl;
R$_1$ is cycloalkyl, aryl, or heteroaryl, any of which optionally substituted with one or more substituents selected from the group consisting of OH, CN, halogen, —C$_1$-C$_6$alkylaryl, —O—C$_1$-C$_6$alkylaryl, O—R$_{10}$, OPO$_3^{-2}$M$_2$, OP(O)(OH)$_2$, SH, S—R$_{10}$, C$_1$-C$_5$ alkyl, branched alkyl, NH$_2$, NHR$_{10}$, NHS(O)$_2$R$_{10}$, N(R$_{10}$)(R$_{10}$'), and NHCOR$_{10}$ where M is a monovalent metal cation;
X is selected from O, S, —S(O)—, and —S(O)$_2$—;
Y and Y' are independently H, halogen, or C$_1$-C$_5$ alkyl;
L$_2$ is a bond, —(CH$_2$)$_n$— or —(CHR$_{11}$)$_n$—;
each R$_{11}$ is independently selected from the group consisting of H, —C$_1$-C$_5$ alkylenyl-, —CO—C$_1$-C$_5$alkylenyl-, and -alkylenyl-CO-alkylenyl-;

R₂ is phenyl, naphthyl, heteroaryl or bicyclic heteroaryl, each of which is optionally substituted with one or more substituents selected from the group consisting of halogen, OH, $C_1$-$C_6$alkyl, $OR_{10}$, CN, $NH_2$, $NHR_{10}$, $N(R_{10})(R_{10}')$, -nitro, SH, $SR_{10}$, $SOR_{10}$, $SO_2R_{10}$, $SO_2NHR_{10}$, $SO_2N(R_{10})(R_{10}')$, $CONH_2$, $CONR_{10}$, and $CON(R_{10})(R_{10}')$; and n is 1, 2, or 3;

wherein cycloalkyl is a monocyclic saturated carbon ring containing 3-18 carbon atoms, and wherein heteroaryl is a monocyclic, bicyclic or polycyclic aromatic radical of 5 to 10 ring atoms and containing one or more ring heteroatoms selected from N, O, or S, the remaining ring atoms being C, and when containing two fused rings, the aryl groups may have an unsaturated or partially saturated ring fused with a fully saturated ring.

2. The compound of claim 1, or a pharmaceutically acceptable salt, tautomer, or stereoisomer thereof, wherein $L_2$ is a bond and $R_2$ is phenyl optionally substituted with one or more halogen, OH, $OR_{10}$, CN, $NH_2$, $NHR_{10}$, $N(R_{10})(R_{10}')$, SH, $SR_{10}$, $SOR_{10}$, $SO_2R_{10}$, $SO_2NHR_{10}$, $SO_2N(R_{10})(R_{10}')$, $CONH_2$, $CONR_{10}$, $CON(R_{10})(R_{10}')$.

3. The compound of claim 2, or a pharmaceutically acceptable salt, tautomer, or stereoisomer thereof, wherein X is O.

4. The compound of claim 2, or a pharmaceutically acceptable salt, tautomer, or stereoisomer thereof, wherein $R_1$ is aryl or heteroaryl each of which is substituted with one or more substituents selected from the group consisting of OH, halogen, $OR_{10}$, SH, $SR_{10}$, $NH_2$, $NHR_{10}$ and $NHCOR_{10}$.

5. The compound of claim 2, or a pharmaceutically acceptable salt, tautomer, or stereoisomer thereof, wherein Y and Y' are hydrogen.

6. A compound of formula Ia:

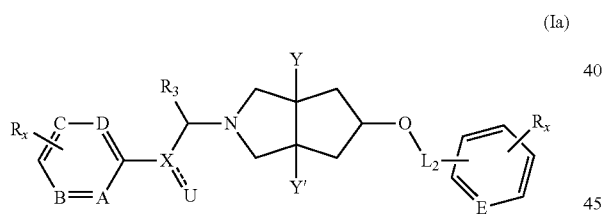

(Ia)

or a pharmaceutically acceptable salt, tautomer, or stereoisomer thereof wherein:

A, B, C, D, and E are independently N or $CR_x$;

------ is an optional double bond;

X is CH or C;

U is OH or O;

Y and Y' are independently H, halogen, or C1-C6 alkyl;

$R_3$ is H;

each $R_x$ is independently H, $C_1$-$C_6$ alkyl, halogen, —OH, —$NHS(O)_2R_{10}$, or —$OC_1$-$C_6$ alkyl;

$R_{10}$ is selected from the group consisting of H; $C_1$-$C_6$ alkyl optionally substituted with one or more substituents selected from the group consisting of OH, O—$C_1$-$C_5$ alkyl, $OPO_3^{-2}M_2$, $OP(O)(OH)_2$, OC(O) alkyl, and OC(O)O-alkyl where M is a monovalent metal cation; and cycloalkyl optionally substituted with one or more substituents selected from the group consisting of OH and O—$C_1$-$C_5$ alkyl provided that no more than one oxygen is attached to any carbon; and $L_2$ is a bond or $(CH_2)_n$, wherein n is 1 or 2.

7. A compound of claim 1, or a pharmaceutically acceptable salt, tautomer, or stereoisomer thereof, selected from the group consisting of:

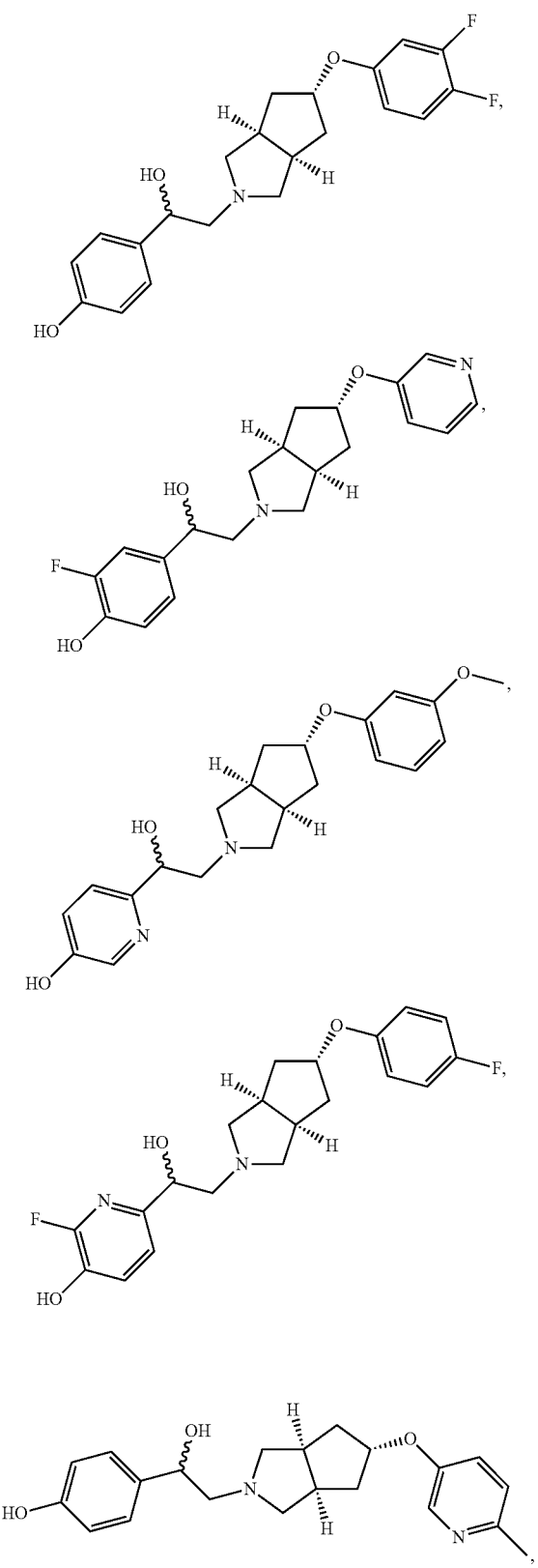

-continued
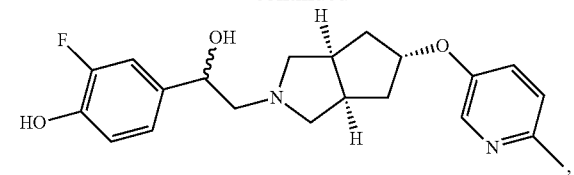
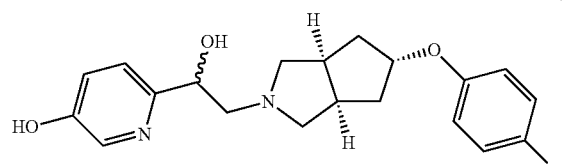
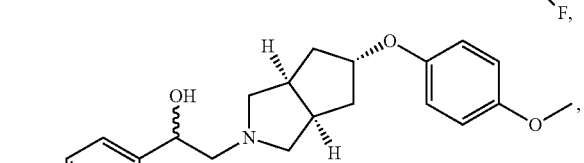
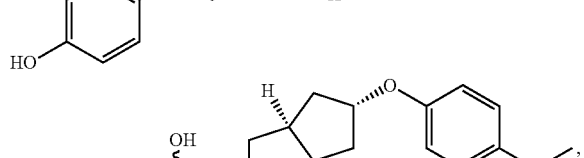
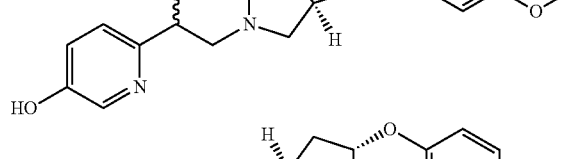
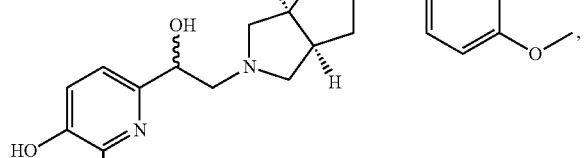
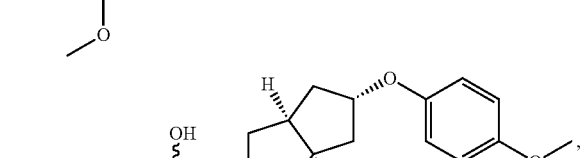
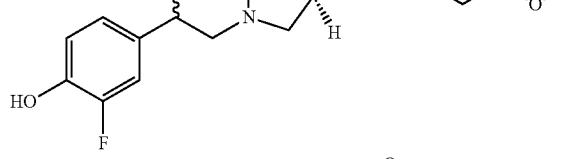
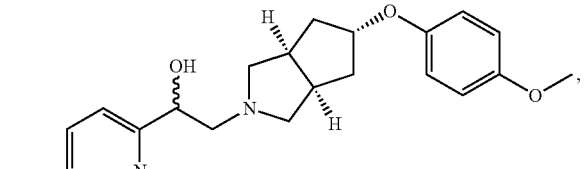
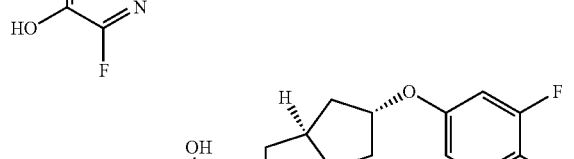
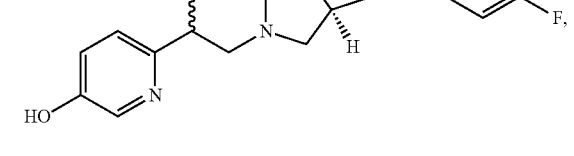
-continued
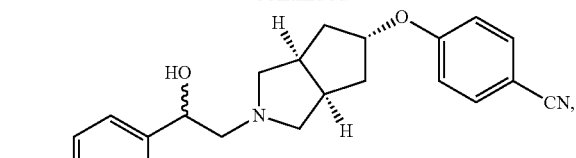
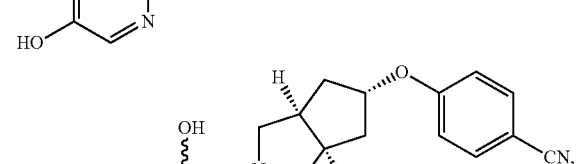
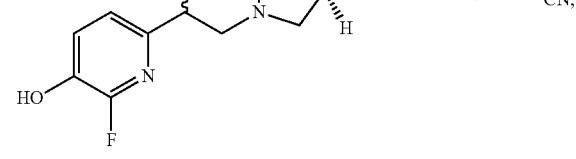
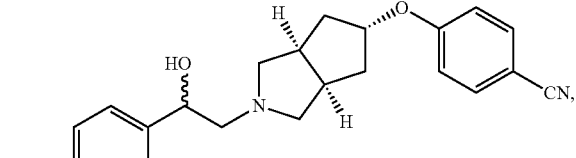
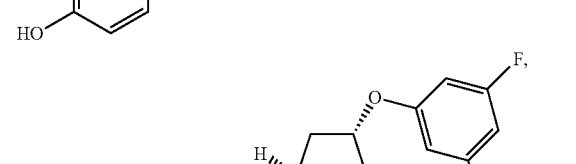
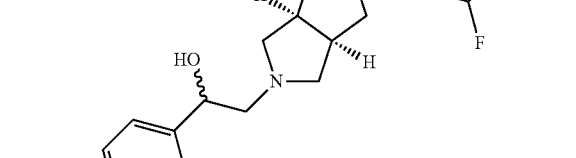
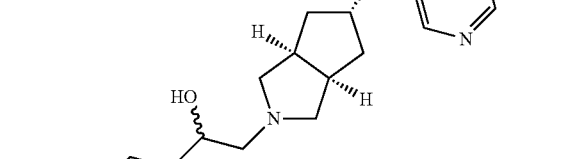
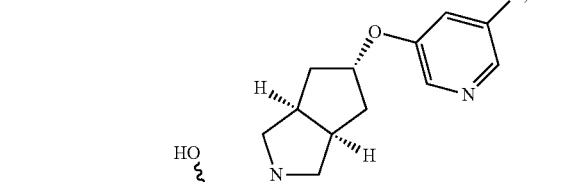
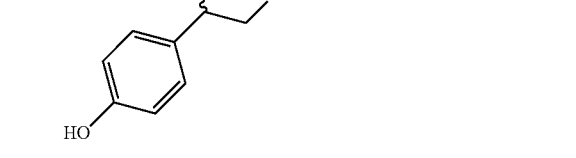

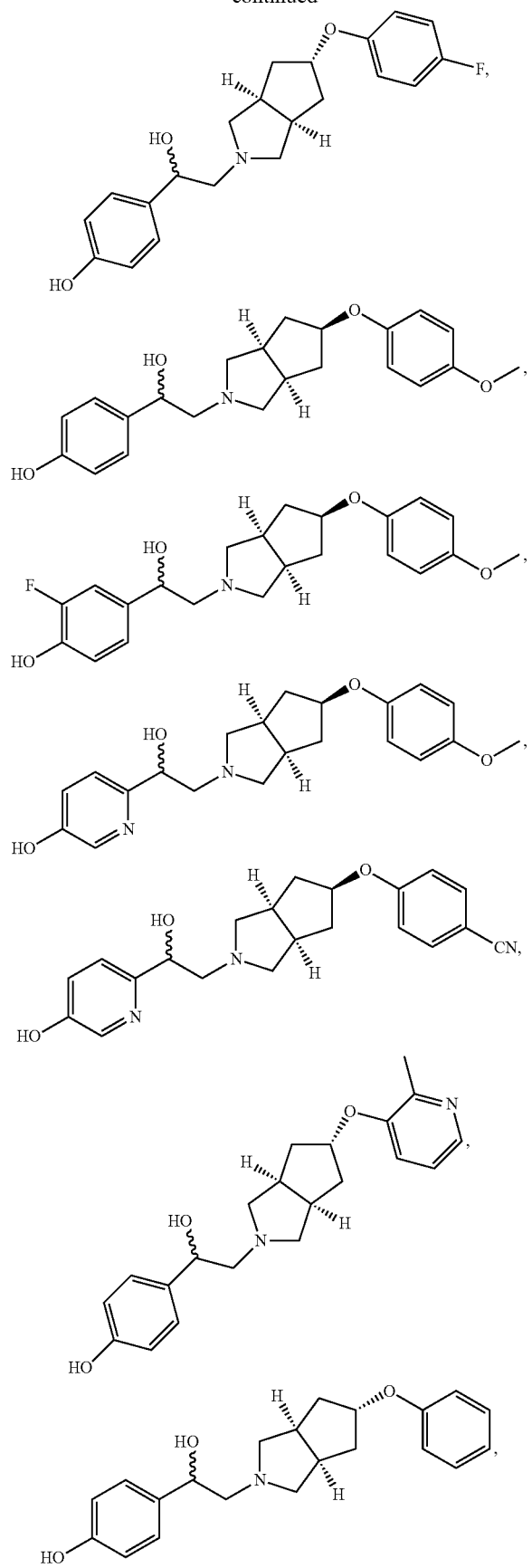
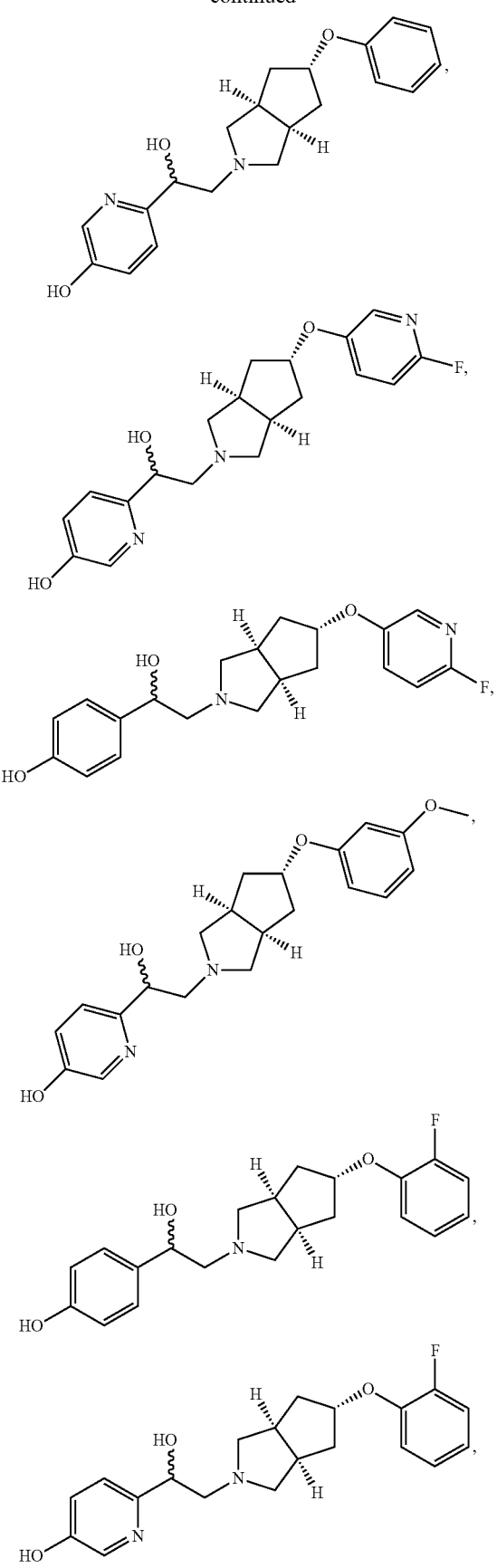

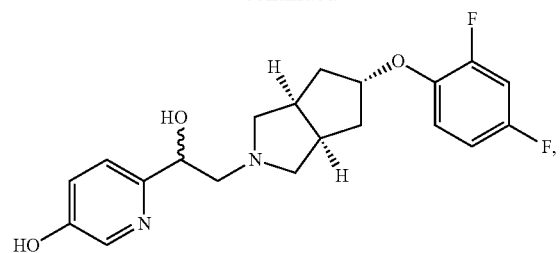
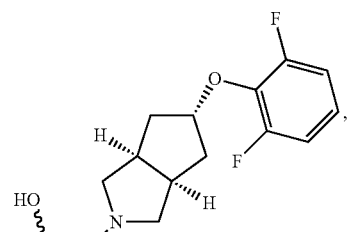
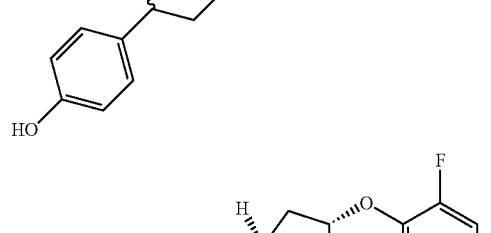
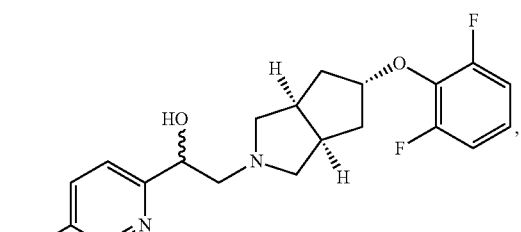
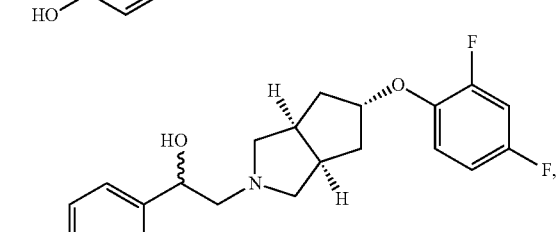
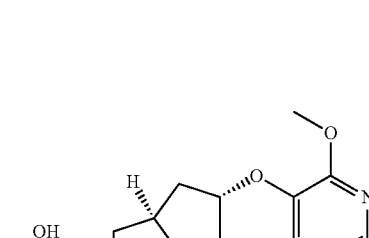
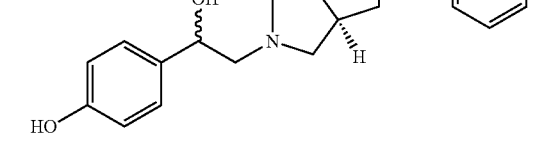
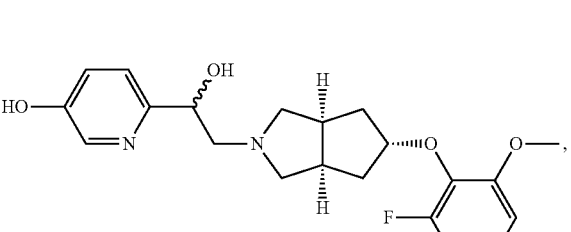
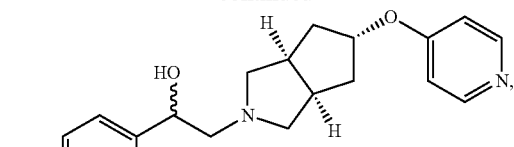
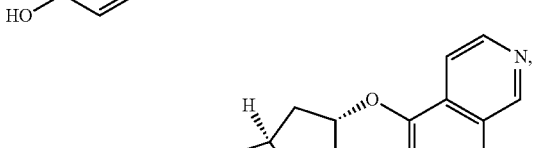
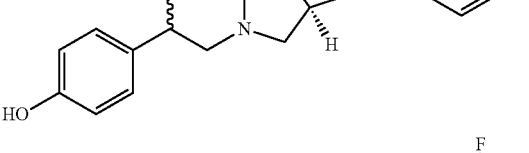
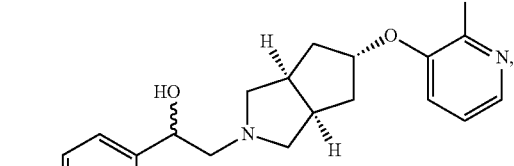
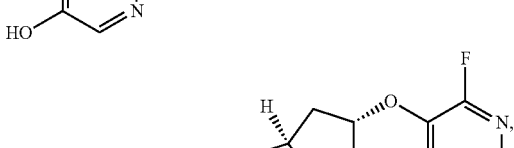
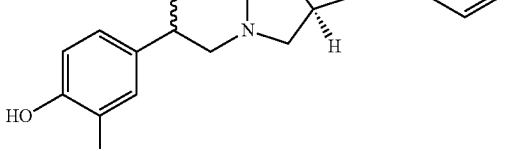
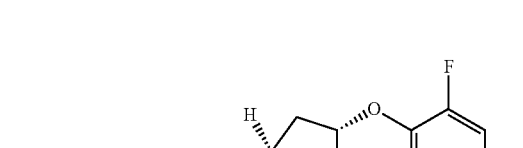
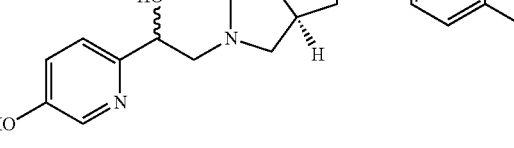
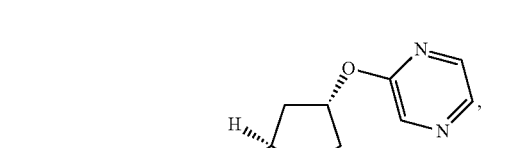
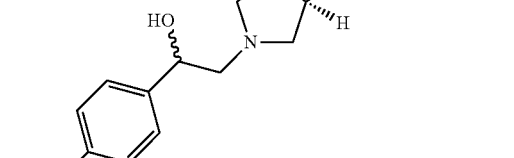

-continued
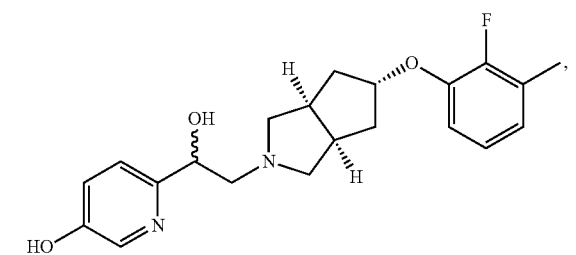
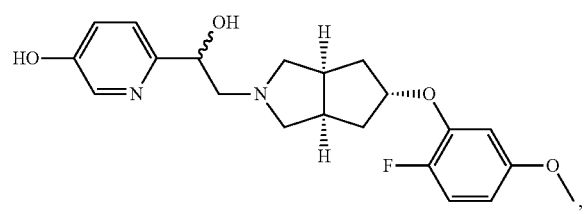
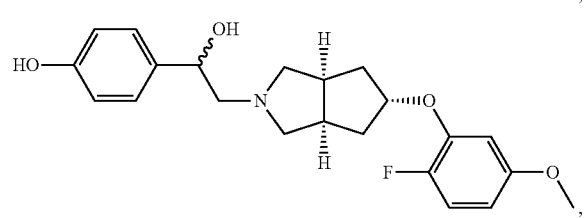
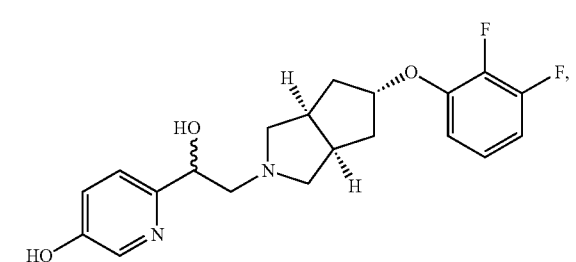
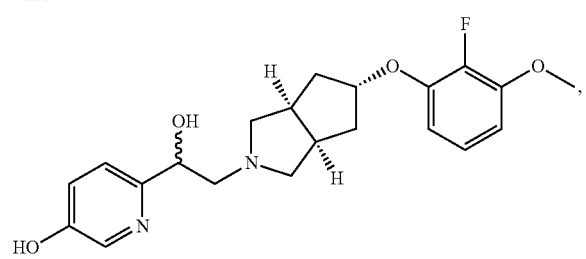
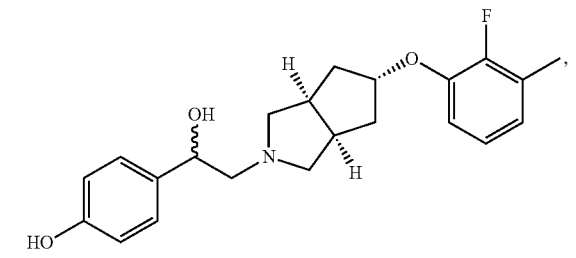
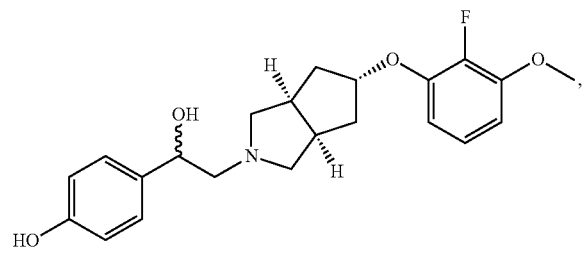
-continued
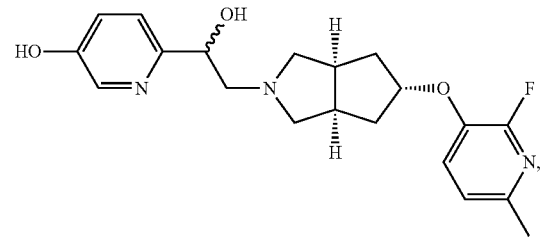
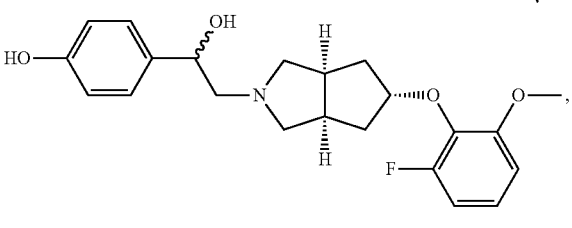
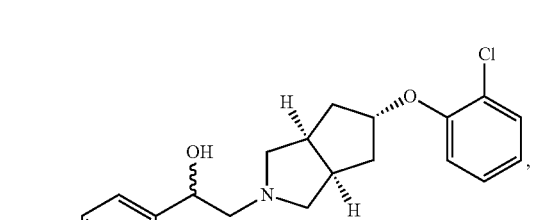
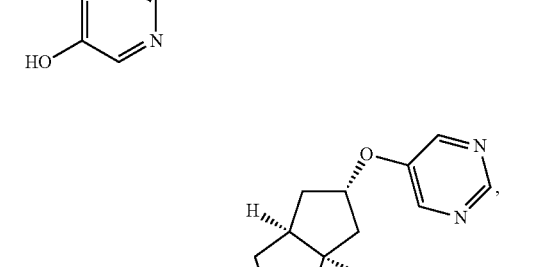
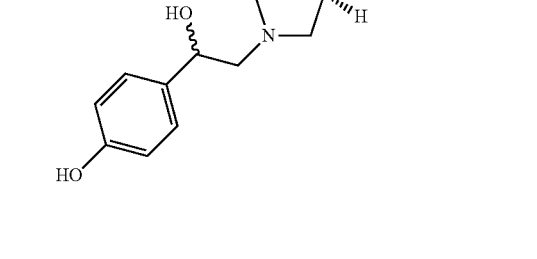
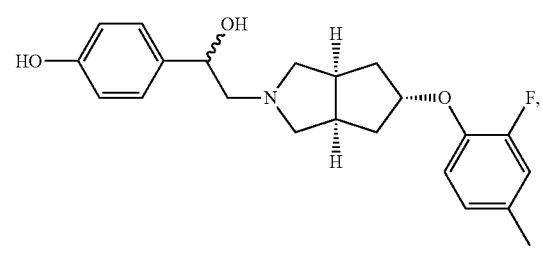
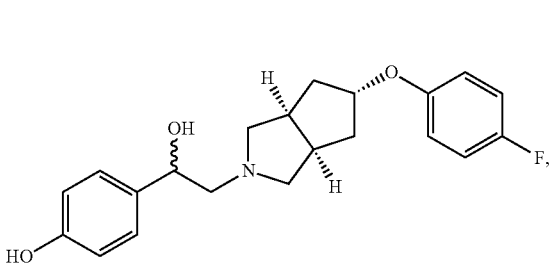

197
-continued
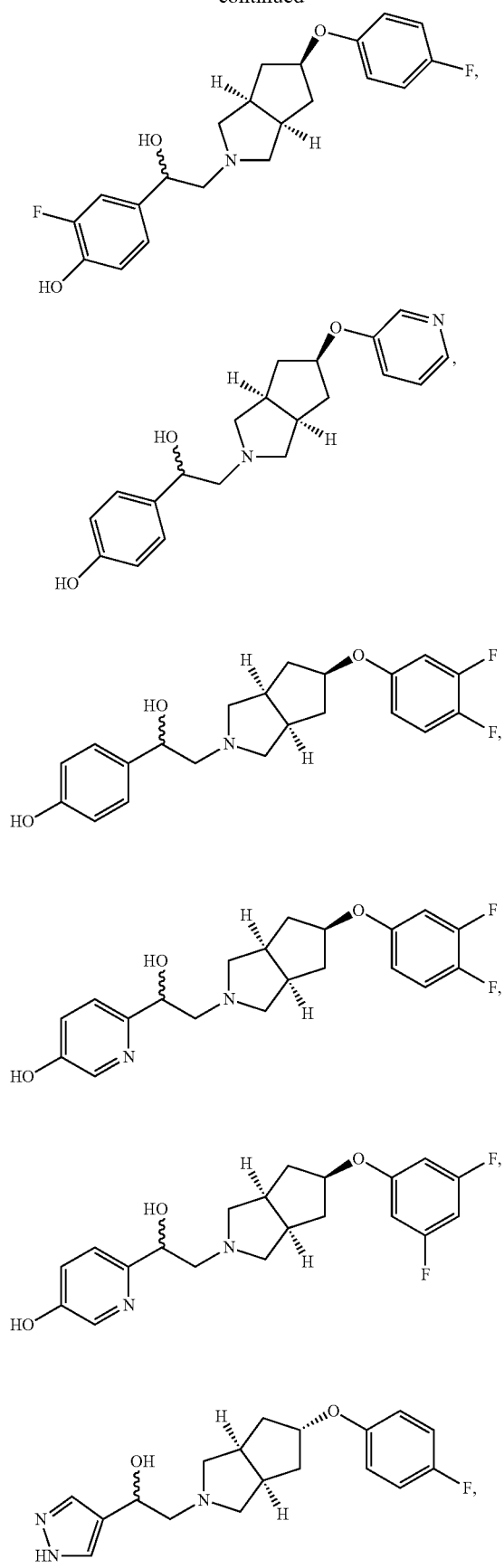
198
-continued
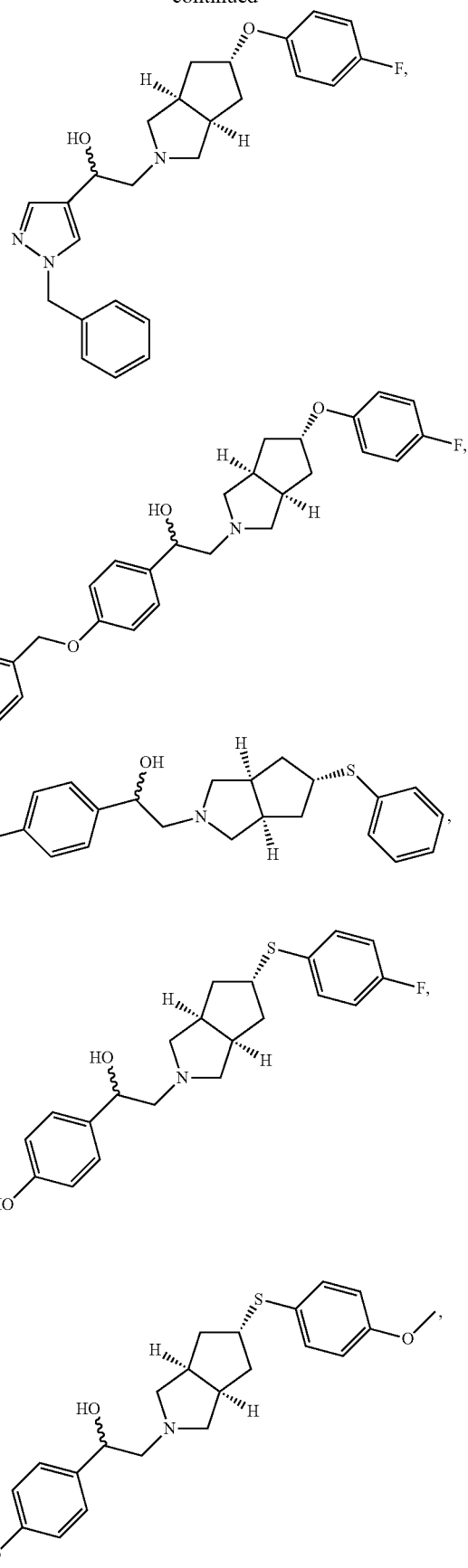

-continued

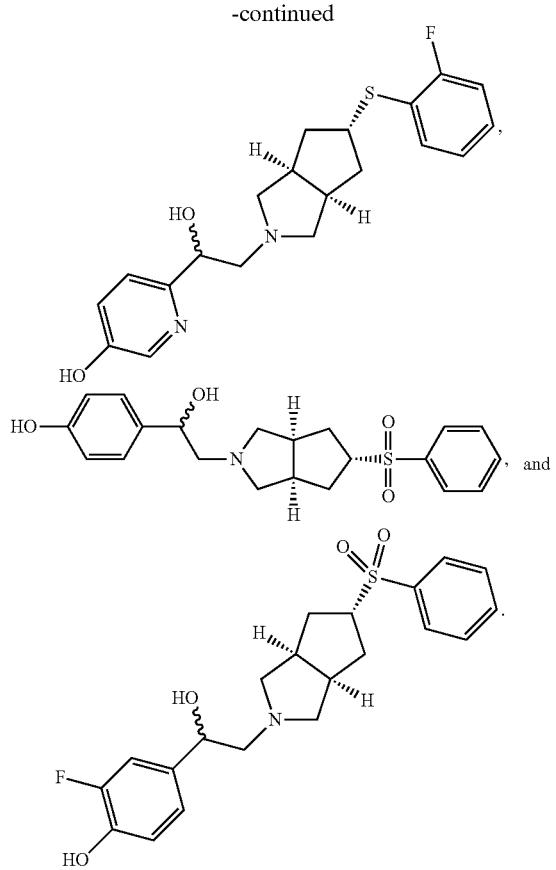

, and

8. A pharmaceutical composition comprising a compound of claim 1, or a pharmaceutically acceptable salt, tautomer, or stereoisomer thereof, and a pharmaceutically acceptable carrier.

9. The compound of claim 7, or a pharmaceutically acceptable salt thereof, which is

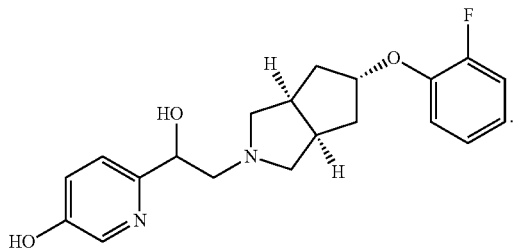 [SMILES: Oc1ccc(C(O)CN2C[C@H]3C[C@H](Oc4ccccc4F)C[C@H]3C2)nc1]

10. The compound of claim 7, or a pharmaceutically acceptable salt thereof, which is

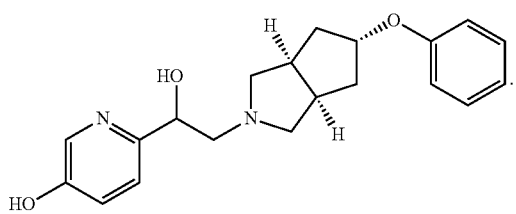 [SMILES: Oc1ccc(C(O)CN2C[C@H]3C[C@H](Oc4ccccc4)C[C@H]3C2)nc1]

11. A compound of the following structure:

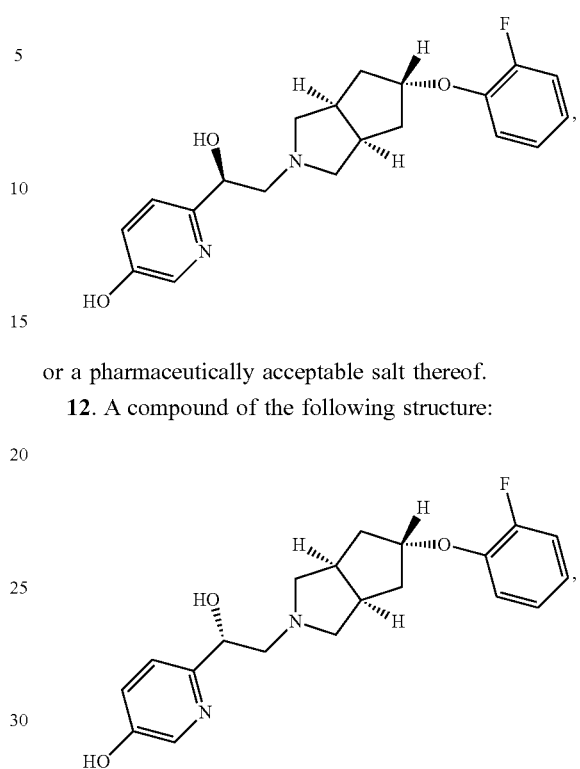

or a pharmaceutically acceptable salt thereof.

12. A compound of the following structure:

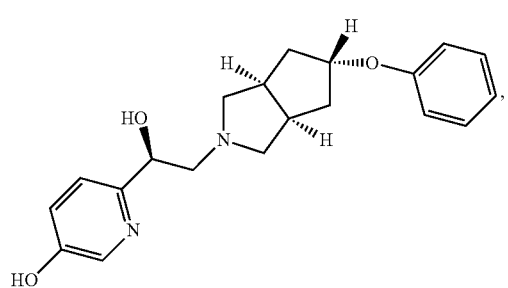 [SMILES: Oc1ccc([C@@H](O)CN2C[C@H]3C[C@H](Oc4ccccc4)C[C@H]3C2)nc1]

or a pharmaceutically acceptable salt thereof.

13. A compound of the following structure:

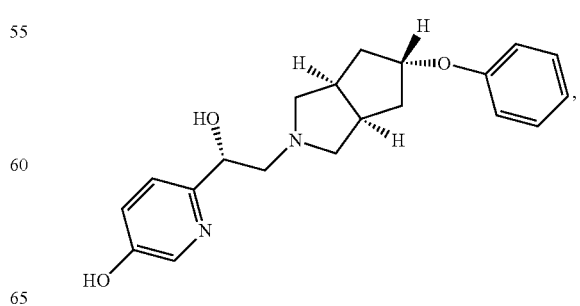

or a pharmaceutically acceptable salt thereof.

14. A compound of the following structure:

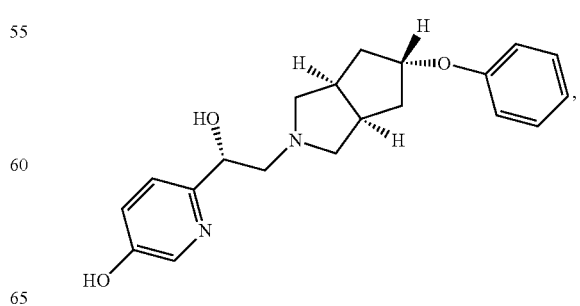

or a pharmaceutically acceptable salt thereof.

15. A compound of claim 6, or a pharmaceutically acceptable salt, tautomer, or stereoisomer thereof, selected from the group consisting of:
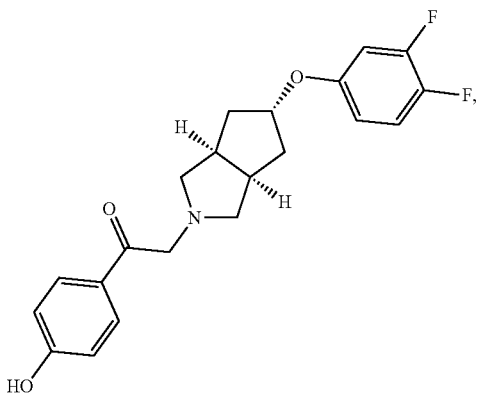
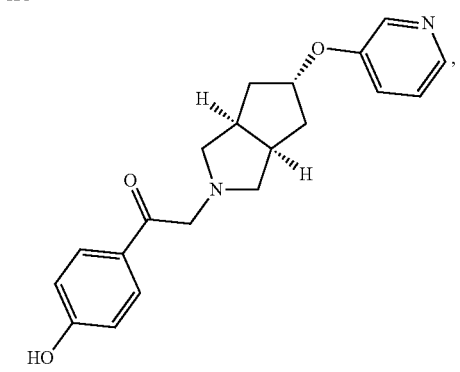
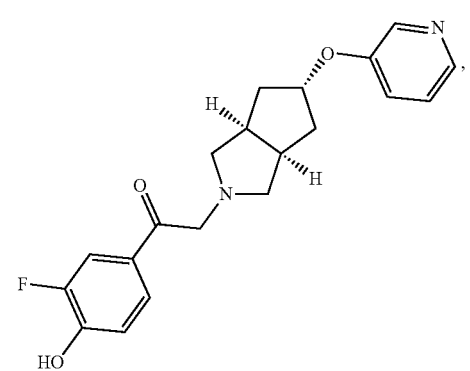
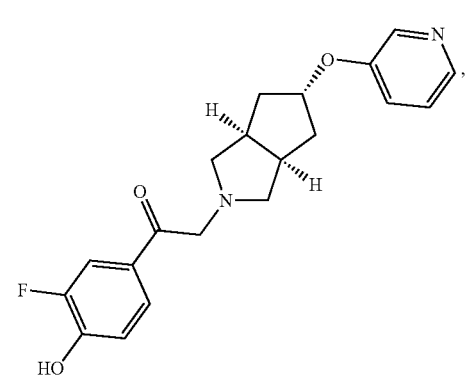
-continued
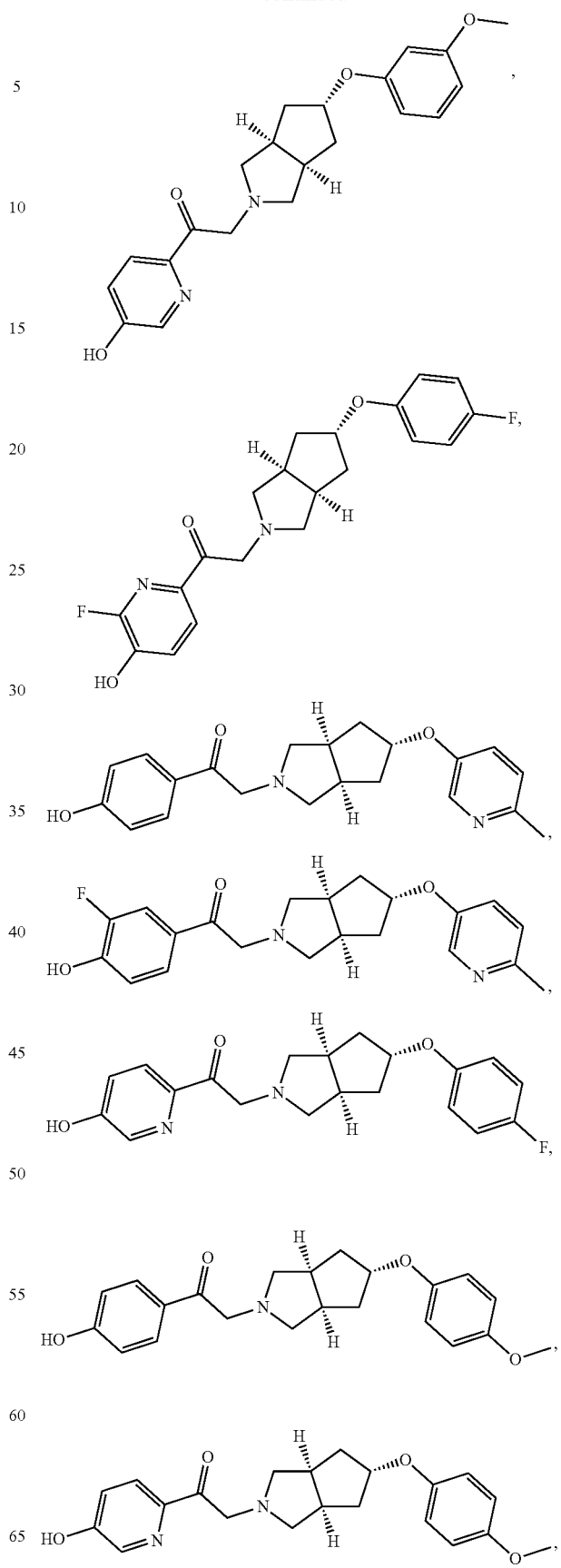

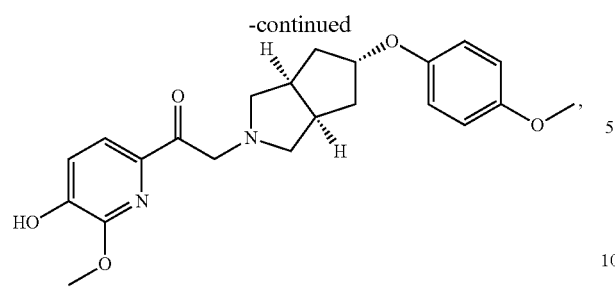
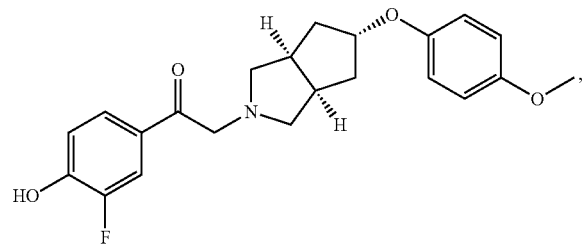
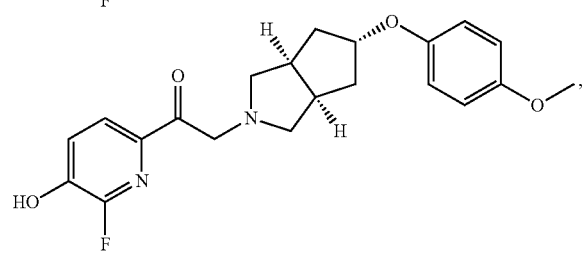
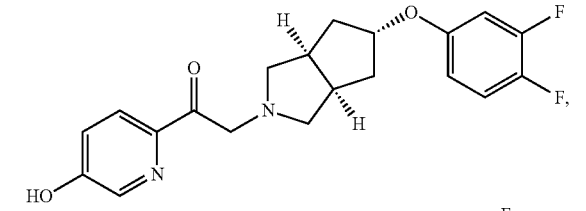
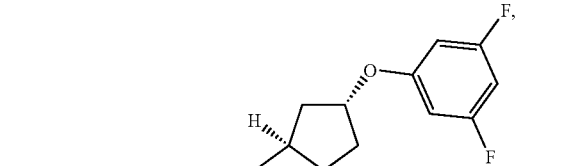
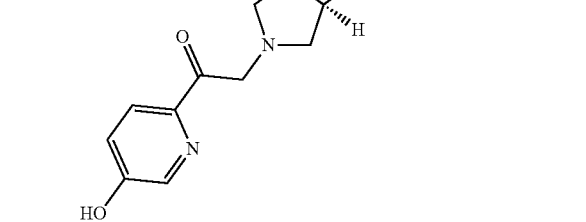
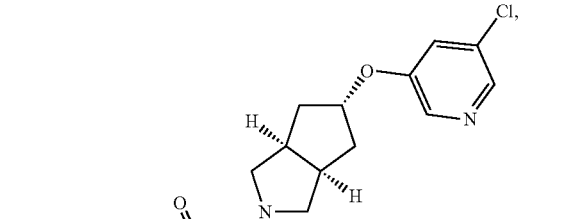
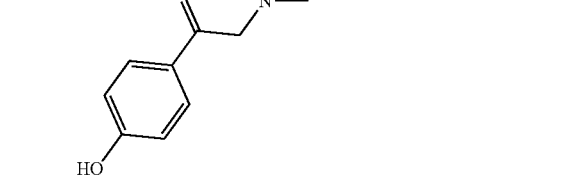
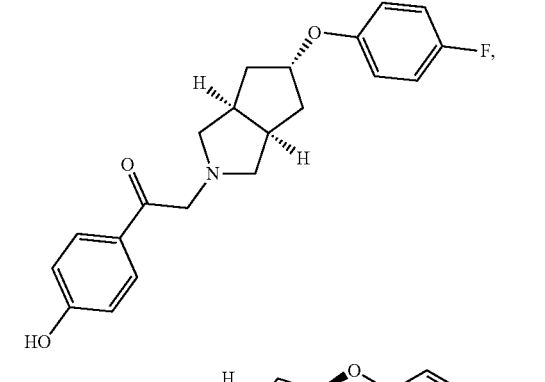
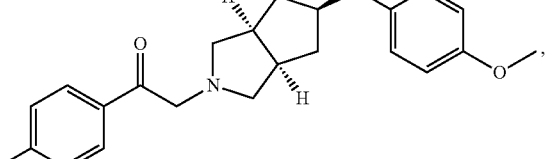
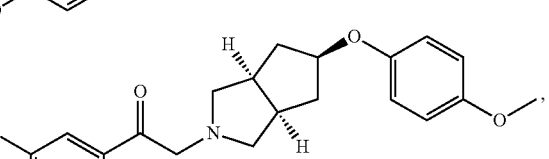
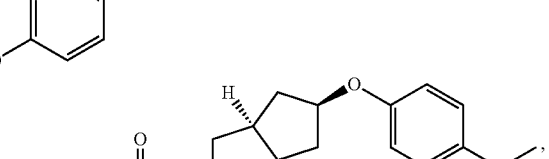
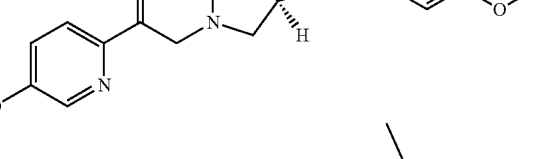
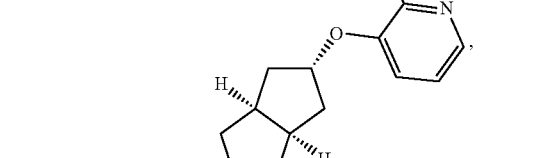
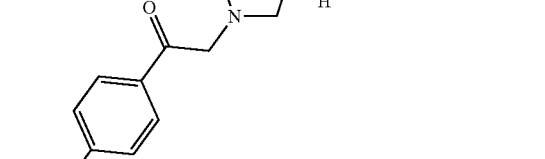
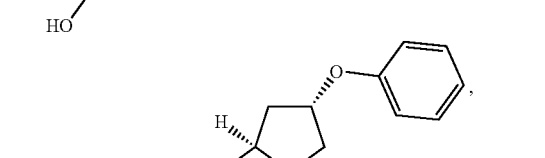
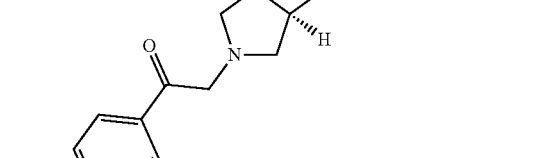

-continued
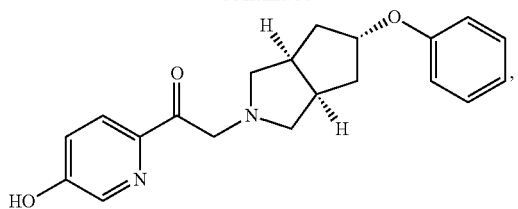
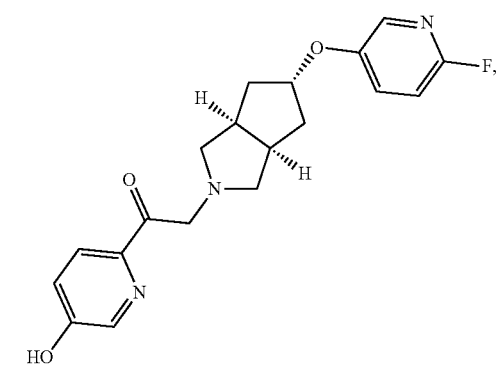
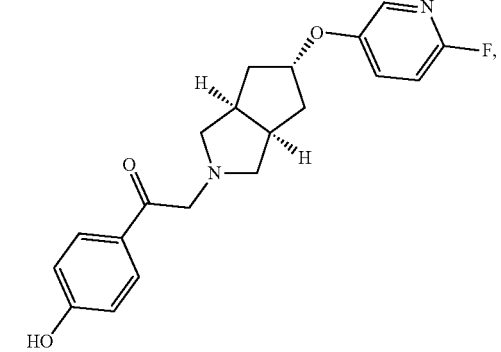
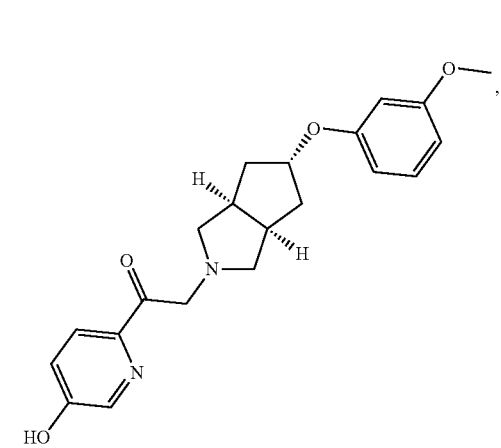
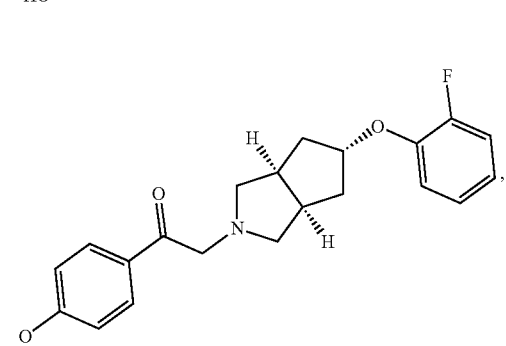
-continued
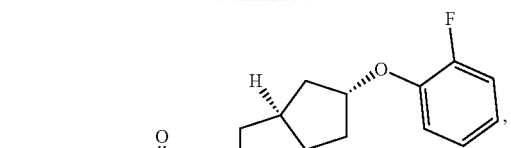
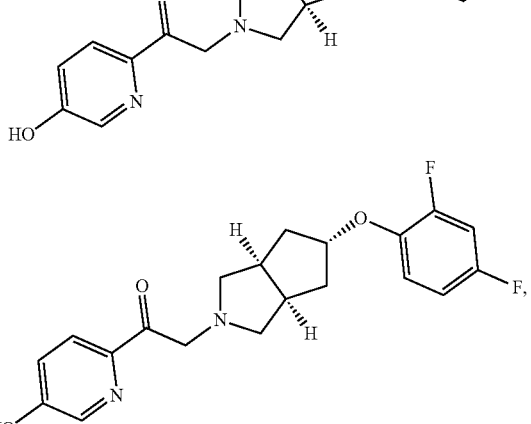
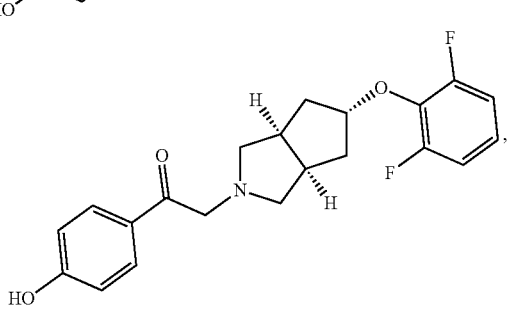
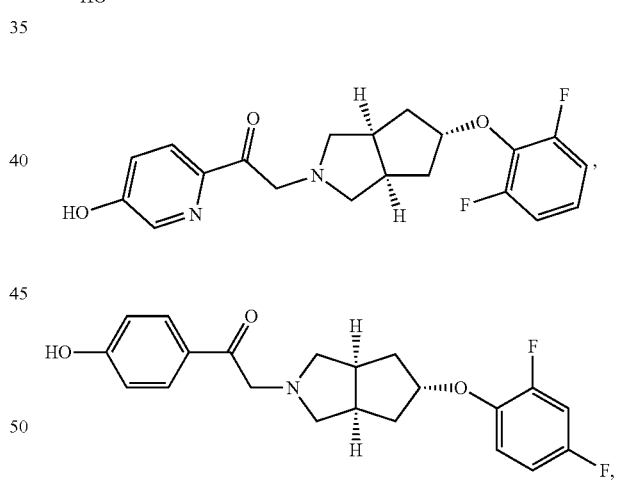
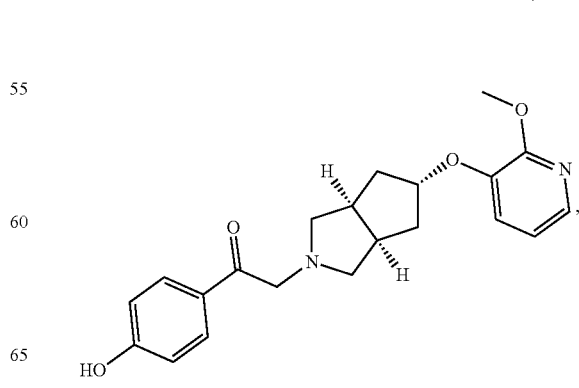

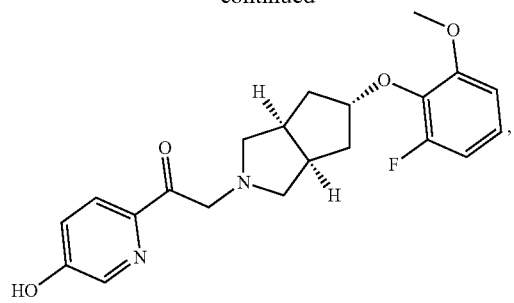
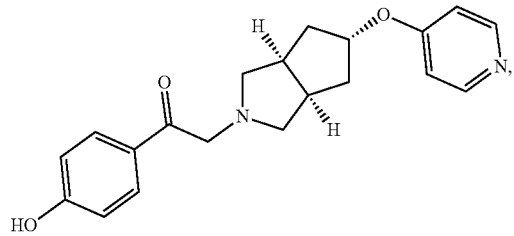
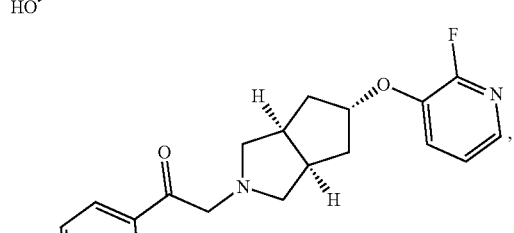
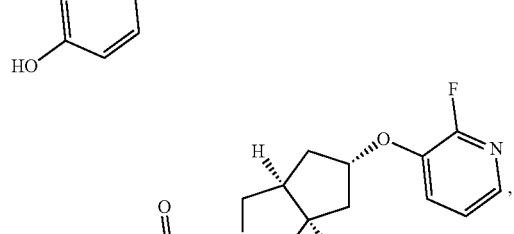
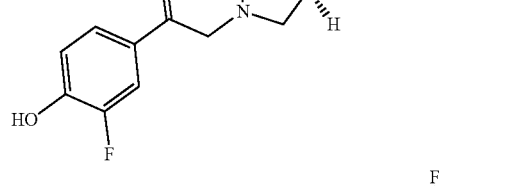
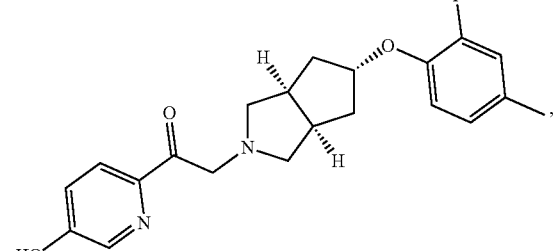
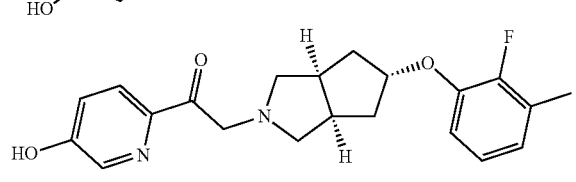
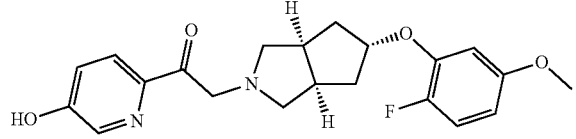
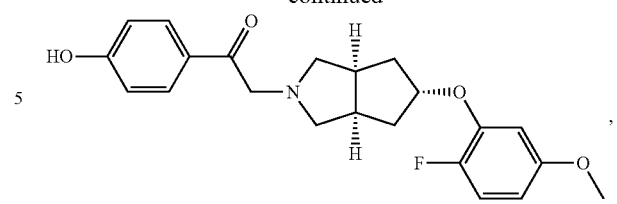
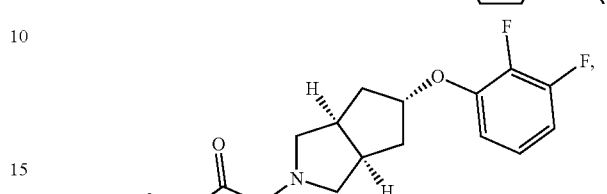
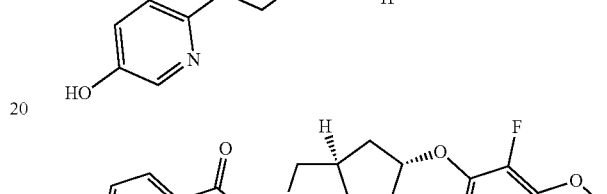
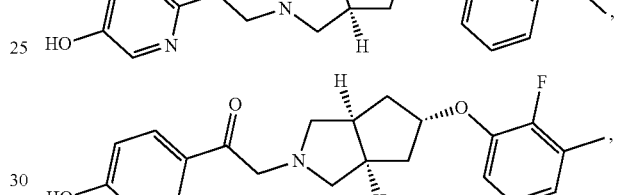
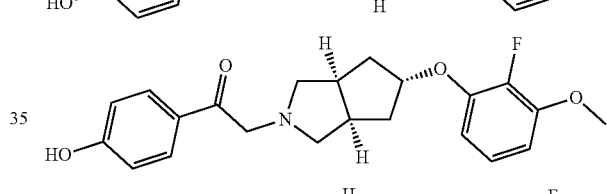
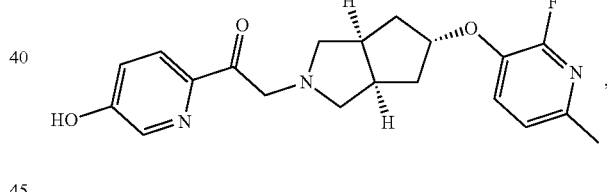
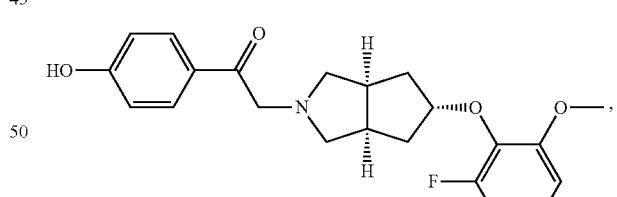
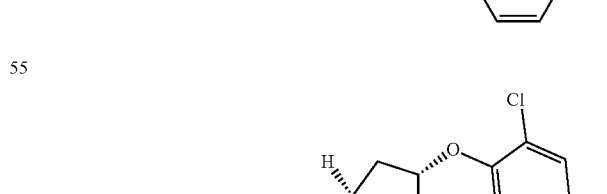
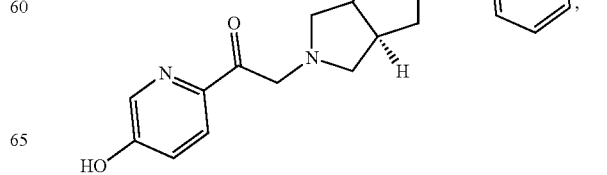

209
-continued
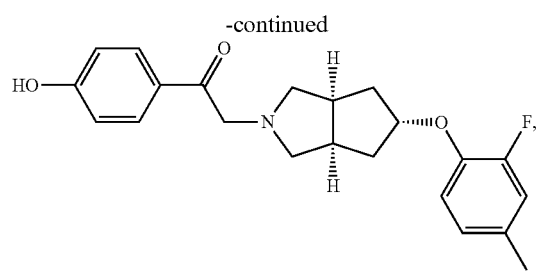
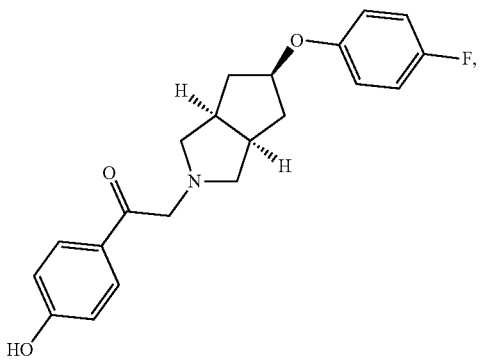
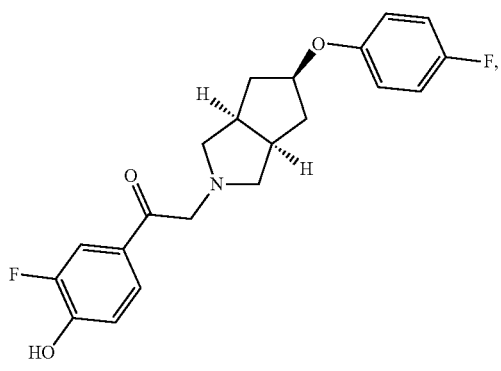
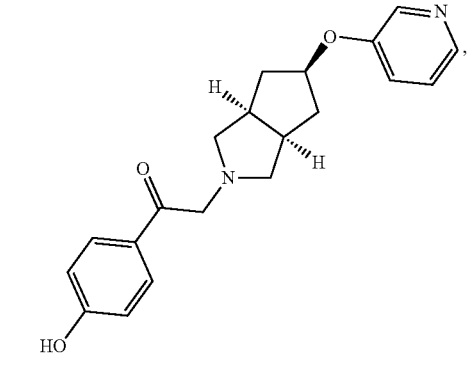
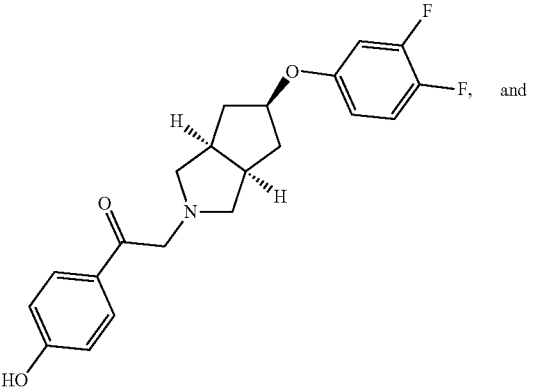
210
-continued
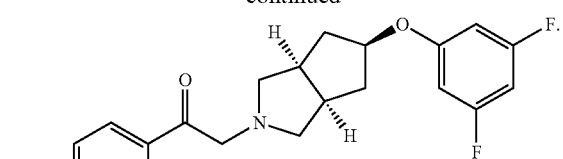
16. A compound, or a pharmaceutically acceptable salt, tautomer, or stereoisomer thereof, selected from the group consisting of:
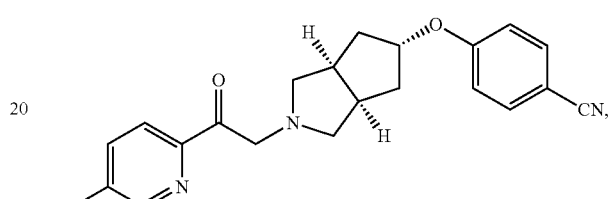
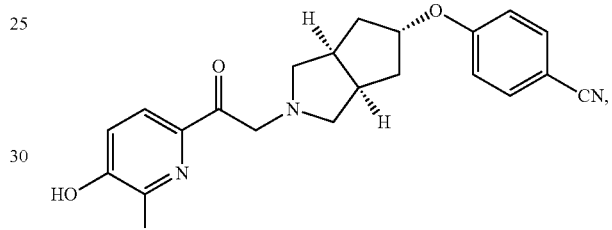
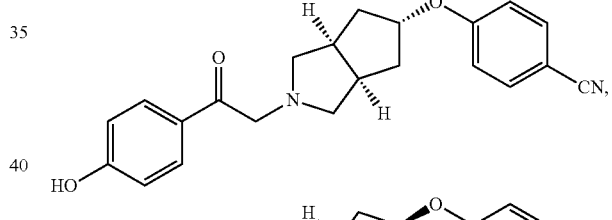
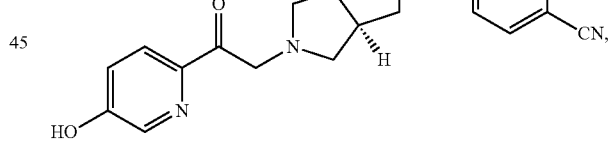
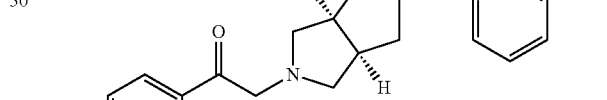
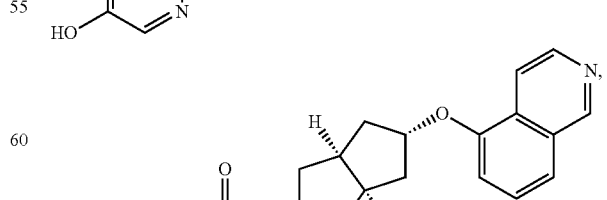
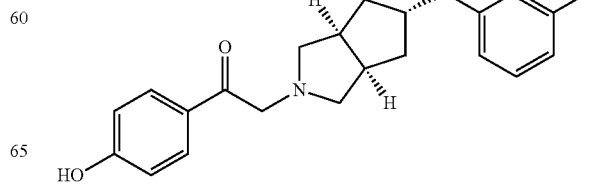

-continued
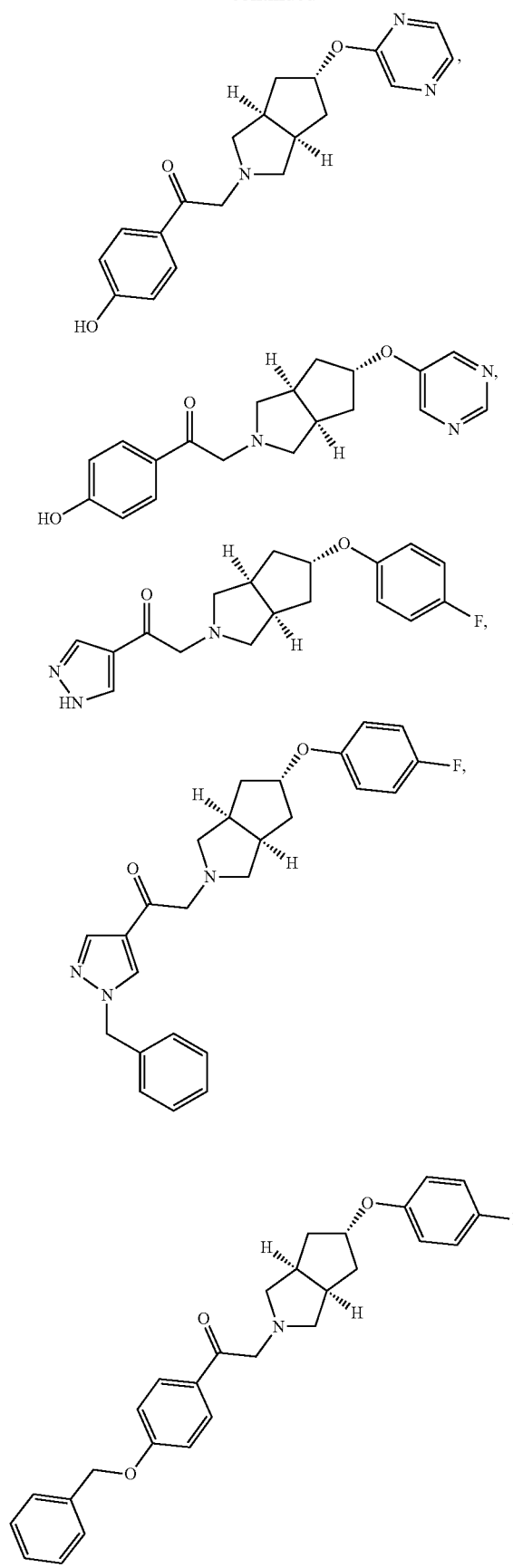
-continued
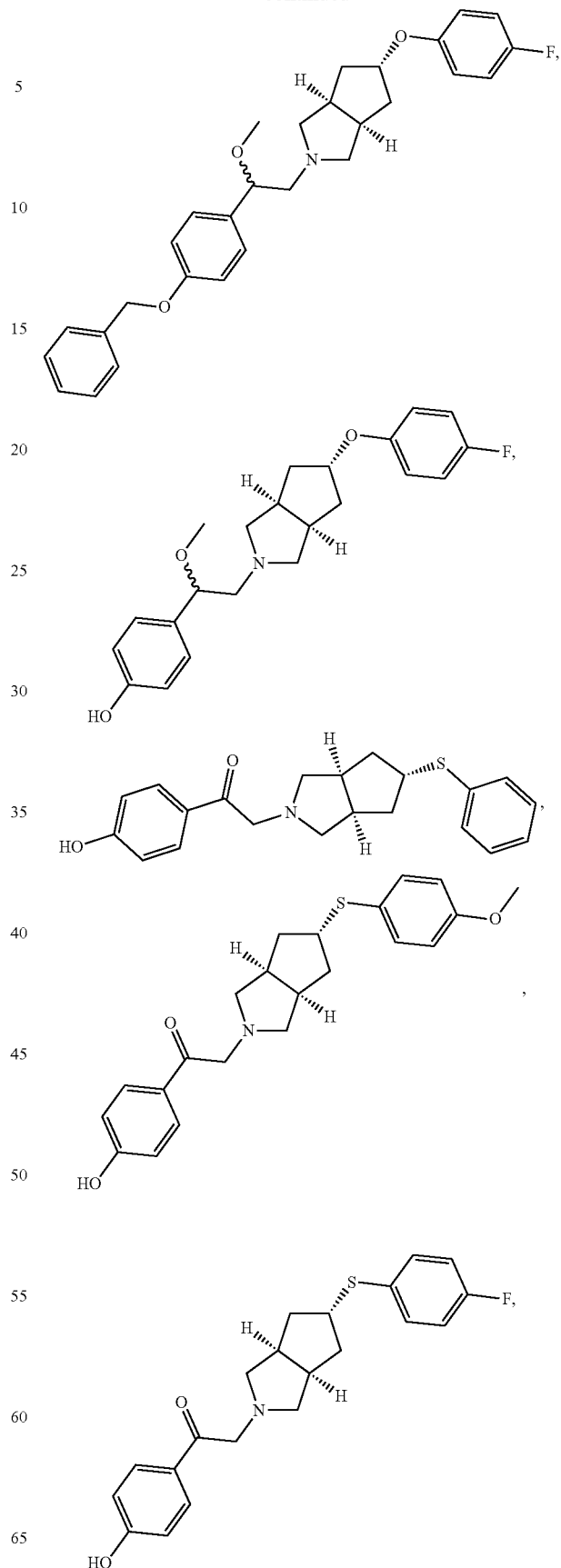

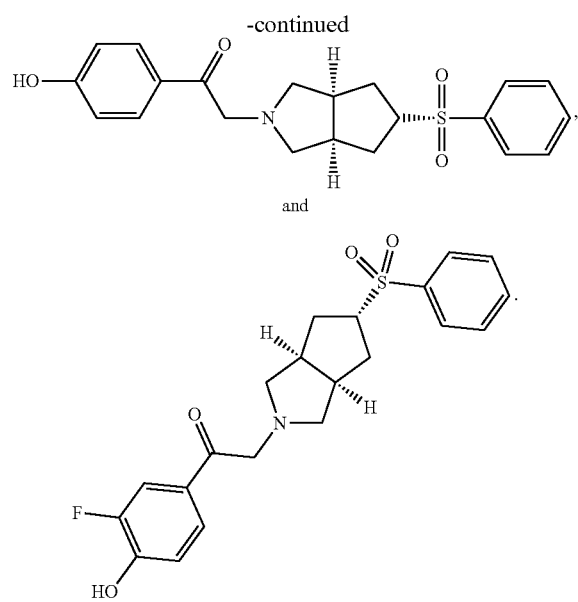

17. A pharmaceutical composition comprising a compound of claim 6, or a pharmaceutically acceptable salt, tautomer, or stereoisomer thereof, and a pharmaceutically acceptable carrier.

18. A pharmaceutical composition comprising a compound of claim 11, or a pharmaceutically acceptable salt thereof, and a pharmaceutically acceptable carrier.

19. A pharmaceutical composition comprising a compound of claim 12, or a pharmaceutically acceptable salt thereof, and a pharmaceutically acceptable carrier.

20. A pharmaceutical composition comprising a compound of claim 13, or a pharmaceutically acceptable salt thereof, and a pharmaceutically acceptable carrier.

21. A pharmaceutical composition comprising a compound of claim 14, or a pharmaceutically acceptable salt thereof, and a pharmaceutically acceptable carrier.

22. A pharmaceutical composition comprising a compound of claim 16, or a pharmaceutically acceptable salt thereof, and a pharmaceutically acceptable carrier.

* * * * *